United States Patent
Nilsson et al.

(10) Patent No.: US 12,227,796 B2
(45) Date of Patent: *Feb. 18, 2025

(54) RNA TEMPLATED LIGATION

(71) Applicant: 10x Genomics, Inc., Pleasanton, CA (US)

(72) Inventors: Mats Nilsson, Drottningholm (SE); Malte Kühnemund, Stockholm (SE); Tomasz Krzywkowski, Skarpnäck (SE)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,291

(22) Filed: Jul. 19, 2023

(65) Prior Publication Data
US 2023/0366010 A1    Nov. 16, 2023

Related U.S. Application Data

(63) Continuation of application No. 18/154,592, filed on Jan. 13, 2023, which is a continuation of application No. 16/647,860, filed as application No. PCT/EP2018/077161 on Oct. 5, 2018, now Pat. No. 11,597,965.

(30) Foreign Application Priority Data

Oct. 6, 2017 (GB) .................................. 1716407
Nov. 1, 2017 (GB) .................................. 1718095
Nov. 1, 2017 (GB) .................................. 1718098

(51) Int. Cl.
  *C12Q 1/682* (2018.01)
  *C12N 15/11* (2006.01)
  *C12P 19/34* (2006.01)
  *C12Q 1/6806* (2018.01)
  *C12Q 1/6876* (2018.01)

(52) U.S. Cl.
  CPC .............. *C12Q 1/682* (2013.01); *C12N 15/11* (2013.01); *C12P 19/34* (2013.01); *C12Q 1/6806* (2013.01); *C12Q 1/6876* (2013.01); *C12N 2310/532* (2013.01)

(58) Field of Classification Search
  CPC .................................. C12Q 1/68; C07H 21/00
  See application file for complete search history.

(56) References Cited

U.S. PATENT DOCUMENTS

| | | |
|---|---|---|
| 4,336,173 A | 6/1982 | Ugelstad |
| 4,883,867 A | 11/1989 | Lee |
| 5,001,050 A | 3/1991 | Blanco et al. |
| 5,321,130 A | 6/1994 | Yue et al. |
| 5,410,030 A | 4/1995 | Yue et al. |
| 5,436,134 A | 7/1995 | Haugland et al. |
| 5,582,977 A | 12/1996 | Yue et al. |
| 5,635,352 A | 6/1997 | Urdea et al. |
| 5,658,751 A | 8/1997 | Yue et al. |
| 5,695,940 A | 12/1997 | Drmanac et al. |
| 5,863,753 A | 1/1999 | Haugland et al. |
| 5,871,921 A | 2/1999 | Landegren et al. |
| 5,942,391 A | 8/1999 | Zhang et al. |
| 5,989,823 A | 11/1999 | Jayasena et al. |
| 6,117,635 A | 9/2000 | Nazarenko et al. |
| 6,248,526 B1 | 6/2001 | Weimer |
| 6,306,597 B1 | 10/2001 | Macevicz |
| 6,326,145 B1 | 12/2001 | Whitcombe et al. |
| 6,372,424 B1 | 4/2002 | Arnold et al. |
| 6,534,266 B1 | 3/2003 | Singer |
| RE38,442 E | 2/2004 | Zhang et al. |
| 7,255,994 B2 | 8/2007 | Lao |

(Continued)

FOREIGN PATENT DOCUMENTS

| | | |
|---|---|---|
| CA | 2136764 | 12/1993 |
| EP | 1916312 | 4/2008 |

(Continued)

OTHER PUBLICATIONS

U.S. Appl. No. 18/154,592, filed Jan. 13, 2023, by Mats Nilsson et al. (Copy not submitted herewith pursuant to the waiver of 37 C.F.R. § 1.98(a)(2)(iii) issued by the Office on Sep. 21, 2004).
Berthet et al., "Phi29 polymerase based random amplification of viral RNA as an alternative to random RT-PCR", BMC Molecular Biology. (2008), 9:77 (7 pages).
Bibikova et al., "Quantitative gene expression profiling in formalin-fixed, paraffin-embedded tissues using universal bead arrays," Am J Pathol. Nov. 2004; 165(5):1799-807.

(Continued)

*Primary Examiner* — Ethan C Whisenant
(74) *Attorney, Agent, or Firm* — MORRISON & FOERSTER LLP

(57) ABSTRACT

The present application provides methods for detecting a target nucleic acid molecule in a sample comprising contacting said sample with a ligatable probe comprising one or more parts and allowing said probe to hybridise to the target nucleic acid molecule, ligating any probe which has hybridised to the target nucleic acid molecule, amplifying the ligated probe, and detecting the amplification product, thereby to detect the target nucleic acid molecule, wherein said probes comprise at least one ribonucleotide at or near to a ligation site and/or wherein the probe or a probe part comprises an additional sequence 5' to a target-specific binding site which is not hybridised to the target nucleic acid molecule upon hybridisation of the probe to the target nucleic acid molecule and forms a 5' flap containing one or more nucleotides at its 3' end that is cleaved prior to ligation, and methods of synthesising a DNA molecule with Phi29 DNA polymerase using a template nucleic acid molecule comprising at least one ribonucleotide. Probes for use in the detection methods are provided.

30 Claims, 36 Drawing Sheets
Specification includes a Sequence Listing.

(56) References Cited

U.S. PATENT DOCUMENTS

| | | |
|---|---|---|
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,655,898 B2 | 2/2010 | Miller |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,008,010 B1 | 8/2011 | Kuersten et al. |
| 8,016,050 B2 | 9/2011 | Teodorescu |
| 8,053,188 B2 | 11/2011 | Gullberg et al. |
| 8,124,751 B2 | 2/2012 | Pierce et al. |
| 8,199,999 B2 | 6/2012 | Hoyt et al. |
| 8,206,904 B2 | 6/2012 | Allawi et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,518,640 B2 | 8/2013 | Drmanac et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,709,727 B2 | 4/2014 | Stromberg et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,422,601 B2 | 8/2016 | Kim et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,597,965 B2 * | 3/2023 | Nilsson ............... C12Q 1/6841 |
| 11,643,679 B2 | 5/2023 | Glezer et al. |
| 11,999,999 B2 | 6/2024 | Ju et al. |
| 2003/0175750 A1 | 9/2003 | Barany et al. |
| 2005/0158716 A1 | 7/2005 | Dahlberg et al. |
| 2005/0287526 A1 | 12/2005 | Landegren et al. |
| 2008/0241831 A1 | 10/2008 | Fan et al. |
| 2010/0112556 A1 | 5/2010 | Sampson et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2014/0120534 A1 * | 5/2014 | Bernitz ............... C12Q 1/6809 435/6.11 |
| 2014/0170654 A1 * | 6/2014 | Landegren ........... C12Q 1/6876 536/24.3 |
| 2014/0171338 A1 | 6/2014 | Terbureggen et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0159033 A1 | 6/2017 | Kamtekar et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0332368 A1 | 10/2020 | Ferree et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |

(56) References Cited

U.S. PATENT DOCUMENTS

| | | |
|---|---|---|
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava et al. |
| 2022/0282319 A1 | 9/2022 | Verheyen et al. |
| 2022/0372570 A1 | 11/2022 | Costa |
| 2022/0380838 A1 | 12/2022 | Kuhnemund et al. |
| 2022/0403458 A1 | 12/2022 | Bava et al. |
| 2023/0012607 A1 | 1/2023 | Kuhnemund et al. |
| 2023/0013775 A1 | 1/2023 | Chen |
| 2023/0015226 A1 | 1/2023 | Chen |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen et al. |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund et al. |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0227894 A1 | 7/2023 | Nilsson et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund et al. |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Levin |
| 2023/0323430 A1 | 10/2023 | Shastry |
| 2023/0323437 A1 | 10/2023 | Chen |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Costa |
| 2024/0026427 A1 | 1/2024 | Kuhnemund et al. |
| 2024/0026439 A1 | 1/2024 | Sasaki et al. |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava et al. |
| 2024/0084373 A1 | 3/2024 | Shastry |
| 2024/0084378 A1 | 3/2024 | Marks et al. |
| 2024/0101978 A1 | 3/2024 | Boghospor |
| 2024/0132938 A1 | 4/2024 | Kuhnemund et al. |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |

FOREIGN PATENT DOCUMENTS

| | | |
|---|---|---|
| EP | 2361991 | 8/2011 |
| WO | WO 2003/044229 | 5/2003 |
| WO | WO 2004/027082 | 4/2004 |
| WO | WO 2005/010199 | 2/2005 |
| WO | WO 2006/020515 | 2/2006 |
| WO | WO 2009/091719 | 7/2009 |
| WO | WO 2013/122996 | 8/2013 |
| WO | WO 2013/123238 | 8/2013 |
| WO | WO 2014/030066 | 2/2014 |
| WO | WO 2015/075198 | 2/2017 |
| WO | WO 2017/019481 | 2/2017 |
| WO | WO 2017/035090 | 3/2017 |
| WO | WO 2017/143155 | 8/2017 |
| WO | WO 2017/223026 | 12/2017 |
| WO | WO 2019/068880 | 4/2019 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | 2021/138676 | 7/2021 |
| WO | WO 2021/155063 | 8/2021 |
| WO | WO 2021/168326 | 8/2021 |
| WO | 2023/108139 | 6/2023 |
| WO | 2023/141476 | 7/2023 |
| WO | 2023/172915 | 9/2023 |
| WO | 2023/192302 | 10/2023 |
| WO | 2024/148300 | 7/2024 |

OTHER PUBLICATIONS

Capodieci et al., "Gene expression profiling in single cells within tissue," Nat Methods. (2005) 2(9): 663-5.

Conze et al., "Single molecule analysis of combinatorial splicing," Nucleic Acids Res. (2010) 38(16): e163.

Credle et al., "Multiplexed analysis of fixed tissue RNA using Ligation in situ Hybridization," Nucleic Acids Res. (2017) 45(14): e128.

Demidov., "Rolling Circle Amplification (RCA) Towards New Clinical Diagnostics and Therapeutics", Springer, (2016), 180 pages, ISBN 978-3-319-42224-4.

Drmanac et al., "Human genome sequencing using unchained base reads on self-assembling DNA nanoarrays," Science. (2010) 327(5961): 78-81.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Guan et al., "Preparation of Circular Templates by T4 RNA Ligase 2 for Rolling Circle Amplification of Target microRNAs with High

(56) References Cited

OTHER PUBLICATIONS

Specificity and Sensitivity", Rolling Circle Amplification (RCA): Toward New Clinical Diagnostics and Therapeutics, Chapter 3, pp. 25-35, 2016.
Gunderson et al. "Decoding randomly ordered DNA arrays." Genome research 14.5 (2004): 870-877.
Han et al., "Quantum-dot-tagged microbeads for multiplexed optical coding of biomolecules," Nat Biotechnol. (2001) 19(7): 631-5.
Hardenbol et al., "Multiplexed genotyping with sequence-tagged molecular inversion probes," Nat Biotechnol. (2003) 21(6): 673-678.
Heid et al., "Real time quantitative PCR," Genome Res. (1996) 6(10): 986-94.
Holland et al., "Detection of specific polymerase chain reaction product by utilizing the 5'----3' exonuclease activity of Thermus aquaticus DNA polymerase," Proc Natl Acad Sci USA. (1991) 88(16): 7276-7280.
Hu et al., "Sensitive quantification of messenger RNA with a real-time ligase chain reaction by using a ribonucleotide-modified DNA probe," Chem Commun (Camb). (2014) 50(86):13093-5.
Hu et al., Supplementary Information for Chem.Commun. paper. Chem. Commun. 50:13093 (Year: 2014).
International Search Report and Written Opinion of the International Searching Authority, dated Jan. 22, 2019, ssued in Application No. PCT/EP2018/077161, 30 pages.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Jain, "Textbook of Personalized Medicine, Chapter 2, Molecular Diagnostics as a Basis of Personalized Medicine" 2009, 31 pages, DOI 10.1007/978-1-4419-0769-1_2.
Jonstrup et al., "A microRNA detection system based on padlock probes and rolling circle amplification," RNA (2006) 12(9): 1747-1752.
Kao et al., "Cleavage Specificity of *Saccharomyces cerevisiae* Flap Endonuclease 1 Suggests a Double-Flap Structure as the Cellular Substrate," J of Bio Chem. vol. 277, No. 17, Issue of Apr. 26, pp. 14379-14389, 2002.
Kao et al., "On the Roles of *Saccharomyces cerevisiae* Dna2p and Flap Endonuclease 1 in Okazaki Fragment Processing" J of Bio Chem. vol. 279, No. 15, pp. 15014-15024, 2004.
Kasiviswanathan et al., "Ribonucleotide discrimination and reverse transcription by the human mitochondrial DNA polymerase," J Biol Chem. (2011) 286(36): 31490-500.
Ke et al., "In situ sequencing for RNA analysis in preserved tissue and cells," Nat Methods. (2013) 10(9):857-60.
Krzywkowski et al., "Chimeric padlock and iLock probes for increased efficiency of targeted RNA detection", RNA, 2018, 24 pages, Cold Spring Harbor Laboratory Press, XP055521430A.
Krzywkowski et al., "Chimeric padlock and iLock probes for increased efficiency of targeted RNA detection," RNA. (2019) 25(1):82-89.
Krzywkowski et al., "Detection of miRNAs using chimeric DNA/RNA iLock probes utilizing novel activity of PBCV-1-DNA ligase: RNA-templaled ligation of ssRNA", 1 sheet, 2017, Accessed from DiVA Portal Website on Jul. 11, 2018 at http://www.diva-portal.org/smash/record.jsf?pid=diva2%3A1148311&dswid=1138.
Krzywkowski et al., "Fidelity of RNA templated end-joining by chlorella virus DNA ligase and a novel iLock assay with improved direct RNA detection accuracy," Nucleic Acids Res. (2017) 45(18): e161.
Krzywkowski et al., "Limited reverse transcriptase activity of phi29 DNA polymerase," Nucleic Acids Res. (2018) 46(7): 3625-3632.
Krzywkowski et al., "Reverse-transcriplase activity of Phi29 DNA polymerase", Abstract only, 1 sheet, J017, URN: urn:nbm:se:su:diva-147733.
Krzywkowski, "iLocks: a novel tool for RNA assays with improved specificity", Department of Biochemistry and Biophysics, Stockholm University, 2017 Thesis, 62 pages. ISBN 978-91-7797-043-9.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Lasda, Eric et al., "Circular RNAs: diversty of form and function", RNA. 2014, vol. 20, No. 12, pp. 1829-1842.
Lee et al., "Allelic discrimination by nick-translation PCR with fluorogenic probes," Nucleic Acids Res. (1993) 21(16): 3761-3766.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Liu et al., "Direct Visualization of RNA-DNA Primer Removal from Okazaki Fragments Provides Support for rlap Cleavage and Exonucleolylic Pathways in Eukaryotic Cells" Journal of Biological Chemistry, 2017, vol. 292, No. 12, pp. 4777-4788.
Lohman et al., "Efficient DNA ligation in DNA-RNA hybrid helices by Chlorella virus DNA ligase," Nucleic Acids Res. (2014) 42(3):1831-44.
Lyamichev et al., "Comparison of the 5' nuclease activities of taq DNA polymerase and its isolated nuclease domain," Proc Natl Acad Sci USA. (1999) 96(11): 6143-6148.
Ma et al., "RNA template-dependent 5' nuclease activity of Thermus aquaticus and Thermus thermophilus DNA polymerases," J Biol Chem. (2000) 275(32): 24693-700.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Nazarenko et al., "A closed tube format for amplification and detection of DNA based on energy transfer," Nucleic Acids Res. (1997) 25(12): 2516-21.
Nilsson et al., "Enhanced detection and distinction of RNA by enzymatic probe ligation," Nat Biotechnol. (2000) 18(7): 791-793.
Nilsson et al., "RNA-templated DNA ligation for transcript analysis," Nucleic Acids Res. (2001) 29(2):578-81.
Payne et al. "In situ genome sequencing resolves DNA sequence and structure in intact biological samples," Science. (2021) 371(6532): eaay3446. doi: 10.1126/science.aay3446. Epub Dec. 31, 2020.
Raj et al., "Imaging individual mRNA molecules using multiple singly labeled probes," Nat Methods. (2008) 5(10): 877-879.
Rouhanifard et al. "ClampFISH detects individual nucleic acid molecules using click chemistry-based amplification," Nat Biotechnol. (2018) 17 pages. doi: 10.1038/nbt.4286.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Tang et al., "Suppression of rolling circle amplification by nucleotide analogs in circular template for three DNA polymerases", Bioscience, Biotechnology, and Biochemistry, 2016, vol. 80, No. 8, 1555-1561.
Tyagi et al., "Molecular Beacons: Probes that Fouresce upon Hybridization," Nature Biotechnology. (1996) 14:303-308.
UKIPO Search Report dated Aug. 10, 2018 issued in Application No. GB1718095.1, 3 pages.
UKIPO Search Report dated Aug. 15, 2018 issued in Application No. GB1718098.5, pages.
UKIPO Search Report dated Jul. 16, 2018 issued in Application No. GB1716407.0, 5 pages.

(56) References Cited

OTHER PUBLICATIONS

Wählby et al., "Sequential immunofluorescence staining and image analysis for detection of large Nos. of antigens in individual cell nuclei," Cytometry. (2002) 47(1): 32-41.

Weibrecht et al., "In situ detection of individual mRNA molecules and protein complexes or post-translational modifications using padlock probes combined with the in situ proximity ligation assay," Nat Protoc. (2013) 8(2):355-72.

Weibrecht et al., "Simultaneous visualization of both signaling cascade activity and end-point gene expression in single cells," PLoS One. (2011) 6(5): e20148.

Whitcombe et al., "Detection of PCR products using self-probing amplicons and fluorescence," Nat Biotechnol. (1999) 17(8): 804-807.

Wilson et al., "Encoded microcarriers for high-throughput multiplexed detection," Angew Chem Int Ed Engl. (2006) 18;45(37): 6104-17.

Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Zhang et al., "Ultrasensitive quantification of mature microRNAs by real-time PCR based on ligation of a ribonucleotide-modified DNA probe," Chem Commun (Camb). (2011) 47(33): 9465-9467.

Zhao et al., "Advances of multiplex and high throughput biomolecular detection technologies based on encoding microparticles," Sci China Chem. (2011) 54(8):1185.

Zhao et al., "Discriminative identification of miRNA let-7 family members with high specificity and sensitivity using rolling circle amplification," Acta Biochim Biophys Sin (Shanghai). (2015) 47(2): 130-6.

Cheng et al., "Highly sensitive determination of microRNA using target-primed and branched rolling-circle amplification," Angew Chem Int Ed Engl. (2009) 48(18):3268-72.

\* cited by examiner

A

B gapfill invader on RNA OncoDG1

A

B

C

SEQUENCE LISTING

```
Sequence total quantity: 294
SEQ ID NO: 1            moltype = RNA   length = 41
FEATURE                 Location/Qualifiers
source                  1..41
                        mol_type = unassigned RNA
                        organism = Homo sapiens
SEQUENCE: 1
aacttgtggt agttggagct ggtggcgtag gcaagagtgc c                   41

SEQ ID NO: 2            moltype = DNA   length = 70
FEATURE                 Location/Qualifiers
misc_feature            1..70
                        note = KRASwt_PLP
misc_feature            1
                        note = 5' Phosphate
source                  1..70
                        mol_type = other DNA
                        organism = synthetic construct
SEQUENCE: 2
agctccaact accacaaaaa aaaaaagtag ccgtgactat cgactaaaaa aaaaacttgc   60
ctacgccacc                                                          70

SEQ ID NO: 3            moltype = RNA   length = 22
FEATURE                 Location/Qualifiers
source                  1..22
                        mol_type = unassigned RNA
                        organism = Homo sapiens
SEQUENCE: 3
tgaggtagga ggttgtatag tt                                         22

SEQ ID NO: 4            moltype = RNA   length = 22
FEATURE                 Location/Qualifiers
source                  1..22
                        mol_type = unassigned RNA
                        organism = Homo sapiens
SEQUENCE: 4
agaggtagta ggttgcatag tt                                         22

SEQ ID NO: 5            moltype = DNA   length = 65
FEATURE                 Location/Qualifiers
misc_feature            1..65
                        note = let7-a_PLP_1
misc_feature            1
                        note = 5' Phosphate
source                  1..65
                        mol_type = other DNA
                        organism = synthetic construct
SEQUENCE: 5
```

```
ctactacctc aaaaaaaaaa acctcaatgc acatgtttgg ctccaaaaaa aaaaaactat    60
acaac                                                                65

SEQ ID NO: 6            moltype = DNA  length = 65
FEATURE                 Location/Qualifiers
misc_feature            1..65
                        note = let7-f_PLP_1
misc_feature            1
                        note = 5' Phosphate
source                  1..65
                        mol_type = other DNA
                        organism = synthetic construct
SEQUENCE: 6
ctactacctc aaaaaaaaaa acctcaatgc acatgtttgg ctccaaaaaa aaaaaactat    60
acaat                                                                65

SEQ ID NO: 7            moltype = DNA  length = 65
FEATURE                 Location/Qualifiers
misc_feature            1..65
                        note = let7-e_PLP_1
misc_feature            1
                        note = 5' Phosphate
source                  1..65
                        mol_type = other DNA
                        organism = synthetic construct
SEQUENCE: 7
ctcctacctc aaaaaaaaaa acctcaatgc acatgtttgg ctccaaaaaa aaaaaactat    60
acaac                                                                65

SEQ ID NO: 8            moltype = DNA  length = 65
FEATURE                 Location/Qualifiers
misc_feature            1..65
                        note = let7-d_PLP_1
misc_feature            1
                        note = 5' Phosphate
source                  1..65
                        mol_type = other DNA
                        organism = synthetic construct
SEQUENCE: 8
ctactacctc taaaaaaaaa acctcaatgc acatgtttgg ctccaaaaaa aaaaaactat    60
gcaac                                                                65

SEQ ID NO: 9            moltype = DNA  length = 65
FEATURE                 Location/Qualifiers
misc_feature            1..65
                        note = let7-a_PLP_RNA_1
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 9
ctactacctc aaaaaaaaaa acctcaatgc acatgtttgg ctccaaaaaa aaaaaactat    60
acaac                                                                65

SEQ ID NO: 10           moltype = DNA  length = 65
FEATURE                 Location/Qualifiers
misc_feature            1..65
                        note = let7-f_PLP_RNA_1
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 10
ctactacctc aaaaaaaaaa acctcaatgc acatgtttgg ctccaaaaaa aaaaaactat    60
acaat                                                                65

SEQ ID NO: 11           moltype = DNA  length = 65
FEATURE                 Location/Qualifiers
misc_feature            1..65
```

```
                         note = let7-e_PLP_RNA_1
misc_feature             1
                         note = 5' Phosphate
misc_feature             1..64
                         note = DNA
misc_feature             65
                         note = RNA
source                   1..65
                         mol_type = other DNA
                         organism = synthetic construct
SEQUENCE: 11
ctcctacctc aaaaaaaaaa acctcaatgc acatgtttgg ctccaaaaaa aaaaaactat    60
acaac                                                                65

SEQ ID NO: 12            moltype = DNA  length = 65
FEATURE                  Location/Qualifiers
misc_feature             1..65
                         note = let7-d_PLP_RNA_1
misc_feature             1
                         note = 5' Phosphate
misc_feature             1..64
                         note = DNA
misc_feature             65
                         note = RNA
source                   1..65
                         mol_type = other DNA
                         organism = synthetic construct
SEQUENCE: 12
ctactacctc taaaaaaaaa acctcaatgc acatgtttgg ctccaaaaaa aaaaaactat    60
gcaac                                                                65

SEQ ID NO: 13            moltype = RNA  length = 25
FEATURE                  Location/Qualifiers
misc_feature             1..25
                         note = benchm_templ_C
source                   1..25
                         mol_type = other RNA
                         organism = synthetic construct
SEQUENCE: 13
tctcgctgtc atccctatat cctcg                                          25

SEQ ID NO: 14            moltype = RNA  length = 25
FEATURE                  Location/Qualifiers
misc_feature             1..25
                         note = benchm_templ_A
source                   1..25
                         mol_type = other RNA
                         organism = synthetic construct
SEQUENCE: 14
tctcgctgtc atacctatat cctcg                                          25

SEQ ID NO: 15            moltype = RNA  length = 25
FEATURE                  Location/Qualifiers
misc_feature             1..25
                         note = benchm_templ_G
source                   1..25
                         mol_type = other RNA
                         organism = synthetic construct
SEQUENCE: 15
tctcgctgtc atgcctatat cctcg                                          25

SEQ ID NO: 16            moltype = RNA  length = 25
FEATURE                  Location/Qualifiers
misc_feature             1..25
                         note = benchm_templ_U
source                   1..25
                         mol_type = other RNA
                         organism = synthetic construct
SEQUENCE: 16
tctcgctgtc attcctatat cctcg                                          25

SEQ ID NO: 17            moltype = DNA  length = 65
FEATURE                  Location/Qualifiers
misc_feature             1..65
                         note = 3'T_PLP_2
misc_feature             1
                         note = 5' Phosphate
source                   1..65
                         mol_type = other DNA
```

```
                        organism = synthetic construct
SEQUENCE: 17
atgacagcga gaaaaaaaaa aaagtagccg tgactatcga ctaaaaaaaa aacgaggata    60
taggt                                                                65

SEQ ID NO: 18           moltype = DNA   length = 65
FEATURE                 Location/Qualifiers
misc_feature            1..65
                        note = 3'G_PLP_2
misc_feature            1
                        note = 5' Phosphate
source                  1..65
                        mol_type = other DNA
                        organism = synthetic construct
SEQUENCE: 18
atgacagcga gaaaaaaaaa aaagtagccg tgactatcga ctaaaaaaaa aacgaggata    60
taggg                                                                65

SEQ ID NO: 19           moltype = DNA   length = 65
FEATURE                 Location/Qualifiers
misc_feature            1..65
                        note = 3'A_PLP_2
misc_feature            1
                        note = 5' Phosphate
source                  1..65
                        mol_type = other DNA
                        organism = synthetic construct
SEQUENCE: 19
atgacagcga gaaaaaaaaa aaagtagccg tgactatcga ctaaaaaaaa aacgaggata    60
tagga                                                                65

SEQ ID NO: 20           moltype = DNA   length = 65
FEATURE                 Location/Qualifiers
misc_feature            1..65
                        note = 3'C_PLP_2
misc_feature            1
                        note = 5' Phosphate
source                  1..65
                        mol_type = other DNA
                        organism = synthetic construct
SEQUENCE: 20
atgacagcga gaaaaaaaaa aaagtagccg tgactatcga ctaaaaaaaa aacgaggata    60
taggc                                                                65

SEQ ID NO: 21           moltype = DNA   length = 65
FEATURE                 Location/Qualifiers
misc_feature            1..65
                        note = 3'rT_PLP_2
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 21
atgacagcga gaaaaaaaaa aaagtagccg tgactatcga ctaaaaaaaa aacgaggata    60
taggt                                                                65

SEQ ID NO: 22           moltype = DNA   length = 65
FEATURE                 Location/Qualifiers
misc_feature            1..65
                        note = 3'rG_PLP_2
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 22
atgacagcga gaaaaaaaaa aaagtagccg tgactatcga ctaaaaaaaa aacgaggata    60
taggg                                                                65

SEQ ID NO: 23           moltype = DNA   length = 65
```

```
FEATURE                 Location/Qualifiers
misc_feature            1..65
                        note = 3'rA_PLP_2
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 23
atgacagcga gaaaaaaaaa aaagtagccg tgactatcga ctaaaaaaaa aacgaggata    60
tagga                                                                65

SEQ ID NO: 24           moltype = DNA   length = 65
FEATURE                 Location/Qualifiers
misc_feature            1..65
                        note = 3'rC_PLP_2
misc_feature            1
                        note = 5' Phosphate
misc_feature            1..64
                        note = DNA
misc_feature            65
                        note = RNA
source                  1..65
                        mol_type = other DNA
                        organism = synthetic construct
SEQUENCE: 24
atgacagcga gaaaaaaaaa aaagtagccg tgactatcga ctaaaaaaaa aacgaggata    60
taggc                                                                65

SEQ ID NO: 25           moltype = DNA   length = 24
FEATURE                 Location/Qualifiers
misc_feature            1..24
                        note = Decorator probe_1
misc_feature            1
                        note = 5' Phosphate
misc_feature            1..20
                        note = DNA
misc_feature            21..24
                        note = RNA
modified_base           21..24
                        mod_base = OTHER
                        note = 2' O-Me nucleotide
source                  1..24
                        mol_type = other DNA
                        organism = synthetic construct
SEQUENCE: 25
cctcaatgca catgtttggc tcca                                           24

SEQ ID NO: 26           moltype = DNA   length = 21
FEATURE                 Location/Qualifiers
misc_feature            1..21
                        note = Decorator probe2_2
misc_feature            1
                        note = 5' Phosphate
misc_feature            1..17
                        note = DNA
misc_feature            18..21
                        note = RNA
modified_base           18..21
                        mod_base = OTHER
                        note = 2' O-Me nucleotide
source                  1..21
                        mol_type = other DNA
                        organism = synthetic construct
SEQUENCE: 26
agtagccgtg actatcgact a                                              21

SEQ ID NO: 27           moltype = RNA   length = 22
FEATURE                 Location/Qualifiers
source                  1..22
                        mol_type = unassigned RNA
                        organism = Homo sapiens
SEQUENCE: 27
tgaggtagta ggttgtatag tt                                             22
```

```
SEQ ID NO: 28              moltype = DNA   length = 59
FEATURE                    Location/Qualifiers
misc_feature               1..59
                           note = let-7a_PLP
source                     1..59
                           mol_type = other DNA
                           organism = synthetic construct
SEQUENCE: 28
ctactacctc aaaaaaaacc tcaatgcaca tgtttggctc caaaaaaaaa ctatacaac    59

SEQ ID NO: 29              moltype = DNA   length = 79
FEATURE                    Location/Qualifiers
misc_feature               1..79
                           note = iLock_1
source                     1..79
                           mol_type = other DNA
                           organism = synthetic construct
SEQUENCE: 29
cgcgtgtcgt tgccctacta cctcaaaaaa aaaaacctca atgcacatgt tggctccaa    60
aaaaaaaaaa ctatacaac                                                79

SEQ ID NO: 30              moltype = DNA   length = 79
FEATURE                    Location/Qualifiers
misc_feature               1..79
                           note = iLock-3_1
misc_feature               1..78
                           note = DNA
misc_feature               79
                           note = RNA
source                     1..79
                           mol_type = other DNA
                           organism = synthetic construct
SEQUENCE: 30
cgcgtgtcgt tgccctacta cctcaaaaaa aaaaacctca atgcacatgt tggctccaa    60
aaaaaaaaaa ctatacaac                                                79

SEQ ID NO: 31              moltype = DNA   length = 79
FEATURE                    Location/Qualifiers
misc_feature               1..79
                           note = iLock-3D_1
misc_feature               1..78
                           note = DNA
misc_feature               79
                           note = RNA
source                     1..79
                           mol_type = other DNA
                           organism = synthetic construct
SEQUENCE: 31
cgcgtgtcgt tgccctacta cctcaaaaaa aaaaacctca atgcacatgt tggctccaa    60
aaaaaaaaaa ctatacaac                                                79

SEQ ID NO: 32              moltype = DNA   length = 79
FEATURE                    Location/Qualifiers
misc_feature               1..79
                           note = iLock-3D5_1
misc_feature               1..78
                           note = DNA
misc_feature               79
                           note = RNA
source                     1..79
                           mol_type = other DNA
                           organism = synthetic construct
SEQUENCE: 32
cgcgtgtcgt tgccctacta cctcaaaaaa aaaaacctca atgcacatgt tggctccaa    60
aaaaaaaaaa ctatacaac                                                79

SEQ ID NO: 33              moltype = DNA   length = 79
FEATURE                    Location/Qualifiers
misc_feature               1..79
                           note = iLock-3DF_1
misc_feature               1..14
                           note = RNA
misc_feature               15..78
                           note = DNA
misc_feature               79
                           note = RNA
source                     1..79
                           mol_type = other DNA
                           organism = synthetic construct
```

SEQUENCE: 33
cgcgtgtcgt tgccctacta cctcaaaaaa aaaaacctca atgcacatgt ttggctccaa    60
aaaaaaaaaa ctatacaac                                                 79

```
SEQ ID NO: 34           moltype = DNA   length = 79
FEATURE                 Location/Qualifiers
misc_feature            1..79
                        note = iLock-DF_1
misc_feature            1..14
                        note = RNA
misc_feature            15..79
                        note = DNA
source                  1..79
                        mol_type = other DNA
                        organism = synthetic construct
```
SEQUENCE: 34
cgcgtgtcgt tgccctacta cctcaaaaaa aaaaacctca atgcacatgt ttggctccaa    60
aaaaaaaaaa ctatacaac                                                 79

```
SEQ ID NO: 35           moltype = RNA   length = 25
FEATURE                 Location/Qualifiers
misc_feature            1..25
                        note = benchm_templ_C
source                  1..25
                        mol_type = other RNA
                        organism = synthetic construct
```
SEQUENCE: 35
tctcgctgtc atccctatat cctcg                                          25

```
SEQ ID NO: 36           moltype = RNA   length = 25
FEATURE                 Location/Qualifiers
misc_feature            1..25
                        note = benchm_templ_A
source                  1..25
                        mol_type = other RNA
                        organism = synthetic construct
```
SEQUENCE: 36
tctcgctgtc atacctatat cctcg                                          25

```
SEQ ID NO: 37           moltype = RNA   length = 25
FEATURE                 Location/Qualifiers
misc_feature            1..25
                        note = benchm_templ_G
source                  1..25
                        mol_type = other RNA
                        organism = synthetic construct
```
SEQUENCE: 37
tctcgctgtc atgcctatat cctcg                                          25

```
SEQ ID NO: 38           moltype = RNA   length = 25
FEATURE                 Location/Qualifiers
misc_feature            1..25
                        note = benchm_templ_U
source                  1..25
                        mol_type = other RNA
                        organism = synthetic construct
```
SEQUENCE: 38
tctcgctgtc attcctatat cctcg                                          25

```
SEQ ID NO: 39           moltype = DNA   length = 79
FEATURE                 Location/Qualifiers
misc_feature            1..79
                        note = 3'T_iLock_3
source                  1..79
                        mol_type = other DNA
                        organism = synthetic construct
```
SEQUENCE: 39
tatatcccta tattatgaca gcgagaaaaa aaaaaagta gccgtgacta tcgactaaaa     60
aaaaaacgag gatataggt                                                 79

```
SEQ ID NO: 40           moltype = DNA   length = 79
FEATURE                 Location/Qualifiers
misc_feature            1..79
                        note = 3'G_iLock_3
source                  1..79
                        mol_type = other DNA
                        organism = synthetic construct
```
SEQUENCE: 40
tatatcccta tatgatgaca gcgagaaaaa aaaaaaagta gccgtgacta tcgactaaaa    60

-continued

```
aaaaaacgag gatataggg                                                         79

SEQ ID NO: 41            moltype = DNA  length = 79
FEATURE                  Location/Qualifiers
misc_feature             1..79
                         note = 3'A_iLock_3
source                   1..79
                         mol_type = other DNA
                         organism = synthetic construct
SEQUENCE: 41
tatatcccta tataatgaca gcgagaaaaa aaaaaagta gccgtgacta tcgactaaaa             60
aaaaaacgag gatatagga                                                         79

SEQ ID NO: 42            moltype = DNA  length = 79
FEATURE                  Location/Qualifiers
misc_feature             1..79
                         note = 3'C_iLock_3
source                   1..79
                         mol_type = other DNA
                         organism = synthetic construct
SEQUENCE: 42
tatatcccta tatcatgaca gcgagaaaaa aaaaaagta gccgtgacta tcgactaaaa             60
aaaaaacgag gatataggc                                                         79

SEQ ID NO: 43            moltype = DNA  length = 79
FEATURE                  Location/Qualifiers
misc_feature             1..79
                         note = 3'U_iLock_RNA_3
misc_feature             14
                         note = RNA
misc_feature             1..13
                         note = DNA
misc_feature             15..78
                         note = DNA
misc_feature             79
                         note = RNA
source                   1..79
                         mol_type = other DNA
                         organism = synthetic construct
SEQUENCE: 43
tatatcccta tattatgaca gcgagaaaaa aaaaaagta gccgtgacta tcgactaaaa             60
aaaaaacgag gatataggt                                                         79

SEQ ID NO: 44            moltype = DNA  length = 79
FEATURE                  Location/Qualifiers
misc_feature             1..79
                         note = 3'G_iLock_RNA_3
misc_feature             13
                         note = RNA
misc_feature             1..12
                         note = DNA
misc_feature             14..78
                         note = DNA
misc_feature             79
                         note = RNA
source                   1..79
                         mol_type = other DNA
                         organism = synthetic construct
SEQUENCE: 44
tatatcccta tatgatgaca gcgagaaaaa aaaaaagta gccgtgacta tcgactaaaa             60
aaaaaacgag gatataggg                                                         79

SEQ ID NO: 45            moltype = DNA  length = 79
FEATURE                  Location/Qualifiers
misc_feature             1..79
                         note = 3'A_iLock _RNA_3
misc_feature             13
                         note = RNA
misc_feature             14..78
                         note = DNA
misc_feature             1..12
                         note = DNA
misc_feature             79
                         note = RNA
source                   1..79
                         mol_type = other DNA
                         organism = synthetic construct
SEQUENCE: 45
tatatcccta tataatgaca gcgagaaaaa aaaaaagta gccgtgacta tcgactaaaa             60
```

```
aaaaaacgag gatatagga                                                    79

SEQ ID NO: 46           moltype = DNA   length = 79
FEATURE                 Location/Qualifiers
misc_feature            1..79
                        note = 3'C_iLock _RNA_3
misc_feature            13
                        note = RNA
misc_feature            1..12
                        note = DNA
misc_feature            14..78
                        note = DNA
misc_feature            79
                        note = RNA
source                  1..79
                        mol_type = other DNA
                        organism = synthetic construct
SEQUENCE: 46
tatatcccta tatcatgaca gcgagaaaaa aaaaaagta gccgtgacta tcgactaaaa        60
aaaaaacgag gatataggc                                                    79

SEQ ID NO: 47           moltype = DNA   length = 24
FEATURE                 Location/Qualifiers
misc_feature            1..24
                        note = Decorator probe_1
source                  1..24
                        mol_type = other DNA
                        organism = synthetic construct
SEQUENCE: 47
cctcaatgca catgtttggc tcca                                              24

SEQ ID NO: 48           moltype = DNA   length = 21
FEATURE                 Location/Qualifiers
misc_feature            1..21
                        note = Decorator probe_2
source                  1..21
                        mol_type = other DNA
                        organism = synthetic construct
SEQUENCE: 48
tgcgtctatt tagtggagcc a                                                 21

SEQ ID NO: 49           moltype = DNA   length = 21
FEATURE                 Location/Qualifiers
misc_feature            1..21
                        note = Decorator probe_3
source                  1..21
                        mol_type = other DNA
                        organism = synthetic construct
SEQUENCE: 49
agtagccgtg actatcgact a                                                 21

SEQ ID NO: 50           moltype = RNA   length = 22
FEATURE                 Location/Qualifiers
source                  1..22
                        mol_type = unassigned RNA
                        organism = Homo sapiens
SEQUENCE: 50
tgaggtagta ggttgtatag tt                                                22

SEQ ID NO: 51           moltype = RNA   length = 22
FEATURE                 Location/Qualifiers
source                  1..22
                        mol_type = unassigned RNA
                        organism = Homo sapiens
SEQUENCE: 51
tgaggtagta gattgtatag tt                                                22

SEQ ID NO: 52           moltype = RNA   length = 22
FEATURE                 Location/Qualifiers
source                  1..22
                        mol_type = unassigned RNA
                        organism = Homo sapiens
SEQUENCE: 52
tgaggtagga ggttgtatag tt                                                22

SEQ ID NO: 53           moltype = RNA   length = 22
FEATURE                 Location/Qualifiers
source                  1..22
                        mol_type = unassigned RNA
```

```
                            organism = Homo sapiens
SEQUENCE: 53
agaggtagta ggttgcatag tt                                              22

SEQ ID NO: 54           moltype = DNA   length = 69
FEATURE                 Location/Qualifiers
misc_feature            1..69
                        note = let-7a_seqRNA
misc_feature            1..13
                        note = DNA
misc_feature            15..68
                        note = DNA
misc_feature            14
                        note = RNA
misc_feature            69
                        note = RNA
source                  1..69
                        mol_type = other DNA
                        organism = synthetic construct
SEQUENCE: 54
aaagatgcga tacactacct catgcgtcta tttagtggag cccgctatct tctttaacta     60
tacaaccta                                                             69

SEQ ID NO: 55           moltype = DNA   length = 69
FEATURE                 Location/Qualifiers
misc_feature            1..69
                        note = let-7e_seqRNA
misc_feature            1..13
                        note = DNA
misc_feature            15..68
                        note = DNA
misc_feature            14
                        note = RNA
misc_feature            69
                        note = RNA
source                  1..69
                        mol_type = other DNA
                        organism = synthetic construct
SEQUENCE: 55
aaaatgtcgt tgccctccta cctcatgcgt ctatttagtg gagccgccta tcttctttaa     60
ctatacaac                                                             69

SEQ ID NO: 56           moltype = DNA   length = 69
FEATURE                 Location/Qualifiers
misc_feature            1..69
                        note = let-7d_seqRNA
misc_feature            1..13
                        note = DNA
misc_feature            15..68
                        note = DNA
misc_feature            14
                        note = RNA
misc_feature            69
                        note = RNA
source                  1..69
                        mol_type = other DNA
                        organism = synthetic construct
SEQUENCE: 56
aaaatgtcgt tgccctacta cctcttgcgt ctatttagtg gagccatcta tcttctttaa     60
ctatgcaac                                                             69

SEQ ID NO: 57           moltype = DNA   length = 69
FEATURE                 Location/Qualifiers
misc_feature            1..69
                        note = let-7f_seqRNA
misc_feature            1..13
                        note = DNA
misc_feature            15..68
                        note = DNA
misc_feature            14
                        note = RNA
misc_feature            69
                        note = RNA
source                  1..69
                        mol_type = other DNA
                        organism = synthetic construct
SEQUENCE: 57
aaaatgtcgt tgctctacta cctcatgcgt ctatttagtg gagcctacta tcttctttaa     60
ctatacaat                                                             69
```

```
SEQ ID NO: 58            moltype = DNA   length = 69
FEATURE                  Location/Qualifiers
misc_feature             1..69
                         note = let-7a_seq
source                   1..69
                         mol_type = other DNA
                         organism = synthetic construct
SEQUENCE: 58
aaagatgcga tacactacct catgcgtcta tttagtggag cccgctatct tctttaacta    60
tacaaccta                                                            69

SEQ ID NO: 59            moltype = DNA   length = 69
FEATURE                  Location/Qualifiers
misc_feature             1..69
                         note = let-7e_seq
source                   1..69
                         mol_type = other DNA
                         organism = synthetic construct
SEQUENCE: 59
aaaatgtcgt tgccctccta cctcatgcgt ctatttagtg agccgccta tcttctttaa     60
ctatacaac                                                            69

SEQ ID NO: 60            moltype = DNA   length = 69
FEATURE                  Location/Qualifiers
misc_feature             1..69
                         note = let-7d_seq
source                   1..69
                         mol_type = other DNA
                         organism = synthetic construct
SEQUENCE: 60
aaaatgtcgt tgccctacta cctcttgcgt ctatttagtg agccatcta tcttctttaa     60
ctatgcaac                                                            69

SEQ ID NO: 61            moltype = DNA   length = 69
FEATURE                  Location/Qualifiers
misc_feature             1..69
                         note = let-7f_seq
source                   1..69
                         mol_type = other DNA
                         organism = synthetic construct
SEQUENCE: 61
aaaatgtcgt tgctctacta cctcatgcgt ctatttagtg agcctacta tcttctttaa     60
ctatacaat                                                            69

SEQ ID NO: 62            moltype = DNA   length = 21
FEATURE                  Location/Qualifiers
misc_feature             1..21
                         note = Decorator probe
misc_feature             1
                         note = 5' Cy3
source                   1..21
                         mol_type = other DNA
                         organism = synthetic construct
SEQUENCE: 62
tgcgtctatt tagtggagcc a                                              21

SEQ ID NO: 63            moltype = DNA   length = 21
FEATURE                  Location/Qualifiers
misc_feature             1..21
                         note = anchor primer
misc_feature             1
                         note = 5' AlexaFluor750
source                   1..21
                         mol_type = other DNA
                         organism = synthetic construct
SEQUENCE: 63
tgcgtctatt tagtggagcc a                                              21

SEQ ID NO: 64            moltype =       length =
SEQUENCE: 64
000

SEQ ID NO: 65            moltype =       length =
SEQUENCE: 65
000

SEQ ID NO: 66            moltype =       length =
SEQUENCE: 66
```

```
000

SEQ ID NO: 67            moltype =    length =
SEQUENCE: 67
000

SEQ ID NO: 68            moltype = DNA   length = 54
FEATURE                  Location/Qualifiers
source                   1..54
                         mol_type = unassigned DNA
                         organism = Mus musculus
SEQUENCE: 68
ggcctgtaca ctgacttgag accaataaaa gtgcacacct taccttacac aaac          54

SEQ ID NO: 69            moltype = DNA   length = 94
FEATURE                  Location/Qualifiers
source                   1..94
                         mol_type = unassigned DNA
                         organism = Homo sapiens
SEQUENCE: 69
tacctgtaca ctgacttgag accagttgaa taaaagtgca cacttaaaa atgaaaaaaa     60
aaaaaaaaaa aaaaaaaaaa aaaaaaaaaa aaaa                                94

SEQ ID NO: 70            moltype = DNA   length = 69
FEATURE                  Location/Qualifiers
misc_feature             1..69
                         note = Mouse PLP
source                   1..69
                         mol_type = other DNA
                         organism = synthetic construct
SEQUENCE: 70
taaggtgtgc aaaaagtagc cgtgactatc gactaaaagt agccgtgact atcgactgtt    60
tgtgtaagg                                                            69

SEQ ID NO: 71            moltype = DNA   length = 68
FEATURE                  Location/Qualifiers
misc_feature             1..68
                         note = Human PLP
source                   1..68
                         mol_type = other DNA
                         organism = synthetic construct
SEQUENCE: 71
taaggtgtgc aagtcggaag tactactctc taaaagtcgg aagtactact ctcttttttt    60
ttcatttt                                                             68

SEQ ID NO: 72            moltype = DNA   length = 69
FEATURE                  Location/Qualifiers
misc_feature             1..69
                         note = Mouse cPLP
misc_feature             1..68
                         note = DNA
misc_feature             69
                         note = RNA
source                   1..69
                         mol_type = other DNA
                         organism = synthetic construct
SEQUENCE: 72
taaggtgtgc aaaaagtagc cgtgactatc gactaaaagt agccgtgact atcgactgtt    60
tgtgtaagg                                                            69

SEQ ID NO: 73            moltype = DNA   length = 68
FEATURE                  Location/Qualifiers
misc_feature             1..68
                         note = Human cPLP
misc_feature             1..67
                         note = DNA
misc_feature             68
                         note = RNA
source                   1..68
                         mol_type = other DNA
                         organism = synthetic construct
SEQUENCE: 73
taaggtgtgc aagtcggaag tactactctc taaaagtcgg aagtactact ctcttttttt    60
ttcatttt                                                             68

SEQ ID NO: 74            moltype = DNA   length = 83
FEATURE                  Location/Qualifiers
misc_feature             1..83
                         note = Mouse iLock
```

```
source                  1..83
                        mol_type = other DNA
                        organism = synthetic construct
SEQUENCE: 74
tatatcccta tatgtaaggt gtgcaaaaag tagccgtgac tatcgactaa aagtagccgt    60
gactatcgac tgtttgtgta agg                                            83

SEQ ID NO: 75           moltype = DNA   length = 82
FEATURE                 Location/Qualifiers
misc_feature            1..82
                        note = Human iLock
source                  1..82
                        mol_type = other DNA
                        organism = synthetic construct
SEQUENCE: 75
tatatcccta tatttaaggt gtgcaagtcg gaagtactac tctctaaaag tcggaagtac    60
tactctcttt tttttttcatt tt                                            82

SEQ ID NO: 76           moltype = DNA   length = 83
FEATURE                 Location/Qualifiers
misc_feature            1..83
                        note = Mouse ciLock
misc_feature            1..13
                        note = DNA
misc_feature            15..82
                        note = DNA
misc_feature            14
                        note = RNA
misc_feature            83
                        note = RNA
source                  1..83
                        mol_type = other DNA
                        organism = synthetic construct
SEQUENCE: 76
tatatcccta tatgtaaggt gtgcaaaaag tagccgtgac tatcgactaa aagtagccgt    60
gactatcgac tgtttgtgta agg                                            83

SEQ ID NO: 77           moltype = DNA   length = 82
FEATURE                 Location/Qualifiers
misc_feature            1..82
                        note = Human ciLock
misc_feature            1..13
                        note = DNA
misc_feature            15..81
                        note = DNA
misc_feature            14
                        note = RNA
misc_feature            82
                        note = RNA
source                  1..82
                        mol_type = other DNA
                        organism = synthetic construct
SEQUENCE: 77
tatatcccta tatttaaggt gtgcaagtcg gaagtactac tctctaaaag tcggaagtac    60
tactctcttt tttttttcatt tt                                            82

SEQ ID NO: 78           moltype = RNA   length = 37
FEATURE                 Location/Qualifiers
misc_feature            1..37
                        note = miR21_BIO
source                  1..37
                        mol_type = other RNA
                        organism = synthetic construct
SEQUENCE: 78
tttttttttt tttttagct tatcagactg atgttga                              37

SEQ ID NO: 79           moltype = DNA   length = 55
FEATURE                 Location/Qualifiers
misc_feature            1..55
                        note = miR21B2D0_PLP
misc_feature            1
                        note = 5' Phosphate
source                  1..55
                        mol_type = other DNA
                        organism = synthetic construct
SEQUENCE: 79
ctgataagct agccgaatct aagagtagcc gtgactatcg actaaaacta cacca         55

SEQ ID NO: 80           moltype = DNA   length = 68
```

```
                        FEATURE                 Location/Qualifiers
                        misc_feature            1..68
                                                note = miR21B2D0_iLock
                        source                  1..68
                                                mol_type = other DNA
                                                organism = synthetic construct
SEQUENCE: 80
ccgtcgctgc gttctgataa gctaaaaaaa agtagccgtg actatcgact aaaaaaatca   60
acatcagt                                                            68

SEQ ID NO: 81           moltype = DNA  length = 66
FEATURE                 Location/Qualifiers
misc_feature            1..66
                        note =  miR21 B2D0_rPLP
misc_feature            1
                        note = 5' Phosphate
misc_feature            1..65
                        note = DNA
misc_feature            66
                        note = RNA
source                  1..66
                        mol_type = other DNA
                        organism = synthetic construct
SEQUENCE: 81
ctgataagct agccgaatct aagagtagcc gtgactatcg actaaaacta caccatcaac   60
atcagt                                                              66

SEQ ID NO: 82           moltype = DNA  length = 68
FEATURE                 Location/Qualifiers
misc_feature            1..68
                        note = miR21B2D0_RiLock
misc_feature            1..12
                        note = DNA
misc_feature            14..67
                        note = DNA
misc_feature            13
                        note = RNA
misc_feature            68
                        note = RNA
source                  1..68
                        mol_type = other DNA
                        organism = synthetic construct
SEQUENCE: 82
ccgtcgctgc gttctgataa gctaaaaaaa agtagccgtg actatcgact aaaaaaatca   60
acatcagt                                                            68

SEQ ID NO: 83           moltype = DNA  length = 20
FEATURE                 Location/Qualifiers
misc_feature            1..20
                        note = B2D0_Cy3
misc_feature            1
                        note = 5' Cy3
source                  1..20
                        mol_type = other DNA
                        organism = synthetic construct
SEQUENCE: 83
agtagccgtg actatcgact                                               20

SEQ ID NO: 84           moltype = DNA  length = 22
FEATURE                 Location/Qualifiers
misc_feature            1..22
                        note = antimiR21_FAM
misc_feature            1
                        note = 5' FAM
source                  1..22
                        mol_type = other DNA
                        organism = synthetic construct
SEQUENCE: 84
tcaacatcag tctgataagc ta                                            22

SEQ ID NO: 85           moltype = DNA  length = 99
FEATURE                 Location/Qualifiers
source                  1..99
                        mol_type = unassigned DNA
                        organism = Homo sapiens
SEQUENCE: 85
acatttcat tattttattt ataaggcctg ctgaaaatga ctgaatataa acttgtggta    60
gttggagctg gtggcgtagg caagagtgcc ttgacgata                          99
```

| | | |
|---|---|---|
| SEQ ID NO: 86 | moltype = DNA   length = 77 | |
| FEATURE | Location/Qualifiers | |
| misc_feature | 1..77 | |
| | note = wt KRAS PLP | |
| source | 1..77 | |
| | mol_type = other DNA | |
| | organism = synthetic construct | |
| SEQUENCE: 86 | | |
| agctccaact accacaaagt cgatagtcac ggctactcag acgtaacgcg ttcagtgatg | | 60 |
| cccttgccta cgccacc | | 77 |
| | | |
| SEQ ID NO: 87 | moltype = RNA   length = 41 | |
| FEATURE | Location/Qualifiers | |
| source | 1..41 | |
| | mol_type = unassigned RNA | |
| | organism = Homo sapiens | |
| SEQUENCE: 87 | | |
| aacttgtggt agttggagct ggtggcgtag gcaagagtgc c | | 41 |
| | | |
| SEQ ID NO: 88 | moltype = DNA   length = 77 | |
| FEATURE | Location/Qualifiers | |
| misc_feature | 1..77 | |
| | note = chim wt KRAS PLP | |
| misc_feature | 1..76 | |
| | note = DNA | |
| misc_feature | 77 | |
| | note = RNA | |
| source | 1..77 | |
| | mol_type = other DNA | |
| | organism = synthetic construct | |
| SEQUENCE: 88 | | |
| agctccaact accacaaagt cgatagtcac ggctactcag acgtaacgcg ttcagtgatg | | 60 |
| cccttgccta cgccacc | | 77 |
| | | |
| SEQ ID NO: 89 | moltype = DNA   length = 77 | |
| FEATURE | Location/Qualifiers | |
| misc_feature | 1..77 | |
| | note = chim wt KRAS PLP_2 | |
| misc_feature | 1..75 | |
| | note = DNA | |
| misc_feature | 76..77 | |
| | note = RNA | |
| source | 1..77 | |
| | mol_type = other DNA | |
| | organism = synthetic construct | |
| SEQUENCE: 89 | | |
| agctccaact accacaaagt cgatagtcac ggctactcag acgtaacgcg ttcagtgatg | | 60 |
| cccttgccta cgccacc | | 77 |
| | | |
| SEQ ID NO: 90 | moltype = DNA   length = 80 | |
| FEATURE | Location/Qualifiers | |
| misc_feature | 1..80 | |
| | note = mut KRAS PLP | |
| source | 1..80 | |
| | mol_type = other DNA | |
| | organism = synthetic construct | |
| SEQUENCE: 90 | | |
| agctccaact accacaaacct caatgcacat gtttggctcc cagacgtaac gcgttcagtg | | 60 |
| atgcccttgc ctacgccact | | 80 |
| | | |
| SEQ ID NO: 91 | moltype = DNA   length = 80 | |
| FEATURE | Location/Qualifiers | |
| misc_feature | 1..80 | |
| | note = chim mut KRAS PLP | |
| misc_feature | 1..79 | |
| | note = DNA | |
| misc_feature | 80 | |
| | note = RNA | |
| source | 1..80 | |
| | mol_type = other DNA | |
| | organism = synthetic construct | |
| SEQUENCE: 91 | | |
| agctccaact accacaaacct caatgcacat gtttggctcc cagacgtaac gcgttcagtg | | 60 |
| atgcccttgc ctacgccact | | 80 |
| | | |
| SEQ ID NO: 92 | moltype = DNA   length = 15 | |
| FEATURE | Location/Qualifiers | |
| misc_feature | 1..15 | |
| | note = RCA primer | |

```
source                  1..15
                        mol_type = other DNA
                        organism = synthetic construct
SEQUENCE: 92
catcactgaa cgcgt                                                        15

SEQ ID NO: 93           moltype = DNA  length = 23
FEATURE                 Location/Qualifiers
misc_feature            1..23
                        note = mut DO-Cy5
source                  1..23
                        mol_type = other DNA
                        organism = synthetic construct
SEQUENCE: 93
cctcaatgca catgtttggc tcc                                               23

SEQ ID NO: 94           moltype = DNA  length = 20
FEATURE                 Location/Qualifiers
misc_feature            1..20
                        note = wt DO-Cy3
source                  1..20
                        mol_type = other DNA
                        organism = synthetic construct
SEQUENCE: 94
agtcgatagt cacggctact                                                   20

SEQ ID NO: 95           moltype = DNA  length = 91
FEATURE                 Location/Qualifiers
misc_feature            1..91
                        note = KRAS wt invader chim 3-5
misc_feature            1..13
                        note = DNA
misc_feature            15..90
                        note = DNA
misc_feature            14
                        note = RNA
misc_feature            91
                        note = RNA
source                  1..91
                        mol_type = other DNA
                        organism = synthetic construct
SEQUENCE: 95
tatatcccta tatcagctcc aactaccaca aagtcgatag tcacggctac tcagacgtaa       60
cgcgttcagt gatgcccttg cctacgccac c                                      91

SEQ ID NO: 96           moltype = DNA  length = 91
FEATURE                 Location/Qualifiers
misc_feature            1..91
                        note = KRAS wt invader chim 3
misc_feature            1..13
                        note = DNA
misc_feature            15..90
                        note = DNA
misc_feature            14
                        note = RNA
misc_feature            91
                        note = RNA
source                  1..91
                        mol_type = other DNA
                        organism = synthetic construct
SEQUENCE: 96
tatatcccta tatcagctcc aactaccaca aagtcgatag tcacggctac tcagacgtaa       60
cgcgttcagt gatgcccttg cctacgccac c                                      91

SEQ ID NO: 97           moltype = DNA  length = 94
FEATURE                 Location/Qualifiers
misc_feature            1..94
                        note = KRAS mut invader chim 3-5
misc_feature            1..13
                        note = DNA
misc_feature            15..93
                        note = DNA
misc_feature            14
                        note = RNA
misc_feature            94
                        note = RNA
source                  1..94
                        mol_type = other DNA
                        organism = synthetic construct
```

```
SEQUENCE: 97
tatatcccta tattagctcc aactaccaca acctcaatgc acatgtttgg ctcccagacg    60
taacgcgttc agtgatgccc ttgcctacgc cact                                94

SEQ ID NO: 98           moltype = DNA   length = 94
FEATURE                 Location/Qualifiers
misc_feature            1..94
                        note = KRAS mut invader chim 3
misc_feature            1..13
                        note = DNA
misc_feature            15..93
                        note = DNA
misc_feature            14
                        note = RNA
misc_feature            94
                        note = RNA
source                  1..94
                        mol_type = other DNA
                        organism = synthetic construct
SEQUENCE: 98
tatatcccta tattagctcc aactaccaca acctcaatgc acatgtttgg ctcccagacg    60
taacgcgttc agtgatgccc ttgcctacgc cact                                94

SEQ ID NO: 99           moltype = DNA   length = 94
FEATURE                 Location/Qualifiers
misc_feature            1..94
                        note = KRAS gapfill invader
source                  1..94
                        mol_type = other DNA
                        organism = synthetic construct
SEQUENCE: 99
tatatctcta tatagctcca actaccacaa gtagtcgata gtcacggcta ctcagacgta    60
acgcgttcag tgatgagtag gcactcttgc ctac                                94

SEQ ID NO: 100          moltype = DNA   length = 19
FEATURE                 Location/Qualifiers
misc_feature            1..19
                        note = invader_splint_chim
misc_feature            1..18
                        note = DNA
misc_feature            19
                        note = RNA
source                  1..19
                        mol_type = other DNA
                        organism = synthetic construct
SEQUENCE: 100
tatatctcta tatgccacc                                                 19

SEQ ID NO: 101          moltype = DNA   length = 19
FEATURE                 Location/Qualifiers
misc_feature            1..19
                        note = invader_splint
source                  1..19
                        mol_type = other DNA
                        organism = synthetic construct
SEQUENCE: 101
tatatctcta tatgccacc                                                 19

SEQ ID NO: 102          moltype =       length =
SEQUENCE: 102
000

SEQ ID NO: 103          moltype =       length =
SEQUENCE: 103
000

SEQ ID NO: 104          moltype = DNA   length = 15
FEATURE                 Location/Qualifiers
misc_feature            1..15
                        note = RCA primer
source                  1..15
                        mol_type = other DNA
                        organism = synthetic construct
SEQUENCE: 104
catcactgaa cgcgt                                                     15

SEQ ID NO: 105          moltype = DNA   length = 20
FEATURE                 Location/Qualifiers
misc_feature            1..20
```

-continued

```
                        note = DO-Cy3
source                  1..20
                        mol_type = other DNA
                        organism = synthetic construct
SEQUENCE: 105
agtcgatagt cacggctact                                             20

SEQ ID NO: 106          moltype = RNA   length = 41
FEATURE                 Location/Qualifiers
source                  1..41
                        mol_type = unassigned RNA
                        organism = Homo sapiens
SEQUENCE: 106
aacttgtggt agttggagct ggtggcgtag gcaagagtgc c                     41

SEQ ID NO: 107          moltype = DNA   length = 57
FEATURE                 Location/Qualifiers
misc_feature            1..57
                        note = R_KRAS wt1_1
misc_feature            1..19
                        note = DNA
misc_feature            20
                        note = RNA
misc_feature            21..57
                        note = DNA
source                  1..57
                        mol_type = other DNA
                        organism = synthetic construct
SEQUENCE: 107
agctccaact accacaacag acgtaacgcg ttcagtgatg cccttgccta cgccacc    57

SEQ ID NO: 108          moltype = DNA   length = 57
FEATURE                 Location/Qualifiers
misc_feature            1..57
                        note = R_KRAS wt1_2
misc_feature            1..19
                        note = DNA
misc_feature            22..28
                        note = DNA
misc_feature            20..21
                        note = RNA
misc_feature            29..30
                        note = RNA
misc_feature            31..57
                        note = DNA
source                  1..57
                        mol_type = other DNA
                        organism = synthetic construct
SEQUENCE: 108
agctccaact accacaacag acgtaacgcg ttcagtgatg cccttgccta cgccacc    57

SEQ ID NO: 109          moltype = DNA   length = 57
FEATURE                 Location/Qualifiers
misc_feature            1..57
                        note = R_KRAS wt1_3
misc_feature            1..19
                        note = DNA
misc_feature            23..28
                        note = DNA
misc_feature            31..57
                        note = DNA
misc_feature            20..22
                        note = RNA
misc_feature            29..30
                        note = RNA
source                  1..57
                        mol_type = other DNA
                        organism = synthetic construct
SEQUENCE: 109
agctccaact accacaacag acgtaacgcg ttcagtgatg cccttgccta cgccacc    57

SEQ ID NO: 110          moltype = DNA   length = 57
FEATURE                 Location/Qualifiers
misc_feature            1..57
                        note = R_KRAS wt1_4
misc_feature            1..19
                        note = DNA
misc_feature            24..28
                        note = DNA
```

```
misc_feature      31..57
                  note = DNA
misc_feature      20..23
                  note = RNA
misc_feature      29..30
                  note = RNA
source            1..57
                  mol_type = other DNA
                  organism = synthetic construct
SEQUENCE: 110
agctccaact accacaacag acgtaacgcg ttcagtgatg cccttgccta cgccacc      57

SEQ ID NO: 111         moltype = DNA  length = 57
FEATURE                Location/Qualifiers
misc_feature      1..57
                  note = R_KRAS wt1_5
misc_feature      1..19
                  note = DNA
misc_feature      25..28
                  note = DNA
misc_feature      31..57
                  note = DNA
misc_feature      20..24
                  note = RNA
misc_feature      29..30
                  note = RNA
source            1..57
                  mol_type = other DNA
                  organism = synthetic construct
SEQUENCE: 111
agctccaact accacaacag acgtaacgcg ttcagtgatg cccttgccta cgccacc      57

SEQ ID NO: 112         moltype = DNA  length = 57
FEATURE                Location/Qualifiers
misc_feature      1..57
                  note = R_KRAS wt1_7
misc_feature      1..19
                  note = DNA
misc_feature      27..28
                  note = DNA
misc_feature      31..57
                  note = DNA
misc_feature      20..26
                  note = RNA
misc_feature      29..30
                  note = RNA
source            1..57
                  mol_type = other DNA
                  organism = synthetic construct
SEQUENCE: 112
agctccaact accacaacag acgtaacgcg ttcagtgatg cccttgccta cgccacc      57

SEQ ID NO: 113         moltype = DNA  length = 57
FEATURE                Location/Qualifiers
misc_feature      1..57
                  note = R_KRAS wt1_6S
misc_feature      1..19
                  note = DNA
misc_feature      22..23
                  note = DNA
misc_feature      26..27
                  note = DNA
misc_feature      30..57
                  note = DNA
misc_feature      20..21
                  note = RNA
misc_feature      24..25
                  note = RNA
misc_feature      28..29
                  note = RNA
source            1..57
                  mol_type = other DNA
                  organism = synthetic construct
SEQUENCE: 113
agctccaact accacaacag acgtaacgcg ttcagtgatg cccttgccta cgccacc      57

SEQ ID NO: 114         moltype = DNA  length = 50
FEATURE                Location/Qualifiers
misc_feature      1..50
```

```
                            note = R_KRAS wt1_DNA
source                      1..50
                            mol_type = other DNA
                            organism = synthetic construct
SEQUENCE: 114
agctccaact accacaaaaa aaaaaaaaaa aaaaacttgc ctacgccacc              50

SEQ ID NO: 115              moltype = DNA  length = 50
FEATURE                     Location/Qualifiers
misc_feature                1..50
                            note = R_KRAS wt1_RNA
misc_feature                1..49
                            note = DNA
misc_feature                50
                            note = RNA
source                      1..50
                            mol_type = other DNA
                            organism = synthetic construct
SEQUENCE: 115
agctccaact accacaaaaa aaaaaaaaaa aaaaacttgc ctacgccacc              50

SEQ ID NO: 116              moltype = DNA  length = 22
FEATURE                     Location/Qualifiers
misc_feature                1..22
                            note = Decorator probe [1]
misc_feature                1..18
                            note = DNA
misc_feature                19..22
                            note = RNA
modified_base               19..22
                            mod_base = OTHER
                            note = 2' O-Me nucleotide
source                      1..22
                            mol_type = other DNA
                            organism = synthetic construct
SEQUENCE: 116
cctcaatgca catgtttggc tc                                            22

SEQ ID NO: 117              moltype = DNA  length = 20
FEATURE                     Location/Qualifiers
misc_feature                1..20
                            note = Decorator probe2 [2]
misc_feature                1..16
                            note = DNA
misc_feature                17..20
                            note = RNA
modified_base               17..20
                            mod_base = OTHER
                            note = 2' O-Me nucleotide
source                      1..20
                            mol_type = other DNA
                            organism = synthetic construct
SEQUENCE: 117
agtcgatagt cacggctact                                               20

SEQ ID NO: 118              moltype = RNA  length = 41
FEATURE                     Location/Qualifiers
source                      1..41
                            mol_type = unassigned RNA
                            organism = Homo sapiens
SEQUENCE: 118
aacttgtggt agttggagct ggtggcgtag gcaagagtgc c                       41

SEQ ID NO: 119              moltype = DNA  length = 77
FEATURE                     Location/Qualifiers
misc_feature                1..77
                            note = R_KRAS.0
source                      1..77
                            mol_type = other DNA
                            organism = synthetic construct
SEQUENCE: 119
agctccaact accacaaagt cgatagtcac ggctactcag acgtaacgcg ttcagtgatg   60
cccttgccta cgccacc                                                  77

SEQ ID NO: 120              moltype = DNA  length = 77
FEATURE                     Location/Qualifiers
misc_feature                1..77
                            note = R_KRAS.1G
misc_feature                1..39
```

```
                        note = DNA
misc_feature            41..77
                        note = DNA
misc_feature            40
                        note = RNA
source                  1..77
                        mol_type = other DNA
                        organism = synthetic construct
SEQUENCE: 120
agctccaact accacaaagt cgatagtcac ggctactcag acgtaacgcg ttcagtgatg   60
cccttgccta cgccacc                                                 77

SEQ ID NO: 121          moltype = DNA  length = 77
FEATURE                 Location/Qualifiers
misc_feature            1..77
                        note = R_KRAS.1C
misc_feature            1..39
                        note = DNA
misc_feature            41..77
                        note = DNA
misc_feature            40
                        note = RNA
source                  1..77
                        mol_type = other DNA
                        organism = synthetic construct
SEQUENCE: 121
agctccaact accacaaagt cgatagtcac ggctactcac acgtaacgcg ttcagtgatg   60
cccttgccta cgccacc                                                 77

SEQ ID NO: 122          moltype = DNA  length = 77
FEATURE                 Location/Qualifiers
misc_feature            1..77
                        note = R_KRAS.1A
misc_feature            1..39
                        note = DNA
misc_feature            41..77
                        note = DNA
misc_feature            40
                        note = RNA
source                  1..77
                        mol_type = other DNA
                        organism = synthetic construct
SEQUENCE: 122
agctccaact accacaaagt cgatagtcac ggctactcaa acgtaacgcg ttcagtgatg   60
cccttgccta cgccacc                                                 77

SEQ ID NO: 123          moltype = DNA  length = 77
FEATURE                 Location/Qualifiers
misc_feature            1..77
                        note = R_KRAS.1U
misc_feature            1..39
                        note = DNA
misc_feature            41..77
                        note = DNA
misc_feature            40
                        note = RNA
source                  1..77
                        mol_type = other DNA
                        organism = synthetic construct
SEQUENCE: 123
agctccaact accacaaagt cgatagtcac ggctactcat acgtaacgcg ttcagtgatg   60
cccttgccta cgccacc                                                 77

SEQ ID NO: 124          moltype = DNA  length = 77
FEATURE                 Location/Qualifiers
misc_feature            1..77
                        note = R_KRAS.2G
misc_feature            1..39
                        note = DNA
misc_feature            42..48
                        note = DNA
misc_feature            51..77
                        note = DNA
misc_feature            40..41
                        note = RNA
misc_feature            49..50
                        note = RNA
source                  1..77
                        mol_type = other DNA
```

```
                        organism = synthetic construct
SEQUENCE: 124
agctccaact accacaaagt cgatagtcac ggctactcag gcgtaacgcg ttcagtgatg    60
cccttgccta cgccacc                                                  77

SEQ ID NO: 125          moltype = DNA  length = 77
FEATURE                 Location/Qualifiers
misc_feature            1..77
                        note = R_KRAS.2C
misc_feature            1..39
                        note = DNA
misc_feature            42..48
                        note = DNA
misc_feature            51..77
                        note = DNA
misc_feature            40..41
                        note = RNA
misc_feature            49..50
                        note = RNA
source                  1..77
                        mol_type = other DNA
                        organism = synthetic construct
SEQUENCE: 125
agctccaact accacaaagt cgatagtcac ggctactcac ccgtaacgcg ttcagtgatg    60
cccttgccta cgccacc                                                  77

SEQ ID NO: 126          moltype = DNA  length = 77
FEATURE                 Location/Qualifiers
misc_feature            1..77
                        note = R_KRAS.2A
misc_feature            1..39
                        note = DNA
misc_feature            42..48
                        note = DNA
misc_feature            51..77
                        note = DNA
misc_feature            40..41
                        note = RNA
misc_feature            49..50
                        note = RNA
source                  1..77
                        mol_type = other DNA
                        organism = synthetic construct
SEQUENCE: 126
agctccaact accacaaagt cgatagtcac ggctactcaa acgtaacgcg ttcagtgatg    60
cccttgccta cgccacc                                                  77

SEQ ID NO: 127          moltype = DNA  length = 77
FEATURE                 Location/Qualifiers
misc_feature            1..77
                        note = R_KRAS.2U
misc_feature            1..39
                        note = DNA
misc_feature            42..48
                        note = DNA
misc_feature            51..77
                        note = DNA
misc_feature            40..41
                        note = RNA
misc_feature            49..50
                        note = RNA
source                  1..77
                        mol_type = other DNA
                        organism = synthetic construct
SEQUENCE: 127
agctccaact accacaaagt cgatagtcac ggctactcat tcgtaacgcg ttcagtgatg    60
cccttgccta cgccacc                                                  77

SEQ ID NO: 128          moltype = DNA  length = 18
FEATURE                 Location/Qualifiers
misc_feature            1..18
                        note = AluI KRAS RO
source                  1..18
                        mol_type = other DNA
                        organism = synthetic construct
SEQUENCE: 128
cgccaccagc tccaacta                                                 18

SEQ ID NO: 129          moltype = DNA  length = 53
```

```
FEATURE                 Location/Qualifiers
misc_feature            1..53
                        note = PE1
source                  1..53
                        mol_type = other DNA
                        organism = synthetic construct
SEQUENCE: 129
acactctttc cctacacgac gctcttccga tctctggtgg cgtaggcaag ggc          53

SEQ ID NO: 130          moltype = DNA  length = 54
FEATURE                 Location/Qualifiers
misc_feature            1..54
                        note = PE2
source                  1..54
                        mol_type = other DNA
                        organism = synthetic construct
SEQUENCE: 130
gtgactggag ttcagacgtg tgctcttccg atctctccaa ctaccacaaa gtcg         54

SEQ ID NO: 131          moltype = DNA  length = 77
FEATURE                 Location/Qualifiers
misc_feature            1..77
                        note = R_KRAS.3G
misc_feature            1..39
                        note = DNA
misc_feature            43..48
                        note = DNA
misc_feature            51..77
                        note = DNA
misc_feature            40..42
                        note = RNA
misc_feature            49..50
                        note = RNA
source                  1..77
                        mol_type = other DNA
                        organism = synthetic construct
SEQUENCE: 131
agctccaact accacaaagt cgatagtcac ggctactcag ggttaacgcg ttcagtgatg   60
cccttgccta cgccacc                                                  77

SEQ ID NO: 132          moltype = DNA  length = 77
FEATURE                 Location/Qualifiers
misc_feature            1..77
                        note = R_KRAS.3C
misc_feature            1..39
                        note = DNA
misc_feature            43..48
                        note = DNA
misc_feature            51..77
                        note = DNA
misc_feature            40..42
                        note = RNA
misc_feature            49..50
                        note = RNA
source                  1..77
                        mol_type = other DNA
                        organism = synthetic construct
SEQUENCE: 132
agctccaact accacaaagt cgatagtcac ggctactcac ccgtaacgcg ttcagtgatg   60
cccttgccta cgccacc                                                  77

SEQ ID NO: 133          moltype = DNA  length = 77
FEATURE                 Location/Qualifiers
misc_feature            1..77
                        note = R_KRAS.3A
misc_feature            1..39
                        note = DNA
misc_feature            43..48
                        note = DNA
misc_feature            51..77
                        note = DNA
misc_feature            40..42
                        note = RNA
misc_feature            49..50
                        note = RNA
source                  1..77
                        mol_type = other DNA
                        organism = synthetic construct
SEQUENCE: 133
```

```
agctccaact accacaaagt cgatagtcac ggctactcaa agtaacgcg ttcagtgatg    60
cccttgccta cgccacc                                                 77

SEQ ID NO: 134          moltype = DNA   length = 78
FEATURE                 Location/Qualifiers
misc_feature            1..78
                        note = R_KRAS.3U
misc_feature            1..39
                        note = DNA
misc_feature            43..48
                        note = DNA
misc_feature            51..78
                        note = DNA
misc_feature            40..42
                        note = RNA
misc_feature            49..50
                        note = RNA
source                  1..78
                        mol_type = other DNA
                        organism = synthetic construct
SEQUENCE: 134
agctccaact accacaaagt cgatagtcac ggctactcat tcgtaacgc gttcagtgat    60
gcccttgcct acgccacc                                                78

SEQ ID NO: 135          moltype = DNA   length = 77
FEATURE                 Location/Qualifiers
misc_feature            1..77
                        note = R_KRAS.5
misc_feature            1..39
                        note = DNA
misc_feature            45..77
                        note = DNA
misc_feature            40..44
                        note = RNA
source                  1..77
                        mol_type = other DNA
                        organism = synthetic construct
SEQUENCE: 135
agctccaact accacaaagt cgatagtcac ggctactcag acgtaacgcg ttcagtgatg    60
cccttgccta cgccacc                                                 77

SEQ ID NO: 136          moltype = DNA   length = 77
FEATURE                 Location/Qualifiers
misc_feature            1..77
                        note = R_KRAS.6S
misc_feature            1..39
                        note = DNA
misc_feature            42..43
                        note = DNA
misc_feature            46..47
                        note = DNA
misc_feature            50..77
                        note = DNA
misc_feature            40..41
                        note = RNA
misc_feature            44..45
                        note = RNA
misc_feature            48..49
                        note = RNA
source                  1..77
                        mol_type = other DNA
                        organism = synthetic construct
SEQUENCE: 136
agctccaact accacaaagt cgatagtcac ggctactcag acgtaacgcg ttcagtgatg    60
cccttgccta cgccacc                                                 77

SEQ ID NO: 137          moltype = DNA   length = 77
FEATURE                 Location/Qualifiers
misc_feature            1..77
                        note = R_KRAS.3
misc_feature            1..39
                        note = DNA
misc_feature            43..47
                        note = DNA
misc_feature            51..77
                        note = DNA
misc_feature            40..42
                        note = RNA
misc_feature            48..50
```

```
                        note = RNA
source                  1..77
                        mol_type = other DNA
                        organism = synthetic construct
SEQUENCE: 137
agctccaact accacaaagt cgatagtcac ggctactcag acgtaacgcg ttcagtgatg    60
cccttgccta cgccacc                                                  77

SEQ ID NO: 138          moltype = DNA  length = 77
FEATURE                 Location/Qualifiers
misc_feature            1..77
                        note = R_KRAS.3S
misc_feature            1..39
                        note = DNA
misc_feature            41
                        note = DNA
misc_feature            43
                        note = DNA
misc_feature            45..77
                        note = DNA
misc_feature            40
                        note = RNA
misc_feature            42
                        note = RNA
misc_feature            44
                        note = RNA
source                  1..77
                        mol_type = other DNA
                        organism = synthetic construct
SEQUENCE: 138
agctccaact accacaaagt cgatagtcac ggctactcag acgtaacgcg ttcagtgatg    60
cccttgccta cgccacc                                                  77

SEQ ID NO: 139          moltype = DNA  length = 77
FEATURE                 Location/Qualifiers
misc_feature            1..77
                        note = R_KRAS.2
misc_feature            1..39
                        note = DNA
misc_feature            42..48
                        note = DNA
misc_feature            51..77
                        note = DNA
misc_feature            40..41
                        note = RNA
misc_feature            49..50
                        note = RNA
source                  1..77
                        mol_type = other DNA
                        organism = synthetic construct
SEQUENCE: 139
agctccaact accacaaagt cgatagtcac ggctactcag acgtaacgcg ttcagtgatg    60
cccttgccta cgccacc                                                  77

SEQ ID NO: 140          moltype = DNA  length = 77
FEATURE                 Location/Qualifiers
misc_feature            1..77
                        note = R_KRAS.7
misc_feature            1..39
                        note = DNA
misc_feature            47..77
                        note = DNA
misc_feature            40..46
                        note = RNA
source                  1..77
                        mol_type = other DNA
                        organism = synthetic construct
SEQUENCE: 140
agctccaact accacaaagt cgatagtcac ggctactcag acgtaacgcg ttcagtgatg    60
cccttgccta cgccacc                                                  77

SEQ ID NO: 141          moltype = DNA  length = 20
FEATURE                 Location/Qualifiers
misc_feature            1..20
                        note = Detection probe (seq anchor probe)
misc_feature            1
                        note = 5' AlexaFluor750
source                  1..20
                        mol_type = other DNA
```

```
                        organism = synthetic construct
SEQUENCE: 141
tgcgtctatt tagtggagcc                                                    20

SEQ ID NO: 142          moltype =    length =
SEQUENCE: 142
000

SEQ ID NO: 143          moltype = DNA  length = 20
FEATURE                 Location/Qualifiers
misc_feature            1..20
                        note = Seq library 1st base-G
misc_feature            20
                        note = 3' thiophosphate
source                  1..20
                        mol_type = other DNA
                        organism = synthetic construct
SEQUENCE: 143
ggctccacta aatagacgca                                                    20

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype =    length =
SEQUENCE: 154
000

SEQ ID NO: 155          moltype =    length =
SEQUENCE: 155
000

SEQ ID NO: 156          moltype =    length =
SEQUENCE: 156
000

SEQ ID NO: 157          moltype =    length =
SEQUENCE: 157
000

SEQ ID NO: 158          moltype =    length =
SEQUENCE: 158
000
```

```
SEQ ID NO: 159          moltype = DNA   length = 95
FEATURE                 Location/Qualifiers
misc_feature            1..95
                        note = Calb2_1119_RNA
misc_feature            1..94
                        note = DNA
misc_feature            95
                        note = RNA
source                  1..95
                        mol_type = other DNA
                        organism = synthetic construct
SEQUENCE: 159
catcgcagcg gagacgacag ctgattcctt tgactcacat tgcgtctatt tagtggagcc    60
aatgctatct tctttataca gcgaaggaac tcatg                               95

SEQ ID NO: 160          moltype = DNA   length = 95
FEATURE                 Location/Qualifiers
misc_feature            1..95
                        note = Calb2_1328_RNA
misc_feature            1..94
                        note = DNA
misc_feature            95
                        note = RNA
source                  1..95
                        mol_type = other DNA
                        organism = synthetic construct
SEQUENCE: 160
cacacacgtc aagaacacaa ctgattcctt tgactcacat tgcgtctatt tagtggagcc    60
aatgctatct tctttgaagc caaagagaaa aggaa                               95

SEQ ID NO: 161          moltype = DNA   length = 95
FEATURE                 Location/Qualifiers
misc_feature            1..95
                        note = Calb2_164_RNA
misc_feature            1..94
                        note = DNA
misc_feature            95
                        note = RNA
source                  1..95
                        mol_type = other DNA
                        organism = synthetic construct
SEQUENCE: 161
accttcaatg tacccatttc ctgattcctt tgactcacat tgcgtctatt tagtggagcc    60
aatgctatct tctttaagaa gttctctagc tcttt                               95

SEQ ID NO: 162          moltype = DNA   length = 95
FEATURE                 Location/Qualifiers
misc_feature            1..95
                        note = Calb2_500_RNA
misc_feature            1..94
                        note = DNA
misc_feature            95
                        note = RNA
source                  1..95
                        mol_type = other DNA
                        organism = synthetic construct
SEQUENCE: 162
aggttcatca tagggcctgt ctgattcctt tgactcacat tgcgtctatt tagtggagcc    60
aatgctatct tcttttgggt gtactcctgg agctt                               95

SEQ ID NO: 163          moltype = DNA   length = 95
FEATURE                 Location/Qualifiers
misc_feature            1..95
                        note = Calb2_937_RNA
misc_feature            1..94
                        note = DNA
misc_feature            95
                        note = RNA
source                  1..95
                        mol_type = other DNA
                        organism = synthetic construct
SEQUENCE: 163
gtcaagagag tcaggacagc ctgattcctt tgactcacat tgcgtctatt tagtggagcc    60
aatgctatct tctttgggga ggtctgggaa ggagt                               95

SEQ ID NO: 164          moltype = DNA   length = 93
FEATURE                 Location/Qualifiers
misc_feature            1..93
```

```
                         note = Calb2_DO3_CCAA_RNA
misc_feature             1..92
                         note = DNA
misc_feature             93
                         note = RNA
source                   1..93
                         mol_type = other DNA
                         organism = synthetic construct
SEQUENCE: 164
ctcatacaga tccttcagct gattcctttg actcacattg cgtctattta gtggagcccc    60
aactatcttc tttttcatct ccttcttgtt ctt                                 93

SEQ ID NO: 165           moltype = DNA  length = 95
FEATURE                  Location/Qualifiers
misc_feature             1..95
                         note = Chodl_1164_RNA
misc_feature             1..94
                         note = DNA
misc_feature             95
                         note = RNA
source                   1..95
                         mol_type = other DNA
                         organism = synthetic construct
SEQUENCE: 165
cgggctagtt tttgatcttc ctgattcctt tgactcacat tgcgtctatt tagtggagcc    60
agtactatct tctttatcca cagtgtagac tgatt                               95

SEQ ID NO: 166           moltype = DNA  length = 95
FEATURE                  Location/Qualifiers
misc_feature             1..95
                         note = Chodl_1798_RNA
misc_feature             1..94
                         note = DNA
misc_feature             95
                         note = RNA
source                   1..95
                         mol_type = other DNA
                         organism = synthetic construct
SEQUENCE: 166
aaagcaaaga acagaacaa ctgattcctt tgactcacat tgcgtctatt tagtggagcc     60
agtactatct tcttttccta aactttatcg aaccc                               95

SEQ ID NO: 167           moltype = DNA  length = 95
FEATURE                  Location/Qualifiers
misc_feature             1..95
                         note = Chodl_2071_RNA
misc_feature             1..94
                         note = DNA
misc_feature             95
                         note = RNA
source                   1..95
                         mol_type = other DNA
                         organism = synthetic construct
SEQUENCE: 167
attctatagg caacatgtga ctgattcctt tgactcacat tgcgtctatt tagtggagcc    60
agtactatct tctttactct ggggagctat ttgca                               95

SEQ ID NO: 168           moltype = DNA  length = 95
FEATURE                  Location/Qualifiers
misc_feature             1..95
                         note = Chodl_2252_RNA
misc_feature             1..94
                         note = DNA
misc_feature             95
                         note = RNA
source                   1..95
                         mol_type = other DNA
                         organism = synthetic construct
SEQUENCE: 168
gttctgctta gcatcacact ctgattcctt tgactcacat tgcgtctatt tagtggagcc    60
agtactatct tcttttaat cattaatatc agtgt                                95

SEQ ID NO: 169           moltype = DNA  length = 95
FEATURE                  Location/Qualifiers
misc_feature             1..95
                         note = Chodl_293_RNA
misc_feature             1..94
                         note = DNA
misc_feature             95
```

```
                              note = RNA
source                        1..95
                              mol_type = other DNA
                              organism = synthetic construct
SEQUENCE: 169
tcctactccc tccttcccag ctgattcctt tgactcacat tgcgtctatt tagtggagcc   60
agtactatct tcttttcct tgctttcctg ctggg                               95

SEQ ID NO: 170              moltype = DNA   length = 95
FEATURE                     Location/Qualifiers
misc_feature                1..95
                            note = Chodl_789_RNA
misc_feature                1..94
                            note = DNA
misc_feature                95
                            note = RNA
source                      1..95
                            mol_type = other DNA
                            organism = synthetic construct
SEQUENCE: 170
gaactgggag ctgcttccat ctgattcctt tgactcacat tgcgtctatt tagtggagcc   60
agtactatct tcttttcatc agtgtaccag tttcg                              95

SEQ ID NO: 171              moltype = DNA   length = 95
FEATURE                     Location/Qualifiers
misc_feature                1..95
                            note = Chodl_916_RNA
misc_feature                1..94
                            note = DNA
misc_feature                95
                            note = RNA
source                      1..95
                            mol_type = other DNA
                            organism = synthetic construct
SEQUENCE: 171
tgttgcacct gtcgtcattc ctgattcctt tgactcacat tgcgtctatt tagtggagcc   60
agtactatct tctttgcaga tgtaattgtg cttca                              95

SEQ ID NO: 172              moltype = DNA   length = 95
FEATURE                     Location/Qualifiers
misc_feature                1..95
                            note = Cort_326_RNA
misc_feature                1..94
                            note = DNA
misc_feature                95
                            note = RNA
source                      1..95
                            mol_type = other DNA
                            organism = synthetic construct
SEQUENCE: 172
cccgggggta cccctccga cgtgcttgtg gtagcaaata tgcgtctatt tagtggagcc    60
tgatctatct tctttctttc ctggctcttg gacag                              95

SEQ ID NO: 173              moltype = DNA   length = 95
FEATURE                     Location/Qualifiers
misc_feature                1..95
                            note = Cort_529_RNA
misc_feature                1..94
                            note = DNA
misc_feature                95
                            note = RNA
source                      1..95
                            mol_type = other DNA
                            organism = synthetic construct
SEQUENCE: 173
caaagctgac ataagaagaa cgtgcttgtg gtagcaaata tgcgtctatt tagtggagcc   60
tgatctatct tcttttctc acagggcagg ggagg                               95

SEQ ID NO: 174              moltype = DNA   length = 95
FEATURE                     Location/Qualifiers
misc_feature                1..95
                            note = Htr3a_1014_GGAC_RNA
misc_feature                1..94
                            note = DNA
misc_feature                95
                            note = RNA
source                      1..95
                            mol_type = other DNA
                            organism = synthetic construct
```

```
SEQUENCE: 174
agtgtgtctg acacgatgat cgtgcttgtg gtagcaaata tgcgtctatt tagtggagcc    60
ggacctatct tctttttaccg atggccgttg ctggc                              95

SEQ ID NO: 175           moltype = DNA  length = 95
FEATURE                  Location/Qualifiers
misc_feature             1..95
                         note = Htr3a_1309_GTAA_RNA
misc_feature             1..94
                         note = DNA
misc_feature             95
                         note = RNA
source                   1..95
                         mol_type = other DNA
                         organism = synthetic construct
SEQUENCE: 175
atggctgcag tggtttccca cgtgcttgtg gtagcaaata tgcgtctatt tagtggagcc    60
gtaactatct tctttaagtc ctgaggtcct ccaac                               95

SEQ ID NO: 176           moltype = DNA  length = 95
FEATURE                  Location/Qualifiers
misc_feature             1..95
                         note = Htr3a_1573_TAAC_RNA
misc_feature             1..94
                         note = DNA
misc_feature             95
                         note = RNA
source                   1..95
                         mol_type = other DNA
                         organism = synthetic construct
SEQUENCE: 176
ccaaatggac cagagagtga cgtgcttgtg gtagcaaata tgcgtctatt tagtggagcc    60
taacctatct tctttgtgcc cactcaagaa taatg                               95

SEQ ID NO: 177           moltype = DNA  length = 95
FEATURE                  Location/Qualifiers
misc_feature             1..95
                         note = Htr3a_1750_TATT_RNA
misc_feature             1..94
                         note = DNA
misc_feature             95
                         note = RNA
source                   1..95
                         mol_type = other DNA
                         organism = synthetic construct
SEQUENCE: 177
aagtcagaga gacagactgg cgtgcttgtg gtagcaaata tgcgtctatt tagtggagcc    60
tattctatct tctttgcttt aaagccatga taggg                               95

SEQ ID NO: 178           moltype = DNA  length = 95
FEATURE                  Location/Qualifiers
misc_feature             1..95
                         note = Htr3a_1927_TCGC_RNA
misc_feature             1..94
                         note = DNA
misc_feature             95
                         note = RNA
source                   1..95
                         mol_type = other DNA
                         organism = synthetic construct
SEQUENCE: 178
gcaagacaat ttgcttttct cgtgcttgtg gtagcaaata tgcgtctatt tagtggagcc    60
tcgcctatct tctttcagaa gtctcaggca tctat                               95

SEQ ID NO: 179           moltype = DNA  length = 95
FEATURE                  Location/Qualifiers
misc_feature             1..95
                         note = Htr3a_2045_TGGA_RNA
misc_feature             1..94
                         note = DNA
misc_feature             95
                         note = RNA
source                   1..95
                         mol_type = other DNA
                         organism = synthetic construct
SEQUENCE: 179
attatcccct gctcccattg cgtgcttgtg gtagcaaata tgcgtctatt tagtggagcc    60
tggactatct tctttttaag atatcatagc atttt                               95
```

```
SEQ ID NO: 180          moltype = DNA  length = 95
FEATURE                 Location/Qualifiers
misc_feature            1..95
                        note = Htr3a_21_AAGT_RNA
misc_feature            1..94
                        note = DNA
misc_feature            95
                        note = RNA
source                  1..95
                        mol_type = other DNA
                        organism = synthetic construct
SEQUENCE: 180
gtcccaggca gactgctttt cgtgcttgtg gtagcaaata tgcgtctatt tagtggagcc    60
aagtctatct tctttccacc cgctgccaac ctcat                              95

SEQ ID NO: 181          moltype = DNA  length = 95
FEATURE                 Location/Qualifiers
misc_feature            1..95
                        note = Htr3a_247_CAGC_RNA
misc_feature            1..94
                        note = DNA
misc_feature            95
                        note = RNA
source                  1..95
                        mol_type = other DNA
                        organism = synthetic construct
SEQUENCE: 181
gtctgacagc cttagtagag cgtgcttgtg gtagcaaata tgcgtctatt tagtggagcc    60
cagcctatct tcttttgta gttagccagg aggtg                               95

SEQ ID NO: 182          moltype = DNA  length = 95
FEATURE                 Location/Qualifiers
misc_feature            1..95
                        note = Htr3a_424_CGGT_RNA
misc_feature            1..94
                        note = DNA
misc_feature            95
                        note = RNA
source                  1..95
                        mol_type = other DNA
                        organism = synthetic construct
SEQUENCE: 182
agtccactgc agaaactcat cgtgcttgtg gtagcaaata tgcgtctatt tagtggagcc    60
cggtctatct tctttacatt gtcgaagtcc tcagg                              95

SEQ ID NO: 183          moltype = DNA  length = 95
FEATURE                 Location/Qualifiers
misc_feature            1..95
                        note = Htr3a_89_CACT_RNA
misc_feature            1..94
                        note = DNA
misc_feature            95
                        note = RNA
source                  1..95
                        mol_type = other DNA
                        organism = synthetic construct
SEQUENCE: 183
ctcagagcag ccactcagga cgtgcttgtg gtagcaaata tgcgtctatt tagtggagcc    60
cactctatct tctttcttcc cagatgtggg agggc                              95

SEQ ID NO: 184          moltype = DNA  length = 95
FEATURE                 Location/Qualifiers
misc_feature            1..95
                        note = Htr3a_955_GCTC_RNA
misc_feature            1..94
                        note = DNA
misc_feature            95
                        note = RNA
source                  1..95
                        mol_type = other DNA
                        organism = synthetic construct
SEQUENCE: 184
agagactctc tcaccgctgt cgtgcttgtg gtagcaaata tgcgtctatt tagtggagcc    60
gctcctatct tctttagaag gagtgtgatc ttgaa                              95

SEQ ID NO: 185          moltype = DNA  length = 95
FEATURE                 Location/Qualifiers
misc_feature            1..95
                        note = Neurod6_1033_RNA
```

| | | |
|---|---|---|
| misc_feature | 1..94 | |
| | note = DNA | |
| misc_feature | 95 | |
| | note = RNA | |
| source | 1..95 | |
| | mol_type = other DNA | |
| | organism = synthetic construct | |

SEQUENCE: 185
```
tagaaggatt catatgcact ctgattcctt tgactcacat tgcgtctatt tagtggagcc   60
ttgcctatct tctttactca ggggaggtac tttca                              95
```

| | | |
|---|---|---|
| SEQ ID NO: 186 | moltype = DNA   length = 95 | |
| FEATURE | Location/Qualifiers | |
| misc_feature | 1..95 | |
| | note = Neurod6_108_RNA | |
| misc_feature | 1..94 | |
| | note = DNA | |
| misc_feature | 95 | |
| | note = RNA | |
| source | 1..95 | |
| | mol_type = other DNA | |
| | organism = synthetic construct | |

SEQUENCE: 186
```
ctgctagtga cgtcacaggg ctgattcctt tgactcacat tgcgtctatt tagtggagcc   60
ttgcctatct tctttagagc tggtacccat gccat                              95
```

| | | |
|---|---|---|
| SEQ ID NO: 187 | moltype = DNA   length = 95 | |
| FEATURE | Location/Qualifiers | |
| misc_feature | 1..95 | |
| | note = Neurod6_1524_RNA | |
| misc_feature | 1..94 | |
| | note = DNA | |
| misc_feature | 95 | |
| | note = RNA | |
| source | 1..95 | |
| | mol_type = other DNA | |
| | organism = synthetic construct | |

SEQUENCE: 187
```
tgtgatacag acaagaggga ctgattcctt tgactcacat tgcgtctatt tagtggagcc   60
ttgcctatct tctttagaga gagagagaat cacag                              95
```

| | | |
|---|---|---|
| SEQ ID NO: 188 | moltype = DNA   length = 95 | |
| FEATURE | Location/Qualifiers | |
| misc_feature | 1..95 | |
| | note = Neurod6_168_RNA | |
| misc_feature | 1..94 | |
| | note = DNA | |
| misc_feature | 95 | |
| | note = RNA | |
| source | 1..95 | |
| | mol_type = other DNA | |
| | organism = synthetic construct | |

SEQUENCE: 188
```
tctcattgat ctctaaaaag ctgattcctt tgactcacat tgcgtctatt tagtggagcc   60
ttgcctatct tctttatctg tgtgtatctg cacta                              95
```

| | | |
|---|---|---|
| SEQ ID NO: 189 | moltype = DNA   length = 95 | |
| FEATURE | Location/Qualifiers | |
| misc_feature | 1..95 | |
| | note = Neurod6_1688_RNA | |
| misc_feature | 1..94 | |
| | note = DNA | |
| misc_feature | 95 | |
| | note = RNA | |
| source | 1..95 | |
| | mol_type = other DNA | |
| | organism = synthetic construct | |

SEQUENCE: 189
```
agacattgaa gtatgctgtg ctgattcctt tgactcacat tgcgtctatt tagtggagcc   60
ttgcctatct tctttcataa ctgtacaact gaaat                              95
```

| | | |
|---|---|---|
| SEQ ID NO: 190 | moltype = DNA   length = 95 | |
| FEATURE | Location/Qualifiers | |
| misc_feature | 1..95 | |
| | note = Neurod6_2041_RNA | |
| misc_feature | 1..94 | |
| | note = DNA | |
| misc_feature | 95 | |
| | note = RNA | |

```
                           -continued source                     1..95
                           mol_type = other DNA
                           organism = synthetic construct
SEQUENCE: 190
aacaatacaa aacaagtgct ctgattcctt tgactcacat tgcgtctatt tagtggagcc   60
ttgcctatct tctttacctg tacagaaaaa tcctg                             95

SEQ ID NO: 191             moltype = DNA   length = 95
FEATURE                    Location/Qualifiers
misc_feature               1..95
                           note = Neurod6_228_RNA
misc_feature               1..94
                           note = DNA
misc_feature               95
                           note = RNA
source                     1..95
                           mol_type = other DNA
                           organism = synthetic construct
SEQUENCE: 191
ttttcaggct gagtgtcgca ctgattcctt tgactcacat tgcgtctatt tagtggagcc   60
ttgcctatct tctttcattt tggatcttcc aaatc                             95

SEQ ID NO: 192             moltype = DNA   length = 95
FEATURE                    Location/Qualifiers
misc_feature               1..95
                           note = Neurod6_315_RNA
misc_feature               1..94
                           note = DNA
misc_feature               95
                           note = RNA
source                     1..95
                           mol_type = other DNA
                           organism = synthetic construct
SEQUENCE: 192
gtagtgttaa catggttctt ctgattcctt tgactcacat tgcgtctatt tagtggagcc   60
ttgcctatct tcttttacga cagactcgtc aaacg                             95

SEQ ID NO: 193             moltype = DNA   length = 95
FEATURE                    Location/Qualifiers
misc_feature               1..95
                           note = Neurod6_495_RNA
misc_feature               1..94
                           note = DNA
misc_feature               95
                           note = RNA
source                     1..95
                           mol_type = other DNA
                           organism = synthetic construct
SEQUENCE: 193
tgtcttcttc ctcctcttct ctgattcctt tgactcacat tgcgtctatt tagtggagcc   60
ttgcctatct tctttattct catcttcttc ctctc                             95

SEQ ID NO: 194             moltype = DNA   length = 95
FEATURE                    Location/Qualifiers
misc_feature               1..95
                           note = Neurod6_648_RNA
misc_feature               1..94
                           note = DNA
misc_feature               95
                           note = RNA
source                     1..95
                           mol_type = other DNA
                           organism = synthetic construct
SEQUENCE: 194
tgtccagagc atcattgagg ctgattcctt tgactcacat tgcgtctatt tagtggagcc   60
ttgcctatct tctttgggga ccacttttcg caaat                             95

SEQ ID NO: 195             moltype = DNA   length = 95
FEATURE                    Location/Qualifiers
misc_feature               1..95
                           note = Neurod6_714_RNA
misc_feature               1..94
                           note = DNA
misc_feature               95
                           note = RNA
source                     1..95
                           mol_type = other DNA
                           organism = synthetic construct
SEQUENCE: 195
```

```
gtcgtaaagt ttctattttg ctgattcctt tgactcacat tgcgtctatt tagtggagcc    60
ttgcctatct tctttccaga tgtaattttt ggcca                                95

SEQ ID NO: 196         moltype = DNA   length = 95
FEATURE                Location/Qualifiers
misc_feature           1..95
                       note = Neurod6_971_RNA
misc_feature           1..94
                       note = DNA
misc_feature           95
                       note = RNA
source                 1..95
                       mol_type = other DNA
                       organism = synthetic construct
SEQUENCE: 196
cccatgccct gggggagtgg ctgattcctt tgactcacat tgcgtctatt tagtggagcc    60
ttgcctatct tctttgactt ggaattatca agagt                                95

SEQ ID NO: 197         moltype = DNA   length = 92
FEATURE                Location/Qualifiers
misc_feature           1..92
                       note = Nov_DO2_ATGC_RNA
misc_feature           1..91
                       note = DNA
misc_feature           92
                       note = RNA
source                 1..92
                       mol_type = other DNA
                       organism = synthetic construct
SEQUENCE: 197
ggagaaagtt catgcacactc tacgatttta ccagtggctg cgtctattta gtggagccat   60
gcctatcttc tttgagtcgg tttgtctata at                                   92

SEQ ID NO: 198         moltype = DNA   length = 95
FEATURE                Location/Qualifiers
misc_feature           1..95
                       note = Pcp4_120_RNA
misc_feature           1..94
                       note = DNA
misc_feature           95
                       note = RNA
source                 1..95
                       mol_type = other DNA
                       organism = synthetic construct
SEQUENCE: 198
tcagaaggca atgctcaggg ctgattcctt tgactcacat tgcgtctatt tagtggagcc    60
atccctatct tctttgctag gtcccacaga acagc                                95

SEQ ID NO: 199         moltype = DNA   length = 95
FEATURE                Location/Qualifiers
misc_feature           1..95
                       note = Pcp4_181_RNA
misc_feature           1..94
                       note = DNA
misc_feature           95
                       note = RNA
source                 1..95
                       mol_type = other DNA
                       organism = synthetic construct
SEQUENCE: 199
tccggcactt tgtctctcac ctgattcctt tgactcacat tgcgtctatt tagtggagcc    60
atccctatct tcttttgtc ttttccgttg gtcgc                                 95

SEQ ID NO: 200         moltype = DNA   length = 95
FEATURE                Location/Qualifiers
misc_feature           1..95
                       note = Pcp4_305_RNA
misc_feature           1..94
                       note = DNA
misc_feature           95
                       note = RNA
source                 1..95
                       mol_type = other DNA
                       organism = synthetic construct
SEQUENCE: 200
actgagactg aatggccaca ctgattcctt tgactcacat tgcgtctatt tagtggagcc    60
atccctatct tctttttct tctggaattt tctga                                 95

SEQ ID NO: 201         moltype = DNA   length = 95
```

```
FEATURE                 Location/Qualifiers
misc_feature            1..95
                        note = Pcp4_386_RNA
misc_feature            1..94
                        note = DNA
misc_feature            95
                        note = RNA
source                  1..95
                        mol_type = other DNA
                        organism = synthetic construct
SEQUENCE: 201
aacttggtgt cttcaggtgg ctgattcctt tgactcacat tgcgtctatt tagtggagcc    60
atccctatct tctttttctt gatggatggt ggttg                               95

SEQ ID NO: 202          moltype = DNA   length = 95
FEATURE                 Location/Qualifiers
misc_feature            1..95
                        note = Pcp4_472_RNA
misc_feature            1..94
                        note = DNA
misc_feature            95
                        note = RNA
source                  1..95
                        mol_type = other DNA
                        organism = synthetic construct
SEQUENCE: 202
ttcaggtttg tagcagggtg ctgattcctt tgactcacat tgcgtctatt tagtggagcc    60
atccctatct tctttatggg tttctcttca tgcat                               95

SEQ ID NO: 203          moltype = DNA   length = 95
FEATURE                 Location/Qualifiers
misc_feature            1..95
                        note = Pde1a_1081_RNA
misc_feature            1..94
                        note = DNA
misc_feature            95
                        note = RNA
source                  1..95
                        mol_type = other DNA
                        organism = synthetic construct
SEQUENCE: 203
ttctctgttg agtccgtcag tctacgagtt tgcagtcacg tgcgtctatt tagtggagcc    60
atcgctatct tctttctata agaggaatga caatt                               95

SEQ ID NO: 204          moltype = DNA   length = 95
FEATURE                 Location/Qualifiers
misc_feature            1..95
                        note = Pde1a_120_RNA
misc_feature            1..94
                        note = DNA
misc_feature            95
                        note = RNA
source                  1..95
                        mol_type = other DNA
                        organism = synthetic construct
SEQUENCE: 204
actttggttt ttcttcaggc tctacgagtt tgcagtcacg tgcgtctatt tagtggagcc    60
atcgctatct tctttagcat ggacaatgct gcgaa                               95

SEQ ID NO: 205          moltype = DNA   length = 95
FEATURE                 Location/Qualifiers
misc_feature            1..95
                        note = Pde1a_1216_RNA
misc_feature            1..94
                        note = DNA
misc_feature            95
                        note = RNA
source                  1..95
                        mol_type = other DNA
                        organism = synthetic construct
SEQUENCE: 205
tcacacacgg agccttttgt tctacgagtt tgcagtcacg tgcgtctatt tagtggagcc    60
atcgctatct tctttagtct ggggcatagc tccca                               95

SEQ ID NO: 206          moltype = DNA   length = 95
FEATURE                 Location/Qualifiers
misc_feature            1..95
                        note = Pde1a_273_RNA
misc_feature            1..94
```

```
                    note = DNA
misc_feature        95
                    note = RNA
source              1..95
                    mol_type = other DNA
                    organism = synthetic construct
SEQUENCE: 206
catttaaggc aaatacatca tctacgagtt tgcagtcacg tgcgtctatt tagtggagcc    60
atcgctatct tctttgctat gctccccgct tgctt                              95

SEQ ID NO: 207      moltype = DNA   length = 95
FEATURE             Location/Qualifiers
misc_feature        1..95
                    note = Pde1a_334_RNA
misc_feature        1..94
                    note = DNA
misc_feature        95
                    note = RNA
source              1..95
                    mol_type = other DNA
                    organism = synthetic construct
SEQUENCE: 207
agatcatatc tggtaaagag tctacgagtt tgcagtcacg tgcgtctatt tagtggagcc    60
atcgctatct tctttgaatc ttgaagcggt tgata                              95

SEQ ID NO: 208      moltype = DNA   length = 95
FEATURE             Location/Qualifiers
misc_feature        1..95
                    note = Pde1a_469_RNA
misc_feature        1..94
                    note = DNA
misc_feature        95
                    note = RNA
source              1..95
                    mol_type = other DNA
                    organism = synthetic construct
SEQUENCE: 208
atataatgca cagtttgagt tctacgagtt tgcagtcacg tgcgtctatt tagtggagcc    60
atcgctatct tcttttgata cctgtatgaa gcatt                              95

SEQ ID NO: 209      moltype = DNA   length = 95
FEATURE             Location/Qualifiers
misc_feature        1..95
                    note = Pde1a_615_RNA
misc_feature        1..94
                    note = DNA
misc_feature        95
                    note = RNA
source              1..95
                    mol_type = other DNA
                    organism = synthetic construct
SEQUENCE: 209
tgtacagaat agcaacgtcc tctacgagtt tgcagtcacg tgcgtctatt tagtggagcc    60
atcgctatct tctttctcaa gcactgagcg gtcgt                              95

SEQ ID NO: 210      moltype = DNA   length = 95
FEATURE             Location/Qualifiers
misc_feature        1..95
                    note = Pde1a_759_RNA
misc_feature        1..94
                    note = DNA
misc_feature        95
                    note = RNA
source              1..95
                    mol_type = other DNA
                    organism = synthetic construct
SEQUENCE: 210
ctgtcgctaa gaccatttca tctacgagtt tgcagtcacg tgcgtctatt tagtggagcc    60
atcgctatct tctttctgaa aatgccctga catgt                              95

SEQ ID NO: 211      moltype = DNA   length = 95
FEATURE             Location/Qualifiers
misc_feature        1..95
                    note = Pde1a_904_RNA
misc_feature        1..94
                    note = DNA
misc_feature        95
                    note = RNA
source              1..95
```

```
                        mol_type = other DNA
                        organism = synthetic construct
SEQUENCE: 211
ctgtagtgca acttccaagt tctacgagtt tgcagtcacg tgcgtctatt tagtggagcc     60
atcgctatct tctttccatt agggccatgg tccat                                95

SEQ ID NO: 212          moltype = DNA  length = 95
FEATURE                 Location/Qualifiers
misc_feature            1..95
                        note = Pde1a_995_RNA
misc_feature            1..94
                        note = DNA
misc_feature            95
                        note = RNA
source                  1..95
                        mol_type = other DNA
                        organism = synthetic construct
SEQUENCE: 212
cttccgatca caaagtggag tctacgagtt tgcagtcacg tgcgtctatt tagtggagcc     60
atcgctatct tctttgactg ggcaaccatt gttga                                95

SEQ ID NO: 213          moltype = DNA  length = 95
FEATURE                 Location/Qualifiers
misc_feature            1..95
                        note = Penk_1282_RNA
misc_feature            1..94
                        note = DNA
misc_feature            95
                        note = RNA
source                  1..95
                        mol_type = other DNA
                        organism = synthetic construct
SEQUENCE: 213
caatactgag cttcaagact tctacgattt taccagtggc tgcgtctatt tagtggagcc     60
gtacctatct tctttacaac atagccataa gagac                                95

SEQ ID NO: 214          moltype = DNA  length = 95
FEATURE                 Location/Qualifiers
misc_feature            1..95
                        note = Penk_286_RNA
misc_feature            1..94
                        note = DNA
misc_feature            95
                        note = RNA
source                  1..95
                        mol_type = other DNA
                        organism = synthetic construct
SEQUENCE: 214
catgggctgt aggagagaag tctacgattt taccagtggc tgcgtctatt tagtggagcc     60
gtacctatct tctttcaaag cctcaggaac cgcgc                                95

SEQ ID NO: 215          moltype = DNA  length = 95
FEATURE                 Location/Qualifiers
misc_feature            1..95
                        note = Penk_638_RNA
misc_feature            1..94
                        note = DNA
misc_feature            95
                        note = RNA
source                  1..95
                        mol_type = other DNA
                        organism = synthetic construct
SEQUENCE: 215
gatatagctc gtccatcttc tctacgattt taccagtggc tgcgtctatt tagtggagcc     60
gtacctatct tcttttttctt cttctggctc catgg                               95

SEQ ID NO: 216          moltype = DNA  length = 95
FEATURE                 Location/Qualifiers
misc_feature            1..95
                        note = Penk_83_RNA
misc_feature            1..94
                        note = DNA
misc_feature            95
                        note = RNA
source                  1..95
                        mol_type = other DNA
                        organism = synthetic construct
SEQUENCE: 216
tgcctgggac tattctatct tctacgattt taccagtggc tgcgtctatt tagtggagcc     60
```

```
gtacctatct tctttgtttc ctgctgttct agtga                              95

SEQ ID NO: 217          moltype = DNA   length = 95
FEATURE                 Location/Qualifiers
misc_feature            1..95
                        note = Penk_882_RNA
misc_feature            1..94
                        note = DNA
misc_feature            95
                        note = RNA
source                  1..95
                        mol_type = other DNA
                        organism = synthetic construct
SEQUENCE: 217
agttgggggc ttcttttgag tctacgattt taccagtggc tgcgtctatt tagtggagcc   60
gtacctatct tctttgctct tttgcttcat cttcc                              95

SEQ ID NO: 218          moltype = DNA   length = 89
FEATURE                 Location/Qualifiers
misc_feature            1..89
                        note = Plcxd2_DO3_GAAA_RNA
misc_feature            1..88
                        note = DNA
misc_feature            89
                        note = RNA
source                  1..89
                        mol_type = other DNA
                        organism = synthetic construct
SEQUENCE: 218
gcactcctac acaatgactg attcctttga ctcacattgc gtctatttag tggagccgaa   60
actatcttct ttgaagatgg tgagggtat                                     89

SEQ ID NO: 219          moltype = DNA   length = 90
FEATURE                 Location/Qualifiers
misc_feature            1..90
                        note = Plcxd2_DO3_GGCC_RNA
misc_feature            1..89
                        note = DNA
misc_feature            90
                        note = RNA
source                  1..90
                        mol_type = other DNA
                        organism = synthetic construct
SEQUENCE: 219
gtggtagaaa atgagaacct gattcctttg actcacattg cgtctattta gtggagccgg   60
ccctatcttt ttttgcttgt agaagggaca                                    90

SEQ ID NO: 220          moltype = DNA   length = 95
FEATURE                 Location/Qualifiers
misc_feature            1..95
                        note = Rorb_2282_RNA
misc_feature            1..94
                        note = DNA
misc_feature            95
                        note = RNA
source                  1..95
                        mol_type = other DNA
                        organism = synthetic construct
SEQUENCE: 220
tcattcagaa ttggattcca ctgattcctt tgactcacat tgcgtctatt tagtggagcc   60
aaatctatct tctttataac caccaaagtg aagtt                              95

SEQ ID NO: 221          moltype = DNA   length = 95
FEATURE                 Location/Qualifiers
misc_feature            1..95
                        note = Rorb_4479_RNA
misc_feature            1..94
                        note = DNA
misc_feature            95
                        note = RNA
source                  1..95
                        mol_type = other DNA
                        organism = synthetic construct
SEQUENCE: 221
tcaattttct gccttaagcc ctgattcctt tgactcacat tgcgtctatt tagtggagcc   60
aaatctatct tctttaagaa gaaaagaag ttcat                               95

SEQ ID NO: 222          moltype = DNA   length = 95
FEATURE                 Location/Qualifiers
```

```
misc_feature          1..95
                      note = Rorb_536_RNA
misc_feature          1..94
                      note = DNA
misc_feature          95
                      note = RNA
source                1..95
                      mol_type = other DNA
                      organism = synthetic construct
SEQUENCE: 222
atgtgaggtc atagataggt ctgattcctt tgactcacat tgcgtctatt tagtggagcc    60
aaatctatct tctttggtaa acaagttggg tacag                              95

SEQ ID NO: 223        moltype = DNA  length = 95
FEATURE               Location/Qualifiers
misc_feature          1..95
                      note = Rorb_6395_RNA
misc_feature          1..94
                      note = DNA
misc_feature          95
                      note = RNA
source                1..95
                      mol_type = other DNA
                      organism = synthetic construct
SEQUENCE: 223
gagaaagtgt cacagatttg ctgattcctt tgactcacat tgcgtctatt tagtggagcc    60
aaatctatct tctttaggta caattaagag aaagg                              95

SEQ ID NO: 224        moltype = DNA  length = 95
FEATURE               Location/Qualifiers
misc_feature          1..95
                      note = Rorb_8435_RNA
misc_feature          1..94
                      note = DNA
misc_feature          95
                      note = RNA
source                1..95
                      mol_type = other DNA
                      organism = synthetic construct
SEQUENCE: 224
tagttgttag ggagtgctgc ctgattcctt tgactcacat tgcgtctatt tagtggagcc    60
aaatctatct tctttaagta atagaaaact ctttt                              95

SEQ ID NO: 225        moltype = DNA  length = 98
FEATURE               Location/Qualifiers
misc_feature          1..98
                      note = Rorb_DO3_CCGG_RNA
misc_feature          1..97
                      note = DNA
misc_feature          98
                      note = RNA
source                1..98
                      mol_type = other DNA
                      organism = synthetic construct
SEQUENCE: 225
agccttttaa agtcatattt ggtctgattc ctttgactca cattgcgtct atttagtgga    60
gccccggcta tcttcttaat cggtcatcat aaaatact                           98

SEQ ID NO: 226        moltype = DNA  length = 87
FEATURE               Location/Qualifiers
misc_feature          1..87
                      note = Rprm_654_RNA
misc_feature          1..86
                      note = DNA
misc_feature          87
                      note = RNA
source                1..87
                      mol_type = other DNA
                      organism = synthetic construct
SEQUENCE: 226
cggtccgtga tggtgcgtgc ttgtggtagc aaatatgcgt ctatttagtg gagccttgtc    60
tatcttcttt gacaggtttg cgttgct                                       87

SEQ ID NO: 227        moltype = DNA  length = 74
FEATURE               Location/Qualifiers
misc_feature          1..74
                      note = Sst_432_AP1SWPLP_RNA
misc_feature          1..73
                      note = DNA
```

```
misc_feature              74
                          note = RNA
source                    1..74
                          mol_type = other DNA
                          organism = synthetic construct
SEQUENCE: 227
taacaggatg tgaatgtctt ctacgatttt accagtggcc tgactatctt cttttaggac    60
aacaatatta aagc                                                      74

SEQ ID NO: 228            moltype = DNA  length = 95
FEATURE                   Location/Qualifiers
misc_feature              1..95
                          note = Synpr_1071_RNA
misc_feature              1..94
                          note = DNA
misc_feature              95
                          note = RNA
source                    1..95
                          mol_type = other DNA
                          organism = synthetic construct
SEQUENCE: 228
catactagag actttaagct tctacgattt taccagtggc tgcgtctatt tagtggagcc    60
attactatct tctttaaggt aatctatgca catta                               95

SEQ ID NO: 229            moltype = DNA  length = 95
FEATURE                   Location/Qualifiers
misc_feature              1..95
                          note = Synpr_1643_RNA
misc_feature              1..94
                          note = DNA
misc_feature              95
                          note = RNA
source                    1..95
                          mol_type = other DNA
                          organism = synthetic construct
SEQUENCE: 229
cctctctgga tgcaaagaaa tctacgattt taccagtggc tgcgtctatt tagtggagcc    60
attactatct tctttaacta tggtgtctaa atctg                               95

SEQ ID NO: 230            moltype = DNA  length = 95
FEATURE                   Location/Qualifiers
misc_feature              1..95
                          note = Synpr_260_RNA
misc_feature              1..94
                          note = DNA
misc_feature              95
                          note = RNA
source                    1..95
                          mol_type = other DNA
                          organism = synthetic construct
SEQUENCE: 230
atgtacacga ccgtggcagc tctacgattt taccagtggc tgcgtctatt tagtggagcc    60
attactatct tctttggtac ttgttctgga agaaa                               95

SEQ ID NO: 231            moltype = DNA  length = 95
FEATURE                   Location/Qualifiers
misc_feature              1..95
                          note = Synpr_591_RNA
misc_feature              1..94
                          note = DNA
misc_feature              95
                          note = RNA
source                    1..95
                          mol_type = other DNA
                          organism = synthetic construct
SEQUENCE: 231
aaggtatctc tgtccagagg tctacgattt taccagtggc tgcgtctatt tagtggagcc    60
attactatct tcttttgctt ctccatgggg tctga                               95

SEQ ID NO: 232            moltype = DNA  length = 98
FEATURE                   Location/Qualifiers
misc_feature              1..98
                          note = Synpr_DO2_ATTA_RNA
misc_feature              1..97
                          note = DNA
misc_feature              98
                          note = RNA
source                    1..98
                          mol_type = other DNA
```

-continued

```
                           organism = synthetic construct
SEQUENCE: 232
cttaaaaatt cttctgctac tggtctacga ttttaccagt ggctgcgtct atttagtgga    60
gccattacta tcttcttcat taataattga ttgaaact                            98

SEQ ID NO: 233              moltype = DNA   length = 95
FEATURE                     Location/Qualifiers
misc_feature                1..95
                            note = Yjefn3_138_RNA
misc_feature                1..94
                            note = DNA
misc_feature                95
                            note = RNA
source                      1..95
                            mol_type = other DNA
                            organism = synthetic construct
SEQUENCE: 233
cactagcgtg cccacatagt cgtgcttgtg gtagcaaata tgcgtctatt tagtggagcc    60
tttactatct tctttggcct tggtcacagc caccg                               95

SEQ ID NO: 234              moltype = DNA   length = 95
FEATURE                     Location/Qualifiers
misc_feature                1..95
                            note = Yjefn3_344_RNA
misc_feature                1..94
                            note = DNA
misc_feature                95
                            note = RNA
source                      1..95
                            mol_type = other DNA
                            organism = synthetic construct
SEQUENCE: 234
cttctcgcac tgcgtggtca cgtgcttgtg gtagcaaata tgcgtctatt tagtggagcc    60
tttactatct tctttgacag gaagggatg tccat                                95

SEQ ID NO: 235              moltype = DNA   length = 95
FEATURE                     Location/Qualifiers
misc_feature                1..95
                            note = Yjefn3_686_RNA
misc_feature                1..94
                            note = DNA
misc_feature                95
                            note = RNA
source                      1..95
                            mol_type = other DNA
                            organism = synthetic construct
SEQUENCE: 235
aaactttcgg cggacgtcat cgtgcttgtg gtagcaaata tgcgtctatt tagtggagcc    60
tttactatct tcttttattt tggcaggtgc aggcc                               95

SEQ ID NO: 236              moltype = DNA   length = 95
FEATURE                     Location/Qualifiers
misc_feature                1..95
                            note = Bgn_412_RNA
misc_feature                1..94
                            note = DNA
misc_feature                95
                            note = RNA
source                      1..95
                            mol_type = other DNA
                            organism = synthetic construct
SEQUENCE: 236
gggcacagtc ttcagaccca tctacgattt taccagtggc tgcgtctatt tagtggagcc    60
ctatctatct tctttgtgtc aggtgagatc tcctt                               95

SEQ ID NO: 237              moltype = DNA   length = 95
FEATURE                     Location/Qualifiers
misc_feature                1..95
                            note = Bgn_851_RNA
misc_feature                1..94
                            note = DNA
misc_feature                95
                            note = RNA
source                      1..95
                            mol_type = other DNA
                            organism = synthetic construct
SEQUENCE: 237
tcagggtctc agggagatct tctacgattt taccagtggc tgcgtctatt tagtggagcc    60
ctatctatct tctttgtggt ccaggtgaag ttcgt                               95
```

```
SEQ ID NO: 238           moltype = DNA   length = 95
FEATURE                  Location/Qualifiers
misc_feature             1..95
                         note = Bgn_1194_RNA
misc_feature             1..94
                         note = DNA
misc_feature             95
                         note = RNA
source                   1..95
                         mol_type = other DNA
                         organism = synthetic construct
SEQUENCE: 238
tcccagtagg gcacagggtt tctacgattt taccagtggc tgcgtctatt tagtggagcc    60
ctatctatct tctttggaag gtggcaggct gcact                              95

SEQ ID NO: 239           moltype = DNA   length = 95
FEATURE                  Location/Qualifiers
misc_feature             1..95
                         note = Bgn_1577_RNA
misc_feature             1..94
                         note = DNA
misc_feature             95
                         note = RNA
source                   1..95
                         mol_type = other DNA
                         organism = synthetic construct
SEQUENCE: 239
aacaatggcg gtggcagtgt tctacgattt taccagtggc tgcgtctatt tagtggagcc    60
ctatctatct tctttaggaa cacatgcctg gatgg                              95

SEQ ID NO: 240           moltype = DNA   length = 95
FEATURE                  Location/Qualifiers
misc_feature             1..95
                         note = Bgn_2309_RNA
misc_feature             1..94
                         note = DNA
misc_feature             95
                         note = RNA
source                   1..95
                         mol_type = other DNA
                         organism = synthetic construct
SEQUENCE: 240
tcagggaccc aggggtgagg tctacgattt taccagtggc tgcgtctatt tagtggagcc    60
ctatctatct tctttgacca tcacctccta ccaca                              95

SEQ ID NO: 241           moltype = DNA   length = 95
FEATURE                  Location/Qualifiers
misc_feature             1..95
                         note = Apq4_879_RNA
misc_feature             1..94
                         note = DNA
misc_feature             95
                         note = RNA
source                   1..95
                         mol_type = other DNA
                         organism = synthetic construct
SEQUENCE: 241
cttaaggcga cgtttgagct ctgattcctt tgactcacat tgcgtctatt tagtggagcc    60
cattctatct tctttgcggc tttgctgaag gcttc                              95

SEQ ID NO: 242           moltype = DNA   length = 95
FEATURE                  Location/Qualifiers
misc_feature             1..95
                         note = Apq4_2186_RNA
misc_feature             1..94
                         note = DNA
misc_feature             95
                         note = RNA
source                   1..95
                         mol_type = other DNA
                         organism = synthetic construct
SEQUENCE: 242
aattacactc acaatgccga ctgattcctt tgactcacat tgcgtctatt tagtggagcc    60
cattctatct tcttttaatt cacacaaatg ggtat                              95

SEQ ID NO: 243           moltype = DNA   length = 95
FEATURE                  Location/Qualifiers
misc_feature             1..95
```

```
                      note = Apq4_3100_RNA
misc_feature          1..94
                      note = DNA
misc_feature          95
                      note = RNA
source                1..95
                      mol_type = other DNA
                      organism = synthetic construct
SEQUENCE: 243
cactggaaat gactgttaaa ctgattcctt tgactcacat tgcgtctatt tagtggagcc    60
cattctatct tcttttgtac catactgaat gctgt                              95

SEQ ID NO: 244        moltype = DNA  length = 95
FEATURE               Location/Qualifiers
misc_feature          1..95
                      note = Apq4_3673_RNA
misc_feature          1..94
                      note = DNA
misc_feature          95
                      note = RNA
source                1..95
                      mol_type = other DNA
                      organism = synthetic construct
SEQUENCE: 244
cggtgtatct gtcagtagct ctgattcctt tgactcacat tgcgtctatt tagtggagcc    60
cattctatct tctttttcc tctctgatct ctgtg                               95

SEQ ID NO: 245        moltype = DNA  length = 95
FEATURE               Location/Qualifiers
misc_feature          1..95
                      note = Apq4_4344_RNA
misc_feature          1..94
                      note = DNA
misc_feature          95
                      note = RNA
source                1..95
                      mol_type = other DNA
                      organism = synthetic construct
SEQUENCE: 245
acagaggcag tgtctctgtg ctgattcctt tgactcacat tgcgtctatt tagtggagcc    60
cattctatct tctttgctct ctggcttcaa ttgtc                              95

SEQ ID NO: 246        moltype = DNA  length = 95
FEATURE               Location/Qualifiers
misc_feature          1..95
                      note = Pdgfra_296_RNA
misc_feature          1..94
                      note = DNA
misc_feature          95
                      note = RNA
source                1..95
                      mol_type = other DNA
                      organism = synthetic construct
SEQUENCE: 246
tgggaggata gagggtaata tctacgagtt tgcagtcacg tgcgtctatt tagtggagcc    60
tgtcctatct tctttacaat cttctcattc tcgtt                              95

SEQ ID NO: 247        moltype = DNA  length = 95
FEATURE               Location/Qualifiers
misc_feature          1..95
                      note = Pdgfra_646_RNA
misc_feature          1..94
                      note = DNA
misc_feature          95
                      note = RNA
source                1..95
                      mol_type = other DNA
                      organism = synthetic construct
SEQUENCE: 247
ggtatgatgg cagagtcatc tctacgagtt tgcagtcacg tgcgtctatt tagtggagcc    60
tgtcctatct tctttccgga tctgtggtgc ggcaa                              95

SEQ ID NO: 248        moltype = DNA  length = 95
FEATURE               Location/Qualifiers
misc_feature          1..95
                      note = Pdgfra_832_RNA
misc_feature          1..94
                      note = DNA
misc_feature          95
```

```
                            note = RNA
source                      1..95
                            mol_type = other DNA
                            organism = synthetic construct
SEQUENCE: 248
gttgctttca aggcataaac tctacgagtt tgcagtcacg tgcgtctatt tagtggagcc    60
tgtcctatct tcttttctcc agattcagtt ctgac                              95

SEQ ID NO: 249              moltype = DNA   length = 95
FEATURE                     Location/Qualifiers
misc_feature                1..95
                            note = Pdgfra_1227_RNA
misc_feature                1..94
                            note = DNA
misc_feature                95
                            note = RNA
source                      1..95
                            mol_type = other DNA
                            organism = synthetic construct
SEQUENCE: 249
ggtaggcctg cacctccacc tctacgagtt tgcagtcacg tgcgtctatt tagtggagcc    60
tgtcctatct tctttccacg atatcctggg cgtcg                              95

SEQ ID NO: 250              moltype = DNA   length = 95
FEATURE                     Location/Qualifiers
misc_feature                1..95
                            note = Pdgfra_1544_RNA
misc_feature                1..94
                            note = DNA
misc_feature                95
                            note = RNA
source                      1..95
                            mol_type = other DNA
                            organism = synthetic construct
SEQUENCE: 250
catccagtcg atttctggaa tctacgagtt tgcagtcacg tgcgtctatt tagtggagcc    60
tgtcctatct tcttttctctt aatatgcttg cagat                             95

SEQ ID NO: 251              moltype = DNA   length = 57
FEATURE                     Location/Qualifiers
misc_feature                1..57
                            note = fwd_index1
source                      1..57
                            mol_type = other DNA
                            organism = synthetic construct
SEQUENCE: 251
aatgatacgg cgaccaccga gatctacaca ggctataaca ctctttccct acacgac       57

SEQ ID NO: 252              moltype = DNA   length = 57
FEATURE                     Location/Qualifiers
misc_feature                1..57
                            note = fwd_index2
source                      1..57
                            mol_type = other DNA
                            organism = synthetic construct
SEQUENCE: 252
aatgatacgg cgaccaccga gatctacacg cctctataca ctctttccct acacgac       57

SEQ ID NO: 253              moltype = DNA   length = 57
FEATURE                     Location/Qualifiers
misc_feature                1..57
                            note = fwd_index3
source                      1..57
                            mol_type = other DNA
                            organism = synthetic construct
SEQUENCE: 253
aatgatacgg cgaccaccga gatctacaca ggataggaca ctctttccct acacgac       57

SEQ ID NO: 254              moltype = DNA   length = 57
FEATURE                     Location/Qualifiers
misc_feature                1..57
                            note = fwd_index4
source                      1..57
                            mol_type = other DNA
                            organism = synthetic construct
SEQUENCE: 254
aatgatacgg cgaccaccga gatctacact cagagccaca ctctttccct acacgac       57

SEQ ID NO: 255              moltype = DNA   length = 57
```

| | | |
|---|---|---|
| FEATURE | Location/Qualifiers | |
| misc_feature | 1..57 | |
| | note = fwd_index5 | |
| source | 1..57 | |
| | mol_type = other DNA | |
| | organism = synthetic construct | |

SEQUENCE: 255
aatgatacgg cgaccaccga gatctacacc ttcgcctaca ctctttccct acacgac      57

| | | |
|---|---|---|
| SEQ ID NO: 256 | moltype = DNA   length = 57 | |
| FEATURE | Location/Qualifiers | |
| misc_feature | 1..57 | |
| | note = fwd_index6 | |
| source | 1..57 | |
| | mol_type = other DNA | |
| | organism = synthetic construct | |

SEQUENCE: 256
aatgatacgg cgaccaccga gatctacact aagattaaca ctctttccct acacgac      57

| | | |
|---|---|---|
| SEQ ID NO: 257 | moltype = DNA   length = 57 | |
| FEATURE | Location/Qualifiers | |
| misc_feature | 1..57 | |
| | note = fwd_index7 | |
| source | 1..57 | |
| | mol_type = other DNA | |
| | organism = synthetic construct | |

SEQUENCE: 257
aatgatacgg cgaccaccga gatctacaca cgtcctgaca ctctttccct acacgac      57

| | | |
|---|---|---|
| SEQ ID NO: 258 | moltype = DNA   length = 57 | |
| FEATURE | Location/Qualifiers | |
| misc_feature | 1..57 | |
| | note = fwd_index8 | |
| source | 1..57 | |
| | mol_type = other DNA | |
| | organism = synthetic construct | |

SEQUENCE: 258
aatgatacgg cgaccaccga gatctacacg tcagtacaca ctctttccct acacgac      57

| | | |
|---|---|---|
| SEQ ID NO: 259 | moltype = DNA   length = 53 | |
| FEATURE | Location/Qualifiers | |
| misc_feature | 1..53 | |
| | note = rev_index1 | |
| source | 1..53 | |
| | mol_type = other DNA | |
| | organism = synthetic construct | |

SEQUENCE: 259
caagcagaag acggcatacg agatcgagta atgtgactgg agttcagacg tgt          53

| | | |
|---|---|---|
| SEQ ID NO: 260 | moltype = DNA   length = 53 | |
| FEATURE | Location/Qualifiers | |
| misc_feature | 1..53 | |
| | note = rev_index2 | |
| source | 1..53 | |
| | mol_type = other DNA | |
| | organism = synthetic construct | |

SEQUENCE: 260
caagcagaag acggcatacg agattctccg gagtgactgg agttcagacg tgt          53

| | | |
|---|---|---|
| SEQ ID NO: 261 | moltype = DNA   length = 53 | |
| FEATURE | Location/Qualifiers | |
| misc_feature | 1..53 | |
| | note = rev_index3 | |
| source | 1..53 | |
| | mol_type = other DNA | |
| | organism = synthetic construct | |

SEQUENCE: 261
caagcagaag acggcatacg agataatgag cggtgactgg agttcagacg tgt          53

| | | |
|---|---|---|
| SEQ ID NO: 262 | moltype = DNA   length = 20 | |
| FEATURE | Location/Qualifiers | |
| misc_feature | 1..20 | |
| | note = P5primer | |
| source | 1..20 | |
| | mol_type = other DNA | |
| | organism = synthetic construct | |

SEQUENCE: 262
aatgatacgg cgaccaccga                                               20

| | | |
|---|---|---|
| SEQ ID NO: 263 | moltype = DNA length = 21 | |
| FEATURE | Location/Qualifiers | |
| misc_feature | 1..21 | |
| | note = P7primer | |
| source | 1..21 | |
| | mol_type = other DNA | |
| | organism = synthetic construct | |
| SEQUENCE: 263 | | |
| caagcagaag acggcatacg a | | 21 |

| | | |
|---|---|---|
| SEQ ID NO: 264 | moltype = DNA length = 77 | |
| FEATURE | Location/Qualifiers | |
| misc_feature | 1..77 | |
| | note = R_KRAS.D3 | |
| misc_feature | 1..23 | |
| | note = DNA | |
| misc_feature | 25..39 | |
| | note = DNA | |
| misc_feature | 41..55 | |
| | note = DNA | |
| misc_feature | 57..77 | |
| | note = DNA | |
| misc_feature | 24 | |
| | note = RNA | |
| misc_feature | 40 | |
| | note = RNA | |
| misc_feature | 56 | |
| | note = RNA | |
| source | 1..77 | |
| | mol_type = other DNA | |
| | organism = synthetic construct | |
| SEQUENCE: 264 | | |
| agctccaact accacaaagt cgatagtcac ggctactcag acgtaacgcg ttcagtgatg | | 60 |
| cccttgccta cgccacc | | 77 |

| | | |
|---|---|---|
| SEQ ID NO: 265 | moltype = DNA length = 77 | |
| FEATURE | Location/Qualifiers | |
| misc_feature | 1..77 | |
| | note = R_KRAS.D8 | |
| misc_feature | 1..17 | |
| | note = DNA | |
| misc_feature | 19..23 | |
| | note = DNA | |
| misc_feature | 25..29 | |
| | note = DNA | |
| misc_feature | 31..35 | |
| | note = DNA | |
| misc_feature | 37..41 | |
| | note = DNA | |
| misc_feature | 43..48 | |
| | note = DNA | |
| misc_feature | 50..55 | |
| | note = DNA | |
| misc_feature | 57..61 | |
| | note = DNA | |
| misc_feature | 63..77 | |
| | note = DNA | |
| misc_feature | 18 | |
| | note = RNA | |
| misc_feature | 24 | |
| | note = RNA | |
| misc_feature | 30 | |
| | note = RNA | |
| misc_feature | 36 | |
| | note = RNA | |
| misc_feature | 42 | |
| | note = RNA | |
| misc_feature | 49 | |
| | note = RNA | |
| misc_feature | 56 | |
| | note = RNA | |
| misc_feature | 62 | |
| | note = RNA | |
| source | 1..77 | |
| | mol_type = other DNA | |
| | organism = synthetic construct | |
| SEQUENCE: 265 | | |
| agctccaact accacaaagt cgatagtcac ggctactcag acgtaacgcg ttcagtgatg | | 60 |
| cccttgccta cgccacc | | 77 |

```
SEQ ID NO: 266           moltype = AA  length = 575
FEATURE                  Location/Qualifiers
source                   1..575
                         mol_type = protein
                         organism = Bacteriophage phi-29
SEQUENCE: 266
MKHMPRKMYS CDFETTTKVE DCRVWAYGYM NIEDHSEYKI GNSLDEFMAW VLKVQADLYF   60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                             575

SEQ ID NO: 267           moltype = DNA  length = 77
FEATURE                  Location/Qualifiers
misc_feature             1..77
                         note = R_KRAS.2G
misc_feature             1..39
                         note = DNA
misc_feature             42..77
                         note = DNA
misc_feature             40..41
                         note = RNA
source                   1..77
                         mol_type = other DNA
                         organism = synthetic construct
SEQUENCE: 267
agctccaact accacaaagt cgatagtcac ggctactcag cgtaacgcg ttcagtgatg    60
cccttgccta cgccacc                                                 77

SEQ ID NO: 268           moltype = DNA  length = 77
FEATURE                  Location/Qualifiers
misc_feature             1..77
                         note = R_KRAS.2C
misc_feature             1..39
                         note = DNA
misc_feature             42..77
                         note = DNA
misc_feature             40..41
                         note = RNA
source                   1..77
                         mol_type = other DNA
                         organism = synthetic construct
SEQUENCE: 268
agctccaact accacaaagt cgatagtcac ggctactcac ccgtaacgcg ttcagtgatg   60
cccttgccta cgccacc                                                 77

SEQ ID NO: 269           moltype = DNA  length = 77
FEATURE                  Location/Qualifiers
misc_feature             1..77
                         note = R_KRAS.2A
misc_feature             1..39
                         note = DNA
misc_feature             42..77
                         note = DNA
misc_feature             40..41
                         note = RNA
source                   1..77
                         mol_type = other DNA
                         organism = synthetic construct
SEQUENCE: 269
agctccaact accacaaagt cgatagtcac ggctactcaa acgtaacgcg ttcagtgatg   60
cccttgccta cgccacc                                                 77

SEQ ID NO: 270           moltype = DNA  length = 77
FEATURE                  Location/Qualifiers
misc_feature             1..77
                         note = R_KRAS.2U
misc_feature             1..39
                         note = DNA
misc_feature             42..77
                         note = DNA
misc_feature             40..41
                         note = RNA
```

| | |
|---|---|
| source | 1..77<br>mol_type = other DNA<br>organism = synthetic construct |

SEQUENCE: 270
agctccaact accacaaagt cgatagtcac ggctactcat tcgtaacgcg ttcagtgatg  60
cccttgccta cgccacc  77

| | |
|---|---|
| SEQ ID NO: 271 | moltype = DNA  length = 77 |
| FEATURE | Location/Qualifiers |
| misc_feature | 1..77<br>note = R_KRAS.3G |
| misc_feature | 1..39<br>note = DNA |
| misc_feature | 43..77<br>note = DNA |
| misc_feature | 40..42<br>note = RNA |
| source | 1..77<br>mol_type = other DNA<br>organism = synthetic construct |

SEQUENCE: 271
agctccaact accacaaagt cgatagtcac ggctactcag ggttaacgcg ttcagtgatg  60
cccttgccta cgccacc  77

| | |
|---|---|
| SEQ ID NO: 272 | moltype = DNA  length = 77 |
| FEATURE | Location/Qualifiers |
| misc_feature | 1..77<br>note = R_KRAS.3C |
| misc_feature | 1..39<br>note = DNA |
| misc_feature | 43..77<br>note = DNA |
| misc_feature | 40..42<br>note = RNA |
| source | 1..77<br>mol_type = other DNA<br>organism = synthetic construct |

SEQUENCE: 272
agctccaact accacaaagt cgatagtcac ggctactcac ccgtaacgcg ttcagtgatg  60
cccttgccta cgccacc  77

| | |
|---|---|
| SEQ ID NO: 273 | moltype = DNA  length = 77 |
| FEATURE | Location/Qualifiers |
| misc_feature | 1..77<br>note = R_KRAS.3A |
| misc_feature | 1..39<br>note = DNA |
| misc_feature | 43..77<br>note = DNA |
| misc_feature | 40..42<br>note = RNA |
| source | 1..77<br>mol_type = other DNA<br>organism = synthetic construct |

SEQUENCE: 273
agctccaact accacaaagt cgatagtcac ggctactcaa aagtaacgcg ttcagtgatg  60
cccttgccta cgccacc  77

| | |
|---|---|
| SEQ ID NO: 274 | moltype = DNA  length = 78 |
| FEATURE | Location/Qualifiers |
| misc_feature | 1..78<br>note = R_KRAS.3U |
| misc_feature | 1..39<br>note = DNA |
| misc_feature | 43..78<br>note = DNA |
| misc_feature | 40..42<br>note = RNA |
| source | 1..78<br>mol_type = other DNA<br>organism = synthetic construct |

SEQUENCE: 274
agctccaact accacaaagt cgatagtcac ggctactcat ttcgtaacgc gttcagtgat  60
gcccttgcct acgccacc  78

| | |
|---|---|
| SEQ ID NO: 275 | moltype = DNA  length = 77 |
| FEATURE | Location/Qualifiers |
| misc_feature | 1..77<br>note = R_KRAS.3 |

```
misc_feature         1..39
                     note = DNA
misc_feature         43..77
                     note = DNA
misc_feature         40..42
                     note = RNA
source               1..77
                     mol_type = other DNA
                     organism = synthetic construct
SEQUENCE: 275
agctccaact accacaaagt cgatagtcac ggctactcag acgtaacgcg ttcagtgatg    60
cccttgccta cgccacc                                                   77

SEQ ID NO: 276       moltype = DNA  length = 77
FEATURE              Location/Qualifiers
misc_feature         1..77
                     note = R_KRAS.2
misc_feature         1..39
                     note = DNA
misc_feature         42..77
                     note = DNA
misc_feature         40..41
                     note = RNA
source               1..77
                     mol_type = other DNA
                     organism = synthetic construct
SEQUENCE: 276
agctccaact accacaaagt cgatagtcac ggctactcag acgtaacgcg ttcagtgatg    60
cccttgccta cgccacc                                                   77

SEQ ID NO: 277       moltype = DNA  length = 57
FEATURE              Location/Qualifiers
misc_feature         1..57
                     note = R_KRAS wt1_2
misc_feature         1..19
                     note = DNA
misc_feature         22..57
                     note = DNA
misc_feature         20..21
                     note = RNA
source               1..57
                     mol_type = other DNA
                     organism = synthetic construct
SEQUENCE: 277
agctccaact accacaacag acgtaacgcg ttcagtgatg cccttgccta cgccacc       57

SEQ ID NO: 278       moltype = DNA  length = 57
FEATURE              Location/Qualifiers
misc_feature         1..57
                     note = R_KRAS wt1_3
misc_feature         1..19
                     note = DNA
misc_feature         23..57
                     note = DNA
misc_feature         20..22
                     note = RNA
source               1..57
                     mol_type = other DNA
                     organism = synthetic construct
SEQUENCE: 278
agctccaact accacaacag acgtaacgcg ttcagtgatg cccttgccta cgccacc       57

SEQ ID NO: 279       moltype = DNA  length = 57
FEATURE              Location/Qualifiers
misc_feature         1..57
                     note = R_KRAS wt1_4
misc_feature         1..19
                     note = DNA
misc_feature         24..57
                     note = DNA
misc_feature         20..23
                     note = RNA
source               1..57
                     mol_type = other DNA
                     organism = synthetic construct
SEQUENCE: 279
agctccaact accacaacag acgtaacgcg ttcagtgatg cccttgccta cgccacc       57

SEQ ID NO: 280       moltype = DNA  length = 57
```

| FEATURE | Location/Qualifiers |
|---|---|
| misc_feature | 1..57 |
| | note = R_KRAS wt1_5 |
| misc_feature | 1..19 |
| | note = DNA |
| misc_feature | 25..57 |
| | note = DNA |
| misc_feature | 20..24 |
| | note = RNA |
| source | 1..57 |
| | mol_type = other DNA |
| | organism = synthetic construct |

SEQUENCE: 280
agctccaact accacaacag acgtaacgcg ttcagtgatg cccttgccta cgccacc     57

| SEQ ID NO: 281 | moltype = DNA length = 57 |
|---|---|
| FEATURE | Location/Qualifiers |
| misc_feature | 1..57 |
| | note = R_KRAS wt1_7 |
| misc_feature | 1..19 |
| | note = DNA |
| misc_feature | 27..57 |
| | note = DNA |
| misc_feature | 20..26 |
| | note = RNA |
| source | 1..57 |
| | mol_type = other DNA |
| | organism = synthetic construct |

SEQUENCE: 281
agctccaact accacaacag acgtaacgcg ttcagtgatg cccttgccta cgccacc     57

| SEQ ID NO: 282 | moltype = DNA length = 37 |
|---|---|
| FEATURE | Location/Qualifiers |
| misc_feature | 1..37 |
| | note = Synthetic construct |
| source | 1..37 |
| | mol_type = other DNA |
| | organism = synthetic construct |

SEQUENCE: 282
atcactgaac gcgttacgtc tgagtagccg tgactat                           37

| SEQ ID NO: 283 | moltype = DNA length = 37 |
|---|---|
| FEATURE | Location/Qualifiers |
| misc_feature | 1..37 |
| | note = Synthetic construct |
| source | 1..37 |
| | mol_type = other DNA |
| | organism = synthetic construct |

SEQUENCE: 283
atcactgaac gcgttacgta tgagtagccg tgactat                           37

| SEQ ID NO: 284 | moltype = DNA length = 37 |
|---|---|
| FEATURE | Location/Qualifiers |
| misc_feature | 1..37 |
| | note = Synthetic construct |
| source | 1..37 |
| | mol_type = other DNA |
| | organism = synthetic construct |

SEQUENCE: 284
atcactgaac gcgttacgaa tgagtagccg tgactat                           37

| SEQ ID NO: 285 | moltype = DNA length = 37 |
|---|---|
| FEATURE | Location/Qualifiers |
| misc_feature | 1..37 |
| | note = Synthetic construct |
| source | 1..37 |
| | mol_type = other DNA |
| | organism = synthetic construct |

SEQUENCE: 285
atcactgaac gcgttacgtt tgagtagccg tgactat                           37

| SEQ ID NO: 286 | moltype = DNA length = 37 |
|---|---|
| FEATURE | Location/Qualifiers |
| misc_feature | 1..37 |
| | note = Synthetic construct |
| source | 1..37 |
| | mol_type = other DNA |
| | organism = synthetic construct |

SEQUENCE: 286

```
atcactgaac gcgttacgtg tgagtagccg tgactat                              37

SEQ ID NO: 287          moltype = DNA   length = 37
FEATURE                 Location/Qualifiers
misc_feature            1..37
                        note = Synthetic construct
source                  1..37
                        mol_type = other DNA
                        organism = synthetic construct
SEQUENCE: 287
atcactgaac gcgttacggg tgagtagccg tgactat                              37

SEQ ID NO: 288          moltype = DNA   length = 37
FEATURE                 Location/Qualifiers
misc_feature            1..37
                        note = Synthetic construct
source                  1..37
                        mol_type = other DNA
                        organism = synthetic construct
SEQUENCE: 288
atcactgaac gcgttacgcc tgagtagccg tgactat                              37

SEQ ID NO: 289          moltype = DNA   length = 37
FEATURE                 Location/Qualifiers
misc_feature            1..37
                        note = Synthetic construct
misc_difference         20
                        note = n = A,T,C or G
source                  1..37
                        mol_type = other DNA
                        organism = synthetic construct
SEQUENCE: 289
atcactgaac gcgttacgtn tgagtagccg tgactat                              37

SEQ ID NO: 290          moltype = DNA   length = 37
FEATURE                 Location/Qualifiers
misc_feature            1..37
                        note = Synthetic construct
misc_difference         19..20
                        note = n = A,T,C or G
source                  1..37
                        mol_type = other DNA
                        organism = synthetic construct
SEQUENCE: 290
atcactgaac gcgttacgnn tgagtagccg tgactat                              37

SEQ ID NO: 291          moltype = DNA   length = 12
FEATURE                 Location/Qualifiers
misc_feature            1..12
                        note = Synthetic construct
source                  1..12
                        mol_type = other DNA
                        organism = synthetic construct
SEQUENCE: 291
actccatcat cc                                                         12

SEQ ID NO: 292          moltype = DNA   length = 13
FEATURE                 Location/Qualifiers
misc_feature            1..13
                        note = Synthetic construct
source                  1..13
                        mol_type = other DNA
                        organism = synthetic construct
SEQUENCE: 292
cgttgctgtg gcg                                                        13

SEQ ID NO: 293          moltype = RNA   length = 22
FEATURE                 Location/Qualifiers
misc_feature            1..22
                        note = Synthetic construct
source                  1..22
                        mol_type = other RNA
                        organism = synthetic construct
```

```
SEQUENCE: 293
tgaggtagta ggttgtatag tt                                                         22

SEQ ID NO: 294          moltype = DNA  length = 11
FEATURE                 Location/Qualifiers
misc_feature            1..11
                        note = Synthetic construct
source                  1..11
                        mol_type = other DNA
                        organism = synthetic construct
SEQUENCE: 294
caacatatca a                                                                     11
```

RNA TEMPLATED LIGATION

CROSS-REFERENCE TO RELATED APPLICATIONS

The present application is a continuation of U.S. patent application Ser. No. 18/154,592, filed on Jan. 13, 2023, which is a continuation of U.S. patent application Ser. No. 16/647,860, which adopts the international filing date of Oct. 5, 2018, now U.S. Pat. No. 11,597,965, issued on Mar. 7, 2023, which is a U.S. National Phase patent application and claims priority to and the benefit of International Application Number PCT/EP2018/077161, filed on Oct. 5, 2018, which claims priority to and the benefit of Great Britain Patent Application Number 1716407.0, filed on Oct. 6, 2017, Great Britain Patent Application Number 1718095.1, filed on Nov. 1, 2017, and Great Britain Patent Application Number 1718098.5, filed on Nov. 1, 2017, the entire contents of all of which are incorporated herein by reference.

REFERENCE TO AN ELECTRONIC SEQUENCE LISTING

The contents of the electronic sequence listing (202412008202SEQLIST.xml; Size: 546,814 bytes; and Date of Creation: Jun. 13, 2023) is herein incorporated by reference in its entirety.

The present invention relates to the field of nucleic acid detection. Specifically, the present invention provides methods for detecting target nucleic acid sequences in a target nucleic acid, and particularly target RNA sequences in a target RNA molecule using ligatable chimeric DNA-RNA probes. Nucleic acid probes for use in such methods are also provided.

The detection of target nucleic acid sequences has applications in many different fields, including personalised medicine, cancer diagnosis and treatment, infectious diseases and biosecurity.

Labelled hybridisation probes complementary to a target nucleic acid sequence may be used for detection of a target nucleic acid sequence, for example in Southern or Northern blot assays. Such probes allow the simple and straightforward detection of target nucleic acid sequences, including target RNA sequences, but hybridisation probes have relatively high lower detection limits, and cannot readily be used to discriminate between similar nucleic acid sequences. Furthermore, such probes cannot readily be adapted for use in multiplexed or automated detection assays.

The sensitivity of detecting target nucleic acid molecules may be enhanced by first amplifying a target sequence. Amplification techniques allow very low levels of a target sequence in a sample to be amplified prior to detection in order to increase the copy number of a target sequence in a sample. Amplification may be performed using any of a variety of techniques available in the art, such as Polymerase Chain Reaction (PCR), Nucleic Acid Specific Based Amplification (NASBA), Ligase Chain Reaction (LCR) and Rolling Circle Amplification (RCA). However, these techniques are principally aimed at amplifying DNA sequences, and typically require a DNA template in order to proceed efficiently.

PCR may be used to amplify a target nucleic acid molecule, and allows exponential amplification to take place using a pair of primers specific for sequences within the target nucleic acid molecule flanking the target nucleic acid sequence. However, target RNA sequences cannot be detected directly by PCR, and instead the detection of RNA requires the formation of a cDNA intermediate using a reverse transcriptase enzyme (RT-PCR), which can subsequently be amplified. NASBA and LCR similarly also require an initial reverse-transcriptase step in order to generate a cDNA template for amplification (CA 2136764).

RCA utilises a strand displacement polymerase enzyme, and requires a circular amplification template. Amplification of the circular template provides a concatenated RCA product, comprising multiple copies of a sequence complementary to that of the amplification template, which may ultimately be detected. The circular RCA template is typically provided by a ligation reaction, and may typically be provided either by circularising a target nucleic acid molecule using a target-specific probe as a template for circularisation, or by circularising a target-specific probe using a target nucleic acid molecule as a template for circularisation.

A circular RCA template may conveniently be provided using a symmetrical selector probe comprising a longer nucleic acid strand overhanging both ends of a shorter nucleic acid strand, which longer strand comprises sequences at its ends complementary to sequences in a target nucleic acid molecule as described in U.S. Pat. No. 7,883,849. Following hybridisation, the selector and the target nucleic acid fragment are joined by ligation to give a circular nucleic acid molecule. Alternative methods for selection and amplification of a nucleic acid involve the general circularisation of genomic fragments as described in Drmanac et al. 2010. Science 327, 78-81, and U.S. Pat. No. 8,518,640. Selector probe-based methods for selecting a target nucleic acid sequence are also provided in WO 03/044229. However, the circularisation and amplification of RNA templates in this way has not been demonstrated.

In alternative techniques, rather than circularising a target nucleic acid, the target nucleic acid may be used as a template for the ligation of a probe or probes. For example, so-called "padlock probes", may be used to detect a target nucleic acid sequence as described e.g. in U.S. Pat. No. 5,871,921. Padlock probes are linear nucleic acid molecules which comprise sequences complementary to a target nucleic acid molecule at their 3' and 5' ends, such that upon hybridisation of a padlock probe to its target nucleic acid molecule the ends of the probe are brought into juxtaposition for ligation. Adaptation of such methods resulted in the development of techniques in which the ends of the probes bind to sequences in the target nucleic acid molecule which are separated by one or more bases, and in which the gap between the respective ends of the probe is filled using a nucleic acid polymerase enzyme (Hardenbol et al. 2003. Nat Biotechnol 21, 673-678), or using a connector (or gap) oligonucleotide (Weibrecht et al. Nature protocols 8, 355-372). Padlock probe-based detection techniques have recently been shown to be effective in detecting pathogens in a sample.

However, padlock probe-based detection and amplification methods typically utilise DNA as a target as well as DNA probes, as this allows a high degree of sequence specificity to be obtained, and permits efficient amplification (and detection) of any formed ligation products. The RNA-templated ligation of DNA probes has been demonstrated, and has been demonstrated to be sufficiently sensitive to distinguish SNPs within an RNA template (Nilsson et al. 2001. Nucleic acids research 29, 578-581). Other studies have also demonstrated the detection of specific miRNAs using DNA padlock probes (Zhao et al. 2015. Acta Biochim Biophys Sin 47, 130-136; Jonstrup et al. 2006. RNA 12, 1747-1752). However, DNA ligation assays typically perform better using a DNA template rather than an RNA template (Nilsson et al. 2000. Nature Biotechnology 18, 791-793), and DNA ligation using an RNA template has been found to be inefficient, and has also been found to have highly variable reaction kinetics, even amongst closely-related sequences. Furthermore, the majority of ligase enzymes do not tolerate RNA templates, and the ones that do have been shown to possess poor end-joining fidelity, or in other words a poor ability to differentiate probes which have hybridised correctly to their target sequence. Thus, typically, the methods of the art generate a cDNA molecule from a target RNA molecule prior to detection.

The target-dependent ligation of ribonucleotide probes, or probes containing both ribonucleotides and deoxyribonucleotides has been demonstrated for an RNA target. (Zhao et al supra.). Specifically, the efficiency of ligation of various combinations of 7-mer ribonucleotide or deoxyribonucleotide probes using an RNA ligation template was tested, and it was shown that the ligation of such probes could be templated by an RNA template. However, amplification of the ligated product containing both ribonucleotides and deoxyribonucleotides was not demonstrated. Furthermore, the polymerase enzymes typically used in RCA methods have poor processivity for templates comprising long stretches of ribonucleotides.

There therefore remains a need for techniques which allow the efficient detection of a broader range of nucleic acid targets, i.e. including RNA targets, which combine both an efficient ligation step, and allow for amplification of the resulting ligation product, in order to allow the target to be detected. Whilst probes and methods have been developed primarily with the intention of detecting RNA targets, it has been found that certain new probes and methods of the present invention also demonstrate advantages in the detection of DNA targets, and thus that they may be more broadly applicable.

The method of the present invention uses a probe provided in one or more parts which is complementary to and hybridises to a target nucleic acid molecule, and which is ligated in a target-dependent manner, wherein the probes are composed primarily of DNA, but comprises ribonucleotides in particular positions relative to the ligation sites which serve to improve the efficiency and fidelity of ligation templated by a target nucleic acid molecule. Once a ligation product has been formed, it is amplified, and the resulting amplification product is detected, thereby to detect the target RNA molecule.

Surprisingly, in the course of making the present invention, it was observed that providing a ribonucleotide rather than a deoxyribonucleotide at or near to a ligatable end of the probe enhanced the efficiency of ligation of a probe, and in particular resulted in an increase in the efficiency of ligation when an RNA ligation template was used. This may also be beneficial in the context of detecting a DNA target (i.e. where a DNA target templates the ligation of the probe) when RNA and DNA targets are being detected together, simultaneously. Ribonucleotide sugar-phosphate backbones in oligonucleotides are known to prefer particular conformations due to the presence of the 2'-OH, which inhibits the C2'-endo conformation in the ribose sugar. Ligase enzymes may also have a greater specificity for probes comprising ribonucleotides when bound to a target RNA molecule than deoxyribonucleotides. Without wishing to be bound by theory, it is believed that the presence of a ribonucleotide at or near to a ligatable end of the probe allows the end(s) of the probe involved in a templated ligation to be recognised and ligated with greater efficiency and fidelity by a ligase enzyme than a corresponding probe which does not comprise ribonucleotides.

It was also observed that the efficiency with which a ligation product could be amplified was not significantly inhibited when the number of consecutive ribonucleotides in a ligated probe composed primarily of DNA was kept to a minimum. Thus, it was found that it was possible to enhance the efficiency of ligation using a probe which comprised one or more ribonucleotides, whilst allowing efficient amplification of the resulting ligation product to be performed.

At its broadest, the present invention provides a method of detecting a target nucleic acid sequence in a target nucleic acid molecule in a sample, said method comprising:

(a) contacting said sample with a ligatable probe and allowing said probe to hybridise to the target nucleic acid molecule;

(b) subjecting said sample to a ligation reaction using a DNA/RNA ligase to ligate any probe which has hybridised to the target nucleic molecule;

(c) amplifying the ligated probe from step (b) with a DNA polymerase; and (d) detecting the amplification product from step (c), thereby to detect the target nucleic acid sequence;

wherein each probe is provided in one or more parts each having at least one target-specific binding site which is complementary to a cognate probe-binding site at or adjacent to the target nucleic acid sequence and hybridises to the target nucleic acid molecule such that, optionally after a step of cleaving the hybridised probe and/or extending the 3' end thereof using the target nucleic acid molecule as a template, ligatable ends of the probe or probe parts are juxtaposed for ligation to each other using the target nucleic acid molecule as a ligation template, to create a ligation site at or adjacent to the target nucleic acid sequence; and wherein said probe comprises at least one ribonucleotide at or near to the ligation site, optionally after said step of cleaving and/or extension, and the ligated probe is comprised primarily of DNA and comprises no more than 4 consecutive ribonucleotides.

The detection method of the invention may therefore be used in the detection of a target DNA sequence in a target DNA molecule, and/or a target RNA sequence in a target RNA molecule. It is particularly preferred that the target nucleic acid sequence is an RNA sequence and that the target nucleic acid molecule is an RNA molecule.

In one embodiment the method comprises detecting both RNA and DNA target sequences, using at least one probe directed towards a RNA target sequence and at least one probe directed towards a DNA target sequence. Thus, the target RNA and DNA molecules may be in the same sample. In such a situation, where a RNA ligase is used, it is beneficial for the DNA-targeting probe, when hybridised with ligatable ends juxtaposed for ligation, also to contain at least one ribonucleotide at or near to the ligation site.

The invention accordingly provides a method which allows the efficient ligation of a probe comprising both DNA and RNA nucleotides, and the subsequent amplification of the ligation product directly from a ligation reaction templated by a target nucleic acid molecule, i.e. without the need first to provide a cDNA molecule complementary to the target molecule. This therefore provides a simplified detection method relative to methods previously known in the art. Furthermore, in the context of detecting RNA, as the requirement to prepare a separate cDNA molecule is dispensed with, detection of a target RNA sequence in a target RNA molecule may be performed more easily alongside the detection of other nucleic acid sequences, such as target DNA sequences. This may, for example, allow target RNA and DNA sequences to be detected simultaneously in the same sample.

Also provided is a probe for use in such a method. More particularly circularisable probes are of particular interest, and in this aspect the invention accordingly provides a chimeric DNA-RNA padlock probe capable of binding to and detecting a target nucleic acid sequence in a target nucleic acid molecule, wherein:

(i) the probe comprises one or more parts each having at least one target specific binding site which is complementary to a cognate probe-binding site at or adjacent to the target nucleic acid sequence and hybridises to the target nucleic acid molecule such that, optionally after a step of cleaving the hybridised probe and/or extending a 3' end thereof using the target nucleic acid molecule as a template, ligatable ends of the probe or probe parts are juxtaposed for ligation to each other using the target nucleic acid molecule as a ligation template, to create one or more ligation sites at or adjacent to the target nucleic acid sequence, wherein ligation at said ligation sites circularises the probe;

(ii) the probe comprises at least one ribonucleotide at or near to a ligation site; and (iii) the probe when ligated to form a circle is composed primarily of DNA and comprises no more than 4 consecutive ribonucleotides.

Thus, in a particular embodiment, the present invention provides a method of detecting a target nucleic acid sequence in a target nucleic acid molecule in a sample, said method comprising:

a) contacting said sample with a padlock probe and allowing said probe to hybridise to the target nucleic acid molecule;

b) subjecting said sample to a ligation reaction using a DNA/RNA ligase to ligate, and thereby circularise, any probe which has hybridised to the target nucleic acid molecule;

c) amplifying the ligated circularised probe from step (b) by rolling circle amplification with a DNA polymerase; and d) detecting the amplification product from step (c), thereby to detect the target nucleic acid sequence;

wherein each padlock probe is provided in one or more parts, each part having at least one target-specific binding site which is complementary to a cognate probe-binding site at or adjacent to the target nucleic acid sequence and hybridises to the target nucleic acid molecule such that, optionally after a step of cleaving the hybridised probe and/or extending a 3' end thereof using the target nucleic acid molecule as a template, ligatable ends of the probe or probe parts are juxtaposed for ligation to each other using the target nucleic acid molecule as a ligation template, to create a ligation site at or adjacent to the target nucleic acid sequence; and wherein said probe comprises at least one ribonucleotide at or near to a ligation site, optionally after said step of cleaving and/or extension, and the ligated circularised probe is composed primarily of DNA and comprises no more than 4 consecutive ribonucleotides.

The probe of the invention may be for the detection of a target DNA sequence in a target DNA molecule and/or a target RNA sequence in a target RNA molecule, as discussed above. Thus, in one preferred embodiment the probe is capable of binding to and detecting a target RNA sequence in a target RNA molecule.

Since the probe may be provided in one or more parts it follows that there may be more than one ligation junction. In other words, one or more probe parts may each comprise, or generate (i.e. by cleavage or extension), ligatable 5' and 3' ends, and the probe as a whole may comprise, or generate, one or more ligatable 5' ends and one or more ligatable 3' ends.

In certain embodiments the probe may comprise two or more parts and two or more ligation junctions may be created. A ligation junction may accordingly be provided between two different probe parts (or more particularly between ligatable ends of, or generated from the ends of, two different probe parts), or between two ends of, or generated from the ends of, a one-part probe.

Following ligation a probe is provided which comprises at least one ribonucleotide at or near to a ligation site. A ligation site is the site of the ligation of a terminal 5' phosphate group at the 5' ligatable end of a probe to the terminal 3' hydroxyl group at the 3' ligatable end of a probe, and ligation may occur when the respective ligatable ends are directly in juxtaposition and hybridised correctly to their respective complementary base pairs in the target nucleic acid molecule. A ligation site, once formed, therefore, is the junction between the nucleotides at the 3' and 5' ligatable ends of the probe or probe parts, and its position is defined by the phosphodiester bond formed between these nucleotides. Thus, according to the methods and probes of the present invention, at least one of the nucleotides participating in the ligation reaction (i.e. the nucleotide providing the terminal 5' phosphate group or 3' hydroxyl group), or a nucleotide near to the ligation site, is a ribonucleotide. Preferably at least one of the nucleotides at or near a ligatable 3' end at a ligation site is a ribonucleotide. In other words, in a preferred embodiment, when hybridised to a target nucleic acid molecule such that the 3' and 5' ends are juxtaposed for ligation, the probe comprises at least one ribonucleotide at or near a ligatable 3' end.

It will therefore be seen that once ligated, the probe comprises at least one ribonucleotide at or near to a ligation site (or, more particularly, at or near one or more ligation sites), the presence of which during the ligation reaction enhances both the specificity and efficiency of ligation. According to the invention where there are two or more ligation junctions, there may be at least one ribonucleotide at or near one or more of these. It is not a requirement, but it is preferred, that there is at least one ribonucleotide at or near each ligation junction. The method of the invention may thus be considered to provide means for enhancing ligation of a primarily DNA probe using a template target nucleic acid molecule, e.g. a target RNA molecule. Expressed another way, the methods of the invention may be used to improve the detection of target nucleic acid molecules in a sample. Significantly, by providing a ligation product which comprises no more than four consecutive ribonucleotides, the method also allows amplification of the ligated product to proceed without significant impedance.

Any one of the nucleotides at or near to the ligation site may be a ribonucleotide as opposed to a deoxyribonucleotide. The term 'near' in this context refers to positions within 5 nucleotides of the ligation site, i.e. the 5 nucleotides 3' to the ligation site and the 5 nucleotides 5' to the ligation site. Accordingly, any one of the ribonucleotides within 5 nucleotides of the ligation site may be a ribonucleotide. A ribonucleotide may preferably be provided at a position within 4 nucleotides of the ligation site, or more preferably within 3 nucleotides of a ligation site. In yet further embodiments, a ribonucleotide may be within 2 nucleotides of a ligation site. Thus, the terminal nucleotide and/or the penultimate nucleotide at a 3' or 5' ligatable end may be a ribonucleotide. In certain embodiments, the penultimate nucleotide at a 3' or 5' ligatable end (preferably a 3' ligatable end) may be a ribonucleotide.

In a preferred embodiment, the ribonucleotide may be at a 3' or 5' ligatable end at a ligation site. The term 'at' in this context refers specifically to the terminal nucleotide at an end of an oligonucleotide, i.e. the nucleotide which provides the hydroxyl or phosphate group for ligation. Thus, in one embodiment, reference to the probe comprising a ribonucleotide at the ligation site refers to either the terminal 3' nucleotide of a 3' ligatable end, or the terminal 5' nucleotide of a 5' ligatable end, being a ribonucleotide. Preferably, the 3' ligatable end at a ligation site is a ribonucleotide.

More than one nucleotide at or near the ligation site may be a ribonucleotide. Accordingly, in certain embodiments, more than one ribonucleotide at or near the ligation site (i.e. any of the 10 nucleotides within 5 nucleotides of the ligation site) may be ribonucleotides in combination, provided that the ligated probe comprises no more than 4 consecutive ribonucleotides as discussed elsewhere.

In a preferred embodiment, the probe comprises the at least one ribonucleotide at a ligatable end of the probe or a part thereof. Preferably, the probe comprises the at least one ribonucleotide at the 3' ligatable end at a ligation site. In other words, the nucleotide at a ligatable 3' end of a probe or part thereof is preferably a ribonucleotide as opposed to a deoxyribonucleotide.

In certain embodiments, the probe or probe part does not comprise a ribonucleotide at or near the 5' ligatable end at a ligation site, and in particular does not comprise a ribonucleotide at the 5' ligatable end at a ligation site. In certain embodiments, where the 5' ligatable end is provided by the 5' end of the probe or probe part (i.e. where the 5' ligatable end is not generated by cleavage of the hybridised probe), the 5' terminal nucleotide of a probe or probe part is preferably not a ribonucleotide. In other words, in a preferred embodiment of the present invention, the nucleotide at a ligatable 5' end of the probe or part thereof is a deoxyribonucleotide. In such embodiments, the ligation of a 3' hydroxyl group from the nucleotide at a ligatable 3' end of the probe or part thereof (be it a ribonucleotide or a deoxyribonucleotide) is to a 5' deoxyribonucleotide.

As described briefly above, the ligatable ends described above which eventually form the ligation site are required to be in direct juxtaposition and hybridised to their respective complementary base pairs in the target nucleic acid molecule in order for ligation to take place. However, the ligatable ends may be brought into juxtaposition for ligation in various ways, depending on the design of the probe and/or its parts.

In a particular embodiment, the 3' end of the probe or part thereof is a ligatable 3' end at the ligation site. Thus, in such an embodiment, the ligatable 3' end is provided at (or, alternatively expressed, by) the 3' end of the probe, or in other words the probe hybridises to the target nucleic acid molecule such that the 3' end of the probe may be ligated to the ligatable 5' end at the ligation site.

Thus, in a preferred embodiment, the probe comprises the at least one ribonucleotide at or near to (but preferably at) the 3' end of the probe or a part thereof. Thus, not only may the probe comprise the at least one ribonucleotide at or near to the ligatable 3' end at the ligation site as described above, the 3' end of the probe or a part thereof itself may be the ligatable 3' end as described herein. In such an embodiment, therefore, the probe or probe part as provided in step (a) of the method of the invention may comprise at or near to its 3' end at least one ribonucleotide, which end hybridises to a target nucleic acid sequence and is a ligatable 3' end for the ligation reaction of step (b). In other words, in such embodiments, the nucleotide at the 3' end of the probe or part thereof participates in a ligation reaction, and is ligated to a ligatable 5' end at a ligation site during the course of the detection method.

In a further embodiment of the invention, the 5' end of the probe is a ligatable 5' end at the ligation site. Thus, the ligatable 5' end may be provided at the 5' end of the probe or a part thereof, or put another way, the probe may hybridise to the target nucleic acid molecule such that the 5' end of the probe or part thereof may be ligated to the ligatable 3' end at the ligation site.

Thus, in one particular embodiment, both of the ligatable ends may be provided at the ends of the probe or probe part, or in other words the probe may hybridise to the target nucleic acid molecule such that ligatable ends of the probe or probe parts are directly juxtaposed for ligation to each other using the target nucleic acid molecule as a ligation template without any further modification or processing (e.g. cleavage or extension) of the probe. Put another way, the probe or each part thereof may comprise the at least one target-specific binding site at its end(s), such that each end of the probe (or its parts) may hybridise to directly adjacent cognate probe binding sites in the target nucleic acid molecule, such that the ligatable ends are provided for ligation. Put another way, in certain embodiments, step (b) may consist of a ligation step without any further steps being required to provide 5' and 3' ends of the probe or probe parts in juxtaposition for ligation.

However, it is not required that a probe comprises target-specific binding sites at its respective ends which hybridise to cognate sequences in the target nucleic acid molecule directly adjacent to one-another in order to bring ligatable ends as described above into juxtaposition for ligation, and optionally one or both of the ligatable ends of the probe may only be generated in one or more processing steps prior to ligation taking place.

In a preferred embodiment of the present invention, a 5' ligatable end of the probe or part thereof may be created by cleavage when the probe is hybridised to a target nucleic acid molecule (i.e. by cleavage of the hybridised probe).

The probe may, therefore, comprise an additional sequence 5' (or externally) to the probe or probe part which provides a 5' ligatable end, such that the 5' ligatable end of the probe or probe part may only be created once said additional sequence has been removed by cleavage (cleaved off). Put another way, the probe or probe part may comprise a 5' additional sequence. The probe or probe part may therefore comprise a first target-specific target binding site situated internally of the 5' end of the probe or probe part, such that the portion of the probe or probe part which hybridises to the target nucleic acid molecule and in due course provides the ligatable 5' end at the ligation site (i.e. the target-specific binding site) comprises an additional sequence at its 5' end which is not hybridised to the target nucleic acid molecule. In this way, once any additional sequence situated 5' to the 5' ligatable end of the probe or probe part has been removed by cleavage, ligation of the probe may proceed.

This additional sequence 5' to the first target-specific binding site which is not hybridised to the target nucleic acid molecule thus forms a 5' flap, which may be removed by cleavage, thereby to create the 5' ligatable end of the probe or probe part.

It will be understood that in a multi-part probe (i.e. a probe comprising two or more parts) more than one 5' flap may be formed. For example in the case of a two part probe (e.g. a padlock probe comprising a backbone oligonucleotide and a gap oligonucleotide which hybridises to the target in between the two hybridised ends of the backbone oligonucleotide, as described further below), the 5' end of the backbone oligonucleotide may form a 5' flap. In a further embodiment the 5' end of the gap oligonucleotide may form a 5' flap and in a still further embodiment the 5' ends of the backbone and gap oligonucleotides may both form 5' flaps. Still further, a multi-part padlock probe may comprise more than one gap oligonucleotide. Thus, two or more gap oligonucleotides may each form 5' flaps.

Thus, after step (a), the method may comprise a step of cleaving any probes which have hybridised to the target nucleic acid molecule. This step removes a (or any) 5' flap which has formed on hybridisation of the probe or probe parts to the target nucleic acid molecule.

The step of cleaving the hybridised probe to remove a 5' flap may be performed using an enzyme. Any enzyme capable of performing a reaction which removes a 5' flap may be used in this step, i.e. any enzyme capable of cleaving, degrading or digesting a 5' single-stranded sequence which is not hybridised to a target nucleic acid molecule, but typically this will be an enzyme with 5' nuclease and/or structure-specific cleavage activity.

A 5' flap formed in this way may be recognised by a structure-specific cleavage enzyme, e.g. an enzyme capable of recognising the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridised to the target nucleic acid molecule, as well as by the 5' and 3' ends of a one-part probe. Enzymes suitable for such cleavage include Flap endonucleases (FENS), which are a class of enzymes having endonucleolytic activity and being capable of catalysing the hydrolytic cleavage of the phosphodiester bond at the junction of single- and double-stranded DNA. Thus, in a preferred embodiment, cleavage of the additional sequence 5' to the first target-specific binding site is performed by a structure-specific cleavage enzyme, e.g. a Flap endonuclease. In preferred embodiments, the enzyme may be a native or recombinant archaeal FEN1 enzyme from *P. furiosus* (Pfu), *A. fulgidus* (Afu), *M. jannaschii* (Mja) or *M. thermoautotrophicum* (Mth) e.g. as described in Ma et al. 2000. JBC 275, 24693-24700.

In other embodiments an enzyme capable of recognising and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognising a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognised the free 5' end, and cleaving the single-stranded region into larger constituent nucleotides (e.g. dinucleotides or trinucleotides), or cleaving the entire 5' single-stranded region, e.g. as described in Lyamichev et al. 1999. PNAS 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

In certain embodiments where a probe or probe part comprises an additional sequence at its 5' end as described above, one or more of the nucleotides within the additional sequence may be complementary to cognate nucleotides in the target nucleic acid molecule, but may not hybridise to the target nucleic acid molecule simultaneously with a 3' ligatable end of the probe or of a probe part (which may be a different probe part, as noted above). In particular one or more nucleotides at the 3' end of said additional sequence (i.e. at the 3' end of the 5' flap) may be complementary to cognate nucleotides in the target nucleic acid molecule in this way. As they are not capable of hybridising to the target nucleic acid molecule, and are prevented from doing so by the 3' ligatable end of the probe or a probe part, the additional sequence may be considered to form a displaced flap, and nucleotides within said additional sequence complementary to cognate nucleotides in the target nucleic acid molecule may be considered to be displaced nucleotides or displaced bases.

Thus, in a preferred embodiment, one or more nucleotides at the 3' end of the additional sequence (i.e. at the end of the additional sequence nearest the first target binding site) are complementary to cognate nucleotides in the target nucleic acid molecule, wherein said nucleotides are not capable of hybridising to the target nucleic acid molecule simultaneously with the 3' ligatable end of the probe or with a 3' ligatable end of another probe part. In other words, one or more of the nucleotides at the 3' end of the additional sequence may be prevented from binding to the target nucleic acid molecule by a 3' ligatable end, or may be thought of as being displaced from the target nucleic acid molecule. Thus, these nucleotides may be referred to as a displaced nucleotide.

Removal of any such additional sequence by cleavage is required before ligation of the probes may take place. Probes having such an additional sequence at their (or a) 5' end (i.e. probes in which the first target-specific binding site is situated internally of the 5' end of the probe or probe part) may thus be regarded as needing to be activated (i.e. by cleavage) prior to ligation.

Surprisingly, the presence of a ribonucleotide in the 5' additional sequence of a probe, in particular at the 3' end of said 5' additional sequence (i.e. the 3' most nucleotide of the additional sequence, has been found to enhance the efficiency of removal (i.e. of cleavage) of the additional sequence, for both DNA and RNA target nucleic acid molecules. This effect is particularly noted in so-called invasive cleavage reactions, described in greater detail below. The additional sequence described above may, therefore, in certain embodiments, comprise one or more ribonucleotides. In certain embodiments of the present invention, one or more of the nucleotides at the 3' end of the 5' additional sequence may be a ribonucleotide. More particularly, one or more nucleotides at the 3' end of the 5' additional sequence which are complementary to cognate nucleotides in the target nucleic acid molecule as described above (i.e. displaced nucleotide as described above) may be a ribonucleotide. In one particular embodiment, the additional sequence may consist entirely of ribonucleotides.

The enhanced cleavage of a 5' additional sequence of a probe is separate to the enhanced ligation efficiency resulting from having a ribonucleotide situated at or near to a ligation site in a chimeric DNA-RNA probe. Thus, the above-described effect may also be seen in a probe which, after cleavage, does not comprise a ribonucleotide at or near to a ligation site.

In another aspect, the present invention therefore provides a method of detecting a target nucleic acid sequence in a target nucleic acid molecule in a sample, said method comprising:
(a) contacting said sample with a ligatable probe and allowing said probe to hybridise to the target nucleic acid molecule;
(b) subjecting said sample to a ligation reaction using a DNA/RNA ligase to ligate any probe which has hybridised to the target nucleic molecule;
(c) amplifying the ligated probe from step (b) with a DNA polymerase; and
(d) detecting the amplification product from step (c), thereby to detect the target nucleic acid sequence;
wherein each probe is provided in one or more parts each having at least one target-specific binding site which is complementary to a cognate probe-binding site at or adjacent to the target nucleic acid sequence and hybridises to the target nucleic acid molecule, wherein one target-specific binding site of the probe or at least one target-specific binding site of a probe part is situated internally of the 5' end of the probe or probe part such that upon hybridisation of the probe or probe part to the target nucleic acid molecule the probe or probe part comprises an additional sequence 5' to the target-specific binding site which is not hybridised to the target nucleic acid molecule and forms a 5' flap, wherein one or more of the nucleotides at or near the 3' end of the 5' additional sequence is a ribonucleotide, and wherein after a step of cleaving the hybridised probe to remove the 5' flap, and optionally after a step of extending the 3' end thereof using the target nucleic acid molecule as a template, ligatable ends of the probe or probe parts are juxtaposed for ligation to each other using the target nucleic acid molecule as a ligation template, to create a ligation site at or adjacent to the target nucleic acid sequence.

In particular, the nucleotide at the 3' end of the 5' additional sequence may be a ribonucleotide. Optionally, one or more nucleotides near the 3' end of the 5' additional sequence may also be ribonucleotides.

The target nucleic acid sequence may be a target DNA sequence or a target RNA sequence, and the target molecule may be a target DNA molecule or a target RNA molecule. As discussed above, this method of this aspect of the invention may also be used to detect more than one target sequence, including in more than one target molecule, and may comprise detecting both RNA and DNA target sequences in RNA and DNA target molecules (e.g. in the same sample).

In another aspect, the present invention therefore provides a probe for use in such a method. This aspect of the invention provides a chimeric DNA-RNA probe capable of binding to and detecting a target nucleic acid sequence in a target nucleic acid molecule, wherein:

(i) the probe comprises one or more parts each having at least one target specific binding site which is complementary to a cognate probe-binding site at or adjacent to the target nucleic acid sequence and hybridises to the target nucleic acid molecule, wherein a first target specific binding site of the probe or a target-specific binding site of a probe part is internal to the 5' end of the probe or a probe part, and the probe or probe part comprises an additional sequence 5' to said target specific binding site, such that when the probe or probe part is hybridised to the target nucleic acid molecule the additional sequence forms a 5' flap which is not hybridised to the target nucleic acid molecule, and which may be removed by cleavage to generate a ligatable 5' end which may be ligated to the 3' end of the probe or a probe part, wherein the additional sequence contains one or more ribonucleotides (preferably at its 3' end), such that after a step of cleaving the hybridised probe or probe part and optionally after a step of extending a 3' end thereof using the target nucleic acid molecule as a template, ligatable ends of the probe or probe parts are juxtaposed for ligation to each other using the target nucleic acid molecule as a ligation template, to create one or more ligation sites at or adjacent to the target nucleic acid sequence.

In a preferred embodiment, the nucleotide at the 3' end of any additional sequence which forms a 5' flap is complementary to the same cognate nucleotide in the target nucleic acid molecule as the nucleotide at the 3' end of the probe. Thus, one or more nucleotides at the 3' end of any additional sequence (i.e. at the end of the additional sequence nearest the first target binding site) may be complementary to cognate nucleotides in the target nucleic acid molecule, wherein said nucleotides are not capable of hybridising to the target nucleic acid molecule simultaneously with the 3' ligatable end of the probe or with a 3' ligatable end of another probe part.

Such a probe may optionally be a one-part or a two (or more) part padlock probe, or a probe comprising two or more parts as defined elsewhere herein, except that it does not comprise a ribonucleotide at or near to a ligation site.

Probes having 5' additional sequences which are required to be removed by cleavage prior to ligation are well-known in the art, for example in the form of Invader probes for use in an Invader assay. An Invader assay of the art typically comprises the use of a first and second probe having target-specific binding sites, wherein the first probe comprises a first target-binding site situated internally of the 5' end of the probe. In such an assay, the first and second probes are typically designed to be complementary and capable of hybridising to cognate binding sites in a target nucleic acid molecule, such that the first probe hybridises to a 5' portion of the target nucleic acid molecule, and the second probe hybridises to a 3' portion of the target nucleic acid molecule directly in juxtaposition to the first probe, and prevents the nucleotide at the 3' end of the additional sequence of the first probe from hybridising to the target nucleic acid molecule. Put another way, in an Invader assay the nucleotide at the 3' end of the 5' additional sequence is a displaced nucleotide as described above. As the 3' end of the additional sequence of the first probe is prevented from hybridising to the target nucleic acid molecule by a second probe, and the 5' additional sequence is subsequently cleaved, such methods are also known as invasive cleavage reactions.

Thus the probes of the invention may be invader probes. Such probes are of particular utility in the detection of single nucleotide polymorphisms. The detection method of the present invention may, therefore, be used in the detection of a single nucleotide polymorphism, or indeed any variant base, in the target nucleic acid sequence. Probes for use in such a method may be designed such that the 3' ligatable end of the probe is complementary to and capable of hybridising to the nucleotide in the target molecule which is of interest (the variant nucleotide), and the nucleotide at the 3' end of the 5' additional sequence at the 5' end of the probe or at the 5' end of another, different, probe part is complementary to the same said nucleotide, but is prevented from hybridising thereto by a 3' ligatable end (i.e. it is a displaced nucleotide as described above). Cleavage of the probe to remove the additional sequence provides a 5' ligatable end, which may be ligated to the 3' ligatable end of the probe or probe part if the 3' ligatable end is hybridised correctly to (i.e. is complementary to) the target nucleic acid molecule. Probes designed according to this principle provide a high degree of discrimination between different variants at the position of interest, as only probes in which the 3' ligatable end is complementary to the nucleotide at the position of interest may participate in a ligation reaction. In one embodiment, the probe is provided in a single part, and the 3' and 5' ligatable ends are provided by the same probe.

Recently, an alternative design for Invader probes has been demonstrated to provide comparable results to the design outlined above (Krzywkowski et al. 2017. Nucleic Acids Research 45, e161). Although this design is disclosed specifically in the context of an Invader assay which utilises a padlock probe, (an "invader padlock" (iLock) probe as described in greater detail below), certain features of such probes may be applied to Invader probes in general.

In this alternative design, the probe (which in the context of an iLock probe is provided as a probe having one part) is designed such that the 3' nucleotide of the 3' target-specific binding site in the padlock probe (a second target-specific binding site as described herein) is complementary and capable of hybridising to the nucleotide in the target nucleic acid molecule 3' of the nucleotide of interest (i.e. to the nucleotide which is immediately 3' to the variant nucleotide), and the 5' nucleotide of the 5' target-specific binding site in the padlock probe (a first target-specific binding site as described herein) is complementary and capable of hybridising to the nucleotide which is of interest in the target nucleic acid molecule (i.e. to the variant nucleotide). Such probes comprise an additional sequence 5' to the first target-specific binding site, such that the first target-specific binding site is situated internally of the 5' end of the probe. The 3' end-most nucleotide of the additional sequence is complementary to the nucleotide in the target nucleic acid molecule 3' of the nucleotide of interest (i.e. immediately 3' to the nucleotide of interest/variant nucleotide), but is prevented from hybridising to the target nucleic acid molecule by the 3' ligatable end of the probe (i.e. the second target-specific binding site), and thus is a displaced nucleotide. As above, an analogous probe design may be provided in which the 5' and 3' target-specific binding sites are provided by different probe parts.

Thus, more generally, probes may be designed such that the 3' ligatable end of the probe or of a probe part is complementary to and capable of hybridising to the nucleotide in the target molecule 3' of the nucleotide of interest (the variant nucleotide), and the nucleotide at the 3' end of the 5' additional sequence of the probe, or at the 5' end of another, different probe part, is complementary to the nucleotide 3' of the nucleotide of interest (the nucleotide which is immediately 3' to the variant nucleotide), but is prevented from hybridising thereto by a 3' ligatable end of the probe or probe part. Cleavage to remove the additional sequence provides a 5' ligatable end, which may be ligated to the 3' ligatable end of the probe or probe part if the 5' ligatable end is hybridised correctly to (i.e. is complementary to) the target nucleic acid molecule. Probes designed according to this principle provide a high degree of discrimination between different variants at the position of interest, as only probes in which the 5' ligatable end is complementary to the nucleotide at the position of interest may participate in a ligation reaction. As described above, in one embodiment, the probe is provided in a single part, and the 3' and 5' ligatable ends are provided by the same probe.

Accordingly, in certain embodiments, the methods of the present invention may be for the detection of a variant base in a target nucleic acid molecule. In particular, probes according to either of the above-mentioned "Invader" designs may be of particular utility in the detection of a variant base in a target nucleic acid molecule.

In such invader probes which create a 5' flap, it is in some embodiments preferred, as noted above, for one or more nucleotides at or near the 3' end of the additional sequence (which creates the 5' flap) to be ribonucleotides. More particularly the, or at least the, 3'-most nucleotide of the additional sequence (or in other words the 3' terminal nucleotide of the cleaved-off 5' flap) is a ribonucleotide.

The invader-type probes may be provided as padlock probes which may be composed of one or more parts, as described further below. Thus the padlock probe may be a one-part padlock which hybridises to the target nucleic acid molecule to form an "invader" structure, or it may comprise two or more parts which hybridise to form one or more "invader" structures with a 5' flap for cleavage.

In one specific representative embodiment, the probe for use in such a method is a padlock probe provided as a single circularisable oligonucleotide comprising a first target-specific binding site situated internally of the 5' end of the probe and a second target-specific binding site situated at the 3' end of the probe, such that upon hybridisation of the probe to the target nucleic acid molecule the probe comprises an additional sequence 5' to the first target binding site which is not hybridised to the target nucleic acid molecule, wherein the nucleotide at the 3' end of the probe is a ribonucleotide and wherein the nucleotide at the 3' end of the probe and the 3' end of the additional sequence are complementary to the same nucleotide, wherein when the nucleotide at the 3' end of the probe and the nucleotide at the 3' end of the additional sequence are complementary to the variant base the nucleotide at the 3' end of the additional sequence is not capable of hybridising to the target nucleic acid molecule simultaneously with the 3' end of the probe and said additional sequence is removed by cleavage thereby to generate the 5' ligatable end of the probe, and wherein when the nucleotide at the 3' end of the additional sequence and the nucleotide at the 3' end of the probe are not complementary to the variant base, the nucleotide at the 3' end of the additional sequence is removed by cleavage and the nucleotide at the 3' end of the probe is not hybridised to the target nucleic acid molecule, thereby preventing ligation.

In another specific representative embodiment the probe is a single circularisable oligonucleotide comprising a first target-specific binding site situated internally of the 5' end of the probe and a second target-specific binding site situated at the 3' end of the probe, such that upon hybridisation of the probe to the target nucleic acid molecule the probe comprises an additional sequence 5' to the first target binding site which is not hybridised to the target nucleic acid molecule, wherein the nucleotide at the 3' end of the probe is a ribonucleotide, and wherein the nucleotide at the 3' end of the probe and the 3' end of the additional sequence are complementary to the same nucleotide, wherein the nucleotide at the 3' end of the probe and the nucleotide at the 3' end of the additional sequence are complementary to the nucleotide at the position 3' to the variant base and wherein the nucleotide at the 3' end of the additional sequence is not capable of hybridising to the target nucleic acid molecule simultaneously with the 3' end of the probe, wherein when the nucleotide at the 5' end of the first target-specific binding site is complementary to the variant base, said additional sequence is removed by cleavage thereby to generate the 5' ligatable end of the probe, and wherein when the nucleotide at the 5' end of the first target-specific binding site is not complementary to the variant base, said nucleotide is also removed by cleavage, thereby generating a gap between the 5' and 3' ligatable ends and preventing ligation.

In other embodiments such invader padlock probes may analogously be provided in two or more parts, e.g. comprising a backbone oligonucleotide and one or more gap oligonucleotides, as described further below.

In certain embodiments, the probe may be designed to bind to two or more non-contiguous sequences within the target nucleic acid molecule. Put another way, the probe, or two probe parts, may hybridise to the target nucleic acid molecule with a gap between the respective target-binding sites of the probe or probe parts. When the ends of the probe or probe parts have hybridised to leave a gap, this may be filled by extending the hybridised 3' end of the probe before ligation to the 5' end, using the target nucleic acid molecule as a template for extension. Once the 3' end of the probe has been extended to be adjacent to the 5' ligatable end, the two ends may be joined by a ligation reaction. In this way, a ligatable 3' end of the probe may be generated by extension.

Such an extension gap-fill embodiment may be of particular utility in the detection of a highly variable target nucleic acid sequence, as a complement of the target nucleic acid sequence is incorporated into a ligated probe. Thus, following amplification, detection of the amplified ligated probe (e.g. by sequencing) allows the sequence of the target nucleic acid sequence to be determined. In further embodiments, such a gap-fill by extension may be combined with the feature of generating a ligatable 5' end by cleavage of a 5' flap. Thus, gap-fill extension may also be used to generate, or provide, a 3' ligatable end in the context of an invader-type probe.

The 'extension gap-fill' embodiment described above requires the incorporation of nucleotides into an extension product, and thus in such embodiments a mixture of nucleoside triphosphates are required in the reaction mixture in order for extension to take place. In certain embodiments, one or more of the nucleoside triphosphates (one, two, three or all four nucleoside triphosphates) (nATP, nGTP, nCTP, dTTP/rUTP) provided may be ribonucleoside triphosphates. This may allow at least one ribonucleotide to be incorporated into the 3' ligatable end during the course of extending the 3' end of a probe. Thus, in one embodiment, three of the nucleoside triphosphate molecules provided may be deoxyribonucleoside triphosphates, and the fourth nucleoside triphosphate molecule may be a ribonucleoside triphosphate. Preferably, the nucleoside triphosphate(s) which are to be provided as a ribonucleoside triphosphate may be selected such that the nucleotide at or near to the 3' end of the resulting extension product following polymerisation (e.g. the 3' terminal nucleotide of the 3' ligatable end at the ligation site) is a ribonucleotide, based on knowledge of the sequence of the target nucleic acid molecule. By way of representative example, if it is known that the nucleotide at the 5' end of the gap between two parts of a probe is "G", a mixture of nucleoside triphosphates comprising rCTP may be used, thereby providing an rCTP nucleotide at the 3' ligatable end of the extended probe.

In some embodiments where the probe or a part thereof is extended to provide a 3' ligatable end, the probe (or part) which is provided and hybridised to the target nucleic acid molecule may be composed entirely of DNA, and ribonucleotides may be introduced by extension as described above. Thus in such an embodiment a DNA probe may be provided and hybridised with the target molecule, and the ligatable probe which is hybridised to the target nucleic acid molecule may become a chimeric DNA-RNA probe by virtue of the extension step. In other words, in the methods of the invention the ligatable probe which is hybridised to the target molecule with ligatable 5' and 3' ends in juxtaposition for ligation (i.e. ready for ligation) may be a chimeric DNA-RNA probe.

In embodiments in which ribonucleotides are introduced into the ligatable probe by an extension reaction, the ribonucleotides may be introduced at or near the ligatable 3' end, e.g. the terminal and/or penultimate 3' nucleotides of the extended sequence may be ribonucleotides, and/or the extension reaction may introduce 5 or less nucleotides, or no more than 4 nucleotides.

Any convenient polymerase enzyme which may use RNA as a template for extension, preferably a non-displacing polymerase, may be used to perform the 'gap-fill' extension described above, including both RNA polymerase and DNA polymerase enzymes. Thus, an RNA-dependent RNA polymerase (RdRP), and/or an RNA-dependent DNA polymerase (RdDP) (e.g. a reverse transcriptase enzyme) may be used in the 'gap-fill' embodiment described above.

In one preferred embodiment, the polymerase may be capable of incorporating both DNA and RNA residues into an extension product using an RNA template, for example the mutated human mitochondrial DNA polymerase gamma comprising the E895A or E895G substitutions, which has surprisingly been found to incorporate both rNTP and dNTP nucleoside triphosphates into an extension product (Kasiviswanathan et al. 2011. JBC 286, 31490-31500).

The probe used in the detection methods disclosed herein may be provided in one or more parts, each part of which comprises at least one target-specific binding site which is complementary to a cognate probe-binding site at or adjacent to the target nucleic acid sequence in the target nucleic acid molecule. Thus, the probe (or each part thereof) is capable of hybridising to the target nucleic acid molecule. The probe or probe parts hybridise to the target nucleic acid molecule in such a way that their ends are juxtaposed for ligation to each other using the target nucleic acid molecule as a ligation template, optionally after a step of cleaving the hybridised probe and/or extending the 3' end thereof using the target nucleic acid molecule as a template. Thus, the ligation reaction of step (b) of the detection method of the present invention comprises the formation of at least one phosphodiester bond between respective ligatable 3' and 5' ends of adjacent probes or parts of a probe hybridised to the target nucleic acid molecule.

In certain embodiments, the probe may be provided in two or more parts, each said part having at least one target-specific binding site complementary to a cognate probe-binding site in the target nucleic acid molecule. Thus, in one embodiment the probe may be provided in two parts, each part of which comprises a target-binding site, and the ligation in step (b) comprises the ligation of the 3' ligatable end of one part of the probe to the 5' ligatable end of the other. As described in greater detail above, the respective ligatable ends of the probes may be generated by cleavage and/or extension prior to ligation.

In other embodiments of the invention, the probe may be provided in two or more parts, e.g. two, three, four, five or more parts, which create two or more ligation junctions. Each part of the probe may provide (i.e. form or comprise) 3' and/or 5' ligatable ends which may be juxtaposed for ligation and be ligated in step (b) of the detection methods of the present invention as outlined above. In certain embodiments, step (b) may, therefore, comprise two or more separate ligation reactions, i.e. between adjacent ligatable ends provided by the two or more parts of a probe.

Thus, the probe may be provided in more than two parts, e.g. in three parts, each said part having at least one target-specific binding site complementary to a cognate probe-binding site in the target nucleic acid molecule. In such an embodiment, ligation in step (b) comprises the ligation of the 5' ligatable end of a first part of the probe to the 3' ligatable end of the second part of the probe, and the ligation of the 5' ligatable end of the second part of the probe to the 3' ligatable end of a third part of the probe.

In particular embodiments, one or more parts of a probe provided in more than two parts may be an oligonucleotide for sequencing by ligation. In the context of the present invention, sequencing by ligation allows a target nucleic acid molecule having an unknown sequence (e.g. a target nucleic acid sequence) which is flanked on at least one end by a known sequence to be detected, thereby allowing said unknown sequence to be determined. One or more of the parts of a probe as described herein may have a target-specific binding site complementary to a cognate probe-specific binding site in the target nucleic acid molecule, and may further comprise at its 5' and/or 3' end a nucleotide which is complementary to a particular nucleotide in the unknown sequence. The parts of the probe may only be ligated when correctly hybridised to the nucleotide in the unknown sequence, and thus the subsequent detection of an amplified ligation product may allow the target nucleic acid sequence to be determined. In a particular embodiment, in the context of a multi-part padlock probe, one or more gap oligonucleotides (as discussed further below) may be an oligonucleotide for sequencing by ligation.

In certain embodiments, and as discussed briefly above, the probe used in the detection method of the present invention may be a padlock probe comprising one or more parts which are ligated together to form a circle, optionally after a cleavage step. In a typical embodiment, a padlock probe may comprise a linear single-stranded oligonucleotide (a backbone oligonucleotide) which comprises two target-specific binding sites complementary to cognate probe-binding sites in a target nucleic acid molecule connected by a sequence which is not complementary to the target nucleic acid (a backbone or linker), and may thus provide (optionally after cleavage and/or extension as discussed above) both 3' and 5' ligatable ends for a ligation reaction. The 5' and 3' ends of a padlock probe may, therefore take part in one or more ligation reactions using the target nucleic acid molecule as a ligation template, thereby to form a circular nucleic acid molecule.

In certain embodiments, a padlock probe may be provided as a single circularisable oligonucleotide comprising a first target-specific binding site at or internally to the 5' end of the probe and a second target-specific binding site at the 3' end of the probe, wherein the first and second target-specific binding sites form or constitute the 5' and 3' ligatable ends of the probe, respectively.

In such embodiments, ligation may be direct, i.e. the 5' and 3' ends of the padlock probe may hybridise to the target nucleic acid molecule directly adjacent to one-another, such that the 3' end of the padlock probe is ligated to the 5' ligatable end of the padlock probe, thereby to form a circular ligation product. Alternatively in such embodiments, the 5' and 3' ends of the padlock probe may hybridise to the target nucleic acid molecule with a gap between its target-specific binding sites, and the 3' end of the probe may be extended as described elsewhere herein to provide the 3' ligatable end of the probe for ligation to the 5' ligatable end of the padlock probe.

A padlock probe provided as a single circularisable oligonucleotide may optionally comprise an additional sequence 5' to its 5' target-binding site, which additional sequence may be cleaved to provide a 5' ligatable end at a ligation site. Thus, in a particular embodiment, the probe may be a single circularisable oligonucleotide comprising a first target-specific target binding site situated internally of the 5' end of the probe and a second target-specific binding site situated at the 3' end of the probe, such that upon hybridisation of the probe to the target nucleic acid molecule the probe comprises an additional sequence 5' to the first target-binding site which is not hybridised to the target nucleic acid molecule, wherein the nucleotide at the 3' end of the additional sequence is a ribonucleotide which is complementary to the cognate nucleotide in the target nucleic acid molecule but is not capable of hybridising to the target nucleic acid molecule simultaneously with the 3' ligatable end of the probe, wherein said additional sequence is removed by cleavage thereby to create the 5' ligatable end of the probe.

A padlock probe may alternatively be provided in two or more parts, i.e. as two or more oligonucleotides, which oligonucleotides are ligated in order to form a circular oligonucleotide. A first oligonucleotide may comprise a first target-specific binding site at or internally to its 5' end and a second target-specific binding site at its 3' end, and may hybridise to the target nucleic acid molecule with a gap in-between its target-specific binding sites. However, rather than extending the 3' end of the padlock probe to provide the 3' ligatable end for ligation, a second oligonucleotide (and optionally third, fourth etc. oligonucleotides) may be provided, which comprises a target-specific binding site(s) complementary to a cognate probe-binding site in the target nucleic acid molecule situated between the respective cognate probe-binding sites for the first and second target-specific binding sites. Circularisation of the padlock probe in such an embodiment comprises the ligation of the 5' and 3' ligatable ends of the first oligonucleotide to the 3' and 5' ligatable ends of these oligonucleotides (e.g. to the 3' and 5' ligatable ends, respectively of a second oligonucleotide). In such embodiments, the second oligonucleotide and subsequent oligonucleotides may be considered to be gap oligonucleotides. A padlock probe provided in two or more parts may therefore be considered to comprise a backbone oligonucleotide (i.e. the oligonucleotide comprising the first and second target-specific binding sites) and one or more gap oligonucleotides.

One or more gap oligonucleotides may be for use in sequencing by ligation as described above.

In certain embodiments, a padlock probe (or more particularly the backbone oligonucleotide of a padlock probe) may itself be provided in two or more parts, preferably in two parts, which may be ligated during the course of circularising the padlock probe at a position other than a ligation site formed between portions of the probe or probe parts which are hybridised to the target nucleic acid molecule. In other words, the backbone oligonucleotide of a padlock probe may be provided in two or more parts, which may be ligated at a position within the sequence which is not complementary to the target nucleic acid (i.e. the backbone or linker as described above). An example of a padlock probe wherein the backbone oligonucleotide is provided in two parts is shown in FIG. 17.

Such ligation of a backbone oligonucleotide provided in two or more parts may be templated by a ligation template, which is capable of hybridising to each of the two or more parts of a backbone oligonucleotide, thereby to bring respective 5' and 3' ends into juxtaposition for ligation. The ligation template thus comprises regions of complementarity to sequences at the ends of each of the two or more parts of a backbone oligonucleotide.

The ligation template may be a separate oligonucleotide, e.g. an oligonucleotide added to the sample together with the probe or separately, or pre-hybridised to the probe, or may be another target nucleic acid molecule, or another part of the same target nucleic acid molecule (i.e. another, separate, target sequence at a different position within the same target nucleic acid molecule). Accordingly, the ligation template may be a synthetic or natural oligonucleotide, and may be an RNA molecule or DNA molecule.

Ligation of parts of a backbone oligonucleotide may be direct or indirect as defined elsewhere herein, or may require gap-fill extension or a further oligonucleotide hybridising to a ligation template in-between the ends of two parts of a backbone oligonucleotide (i.e. analogously to a gap oligonucleotide). Furthermore, ligation may require cleavage of a 5' additional sequence, optionally wherein the nucleotide at the 3' end of an additional sequence is a ribonucleotide, and/or wherein a ribonucleotide is provided at or near to a ligation site, as described elsewhere herein. It will be seen that such a circularisation method (where the backbone oligonucleotide is provided in 2 or more parts) may conveniently be used to introduce ribonucleotides into the backbone oligonucleotide (e.g. by extension using rNTPs) at sites other than the (or a) ligation site on the (primary) target molecule as template. The presence of one or more such ribonucleotides at one or more different sites in the backbone oligonucleotide may be beneficial in the ligated (circularised) padlock probe, as this may act to speed up an RCA reaction, as discussed below.

Where more than one ligation takes place during step (b) (i.e. where two or more ligation sites are formed), any of the ligation sites may comprise at least one ribonucleotide as discussed in greater detail above (i.e. the probe may comprise a ribonucleotide at or near to any of the ligation sites). Thus, where two or more ligation sites are present, one or more of said ligation sites may comprise at least one ribonucleotide as defined herein. In a particular embodiment of the invention, the probe may comprise a ribonucleotide at or near to each ligation site. Thus, in a preferred aspect, any one or all parts of a probe provided in two or more parts may comprise at least one ribonucleotide at or near to the ligatable 3' end at the ligation site, and in one particular embodiment, each of the parts of the probe may comprise at least one ribonucleotide at or near to its ligatable 3' end at the ligation site. More preferably, each of the parts of the probe may comprise the at least one ribonucleotide at or near to the 3' end thereof. It should be noted, however, that where a probe is provided in two or more parts, it may suffice that only one of said two or more parts may comprise at least one ribonucleotide at or near to its ligatable 3' end or at its 3' end.

Where a probe is provided in two or more parts as described above, the 5' ligatable end of any or all of the parts of the probe may be created by cleavage as described elsewhere herein. In particular, a target-specific binding site of any or all of the parts of a probe provided in two or more parts may be situated internally to the 5' end of a probe part (i.e. may comprise an additional sequence 5' to the target binding site which is not hybridised to the target nucleic acid molecule), which additional sequence may be removed by cleavage prior to ligation. Similarly, any two or more parts of a probe may hybridise to non-contiguous sequences in the target nucleic acid molecule and the gap between them filled by extending the 3' end of any or all probes as necessary, as discussed above.

The number of ribonucleotides contained in the probe is not critical as long as the probe meets the requirement that the ligated probe comprises no more than 4 consecutive ribonucleotides. More particularly, the ligated probe may comprise no more than 3 consecutive ribonucleotides, and in a preferred embodiment no more than 2 consecutive ribonucleotides (e.g. 1 or 2 ribonucleotides). Since the probe may comprise more than one ligation site, and ribonucleotides may be present at or near each or multiple ligation sites, it will be understood that ribonucleotides may be present at multiple (i.e. two or more) sites in the ligated probe, but at each site there will not be more than 4 (or 3 or 2) consecutive ribonucleotides. In other words, at each ligation site there may be 1 ribonucleotide or no more than 4 (or 3 or 2) consecutive ribonucleotides, Indeed, there is no limitation on including ribonucleotides at other sites throughout the probe (i.e. not only at ligation sites), within the confines set out above. Surprisingly, it has been found that the presence of ribonucleotides in a circular ligated probe allows rolling circle amplification to proceed more quickly. Probes for use in the methods of the present invention may, therefore, optionally comprise one or more (and up to 4 consecutive) ribonucleotides at one or more sites, including at one or more positions other than at or near to a ligation site.

As described above the probe or a probe part may be provided with an additional sequence 5' of the first target binding site, and this additional sequence forms a 5' flap which may be removed. As described above, the additional sequence (5' flap sequence) may comprise one or more ribonucleotides which may be consecutive and are not limited in number; these ribonucleotides may be removed by cleavage, such that when the probe is ligated there are no more than 4 (or no more than 3 or 2) consecutive ribonucleotides left in the probe.

In some embodiments where the probe is a padlock probe, the backbone oligonucleotide may be composed entirely of DNA and ribonucleotides may be contained in one or more gap oligonucleotides (more particularly at or near the 3' ligatable ends thereof), and/or they may be introduced by extension, as discussed above. In other embodiments the backbone oligonucleotide may contain one or more ribonucleotides, within the confines above, e.g. single ribonucleotides may be interspersed throughout. In another embodiment, the backbone oligonucleotide may contain at least one ribonucleotide at or near the 3' ligatable end. In such an embodiment one or more gap oligonucleotides may also contain at least one ribonucleotide at or near their 3' ligatable end. Alternatively, the ribonucleotides may be provided only in the backbone oligonucleotide. Any combination of these features may be used.

The present invention may therefore alternatively be viewed as providing a method of detecting a target nucleic acid sequence in a target nucleic acid molecule hybridised to a ligatable chimeric DNA-RNA probe, said method comprising:
i) ligating the chimeric DNA-RNA probe hybridised to the target nucleic acid molecule;
ii) amplifying the ligated probe from step (i) with a DNA polymerase; and
iii) detecting the amplification product from step (ii), thereby to detect the target nucleic acid sequence;
wherein the ligatable chimeric DNA-RNA probe is provided in one or more parts each having at least one target-specific binding site which is complementary to a cognate probe-binding site at or adjacent to the target nucleic acid sequence and is hybridised to the target nucleic acid molecule such that ligatable ends of the probe or probe parts are juxtaposed for ligation to each other using the target nucleic acid molecule as a ligation template, to create a ligation site at or adjacent to the target nucleic acid sequence; and
wherein said ligatable chimeric DNA-RNA probe comprises at least one ribonucleotide at or near to the ligation site, and the ligated probe is comprised primarily of DNA and comprises no more than 4 consecutive ribonucleotides.

It will be apparent that according to such a method, the ligatable ends of the probe or probe parts, which are juxtaposed for ligation to each other, may have been generated e.g. following a step of cleavage and/or extension as described in greater detail above.

The target nucleic acid molecule may be any sequence it may be desired to detect, analyse or amplify. Thus it may be DNA or RNA, or a modified variant thereof. Thus the nucleic acid may be made up of ribonucleotides and/or deoxyribonucleotides as well as synthetic nucleotides that are capable of participating in Watson-Crick type or analogous base pair interactions. Thus the nucleic acid may be or may comprise, e.g. bi-sulphite converted DNA, LNA, PNA or any other derivative containing a non-nucleotide backbone.

The target nucleic acid molecule may thus be coding or non-coding DNA, for example genomic DNA or a sub-fraction thereof, or may be derived from genomic DNA, e.g. a copy or amplicon thereof, or it may be cDNA or a sub-fraction thereof, or an amplicon or copy thereof etc.

As noted above, the target nucleic acid molecule may be a target RNA molecule. The target nucleic acid molecule may, for example, it may be an RNA molecule in a pool of RNA or other nucleic acid molecules or nucleotide sequences, for example genomic nucleic acids, whether human or from any source, from a transcriptome, or any other nucleic acid (e.g. organelle nucleic acids, i.e. mitochondrial or plastid nucleic acids), whether naturally occurring or synthetic. The target RNA molecule may thus be or may be derived from coding (i.e. pre-mRNA or mRNA) or non-coding RNA sequences (such as tRNA, rRNA, snoRNA, miRNA, siRNA, snRNA, exRNA, piRNA and long ncRNA). The target RNA molecule may typically be an RNA molecule it is desired to detect in a sample, in the sense of being the target of the assay, i.e. an analyte. In one preferred embodiment, the target nucleic acid molecule is a micro RNA (miRNA). In another preferred embodiment, the target RNA molecule is 16S RNA, preferably wherein the 16S RNA is from and identificatory of a microorganism (e.g. a pathogenic microorganism) in a sample. Alternatively, the target RNA molecule may be genomic RNA, e.g. ssRNA or dsRNA of a virus having RNA as its genetic material. Notable such viruses include Ebola, HIV, SARS, influenza, hepatitis C, West Nile fever, polio and measles. Accordingly, the target RNA molecule may be positive sense RNA, negative sense RNA, or double-stranded RNA from a viral genome, or positive-sense RNA from a retroviral RNA genome.

The method of the present invention has particular advantages for the detection of short target nucleic acid molecules, and in particular short target RNA molecules, which are typically difficult to amplify and characterise by conventional techniques known in the art. Thus, in particular embodiments of the invention, the target nucleic acid molecule may be less than, or up to, 100 nucleotides in length, or more preferably less than, or up to, 90, 80, 70, 60, 50, 40, 30 or 25 nucleotides in length. Particularly preferred such short nucleic acid molecules are miRNA molecules, which are typically 19-25 nucleotides in length. It is shown in WO 2015/071445 that padlock probes having a pair of target-specific binding sites comprising 6 nucleotides each may bind to a target nucleic acid molecule and be ligated in a target-dependent manner. Thus, shorter target (e.g. RNA) molecules, e.g. comprising at least 18, 17, 16, 15, 14, 13 or 12 nucleotides may also be detected in the methods of the present invention. The target nucleic acid molecules may have a number of nucleotides in a range between any of the integers recited above.

The target nucleic acid molecule may be present within a sample. The sample may be any sample which contains any amount of nucleic acid, from any source or of any origin, in which it is desired to detect a target nucleic acid sequence in a target nucleic acid molecule. A sample may thus be any clinical or non-clinical sample, and may be any biological, clinical or environmental sample in which the target nucleic acid molecule may occur.

The sample may be any sample which contains a target nucleic acid molecule, and includes both natural and synthetic samples, that is, materials which occur naturally or preparations which have been made. Naturally occurring samples may be treated or processed before being subjected to the methods of the invention. All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a target nucleic acid molecule, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue green algae, fungi, bacteria, protozoa etc., or a virus. Representative samples thus include whole blood and blood-derived products such as plasma, serum and buffy coat, blood cells, urine, faeces, cerebrospinal fluid or any other body fluids (e.g. respiratory secretions, saliva, milk, etc.), tissues, biopsies, cell cultures, cell suspensions, conditioned media or other samples of cell culture constituents, etc. The sample may be pre-treated in any convenient or desired way to prepare for use in the methods and uses of the invention, for example by cell lysis or purification, isolation of the nucleic acid or RNA, etc.

In one particular embodiment the sample comprises microbial cells or viruses which have been isolated from a clinical sample or from a culture of a clinical sample. In such a sample the target nucleic acid molecule may be a nucleotide sequence present in a microbial cell, e.g. a nucleotide sequence which is characteristic for, or discriminatory or identificatory of a microbial cell or virus, at any level, e.g. at type, group, class, genus, species or strain level.

The probe described herein, and indeed one or more parts of a probe, may comprise one or more further sequences which may serve to introduce a sequence into a ligation product, for example a tag or detection sequence, e.g. a barcode or identificatory motif, or a binding site for a detection probe or primer. Such a further sequence may be found, for example, at a 3' or a 5' end of a probe or probe part (preferably situated at the opposite end to a ligatable end of a probe or probe part), or may be found intermediate to an end of a probe or probe part, for example, in a portion of a circularisable backbone oligonucleotide not hybridised to a target nucleic acid molecule. Tags such as barcodes or probe/primer binding sites may be designed with different needs/purposes, for example, to introduce a universal or common sequence to enable different ligated probes in a multiplex setting to be processed together, e.g. to introduce a binding site for a universal or common amplification primer. This would enable different ligated probes to be amplified together, e.g. in a library amplification by PCR or RCA. Alternatively or additionally, a tag/barcode sequence may be used to "label" different amplified ligated probes so that they may readily be distinguished from one another (i.e. a "target" tag or marker), or to tag different samples etc. so that they may be pooled prior to a common/universal amplification step (i.e. a "sample" tag or marker). Thus, in a multiplex setting, different probes (i.e. probes for different target nucleic acid molecules) may be provided with different tag sequences (e.g. different marker or detection sequences) and/or they may be provided with the same tag sequence(s) e.g. for the introduction of a common or universal sequence. Such methods may preferably be used in conjunction with sequencing by hybridization, sequencing by ligation or other next generation sequencing chemistries, e.g. in the multiplexed detection of multiple target nucleic acids in a sample.

The term "detecting" is used broadly herein to include any means of determining the presence of the target nucleic acid sequence in the target nucleic acid molecule. It will be understood that in the methods of the invention the target nucleic acid is detected by detecting the amplified ligated probe in the sample (i.e. if it is present or not) or any form of measurement of the amplified ligated probe. Thus, the amplification product of step (c) may be detected as the "reporter" for the target nucleic acid sequence. Accordingly, detecting the amplification product in step (d) may include determining, measuring, assessing or assaying the presence or absence or amount or location of the amplified ligated probe in any way. The presence of the amplified ligated probe in the sample (i.e. the confirmation of its presence or amount or ligation) is indicative or identificatory of the presence of the target nucleic acid sequence, as the successful ligation of the probe (which allows amplification to take place) is dependent on the presence of the target nucleic acid molecule, and more particularly of the target nucleic acid sequence therein. Thus, detection of the amplified ligated probe allows the presence of the target nucleic acid sequence to be determined.

Quantitative and qualitative determinations, measurements or assessments are included, including semi-quantitative. Such determinations, measurements or assessments may be relative, for example when two or more different target nucleic acid molecules in a sample are being detected, or absolute. As such, the term "quantifying" when used in the context of quantifying a target nucleic acid molecule(s) in a sample can refer to absolute or to relative quantification. Absolute quantification may be accomplished by inclusion of known concentration(s) of one or more control RNA molecules and/or referencing the detected level of the target nucleic acid molecule with known control RNA molecules (e.g. through generation of a standard curve). Alternatively, relative quantification can be accomplished by comparison of detected levels or amounts between two or more different target nucleic acid molecules to provide a relative quantification of each of the two or more different RNA molecules, i.e., relative to each other.

The sequences of the probes may be chosen or selected with respect to the sequence of the probe and its target nucleic acid molecule. Thus, whilst the target-complementary regions are chosen with respect to the target nucleic acid molecule to which they bind, the sequence of the rest of the probe is not critical. However, the sequences should be chosen to avoid the occurrence of intramolecular hybridization. Once the sequence is selected or identified, the probe may be synthesized using any convenient method.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity in a region of a probe refers to a portion of that region that is capable of forming a duplex (or in other words, binding to its cognate complementary sequence). These terms are also used to refer to base pair interactions which are analogous to Watson-Crick base pairing, including Hoogsteen base pairing which is a rarely observed variation of base pairing which also allows for a third strand to wind around a double-helix assembled in a Watson-Crick pattern to form a triplex.

The amount of probe that is added to a sample may be selected to provide a sufficiently low concentration of probe in the reaction mixture to minimise non-target specific interactions, i.e. to ensure that the probe will not randomly bind to non-target nucleic acid molecules in the sample to any great or substantial degree. Generally, however, the probe will be used in excess to the target molecule. In representative embodiments, the concentration of each probe in the reaction mixture following combination with the sample ranges from about 1 fM to 1 µM, such 10 as from about 1 pM to about 1 nM, including from about 1 pM to about 100 nM, e.g. 1, 2, 5, 10, 20, 50 nM.

A number of different probes may be added to a sample for a multiplex assay (for example in a situation where multiple different target nucleic acid molecules are present in a sample, in order to detect multiple target nucleic acid molecules in parallel. Multiplex assays may involve the detection of tens, hundreds, thousands or even tens of thousands of nucleic acid molecules in a sample. Accordingly, multiplex assays may comprise at least 2 distinct probes, i.e. probes capable of hybridising (directly or indirectly) to different first RCA products and hence, for example, detecting different analytes. For instance, multiplex assays may utilise at 20 least 3, 4, 5, 10, 20, 30, 40 or 50 probes, such as 100, 200, 500, 1000, 10000 or more probes. Furthermore, the detection method of the present invention (i.e. for detecting a target nucleic acid molecule) may be used in combination with broader methods for the detection of other nucleic acid molecules in a sample. In a particular embodiment, wherein the target nucleic acid molecule is a target RNA molecule, this may allow for the detection of a target RNA molecule in combination with broader methods for the detection of other (e.g. non-RNA) nucleic acid molecules in a sample.

Following combination of the sample containing the target nucleic acid molecule and the probe(s), the reaction mixture may be incubated for a period of time sufficient for the probe(s) to bind to its target nucleic acid molecule in the sample. As described above, once the probe has bound to the target nucleic acid molecule, the probe is ligated (optionally after a step of cleaving and/or extending the hybridised probe) to generate a ligation product that may subsequently be amplified, and the amplification product detected thereby to detect the target nucleic acid sequence.

In some representative embodiments, e.g. in situ assays or other assays in which the target nucleic acid molecule is immobilised, wash steps may be included between the addition of probe and ligation and/or amplification of the ligation product. In other words, a target nucleic acid molecule may be captured or immobilised on a solid support or substrate, which may be washed to remove unbound or non-specifically bound probe. In some embodiments, wash steps may be included between ligating the probe and amplification of the ligation product, to remove unligated probes. In other representative embodiments a wash step may be included before ligation takes place.

Where the probe is a multi-part padlock, the backbone oligonucleotide a may be contacted with the sample and allowed to hybridise, and the gap oligonucleotide(s) may then be added, if used, and allowed to hybridise. Alternatively all the parts of a multi-part probe may be added together.

Ligation comprises the formation of a phosphodiester bond between the 3' OH group at the 3' of a probe and the 5' phosphate group at the 5' end of a probe in two adjacent bases hybridised to a target nucleic acid sequence and juxtaposed for ligation. Thus, depending on the design of the probe, the 3' OH group and/or 5' phosphate group may be provided on a ribonucleotide or a deoxyribonucleotide. Accordingly, a ligase enzyme may be selected which is capable of catalysing the formation of a phosphodiester bond in a target-specific manner.

The ligase may be a DNA ligase (i.e. a ligase enzyme characterised by its ability to catalyse the formation of a phosphodiester bond between two adjacent deoxyribonucleotides hybridised to a target nucleic acid molecule), or an RNA ligase (i.e. a ligase enzyme characterised by its ability to catalyse the formation of a phosphodiester bond between two adjacent ribonucleotides hybridised to a target nucleic acid molecule. As demonstrated in the Examples, both DNA and RNA ligase enzymes have now been shown to catalyse the formation of phosphodiester bonds between an adjacent 3' ribonucleotide and a 5' deoxyribonucleotide, and between an adjacent 3' ribonucleotide and a 5' ribonucleotide, which are hybridised to a target nucleic acid molecule, in an efficient and target-dependent manner. Thus, both DNA and RNA ligases may be of utility in the methods of the present invention. Accordingly, reference to a DNA/RNA ligase includes both DNA and RNA ligases which are capable of joining hybridised 3' and 5' nucleotides to form a ligation product comprising a ribonucleotide at or near to the ligation site as described elsewhere herein.

Exemplary ligases which are of particular utility in the detection method of the present invention include *Chlorella* virus DNA ligase (PBCV-1 DNA ligase I), T4DNA ligase, T4RNA ligase 1 (T4RnI1), T4RNA ligase 2 (T4RnI2) and DraRN1 ligase. To date, RNA templated end-joining fidelity of T4 DNA ligase and PBCV-1 ligase has only been characterised for DNA probes. Surprisingly, efficiency and fidelity improvements are observed for ligation when probes as defined herein are used in the detection of a target nucleic acid sequence, compared to DNA-only probes of the prior art.

A suitable ligase and any reagents that are necessary and/or desirable may be combined with the reaction mixture and maintained under conditions sufficient for ligation of the hybridized oligonucleotides to occur. Ligation reaction conditions are well known to those of skill in the art. During ligation, the reaction mixture in certain embodiments may be maintained at a temperature ranging from about 4° C. to about 105° C., about 4 to about 80° C., such as about 10 to about 70° C., about 15 to about 60° C., typically such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM MgCl2, 10 mM DTT, 1 mM ATP, 25 mg/ml BSA, 0.25 units/ml RNaseinhibitor, and T4 DNA ligase at 0.125 units/ml. In yet another representative embodiment, 2.125 mM magnesium ion, 0.2 units/ml RNaseinhibitor; and 0.125 units/ml DNA ligase are employed.

It will be evident that the ligation conditions may depend on the ligase enzyme used in the methods of the invention. Hence, the above-described ligation conditions are merely a representative example and the parameters may be varied according to well-known protocols. However, it will be further understood that the alteration of one parameter, e.g. temperature, may require the modification of other conditions to ensure that other steps of the assay are not inhibited or disrupted, e.g. binding of the probe to the target nucleic acid molecule. Such manipulation of RCA assay methods is routine in the art.

Once the ligated probe is formed, it is amplified in order to increase the copy number of the ligation product in a sample, which may increase the sensitivity of the detection method of the present invention. In certain embodiments, a part or portion of the ligated probe is amplified. The ligated probe (or part thereof) may be amplified using any convenient method known in the art, such as PCR or a variant thereof, SDA, HAD, LAMP of SMAP.

In a preferred embodiment, the probe is circularised by ligation. Preferably in such embodiments, the probe may be amplified by rolling circle amplification (RCA). Rolling circle amplification using a circular template for amplification provides a concatenated RCA product comprising multiple tandem repeats, each having a sequence complementary to the circular template oligonucleotide (i.e. the circularised ligation product). RCA may be performed, for example, by contacting the sample with a separate primer complementary to and capable of hybridising to the resulting circle, and the 3' end of said primer may be extended to provide a concatenated RCA product. Alternatively, the target nucleic acid molecule may comprise or provide a 3' end which can serve as a primer for RCA amplification.

Amplification of the ligated probe is performed using a DNA polymerase enzyme, i.e. a polymerase enzyme capable of synthesising a DNA oligonucleotide from dNTPs. The term "DNA polymerase" as used herein includes any enzyme capable of incorporating dNTPs, and hence includes enzymes which have both DNA and RNA polymerase activity. In particular, the DNA polymerase may be an enzyme whose principle activity or function is to synthesise DNA, but which is also capable of incorporating RNA nucleotides. A DNA polymerase may be selected which is capable of using a chimeric DNA-RNA oligonucleotide as a template for amplification, as the ligated probe comprises at least one ribonucleotide. Representative polymerase enzymes for use in step (c) include Vent DNA polymerase and Bst DNA polymerase.

Surprisingly, it has also been found that Phi29 DNA polymerase is able to synthesise a DNA oligonucleotide using a chimeric template oligonucleotide containing ribonucleotides, including incorporating a deoxyribonucleotide into a synthesis product complementary to a ribonucleotide in a target nucleic acid molecule. In other words, Phi29 is able to function as a reverse transcriptase, and incorporate a DNA nucleotide (dNTP) corresponding to the RNA base which is complementary to the ribonucleotide in the template. Amplification of a ligated probe comprising up to four consecutive ribonucleotides using Phi29 DNA polymerase has been demonstrated. In a preferred embodiment of the methods of the various methods of the invention defined above, the DNA_polymerase enzyme is Phi29 DNA polymerase. However, this surprising newly-observed ability of Phi29 to accept RNA-containing substrates broadens the spectrum of applications for Phi29-mediated amplification, and RCA in particular, and opens up new uses for the enzyme, beyond the detection methods of the invention described above. For example Phi29-based RCA has applications not only in nucleic acid detection, but also oligonucleotide synthesis and library preparation for next generation sequencing technology.

In one aspect, the present invention therefore provides the use of Phi29 DNA polymerase as a reverse transcriptase.

Alternatively viewed, this aspect also provides a method of synthesising a DNA molecule, said method comprising contacting a template nucleic acid molecule comprising both RNA and DNA bases with Phi29 DNA polymerase, and generating a DNA reverse complement thereto.

Although it has been reported that Phi29 DNA polymerase may be converted to have RNA-dependent DNA polymerase activity by introducing particular amino acid substitutions, it has not been demonstrated that wild-type Phi29 DNA polymerase, or any other Phi29 sequence variant which has not been modified with the purpose of increasing reverse transcriptase activity, may have the ability to act in this way.

In particular, the present invention therefore provides the use of Phi29 DNA polymerase as a reverse transcriptase, wherein the sequence of the Phi29 DNA polymerase has not been modified to increase reverse transcriptase activity.

Furthermore, the present invention also provides a method of synthesising a DNA molecule said method comprising contacting a template nucleic acid molecule comprising both RNA and DNA bases with Phi29 DNA polymerase, and generating a DNA reverse complement thereto, wherein the sequence of the Phi29 DNA polymerase has not been modified to increase reverse transcriptase activity.

In particular, the present invention provides a method of synthesising a DNA molecule by rolling circle amplification, said method comprising contacting a circular template nucleic acid molecule comprising at least one ribonucleotide and no more than four consecutive ribonucleotides with a Phi29 DNA polymerase, and generating a DNA molecule comprising multiple tandem repeats of the reverse complement sequence to the template nucleic acid molecule, wherein the sequence of the Phi29 DNA polymerase has not been modified to increase RT activity.

By reference to the sequence of the Phi29 DNA polymerase not having been modified to increase reverse transcriptase activity it is meant that no sequence modifications have been introduced into a Phi29 amino acid sequence with the purpose of introducing (i.e. conferring) or increasing reverse transcriptase activity, that is an activity of the enzyme to act on a template comprising ribonucleotide(s) and to incorporate into a synthesis product a deoxynucleotide complementary to a ribonucleotide in the template. The sequence has therefore not been modified with the purpose to confer or increase reverse transcriptase activity of Phi29 DNA polymerase. This does not preclude that the amino acid sequence of the Phi29 enzyme may have other sequence modifications as compared to a wild-type or native sequence, but that the modifications have not been purposively or deliberately introduced in order to confer or increase the activity. More particularly, any sequence modifications which may present relative to a wild-type or native Phi29 enzyme do not confer or increase RT activity.

By way of representative example, a structure-guided approach for converting Phi29 DNA polymerase to have RNA-dependent DNA polymerase activity is outlined in US 2017/0159033, which proposes a number of amino acid substitutions to provide enzymes which have properties such as increased template-polymerase stability or processivity, reduced exonuclease activity and/or altered template specificity as compared to a corresponding parental polymerase. Exemplary amino acids which may be substituted include those which may clash with an RNA/DNA heteroduplex, or those which may contribute to steric clashing between the polymerase and a template 2'OH moiety, and a number of exemplary substitutions are proposed. Further amino acid substitutions may be those which reduce or eliminate exonuclease activity of Phi29 DNA polymerase, substitutions which increase cognate base affinity in the active site, substitutions which inhibit primer strand binding to the exonuclease domain, substitutions to improve read length and/or processivity, substitutions to decrease interpulse distance, substitutions which enhance thermostability and/or stability of a binary complex including the polymerase and the nucleic acid substrate and/or a ternary complex including the polymerase, a nucleic acid substrate and a cognate nucleotide or nucleotide analogue. Accordingly, preferably, the Phi29 DNA polymerase has not been modified to affect any one or more of the aforementioned properties, and it does not comprise any one or more of the exemplary substitutions suggested in US 2017/0159033 for converting a Phi29 DNA polymerase to an enzyme having RNA-dependent DNA polymerase activity.

However, the Phi29 DNA polymerase according to this aspect of the present invention may according to certain embodiments comprise one or more alternative modifications introduced for a different aim (i.e. other than to increase its reverse transcriptase activity), e.g. in order to alter one or more of its other biochemical properties, and/or to enhance the recombinant expression and/or purification of the enzyme (i.e. to improve its production).

According to certain embodiments, the sequence of the Phi29 DNA polymerase may not be modified relative to a wild-type sequence. According to a particular embodiment, the sequence of the Phi29 DNA polymerase enzyme may therefore be a wild-type, or a native, sequence. Put another way, the sequence of the Phi29 DNA polymerase may be a non-mutant sequence.

In a particular embodiment, the Phi29 DNA polymerase enzyme according to this aspect of the invention may have the sequence set forth in SEQ ID NO:268, or a sequence which has at least 95, 96, 97, 98, or 99% sequence identity thereto.

The template nucleic acid molecule thus comprises at least one ribonucleotide, and the method of this aspect of the invention comprises generating a DNA molecule comprising or having a sequence which is complementary to the template nucleic acid molecule.

In these aspects, it is preferred that the template nucleic acid molecule comprises no more than 4, and preferably no more than 3, or 2 consecutive ribonucleotides (see the discussion above, which applies also in this context). Although better results may in some cases be obtained when the number of consecutive ribonucleotides is no more than 2, it will understood that routine optimisation of the method is possible, particularly in the context of a circular template, such that is not a requirement to limit the number of consecutive ribonucleotides to no more than 2. In certain embodiments, the template nucleic acid molecule therefore may comprise 1, 2, 3 or 4 consecutive ribonucleotides.

This is demonstrated in the Examples below. The template molecule may contain ribonucleotides at multiple sites and the total number of ribonucleotides is not critical or limiting. Thus, the template nucleic acid molecule may comprise no more than 4 (i.e. 4, 3, 2 or 1) ribonucleotides at each of two or more separate or distinct sites. In one embodiment, the template nucleic acid molecule may comprise one or more single ribonucleotides, i.e. a ribonucleotide flanked by at its 5' and 3' sides by deoxyribonucleotides, at more than one position as described elsewhere herein. Each of the ribonucleotide sites is therefore separated by one or more deoxyribonucleotides between. In certain embodiments, two sites may be separated by only a single deoxyribonucleotide.

In a yet further embodiment, the template nucleic acid molecule may comprise ribonucleotides at only a single site within the template nucleic acid molecule. In a particular embodiment, the template nucleic acid molecule may comprise only a single ribonucleotide.

Consecutive ribonucleotides may preferably be pyrimidine nucleotides rather than purine nucleotides, as Phi29 has been demonstrated in the Examples below to have better processivity and higher replication accuracy for pyrimidine ribonucleotides (i.e. C and U) in an amplification template.

It is preferred in this particular aspect of the invention that the template nucleic acid molecule comprises at least one ribonucleotide, rather than a chemical modification, analogue or derivative thereof. Thus, in certain preferred embodiments, the ribonucleotide is not a 2'-O-Me modified ribonucleotide, 2'-F modified ribonucleotide, or locked nucleic acid (LNA).

Factors such as the concentration of salt or of particular metal cations e.g. $Mn^{2+}$, which has been demonstrated to be required for the optimal reverse transcriptase activity of Taq and Bst polymerases described above may be adjusted to optimise Phi29 reverse transcriptase activity. Activity of Phi29 on longer stretches of ribonucleotides and/or on purine RNA bases may be improved by altering RCA reaction conditions.

Chimeric template molecules comprising both RNA and DNA bases may of course be generated by ligation of probes according to the present invention. However, this aspect of the present invention is not limited to use of Phi29 for amplification of the ligated probes according to the methods herein, and includes use in amplification of any chimeric molecule which comprises both ribo- and deoxyribonucleotides. Such a chimeric DNA-RNA molecule may be a circular molecule and can be any circular or circularised probe. Thus, the Phi29 polymerase may be used to amplify any circularised probe (e.g. padlock probe, iLock, molecular inversion probe, selector probe etc.) howsoever generated, in any context. For example the probe may be a molecular inversion probe gap-filled with RNA, or a selector probe which hybridises to a target molecule containing RNA etc. Thus, in certain preferred embodiments, the template nucleic acid molecule may be a circular template, e.g. as formed according to any of the methods disclosed herein.

Other areas of application may include oligonucleotide production and next generation sequencing as mentioned above, as well as RNA-based therapeutics.

In general, any convenient protocol that is capable of detecting the presence of the amplified ligation product may be employed in the detection method of the present invention. The detection protocol may or may not require a separation step. Reference to detection of the amplified ligation product herein refers to the detection of the sequence formed by the ligation of the probe, and/or of a complement thereof (i.e. the complementary sequence thereto).

The amplified ligation product (i.e. amplification product) may be detected using any convenient protocol, where the particular protocol employed may detect the amplified ligation product non-specifically or specifically, as described in greater detail below. For instance, the amplified ligation product may be detected directly, e.g. using gel electrophoresis, or more preferably by hybridizing labelled detection oligonucleotides that hybridize to the amplified ligation product. Alternatively, the amplified product may be detected indirectly, e.g. the product may be amplified by PCR and the amplification products may be detected.

Representative non-specific detection protocols of interest include protocols that employ signal producing systems that selectively detect single or double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo or heterodimer thereof, such as acridine orange, acridine homodimer, ethidium, acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg.

In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazoe, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplified ligation product, as opposed to nucleic acid molecules in general, may be employed to detect the amplification. In these embodiments, the signal producing system may include a nucleic acid or oligonucleotide that specifically binds to a sequence found in the amplified ligation product (i.e. a reporter domain sequence), where the nucleic acid/oligonucleotide may be labelled with a directly or indirectly detectable label. In specific embodiments, an amplified ligated probe may be detected by sequencing by ligation.

A directly detectable label is one that can be directly detected without the use of additional reagents, while an indirectly detectable label is one that is detectable by employing one or more additional reagents, e.g., where the label is a member of a signal producing system made up of two or more components.

In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids (i.e. detection probes) include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled nucleic acids (detection probes) are labelled with "energy transfer" labels. As used herein, "energy transfer" refers to the process by which the fluorescence emission of a fluorescent group is altered by a fluorescence-modifying group. Energy transfer labels are well known in the art, and such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Further examples of detection probes include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference).

Thus, determining the presence of the amplified ligation product may be achieved using any convenient protocol. The reaction mixture may be screened etc. (i.e., assayed, assessed, evaluated, tested, etc.) for the presence of any resultant amplified ligation products in order to detect the presence of the target nucleic acid molecule in the sample being assayed. The particular detection protocol may vary depending on the sensitivity desired and the application in which the method is being practiced.

The amplified ligation product may be detected in a number of different ways. For example, the nucleotides incorporated in the amplified ligation product may be directly labelled, e.g., fluorescently, or otherwise spectrophotometrically, or radioisotopically labelled or with any signal-giving label, such that the amplified ligation product is directly labelled. In some embodiments detection probes as discussed above, e.g., fluorescently labelled probes, molecular beacons (as described above) etc. may be employed to detect to the presence of the amplified ligation product, where these probes are directed to a sequence (e.g. a reporter domain sequence) that is present in the ligation product (i.e. is formed by or during said ligation) and therefore only exists in its entirety in the amplified ligation product.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, although higher or lower amounts may be used and may depend on the type of reaction. For instance, for PCR the amount of $Mg_{2+}$ present in the buffer may be about 1.5 mM, whereas for RCA, the amount of $Mg_{2+}$ present in the buffer may about 10 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C.

Other agents which may be present in the buffer medium include chelating agents, such as EDTA, EGTA and the like.

The next step in the subject methods is signal detection from the labelled products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the amplified ligation product and hence the target nucleic acid molecule. Depending on the particular label employed, detection of a signal may indicate the presence or absence of the target nucleic acid sequence in the target nucleic acid molecule.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or, for example where the sample is a tissue sample on a microscope slide, fluorescence may be detected using a fluorescence microscope. Fluorescence is suitably monitored using a known fluorimeter. The signals from these devices, for instance in the form of photomultiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analysed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring). The data generated as described above can be interpreted in various ways. In its simplest form, an increase or decrease in fluorescence from the sample in the course of or at the end of the amplification reaction is indicative of an increase in the amount of the target analyte present in the sample, e.g. as correlated to the amount of the amplified ligation product detected in the reaction mixture, suggestive of the fact that the amplification reaction has proceeded and therefore the target nucleic acid molecule was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of the amplification product, and hence of target nucleic acid molecule(s). The methods are suitable for detection of a single target nucleic acid molecule as well as multiplex nucleic acid molecules, in which two or more different target nucleic acid molecules are assayed in the sample. In these latter multiplex situations, the number of different probes that may be employed typically ranges from about 2 to about 20 or higher, e.g., as up to 100 or higher, 1000 or higher, etc. wherein the multiple analytes in a sample may be detected in parallel or sequentially. The analysis of many analytes simultaneously and in a single reaction using several different probes (multiplexing) may enhanced by the increased sensitivity, and in certain embodiments also increased specificity, which may be obtained using the methods and probes of the invention. Each probe set can be designed to produce a ligation product that can be used to determine the presence or absence, quantity and/or location of the analytes ultimately being interrogated by the probe.

The amplified ligated probe may be detected using any of the well-established methods for analysis of nucleic acid molecules known from the literature including liquid chromatography, electrophoresis, mass spectrometry, microscopy, real-time PCR, fluorescent probes, microarray, colorimetric analysis such as ELISA, flow cytometry, mass spectrometry (CyTOF) etc.

Detection of the amplified ligated probe further encompasses determining the sequence of the amplified ligated probe. Thus, in certain embodiments, detection may comprise sequencing of all or a part of the amplified ligated probe. The probes and methods of the present invention may be employed homogeneously (i.e. in solution) as described above, or alternatively heterogeneously, using a solid phase, for example, in which the target nucleic acid molecule becomes immobilised on a solid phase, permitting the use of washing steps. This may result from immobilisation of the target nucleic acid molecule, for example in in situ detection procedures. The use of solid phase assays offers advantages, particularly for the detection of difficult samples: washing steps can assist in the removal of unbound and/or unligated probes etc., inhibiting components, and target molecules can be enriched from an undesirably large sample volume. Higher concentrations and greater amounts of probes can be used, as unbound probes and RNA molecules can be removed by washing.

In a preferred embodiment of the present invention, the target nucleic acid molecule is detected in situ. This may allow the level, location or position of a target nucleic acid molecule to be detected directly in a sample. The sample may thus preferably be any sample which reflects the normal or native ("in situ") localisation of the target nucleic acid molecule, i.e. any sample in which it normally or natively occurs. Such a sample will advantageously be a cell or tissue sample. Particularly preferred are samples such as cultured or harvested or biopsied cell or tissue samples in which the target nucleic acid molecule may be detected to reveal the localisation of the target nucleic acid molecule relative to other features of the sample. As well as cell or tissue preparations, such samples may also include, for example, dehydrated or fixed biological fluids, and nuclear material such as chromosome/chromatin preparations, e.g. on microscope slides. The samples may be freshly prepared or they may be prior-treated in any convenient way such as by fixation or freezing. Accordingly, fresh, frozen or fixed cells or tissues may be used, e.g. FFPE tissue (Formalin Fixed Paraffin Embedded).

In alternative embodiments, the target nucleic acid molecule may be immobilised. Immobilisation of the target nucleic acid molecule on a solid phase may be achieved in various ways. Accordingly, several embodiments of solid phase assays are contemplated. In one such embodiment, the molecule can first be captured by an immobilised (or immobilisable) capture probes, the amplified ligation product can generated such that it is attached to the target nucleic acid molecule, for example by virtue of a primer for amplification being or being attached to the target nucleic acid molecule as described elsewhere herein. Alternatively, the amplified ligation product may simply be immobilised to a solid support. For example a primer for amplification may be provided with an immobilisable group or moiety or means for immobilisation, or may be immobilised, prior to amplification.

The immobilised capture probe, target nucleic acid molecule, primer for amplification, or amplified ligation product, may be immobilised, i.e. bound to the support, in any convenient way. Thus the manner or means of immobilisation and the solid support may be selected, according to choice, from any number of immobilisation means and solid supports as are widely known in the art and described in the literature. Thus, the capture probe, target nucleic acid molecule, primer for amplification, or amplified ligation product may be directly bound to the support (e.g. chemically cross-linked), it may be bound indirectly by means of a linker group, or by an intermediary binding group(s) (e.g. by means of a biotin-streptavidin interaction). Thus, capture probe, target nucleic acid molecule, primer for amplification, or amplified ligation product may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support. A capture probe may be immobilised before or after binding to the analyte. Further, such an "immobilisable" capture probe may be contacted with the sample together with the support.

Analogously, a primer for amplification may be immobilised before or after amplification. The capture probe may be, for example, a nucleic acid molecule that is capable of binding to the target nucleic acid molecule specifically. In other words the capture probe may be an immobilised (or immobilisable) probe specific for the target nucleic acid molecule comprising a binding domain complementary thereto. Thus in such an embodiment the target nucleic acid molecule is first captured by the immobilised or immobilisable capture probe which serves only to immobilise the target nucleic acid molecule on the solid phase, and subsequently the immobilised target nucleic acid molecule is subjected to a detection protocol which uses, or leads to the generation of an amplified ligation product. More particularly, such a capture probe binds specifically to the analyte.

The solid support may be any of the well-known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the binding steps.

In a further embodiment, the target nucleic acid molecule itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

As noted above, the present invention also provides certain probes for use in the method of the invention, namely circularisable probes as defined above, which may be provided in one or more parts. The invention thus provides chimeric DNA-RNA padlock probes as defined herein, including invader padlock probes.

In one such embodiment the chimeric DNA-RNA padlock probe is a single circularisable oligonucleotide comprising a first target-specific target binding site situated at or internally of the 5' end of the probe and a second target-specific binding site situated at the 3' end of the probe, and wherein:
 (i) the second target specific binding site comprises one or more ribonucleotides;
 (ii) where the first target specific binding site is internal to the 5' end of the probe, the probe comprises an additional sequence 5' to the first target specific binding site, such that when the probe is hybridised to the target nucleic acid molecule the additional sequence forms a 5' flap which is not hybridised to the target nucleic acid molecule, and which may be removed by cleavage to generate a ligatable 5' end which may be ligated to the 3' end of the probe to circularise the probe, wherein the additional sequence may optionally contain one or more ribonucleotides;

(iii) the probe when ligated to form a circle is composed primarily of DNA and comprises no more than 4 consecutive ribonucleotides.

In another embodiment, the chimeric DNA-RNA padlock probe comprises two or more parts, the first part being a backbone oligonucleotide comprising a first target-specific target binding site situated at or internally of its 5' end and a second target-specific binding site situated at its 3' end, and one or more gap oligonucleotides which each comprise a target-specific binding site complementary to and capable of hybridising to the target nucleic acid molecule in between the first and second target-specific binding sites of the backbone oligonucleotide, and wherein:

(i) the second target specific binding site of the backbone oligonucleotide and/or at the target-specific binding site of at least one gap oligonucleotide comprises one or more ribonucleotides at or near the 3' end thereof;

(ii) where the first target specific binding site is internal to the 5' end of the backbone oligonucleotide, the backbone oligonucleotide comprises an additional sequence 5' to the first target specific binding site, such that when the backbone oligonucleotide is hybridised to the target nucleic acid molecule the additional sequence forms a 5' flap which is not hybridised to the target nucleic acid molecule, and which may be removed by cleavage to generate a ligatable 5' end which may be ligated to the 3' end of a gap oligonucleotide to circularise the probe, wherein the additional sequence may optionally contain one or more ribonucleotides;

(iii) one or more gap oligonucleotides optionally comprise an additional sequence 5' to the target-specific binding site, such that when the gap oligonucleotide is hybridised to the target nucleic acid molecule the additional sequence forms a 5' flap which is not hybridised to the target nucleic acid molecule, and which may be removed by cleavage to generate a ligatable 5' end which may be ligated to the 3' end of another gap oligonucleotide or to the 3' end of the backbone oligonucleotide to circularise the probe, wherein the additional sequence may optionally contain one or more ribonucleotides (iv) the backbone and gap oligonucleotides when ligated form a circle which is composed primarily of DNA and comprises no more than 4 consecutive ribonucleotides.

Such probes may be invader padlock probes, also referred to herein as iLock probes. In a certain embodiments, the probes of the invention (i.e. a probe provided as a single circularisable oligonucleotide, or a part of a probe provided in two or more parts i.e. a backbone oligonucleotide and/or one or more gap oligonucleotides) may therefore comprise an additional sequence 5' to the first target-specific binding site or to a target-binding site of a gap oligonucleotide as described above, wherein the nucleotide at the 3' end of any additional sequence which forms a 5' flap is complementary to the same cognate nucleotide in the target nucleic acid molecule as the nucleotide at the 3' end of the probe, or of a backbone and/or one or more gap oligonucleotides (i.e. a ligatable end of an adjacent part of the probe). When such probes are hybridised to the target nucleic acid molecule the nucleotide at the 3' end of an additional sequence which forms the 5' flap thus is prevented from hybridising to the target nucleic acid molecule by the 3' ligatable end of the probe or the backbone and/or the one or more gap oligonucleotides.

Such invader probes may be suitable for detecting a variant base in a target nucleic acid molecule. In a probe for detecting a variant base in a target nucleic acid molecule:

(i) the nucleotide at the 3' end of the probe or backbone and/or gap oligonucleotides and the nucleotide at the 3' end of the additional sequence described above are complementary to a variant base, and the nucleotide at the 3' end of the additional sequence is not capable of hybridising to the target nucleic acid molecule simultaneously with the 3' end of the probe or backbone or gap oligonucleotide, such that said additional sequence may be removed by cleavage to generate a 5' ligatable end of the probe; or (ii) the nucleotide at the 3' end of the additional sequence and the nucleotide at the 3' end of the probe or backbone and/or gap oligonucleotides are not complementary to the variant base, such that the nucleotide at the 3' end of the probe, or backbone and/or gap oligonucleotide is not capable of hybridising to the target nucleic acid molecule, thereby preventing ligation, and the nucleotide at the 3' end of the additional sequence may also be removed by cleavage.

Alternatively, in a probe for detecting a variant base in a target nucleic acid molecule:

(i) the nucleotide at the 5' end of the first target-specific binding site or at the 5' end of the target-specific binding site of a backbone or gap oligonucleotide is complementary to the variant base, the nucleotide at the 3' end of the probe or backbone and/or gap oligonucleotide and the nucleotide at the 3' end of the additional sequence described above are complementary to the nucleotide at the position 3' to the variant base, and the nucleotide at the 3' end of the additional sequence is not capable of hybridising to the target nucleic acid molecule simultaneously with the 3' end of the probe or backbone or gap oligonucleotide, such that said additional sequence may be removed by cleavage to generate a 5' ligatable end of the probe; or (ii) the nucleotide at the 5' end of the first target-specific binding site or at the 5' end of the target-specific binding site of a backbone or gap oligonucleotide is not complementary to the variant base, said nucleotide is also removed by cleavage, thereby generating a gap between the 5' and 3' ligatable ends and preventing ligation.

In a preferred embodiment, the nucleotide at the 3' end of an additional sequence which forms the 5' flap is a ribonucleotide.

In another aspect, the present invention provides a set of invader probes comprising two or more invader probes for the detection of a variant base in a target nucleic acid molecule, wherein each probe in said set of probes comprises a different nucleotide (e.g. A, G, C or T/U) at a position in the additional sequence and 3' end of the probe or backbone or gap oligonucleotide complementary to the variant base. In certain embodiments, the set of invader probes may comprise three or four probes, each comprising a different nucleotide at said positions.

As discussed above, the total number of ribonucleotides in the probe is not critical as long as the probe, when ligated contains no more than 4, or more preferably no more than 3, or 2 consecutive ribonucleotides (see the discussion above).

In certain embodiments, the second binding site at the 3' end of the one-part probe or at the 3' end of the backbone oligonucleotide, or the target-specific binding site of a gap oligonucleotide may comprise no more than 4 or 5 ribonucleotides.

The present invention may be better understood with reference to the Examples and Figures, in which:

FIG. 1 shows the effect of a RNA nucleotide at the 3' ligatable end at a ligation site using PBCV-1 ligase in the ligation of a padlock probe templated by an RNA. A: Experiment overview. B: Padlock probes (PLP) targeting let-7 family members were designed with RNA or DNA terminal 3' nucleotides. Probes were hybridised with matching templates, ligated with PBCV-1 and amplified. A total number of RCA products (RCP) for each PLP/miRNA pair is shown in the column plot. y-axis shows the number of RCPs while type of miRNA is depicted on x-axis. Error bars±s.d.; n=2.

FIG. 2 shows the effect of a RNA nucleotide at the 3' ligatable end at a ligation site using PBCV-1 or T4RnI2 ligase. Ligation of a 3'-OH(N)/5'-p(N) vs 3'-OH(rN)/5'-p(N) using an RNA template was compared. Full DNA and chimeric padlock probes were hybridised with a corresponding RNA target and ligated with (A) PBCV-1 and (B) T4RnI2. The y-axis shows the number of rolling circle products (RCPs) and the x-axis the RNA template used. Error bars±s.d.; n=2. A greater number of ligation products was seen for all target RNAs for PBCV-1, and a large increase in the number of ligation products was seen for all target RNAs for T4RnI2 ligase when the probe comprised a 3' ribonucleotide at its 3' end.

FIG. 3 shows the effect of 3'-OH(rN) mismatches on nick sealing by PBCV-1 and T4RnI2 ligase. Numbers of RCPs for each RNA template (FIGS. 3B and 3C) were added and presented as percentage within an iLock probe group (FIG. 3A) for each ligase enzyme.

FIG. 4 shows the effect of RNA substitutions at various positions in an Invader padlock (iLock) probe used in an RNA detection assay with PBCV-1 ligase. The recognition of the invader structure and structure-specific nucleolytic activity of Taq DNA polymerase can vary for different RNA substitutions. A: targeting let-7a with iLock probe, showing the arrangement of the first and second target-specific binding sits of the iLock probe, and a 5' additional sequence. RNA nucleotides were introduced at different positions: at the terminal 3' end (3); at the 3'-most nucleotide in the 5' flap which competes with the terminal 3' nucleotide at the end of the probe for target binding (displaced base, D); the base in the first target binding site that becomes the 5' ligatable end (provides the 5'-phosphorylated donor) after cleavage to remove the additional sequence (iLock probe activation) (5); the entire flap sequence (F). B: The circularisation of six iLock designs was assessed: DNA-only iLock; an iLock with the (3) modification (iLock-3); an iLock with the (3) and (D) modifications (iLock-3D); an iLock with the (3), (D) and (5) modifications (iLock-3D5); an iLock with the (3), (D) and (F) modifications (iLock-3DF); and an iLock with the (D) and (F) modifications (iLock-DF). The total number of RCPs detected for each iLock probe is showed on x-axis. Probes comprising the (3) modification, and the (3) modification in combination with the (D) or the (D) and (F) modifications showed a large increase in the number of RCPs generated relative to the DNA-only iLock. The combination of the (3) modification with the (D) and (5) modifications, and of the (D) and (F) modifications, showed a much smaller increase in the relative number of RCPs generated relative to the DNA-only iLock. C: PAGE of the iLock DNA, iLock-3 and iLock-3D probes after activation and ligation, without (lanes 1-3) and with Taq DNA polymerase (lanes 4-6). Non-activated iLock probe (79) is shortened upon activation by 14 nt (65) and ligated (seen as the high molecular weight band at the top of the gel). Lane 4: a band for activated, unligated probe is visible (65 nt), the band for uncleaved probe is clearly visible (79nt) and only a faint band for ligated probe is visible. Lane 5: no band for unligated probe is visible, the band for uncleaved probe is clearly visible (65 nt) and a band for ligated probe is visible. Lane 6: no band for unligated probe is visible, the band for uncleaved probe is faint (65 nt) and a strong band for ligated probe is visible. Together these data show that a ribonuclease at a 3' ligatable end at a ligation site improves ligation (lanes 4 and 5), and that a ribonuclease at the 3'-most position in an additional sequence which is cleaved in an Invader assay improves cleavage (lanes 5 and 6).

FIG. 5 shows a comparison of chimeric and non-chimeric iLock probes ligation. A: 3D and non-chimeric iLock probes performance on longer, non-miRNA targets. Total number of RCPs for each probe on matching polymorphic templates is showed on y-axis. B: a comparison of chimeric and non-chimeric iLock probes on miR21 using PBCV-1 and T4RnI2. Total number of RCPs for chimeric or non-chimeric iLock probes is presented on y-axis. Ligase used is depicted on the x-axis. Error bars±s.d.; n=2. Both ligases demonstrate improved ligation when a chimeric probe is used.

FIG. 6 shows chimeric iLock probe ligation efficiency and fidelity on non-miRNA templates for PBCV-1 and T4RnI2 ligase. A and B: Fidelity of nick sealing by PBCV-1 and T4RnI2 ligases on matching polymorphic RNA templates. C and D: Data presented in (A) and (B) but as a total number of RCPs generated for each iLock probe on each polymorphic template. Error bars±s.d.; n=2.

FIG. 7 shows the multiplexed detection of let-7 miRNA isoforms using chimeric iLock probes and PBCV-1 ligase. A: miRNA-specific barcode (NN) was embedded in the probe backbone, between anchor primer hybridisation region and a sequencing library hybridisation site. During sequencing, anchor primer (AP) hybridises to the RCP and pool of sequencing library oligonucleotides compete with each other for hybridisation based on the nucleotide at their 5' end. Library containing terminal T was 3'-FITC labelled; G-3'Cy3 labelled; A-3'Cy5 labelled. Ligase joins a library oligonucleotide corresponding to a barcode base. B: imaging of a first barcode base by sequencing by ligation (SBL). AP: all RCPs stained with AP. Images of each barcode base is presented as well as merged image. Scale bar 5 µm. C: miRNAs were mixed in stoichiometric ratios as stated on the x-axis. 1:1:1 represents equal ratio and 0:0:0 no template control. Total number of reads is depicted on the y-axis. Error bars±s.d.; n=number of samples imaged=2. A 1:1:3 ratio generated similar number of RCPs for each template.

FIG. 8 shows a comparison of the ligation efficiencies of a padlock probe, and a chimeric padlock probe comprising 1 (R1pd) or 2 (R2pd) ribonucleotides at the 3' end, for PBCV-1 ligase and T4 RN12 ligase at both high and low concentrations, using (A) an RNA template or (B) a DNA template. Chimeric padlock probes were shown to be ligated and amplified more efficiently than DNA-only padlock probes for both RNA and DNA targets for both ligases.

FIG. 9 shows the detection of KRAS wt and mutant RNA in situ using DNA padlock probes or chimeric padlock probes. A: microscopy image showing detection of mutant and WT RNA using padlock probes (top) or chimeric padlock probes (bottom). B: Average number of mutant RCPs and wild type RCPs per cell in both cell lines A549 and OncoDG1. The efficiency of chimeric padlock probes is much higher in both cases. The specificity is high enough to distinguish between mutant and wild type KRAS (more mutant RCPs in A549 and more wild type RCPs in OncoDG1).

FIG. 10 shows the detection of KRAS wt and mutant RNA in situ using chimeric iLock probes. A: microscopy image showing detection of mutant and WT RNA using chimeric iLock probes. B: Average number of mutant RCPs and wild type RCPs per cell in both cell lines A549 and OncoDG1. The specificity is high enough to distinguish between mutant and wild type KRAS (more mutant RCPs in A549 and more wild type RCPs in OncoDG1).

FIGS. 11A-C show detection of target RNA molecules using gap-fill polymerisation and an iLock probe. A: number of RCPs counted in solution after gap-fill polymerization with reverse transcriptase and Taq cleavage+PBCV-1 ligase ligation (all at once) followed by RCA, using chimeric iLock probes. B: in situ detection of RCPs using gap-fill polymerisation and chimeric iLock probes.

FIG. 12 shows a design for a 2-part iLock probe comprising a ribonucleotide at the end of the backbone and gap oligonucleotides. A target RNA molecule (1) is contacted with a 2-part iLock probe comprising a backbone oligonucleotide (2) and a gap-fill oligonucleotide (3). Both the backbone oligonucleotide and the gap-fill oligonucleotide comprise an additional sequence at their 5' end which is not hybridised to the target RNA molecule (4) and a ribonucleotide at their 3' end (5).

FIG. 13 shows the effect of RNA substitutions on rolling circle amplification with Phi29 DNA polymerase. A: Total amount of RCA products (y-axis) generated for padlock probes with/without a terminal 3' RNA and in the absence of synthetic RNA ligation template (template-). B: Circles with 0-7 RNA substations in the backbone were amplified and digitally counted. The y-axis shows the number of rolling circle products (RCPs); error bars±s.d.; n=2. The same RCA reactions with chimeric circles were also monitored in real-time measuring Sybr gold incorporation on a qPCR instrument (C and E). C: RCA reaction curves of circles with 0, 1, 2 or 3 RNA substitutes. D: RCPs from C were imaged on microscope slides and size and intensity of individual RCPs were quantified. Black line, median; upper whisker, highest value that is within 1.5 the interquartile range of the hinge; lower whisker, lowest value within 1.5 the interquartile range of the hinge. E: Real time data of the same RCA reactions as in B with 0-7 RNA substitutes are displayed. Representative samples are presented from a duplicated experiment. To highlight the initial stages of RCA and to see difference between the samples with low RCA efficiency, fluorescence between 4 000 and 6 000 is shown.

FIG. 14 shows that chimeric padlock probes comprising a 3' ribonucleotide are more readily ligated using PBCV-1 ligase than a padlock probe which comprises a deoxyribonucleotide at its 3' end. Lanes 1-6—chimeric padlock probes. Lanes 7-12—non-chimeric padlock probes. A ligated probe product is shown (*) as the heavier fragment. This is clearly visible after 1-2 minutes for chimeric probes (lanes 2-3), whereas this only becomes clearly visible at later time points for non-chimeric probes (lane 12).

Figure 18:
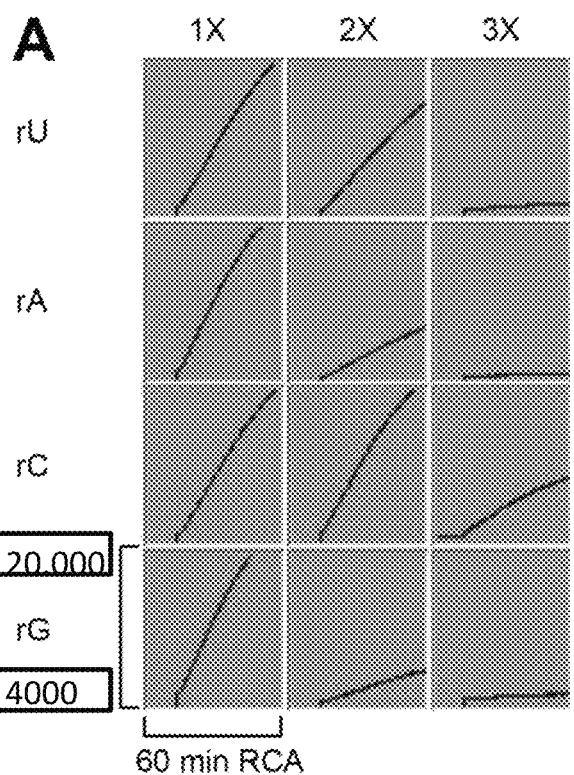
Figure 18:
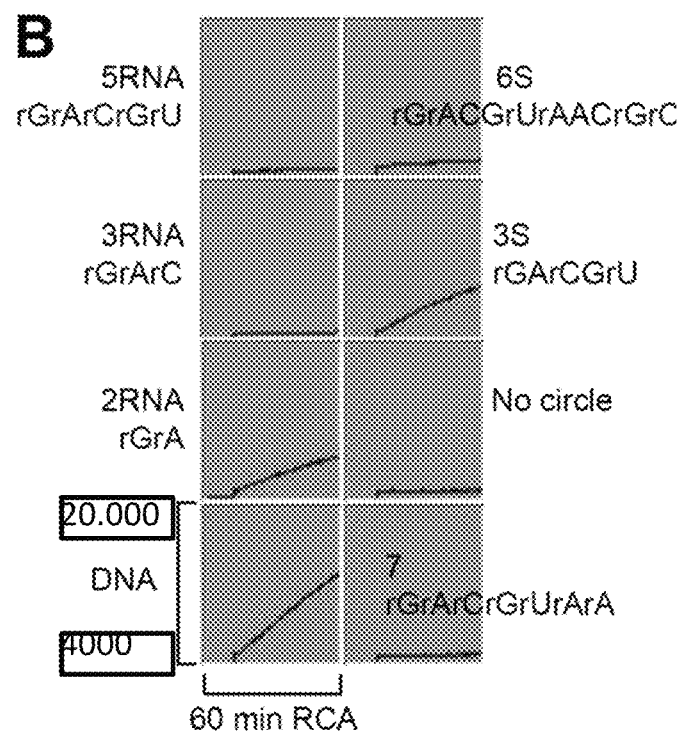

FIG. 18 shows the rates of amplification of circularised padlock probes comprising different ribonucleotides. A: Real-time RCA curves of circles containing 1, 2 or 3 consecutive RNA substitutions of all four RNA bases are displayed. Rate of RCA was monitored by measuring fluorescence build-up (y-axis) resulting from SybrGold incorporation into RCPs. Representative data are shown for each experiment. B: RCA rates for the positive control (pure DNA circle—bottom left), negative control (no circle) and circles with 2, 3, 5 and 7 consecutive RNA substitutions, as well as circles with RNA substitutions interspersed with DNA bases are displayed. Phi29 DNA polymerase exhibits higher RCA rate with circles containing pyrimidine RNA substitutions.

Figure 19:
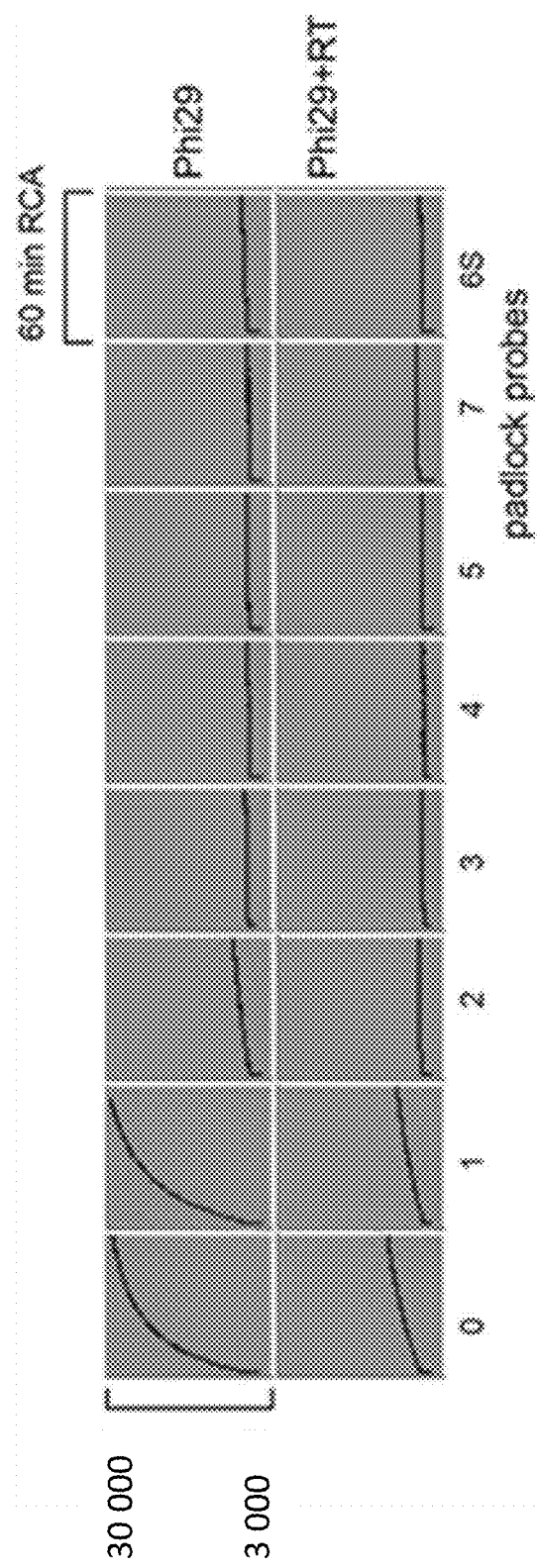

FIG. 19 shows that limited replication of RNA-enriched padlock probes is not recovered in the presence of M-MuLV reverse transcriptase. Amplification curves of padlock probes with 0-7 RNA substations in the backbone are displayed. Rate of RCA was monitored by measuring fluorescence build-up (y-axis; 3000-30000) resulted from SybrGold incorporation into RCPs. Replication is shown for circles without additional reverse-transcriptase (upper panel) and with additional M-MuLV reverse transcriptase (lower panel).

Figure 20:
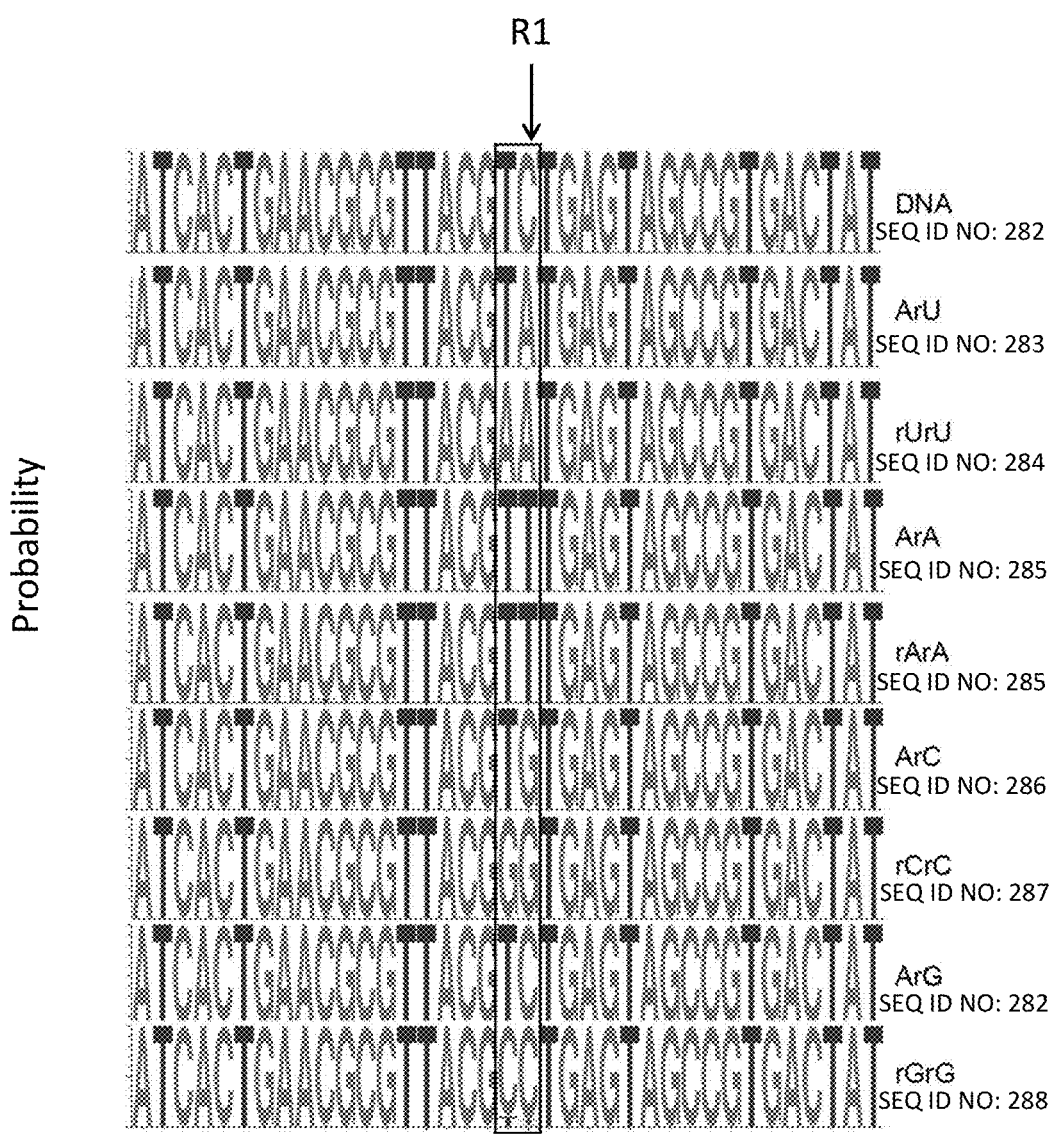

FIG. 20 shows stacked graphs showing incorporation of expected dNTPs during RCA reverse-transcription. RNA-containing padlock probes were amplified, monomerised and sequenced. RCA monomers were generated from the control DNA circle (upper row), and circles containing rA, rC, rG and rU at the first RNA position (R1), and rUrU, rArA, rCrC and rGrG at their R1 and R2 positions (full oligo sequences in table 9). Sequencing reads were aligned and frequency of each base in every position was calculated. Size of each base is proportional to the base frequency. Positions R1 and R2 (relative to RNA positions in the padlock probe backbone) are indicated by the box and position R1 was highlighted (see arrow).

Figure 21:
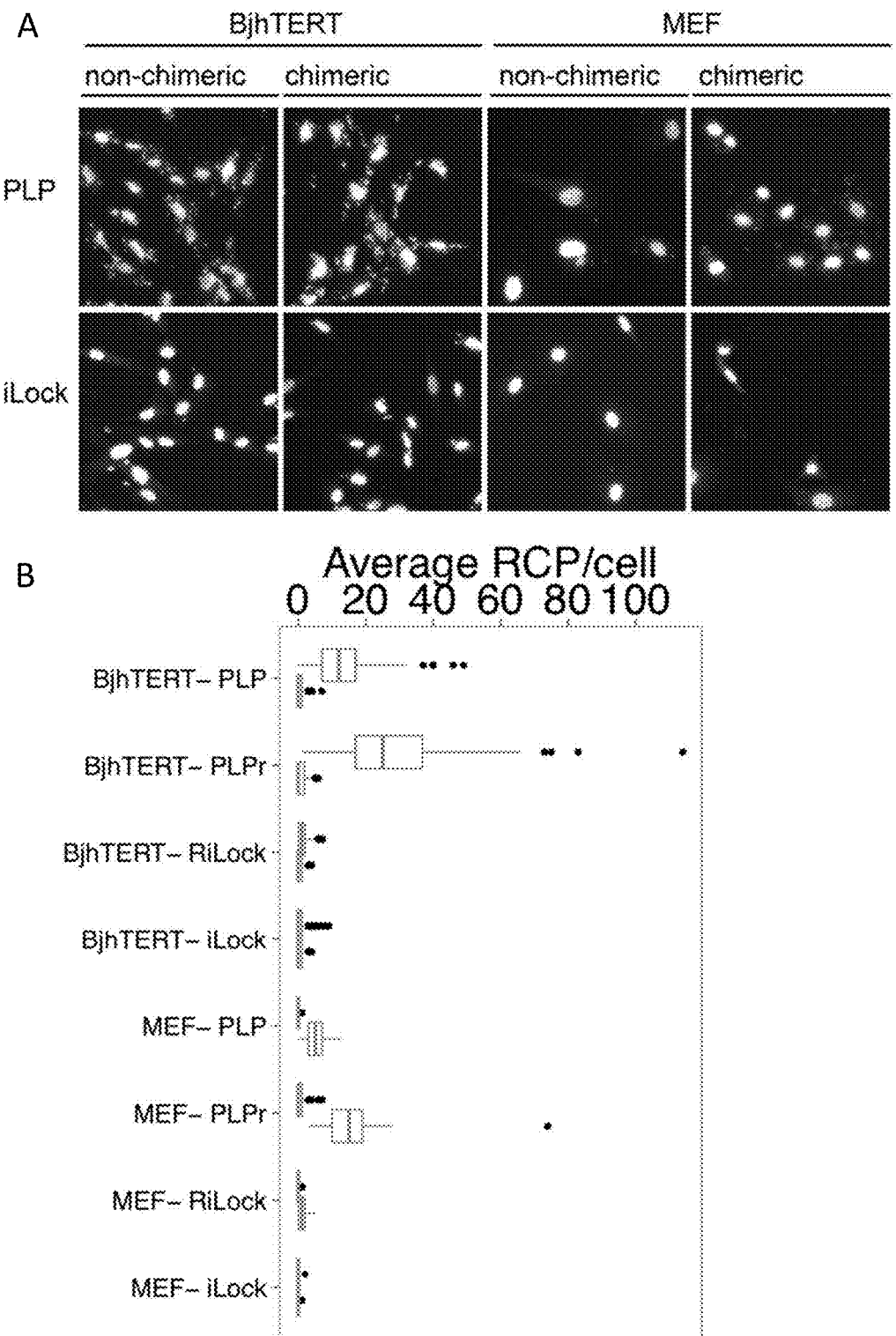

FIG. 21 shows the in situ detection of ACTB mRNA in cultured human (BjhTERT) and mouse (MEF) fibroblasts. A: Detection of human and mouse ACTB mRNA in Bjh-TERT and MEF cells using chimeric and non-chimeric chimeric padlock probes (PLP) and iLock probes. Probes for both targets were included in each sample, and showed good levels of target specificity. B: Average number of RCPs per cell arising from each probe are shown for each cell line using chimeric and DNA-only PLPs and iLocks. PLP: DNA-only padlock probe; PLPr-3'-(rN) PLP; RiLock: RNA iLock; iLock: DNA-only iLock. For each probe, signal from human-specific probes is top, and signal from mouse-specific probes is bottom. In BjhTERT, human ACTB-specific PLP (top box plot) shows fewer blobs than RNA PLPr (second boxplot). Mouse-specific PLP and PLPr shows no signal. For iLock (31d and 4th box plots) RiLocks show a higher median than iLocks (boxplot is a bit shifted) but signal amount is much lower comparing to PLPs. Corresponding data was obtained for MEF mouse cells, with signals from mouse-specific probes higher than for human-specific probes.

Figure 22:
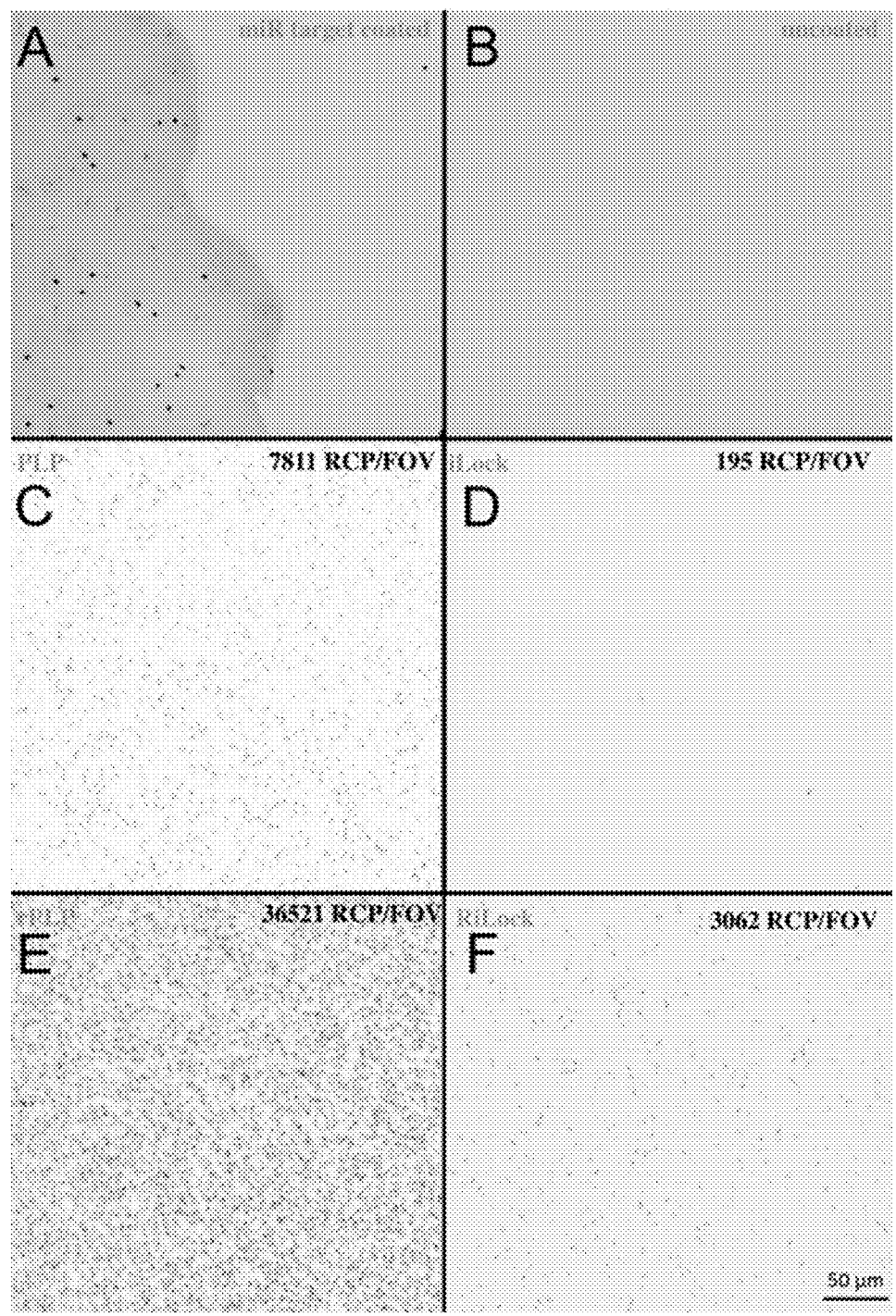

FIG. 22 shows in situ detection of miR21 RNA immobilised on a solid surface. A: miR21 was immobilised and complementary probe (labelled with fluorescent dye) was hybridised. Edge of the silicone chamber was imaged intentionally, to visualise the immobilisation effect; B) When miR21 was not added, complementary probe generated no visible fluorescence; detection of mir21 with non-chimeric PLPs (C) chimeric PLPs (E) iLock probes (D) and chimeric iLock probes (F). Number of RCPs quantified is presented as total number of RCP/field of view (FOV).

Figure 23:
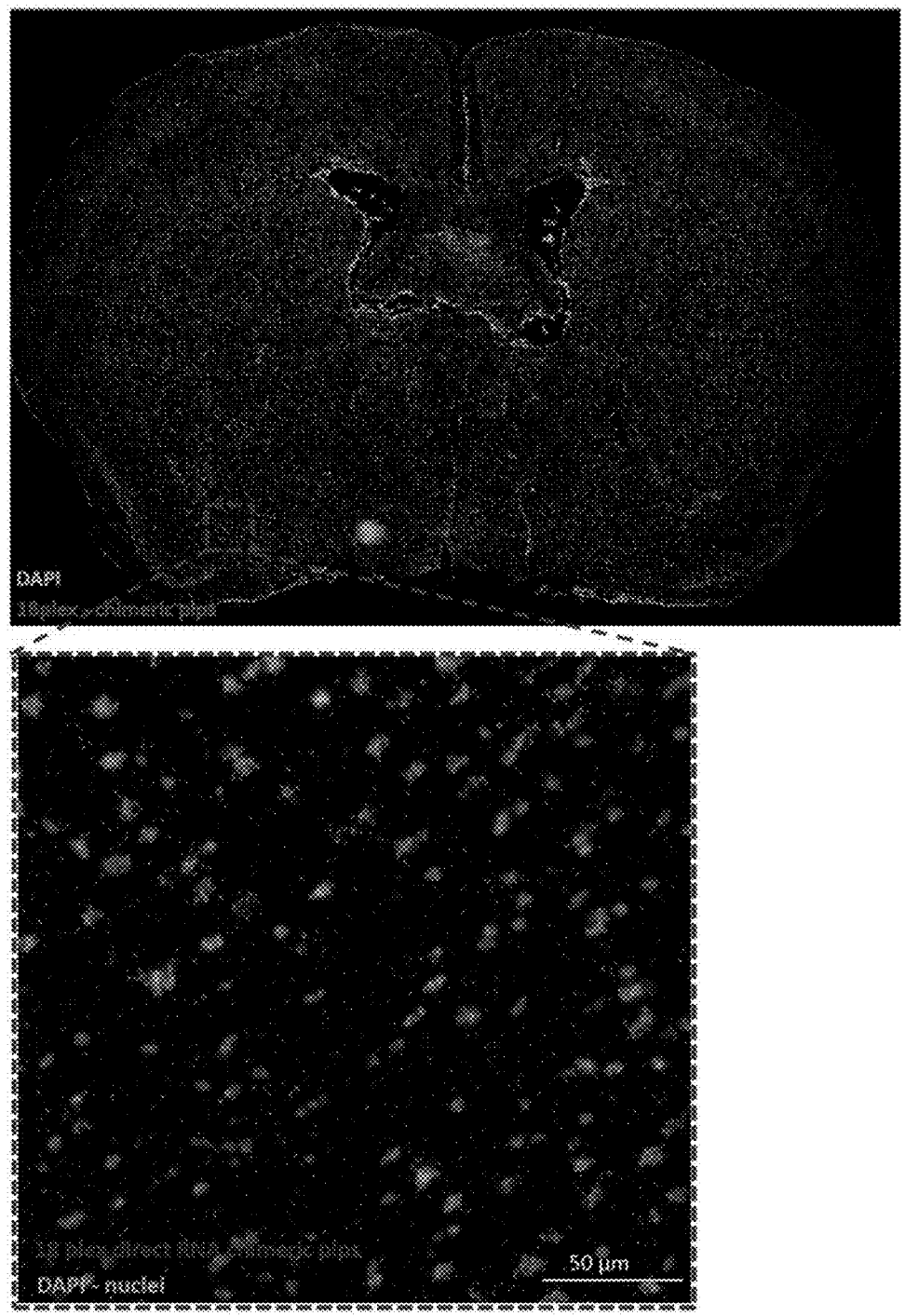

FIG. 23 shows in situ multiplexed RNA detection using chimeric padlock probes and in situ sequencing in mouse brain tissue sections. Upper panel shows an overview image of the mouse brain tissue section with nuclei stained in DAPI and the anchor probe-stained RCA products generated from chimeric PLPs targeting 18 different neuronal genes (with 5 probes per gene each=90 different probes in total). Below, an area of the left overview image where individual cells are visible.

FIGS. 24A-D show Phi29 DNA polymerase exhibits higher RCA rate with circles containing pyrimidine RNA substitutions. (FIGS. 24A-B) Real-time RCA curves of circles containing 1, 2, 3 or 4 consecutive RNA substations of rG, rU, rA, rC RNA bases are displayed (number of consecutive substitutions is indicated above plots). Rate of RCA was monitored by measuring fluorescence build-up (y-axis) resulted from SYBR Gold incorporation into RCPs. Averaged fluorescence intensity for each RCA time point was calculated from a duplicated experiment. RCA was conducted in the presence of $Mg^{2+}$ and $Mn^{2+}$ (solid and dashed lines respectively). (FIG. 24C) Linear, early stage RCA velocity (y-axis) is presented for PLPs from (A) in the presence of $Mg^{2+}$ (solid lines) and $Mn^{2+}$ (dashed lines). (FIG. 24D) RCA for the control PLP (non-chimeric DNA circle, with $Mg^{2+}$ (solid) and $Mn^{2+}$ (dashed line) are displayed.

Figure 25:
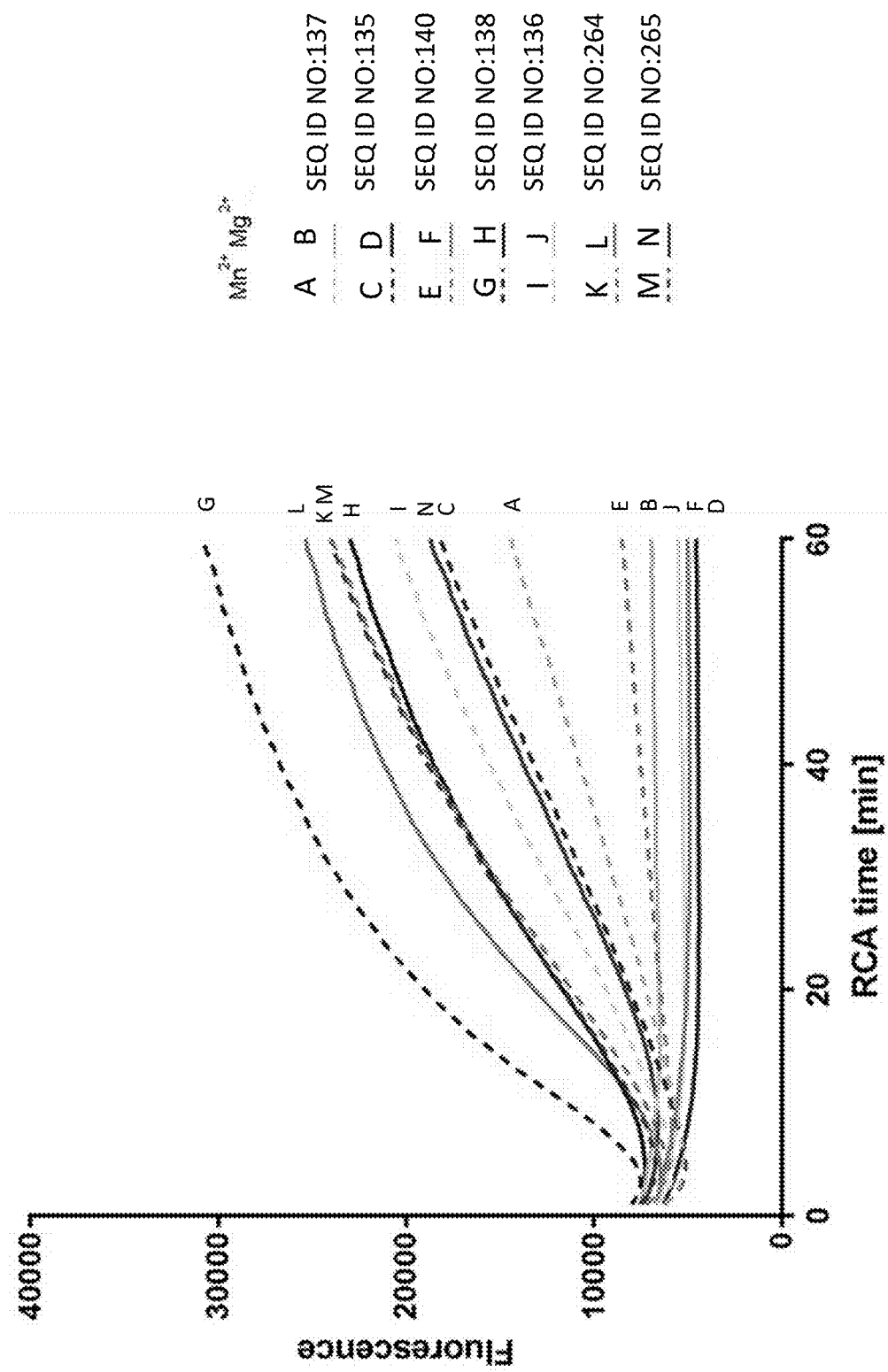

FIG. 25 shows RCA of chimeric circular substrates with RNA substitutions organised in different patterns. Rate of RCA was monitored by measuring fluorescence build-up (y-axis) resulted from SybrGold incorporation into RCPs. 4, 5 and 7 consecutive substitution (yellow, red, green); 3, 6 RNA substitutions interspaced with 1 or 2 DNA bases (blue, grey) as well as 3 and 8 RNA substitutions interspaced with larger number of DNA bases (orange, magenta) were introduced in the PLP backbone as indicated in the legend (only fragment of a backbone fragment is depicted, full PLP sequences as indicated. Averaged data from a duplicated experiment. RCA was conducted in the presence of magnesium and manganese ions (solid and dashed lines respectively).

Figure 26:
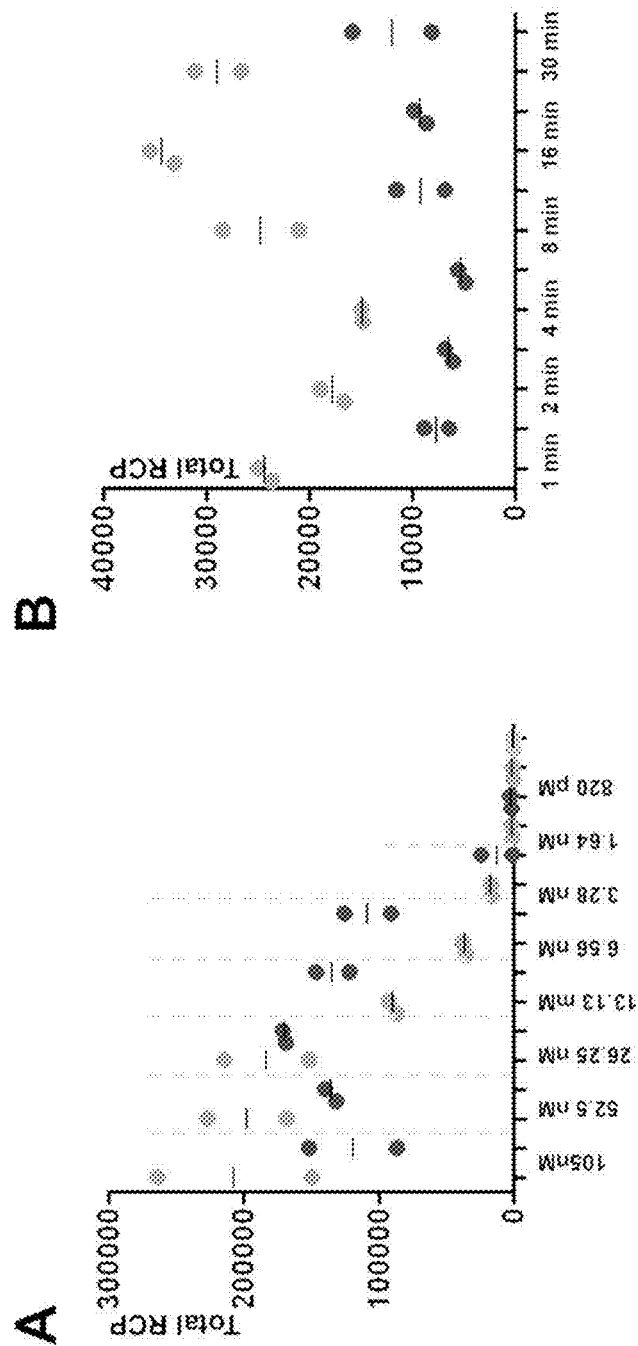

FIG. 26 shows the effect of RNA substitutions on 3'-OH (rG) and 3'-OH(G) padlock probe stability and ligation with PBCV-1 ligase on RNA. A: PBCV-1 ligase titration. Total number of RCPs (y-axis) generated for each ligase concentration (x axis) during 30 min ligation. For each time point, data for chimeric probes are shown on the left and non-chimeric probes are show on the right. B: To evaluate stability of chimeric padlock probes during first minutes of the reaction 26.5 nM (62 mU//µL) concentration was used. Ligation reaction was stopped by heat inactivating enzyme at 70° C. for 10 min. Total number of RCA products (y-axis) for given time point (x-axis) is presented.

Figure 27:
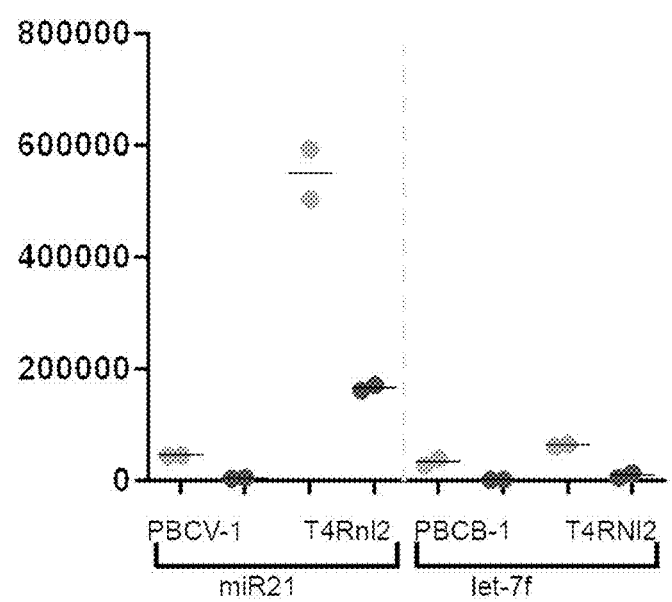

FIG. 27 shows a comparison of chimeric and non-chimeric iLock probes ligation on miR21 and let-7f using PBCV-1 and T4RnI2. Total number of RCPs for chimeric (left) or non-chimeric (right). iLock probes is presented on y-axis with PBCV-1 or T4RnI2 (x-axis). Data is presented for miR21 and let-7f RNA template.

Figure 28:
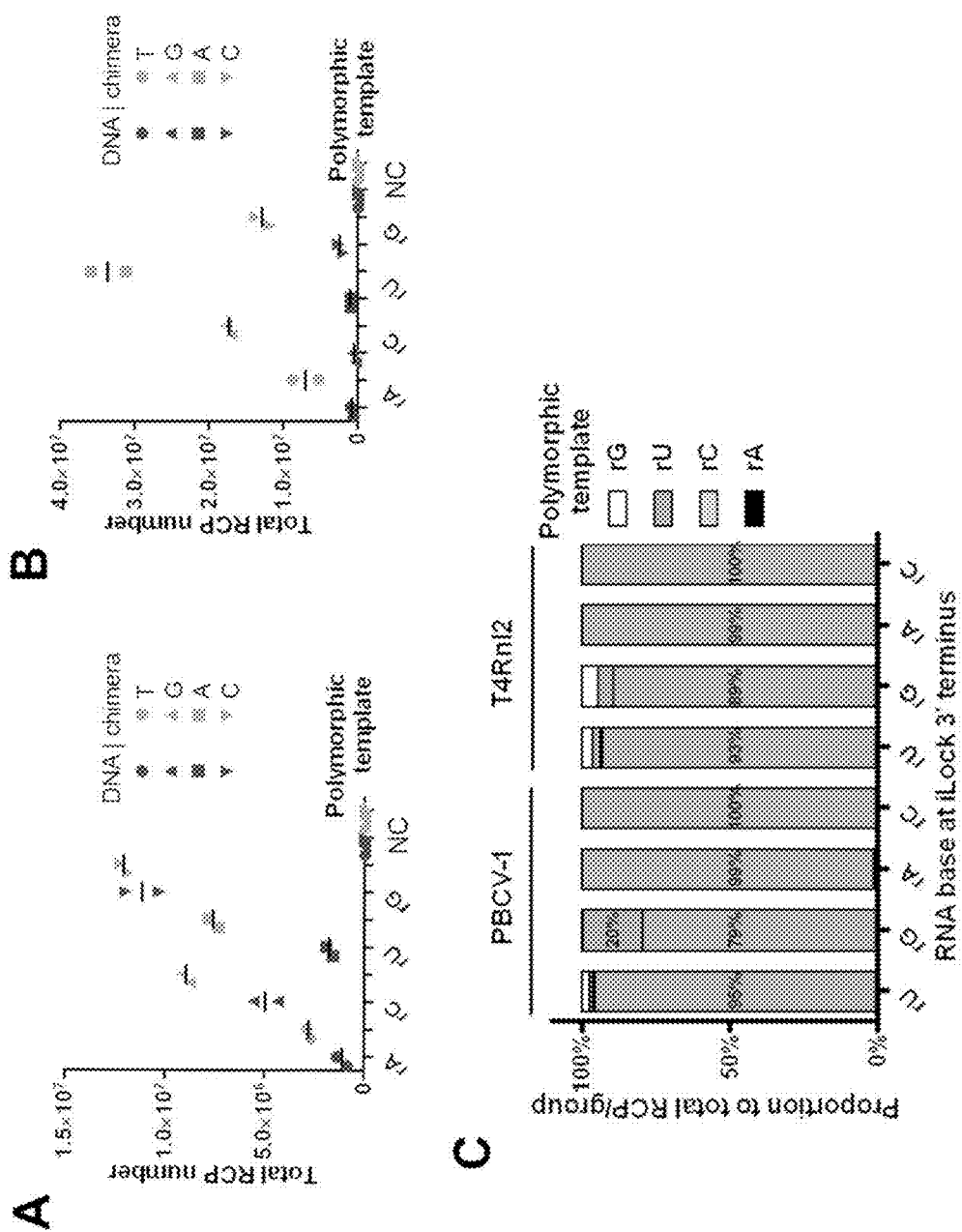

FIG. 28 shows the effect of 3'-OH(rN) mismatches on iLock activation and nick sealing fidelity for PBCV-1 and T4RnI2 ligase. A and B: Chimeric iLock-3D (left) and non-chimeric (right) iLock probes performance on polymorphic RNA targets. Total number of RCPs for each probe on matching polymorphic templates is showed on y-axis for A) PBCV-1 DNA ligase and B) T4RnI2. NC-negative control. C: Fidelity of nick sealing by PBCV-1 DNA ligase (left panel) and T4RnI2 (right panel) using 3D-type iLock probes on RNA. Numbers of RCPs for the same iLock probe on each RNA template were added and presented as percentage within an iLock probe group. Calculated proportion for the expected probe pair is highlighted.

Figure 29:
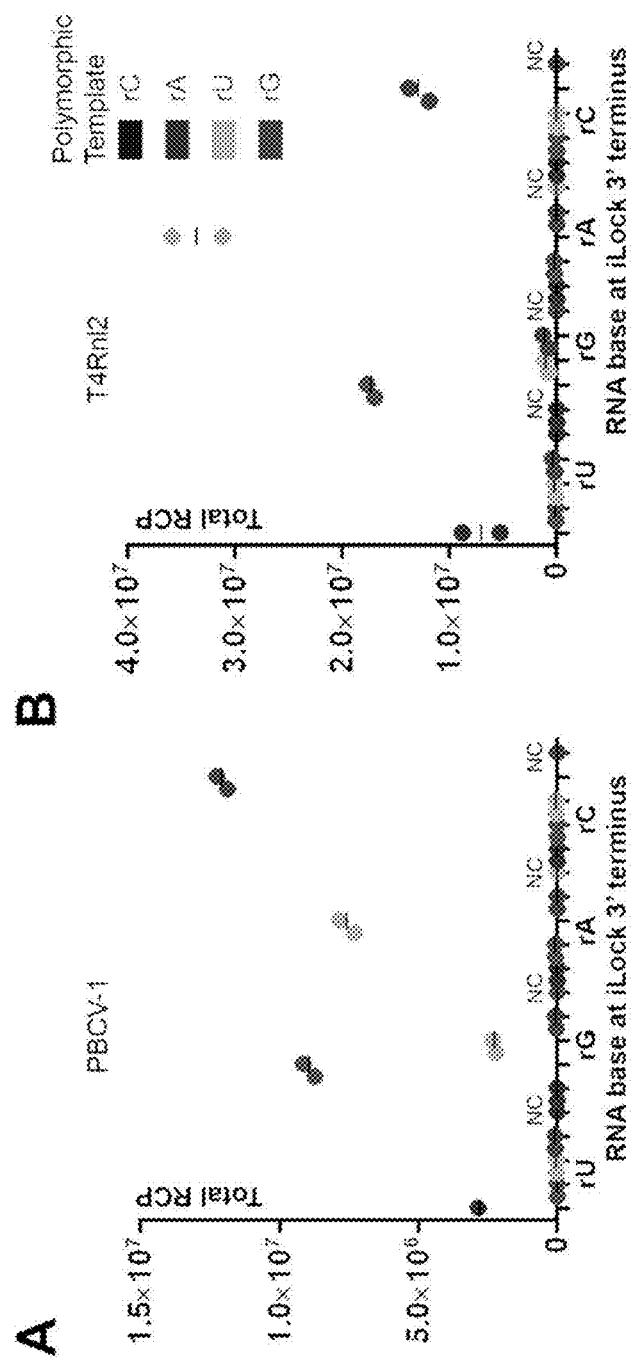

FIG. 29 shows PBCV-1 and T4RnI2 ligase chimeric iLock probes ligation efficiency and fidelity on polymorphic templates. Total number of RCPs generated and quantified (y-axis) for each iLock probe on each polymorphic template is shown in FIG. 28 for A) PBCV-1 DNA ligase and B) T4RnI2.

Figure 30:
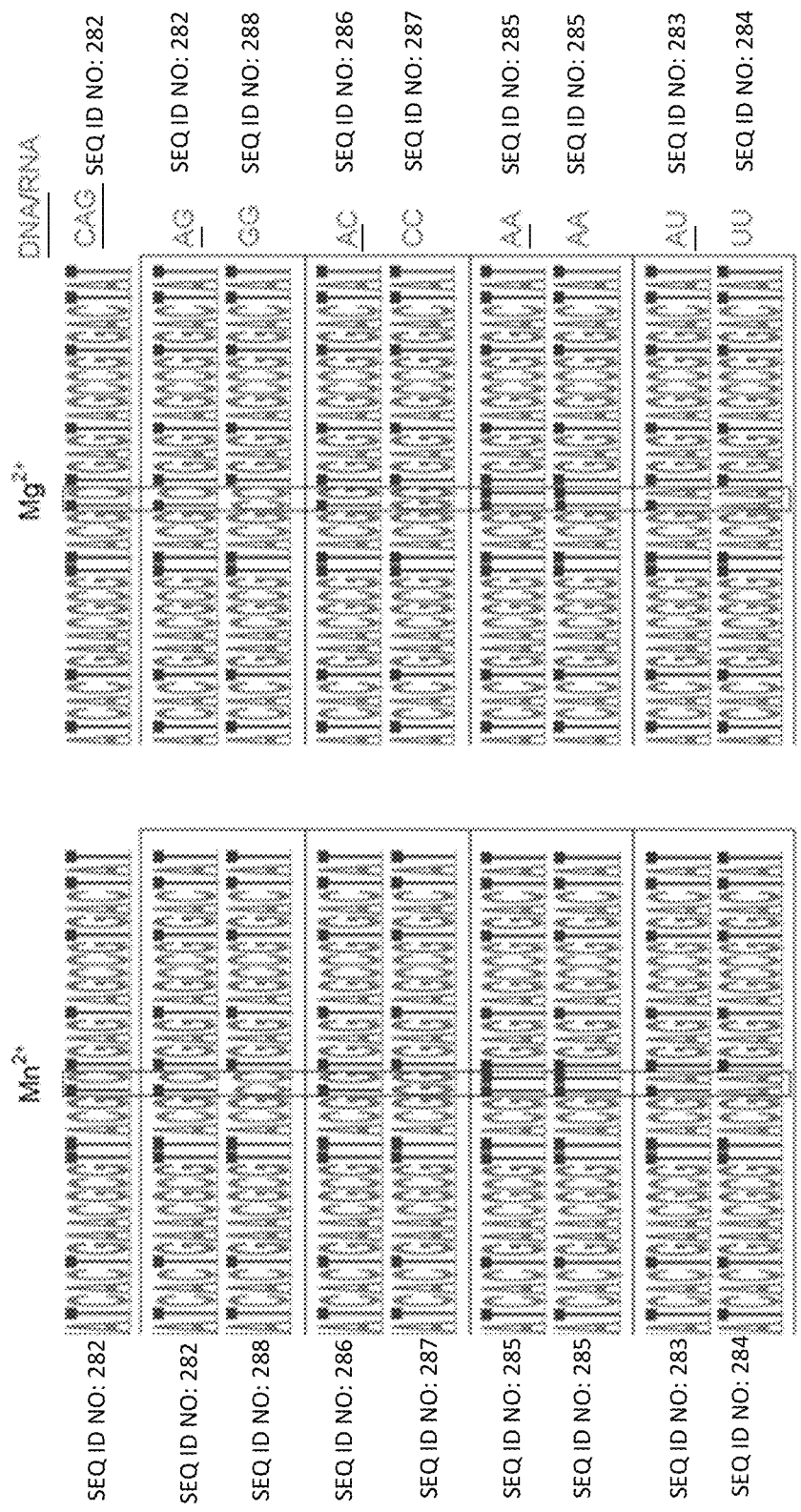

FIG. 30 shows dNTPs incorporation during RCA reverse-transcription. Padlock probes were monomerised, amplified and sequenced, as described in the Examples. Samples with single and double RNA bases were sequenced with this approach as depicted next to individual graphs. Sequencing reads were aligned and frequency of each base in every position was calculated. Size of each base is proportional to the base frequency. RCA reaction was conducted in the presence of magnesium and manganese ions as indicated above graphs. Position of RNA bases is indicated with the box. DNA/RNA sequence present originally in the PLP sequence is depicted on right-hand side.

Figure 31:
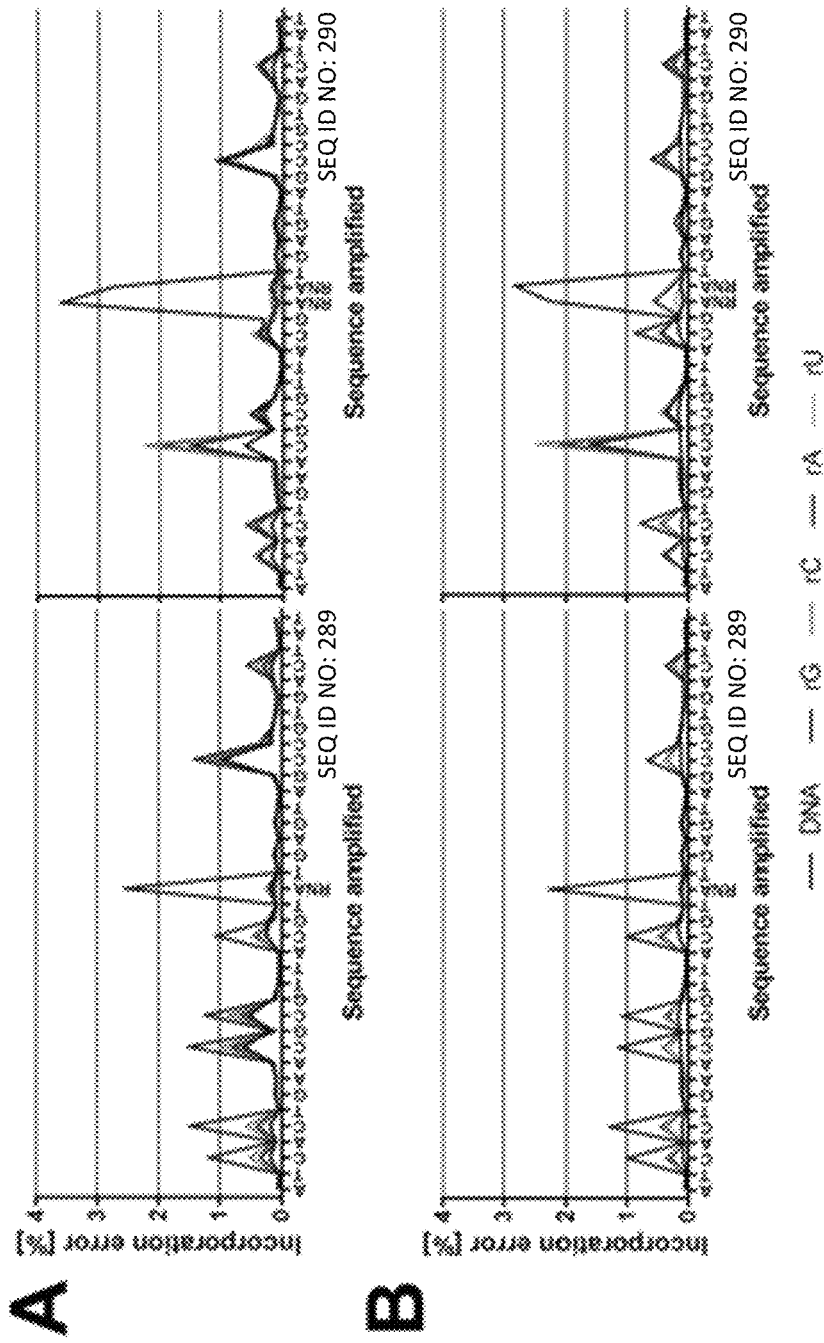

FIG. 31 shows the misincorporation rate for every position in the padlock probe backbone during RCA reverse transcription. Probability of misincorporation of unexpected nucleotide at every position for padlock probes with single- (left hand plots) and double-RNA substitutions (right hand plots) were calculated as Incorporation error [%]=1-number of reads with expected nucleotide/total number of reads. Average error (y-axis) is shown for each base of the sequenced read (x-axis) and for every sample analysed. RCA reaction was conducted in the presence of manganese (A) and magnesium (B).

Figure 32:
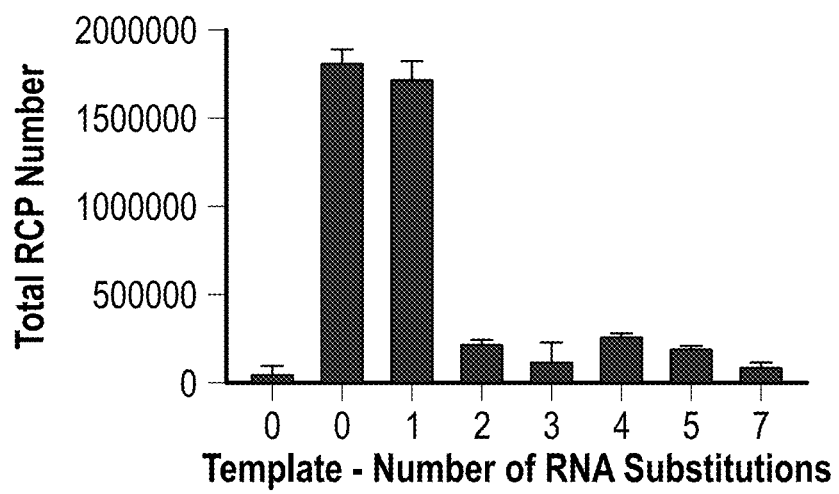
Figure 32:
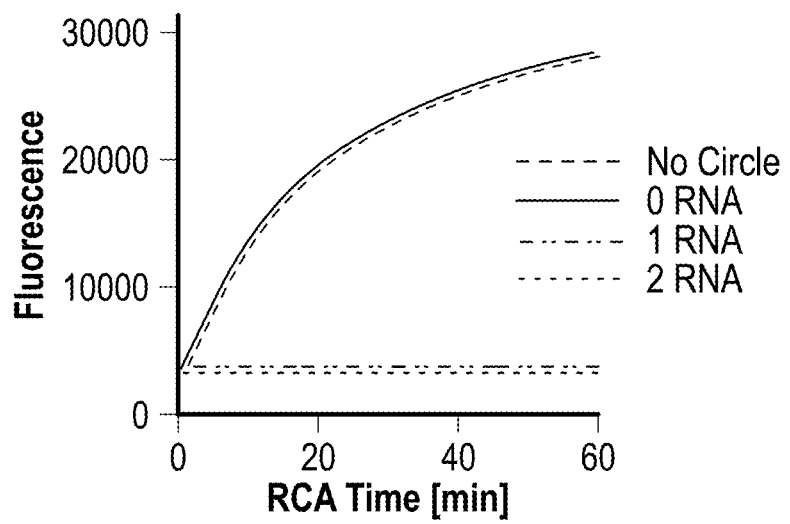
Figure 32:
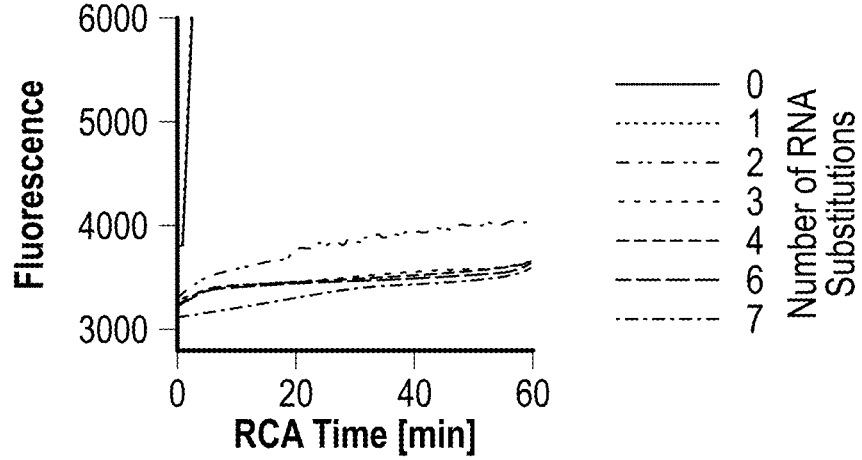

FIG. 32 shows the effect of RNA substitutions in circular templates on rolling circle amplification with phi29DNA polymerase. (A) Circles with 0-7 RNA substitutions in the backbone were amplified and digitally counted. The y-axis shows the number of rolling circle products (RCPs); error bars±S.D.; n=2. The same RCA reactions with chimeric circles were also monitored in real-time by measuring SYBR Gold incorporation on qPCR instrument (B and C). (B) RCA reaction curves of circles with 0, 1 and 2 RNA substitutions. (C) Real-time data of the same RCA reactions as in B with 0-7 RNA substitutes are displayed. Representative samples are presented from a duplicated experiment. To highlight the initial stages of RCA and to show the difference between the samples with low RCA efficiency, fluorescence intensity readout between 3000 and 6000 is presented.

Figure 33:
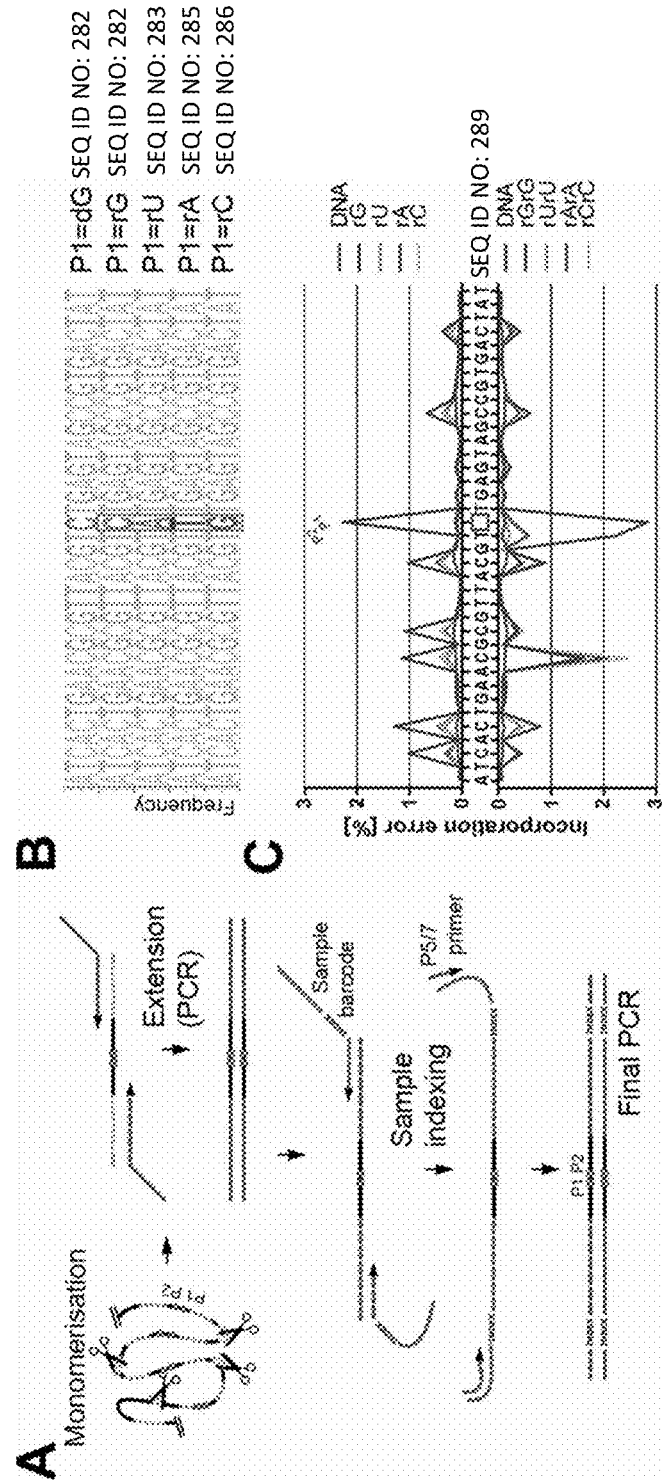

FIG. 33 shows DNA sequencing-based analysis of rolling circle products reveals reverse transcription activity of phi29 DNA polymerase. (A) After RCA, short DNA oligonucleotides were hybridized to an AluI restriction site in the RCA products and RCPs were digested with AluI restriction enzyme, resulting in RCA monomers. Following digestion, monomers were PCR-amplified using primers containing Ilumina adapter sequences. PCR products were extended using Illumina indexed primers. Finally, sequencing library was prepared using indexed primers-specific P5/7 PCR primers. The region of interest containing RNA substitutions in the original padlock probe sequence is indicated with green boxes. (B) Logos showing sequencing frequencies for each position within RCA monomers generated from the control DNA circle (P1=dG), and circles containing single rG, rU, rA and rC substitutions at the RNA position (P1). Positions P1 and P2 are indicated and position P1 was additionally highlighted with the red box. (C) Incorporation of incorrect nucleotides for every position in the sequenced monomers from (B). Error rates, calculated as Incorporation error [%]=1−number of reads with expected nucleotide/total number of reads, is presented for padlock probes with single-(upper plot) and double-RNA substitutions (lower plots). P1 position for the first RNA substitution is indicated with the box.

EXAMPLES

Example 1—Detection of miRNAs Using Chimeric DNA/RNA iLock Probes Utilizing Novel Activity of PBCV-1 DNA Ligase: RNA-Templated Ligation of ssRNA Material and Methods
Oligonucleotides Used in the Study All oligonucleotides used were purchased from IDT (Integrated DNA Technologies, Inc., Coralville, IA, USA) using following synthesis and purification conditions: DNA padlock probes and iLock probes: 4 nM of standard desalted Ultramer® DNA oligonucleotides; chimeric padlock and iLock probes: 4 nM of standard desalted Ultramer® RNA oligonucleotides; decorator probes: HPLC purified DNA oligonucleotides with 5' conjugated fluorophore. All padlock probes were pre-phosphorylated on the 5' terminus to permit ligation. RNA templates harbouring centrally located polymorphic site are shown in Table 1 (benchmark oligonucleotides) with the polymorphism indicated with an asterisk.

Padlock probes were designed, such that terminal arms would form a nicked circle when base paired with attended RNA targets and discriminatory base was localized at the 3' terminus of the probe (table 1). miRNA padlock probes used in this study are shown in table 1. Chimeric padlock probes were ordered with a terminal 3'-OH RNA. iLock probes were used in the present work for comparative purposes (table 2). Standardized chimeric iLock probes design includes RNA substitution on the terminal 3' base as well as a base in the 5' arm that 3' terminal base was competing for target binding with (displaced base, FIG. 4A, table 2). Two types of probe barcoding methods were used: traditional and compatible with sequencing-by-ligation read-out (used in chimeric, miRNA targeting iLock probes). For traditional rolling circle product (RCP) staining and digital quantitation, a reporter sequence was embedded in the sequence linking the probe arms, separated from probe arms with series of 10 adenines (table 2). For the latter, a consensus backbone with unique probe-specific barcode was used (table 3). To allow barcode decoding, common anchoring primer sequence was embedded in the probe backbone, followed by two-bases barcode and a sequencing library anchoring sequence (table 3).

RNA Detection Assay and Digital Quantitation of Amplified iLock and Padlock Probes iLock activation (cleavage) was performed in 4:1 probe to template excess (typically, 2 nM iLock probe was mixed with 0.5 nM RNA template). Duplicate reactions were incubated in a heated-lid thermocycler at 51° C. for 30 min, in a 10 μL volume containing 1 U of Taq DNA polymerase (ThermoFisher Scientific), 4 U RNaseiInhibitor and 1×Taq polymerase buffer supplied with 8 mM MgCl2. Next, 3 μL of sample volume was transferred to a ligation reaction mix supplemented with 3.75 U of PBCV-1 DNA ligase (SplintR, M0375S, NEB) or 4 U of T4RnI2 (M0239S, NEB) in respective buffers in a final volume of 15 μL. The reactions were incubated at 37° C. for 30 min. For padlock probes, identical ligation conditions were applied, excluding the activation step. For RCA, 5 μL of the ligation reaction was incubated with 10 nmole decorator probe, 0.125 mM dNTPs, 0.2 μg/μl BSA, 250 mU of Phi29 Polymerase (Monserate Biotechnology Group) and 1×phi29 reaction buffer (Thermo Fisher) in a final volume of 25 μl at 37° C. for 60 minutes. The polymerase was heat inactivated at 65° C. for 3 minutes and allowed to cool to room temperature. Estimated final concentration of amplified products was 5 pM and 20 pM for padlock and iLock probes respectively, unless stated otherwise. 15 μl of the RCA sample were analysed using the Aquila 400 Detection Unit (Q-linea, Uppsala). If RCPs concentration was outside the instrument's dynamic range, samples were diluted in 4 nM of the decorator probe in 1× labelling solution (20 mM EDTA, 20 mM Tris-HCl (pH 7.5), 0.05% Tween 20 and 1 M NaCl), incubated at 65° C. for 3 min, allowed to cool at room temperature for 15 min and recounted. Template-negative reactions were run in parallel with every experiment as a control.

Multiplexed miRNA Detection Using Chimeric iLock Probes and Sequencing-by Ligation To test if chimeric iLock probes could be used to detect miRNA expression variation in RNA mixtures, we have combined (let-7f):(let-7e):(let-7d) miRNAs in (1):(1):(1), (3):(1):(1), (1):(3):(1) and (1):(1):(3) ratios. Baseline miRNA concentration during iLock activation step was 0.5 nM and 1.5 nM for samples where miRNA concentration was increased. 2 nM cocktail of let-7f, let-7e, let-7d chimeric iLock probes was used, each embedded with a unique two-nucleotide barcode (table 3) and sequencing-by-ligation chemistry sequences. Protocol was conducted as described above (using PBCV-1 ligase) except that 10 μL droplets of RCA products were spotted on positively charged microscope slides (Superfrost Plus, Menzel Glaser) and evaporated at 55° C. for 10 min. 50 μL volume silicone chamber (Secure-Seal hybridization chamber, Sigma) was mounted over each droplet and samples were washed 3× with 1×TBS. 0.5 μM anchor primer was hybridised in 2×SSC, 20% formamide at room temperature for 30 min. Followed by 3× washes with 1×TBS, RCPs were mixed with sequencing mixture, containing 1×T4 DNA Ligase buffer, 10 μg BSA, 1 mM ATP, 0.1 μM sequencing oligonucleotides (table 3) and 5 U of T4 DNA Ligase. Slides were incubated at room temperature for 60 min. After 3× washes with 1×TBS, silicone chambers were removed, slides rinsed with 100% ETOH, air-dried and mounted (SlowFade antifade, ThermoFisher). Images of RCPs were acquired using 20× objective.

To visualise activation and ligation efficiency of various chimeric iLock probes (table 2) products were separated electrophoretically. 5 μM synthetic RNA and 2.5 μM probe were processed as above. Following the ligation, 50 nM of sample was diluted in Novex® TBE-Urea Sample Buffer (LC6876, ThermoFisher Scientific) to a final volume of 12 μL. Samples were denatured at 70° C. for 3 min, placed on ice for min, 10 μL was loaded onto 15% Novex® TBE-Urea Gel (EC6885BOX, ThermoFisher Scientific) and separated in XCell SureLock™ Mini-Cell Electrophoresis System (ThermoFisher Scientific) using PowerPac Basic Power Supply (Bio-Rad) for ~90 min at 170V. Gels were stained using 1× SybrGold (S11194, Invitrogen) in 1×TBE running buffer for 15 min followed by imaging in Gel Doc XR System (Bio-Rad). In chimeric probes binding assay, concentrations of template and padlock probes as stated above were incubated with 62 mU/µL PBCV-1 DNA ligase and 0.4 U/µL RNaseinhibitor at room temperature for 10 minutes. Reactions were stopped by adding 1 µL 0.5 M EDTA and 5 µL 100 formamide.

Results

Figure 14:
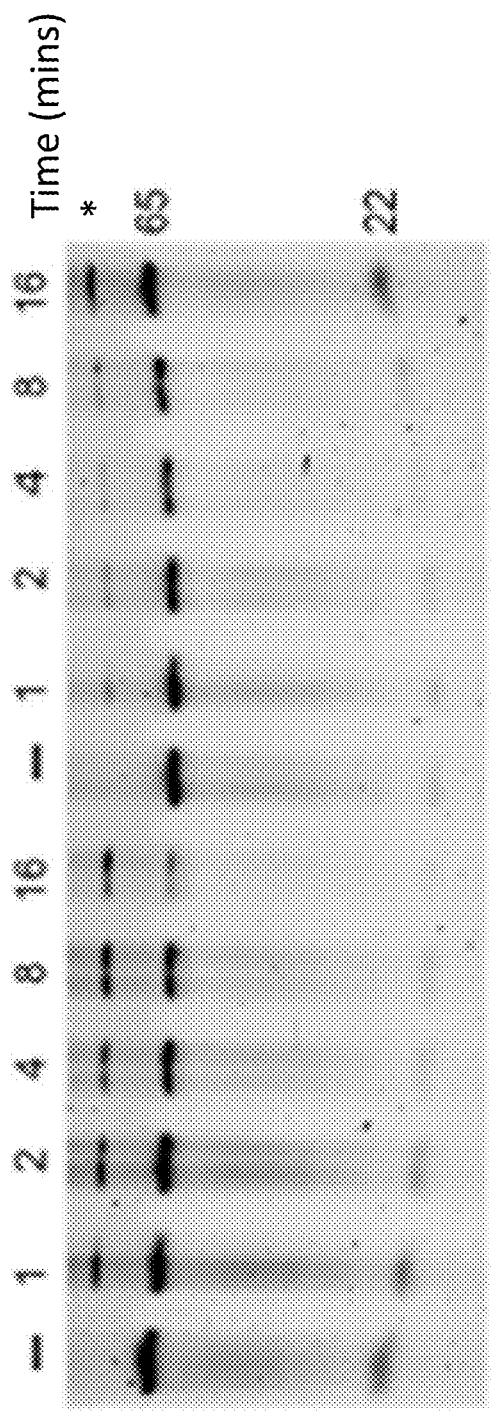
Figure 15:
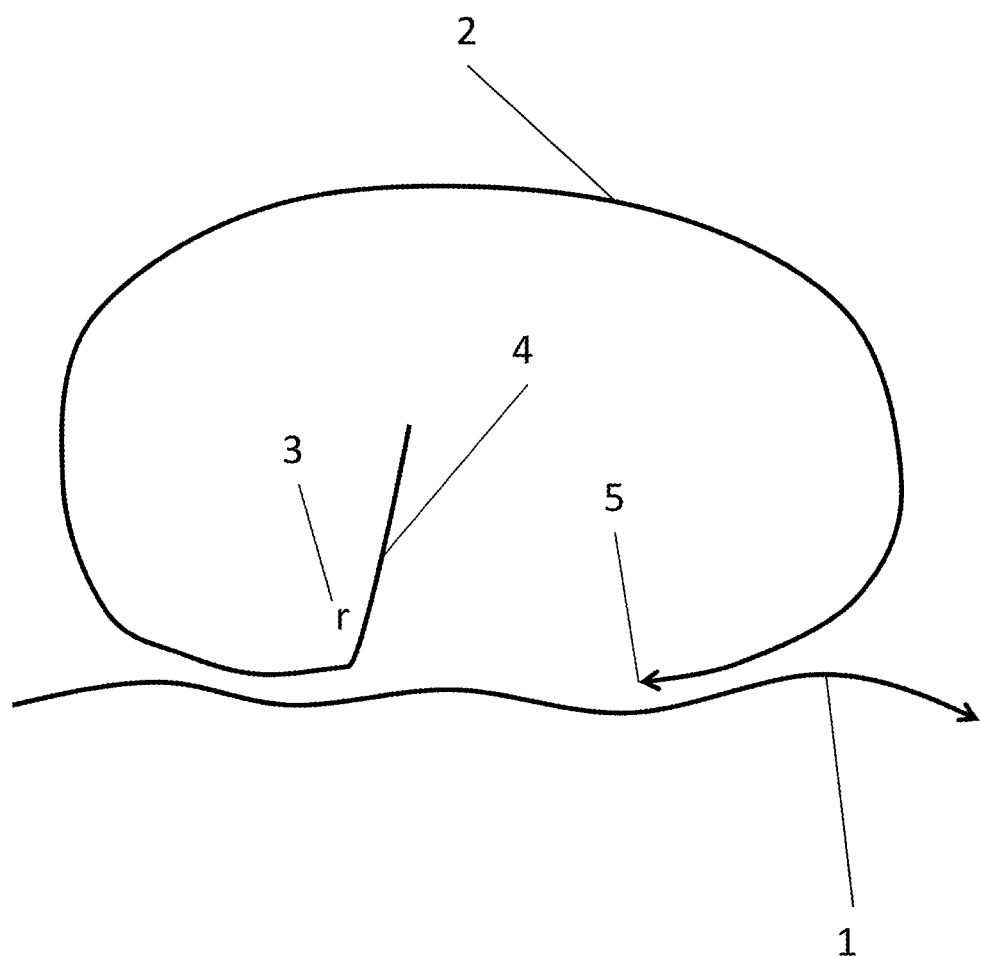
FIG. 15 shows a gap-fill padlock probe (2) comprising a ribonucleotide (3) at the 3' end of a 5' additional sequence (4), which is cleaved prior to ligation. A 3' end of the probe (5) hybridised to the target nucleic acid molecule (1) may be extended by gap-fill polymerisation.
Figure 16:
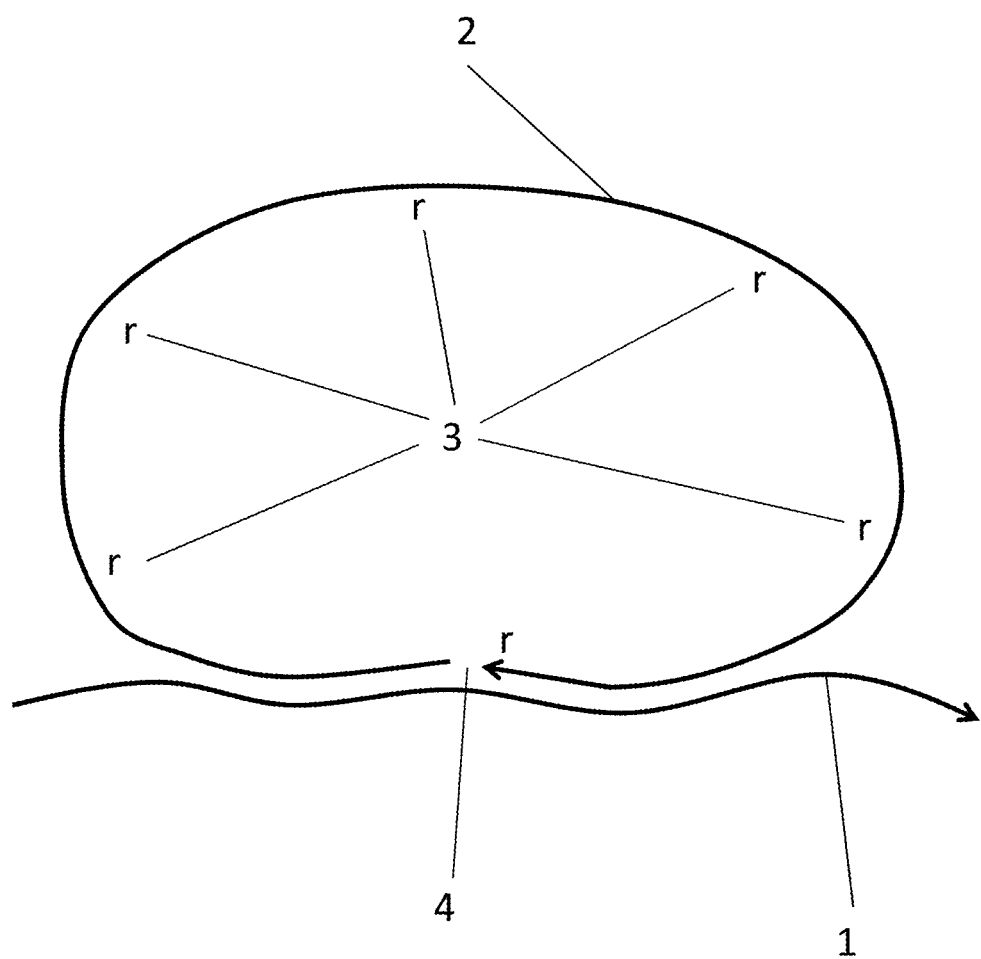
FIG. 16 shows a padlock probe (2), which comprising ribonucleotides (3) at positions other than at or near to a ligation site (4) hybridised to a target nucleic acid molecule (1).
Figure 17:
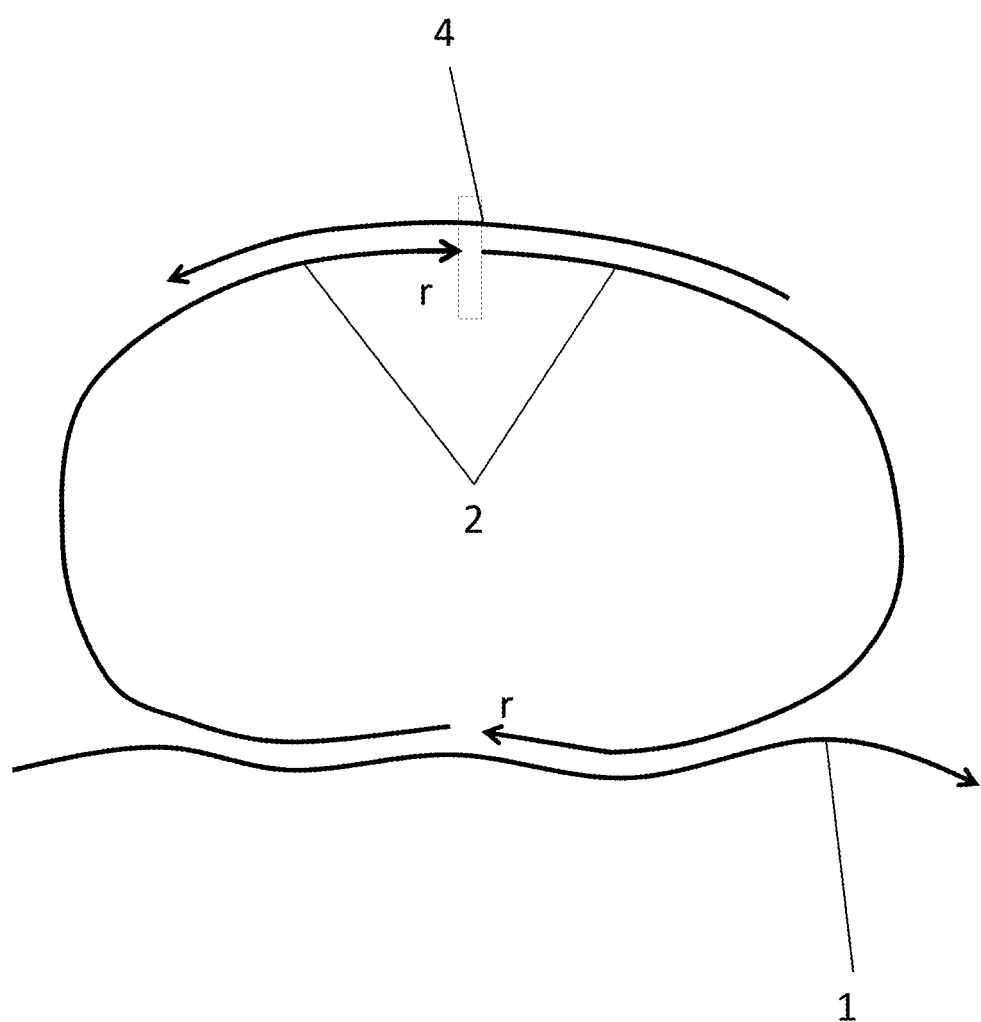
FIG. 17 shows a padlock probe (2) comprising a backbone oligonucleotide provided in two parts, and a ligation template (4) which hybridises to each part of the backbone oligonucleotide in order to template ligation. As shown, the nucleotide at the 3' ligatable end in this ligation site is a ribonucleotide.

Effect of 3'-OH RNA on PBCV-1 DNA Ligase RNA-Dependent Ligation: RNA End Joining for Different RNA Substrates We compared the ability of PBCV-1 ligase to circularize padlock probes hybridised to let-7a, where the 5' end of the probe is DNA, and the 3' end was either DNA or RNA. While the ability of T4RnI2 to join chimeric 3' RNA acceptor strands with 5' donor strands on RNA is well characterised, this has only been demonstrated for PBCV-1 DNA ligase on DNA templates. We compared the ligation efficiency of chimeric padlock probes versus DNA padlocks probes over reaction time by PAGE separation (FIG. 14). Moreover, we measured the ligation efficiency as total number of rolling circle amplification products (RCP), digitally counted for each padlock/template pair (FIG. 1A).

Figure 1:
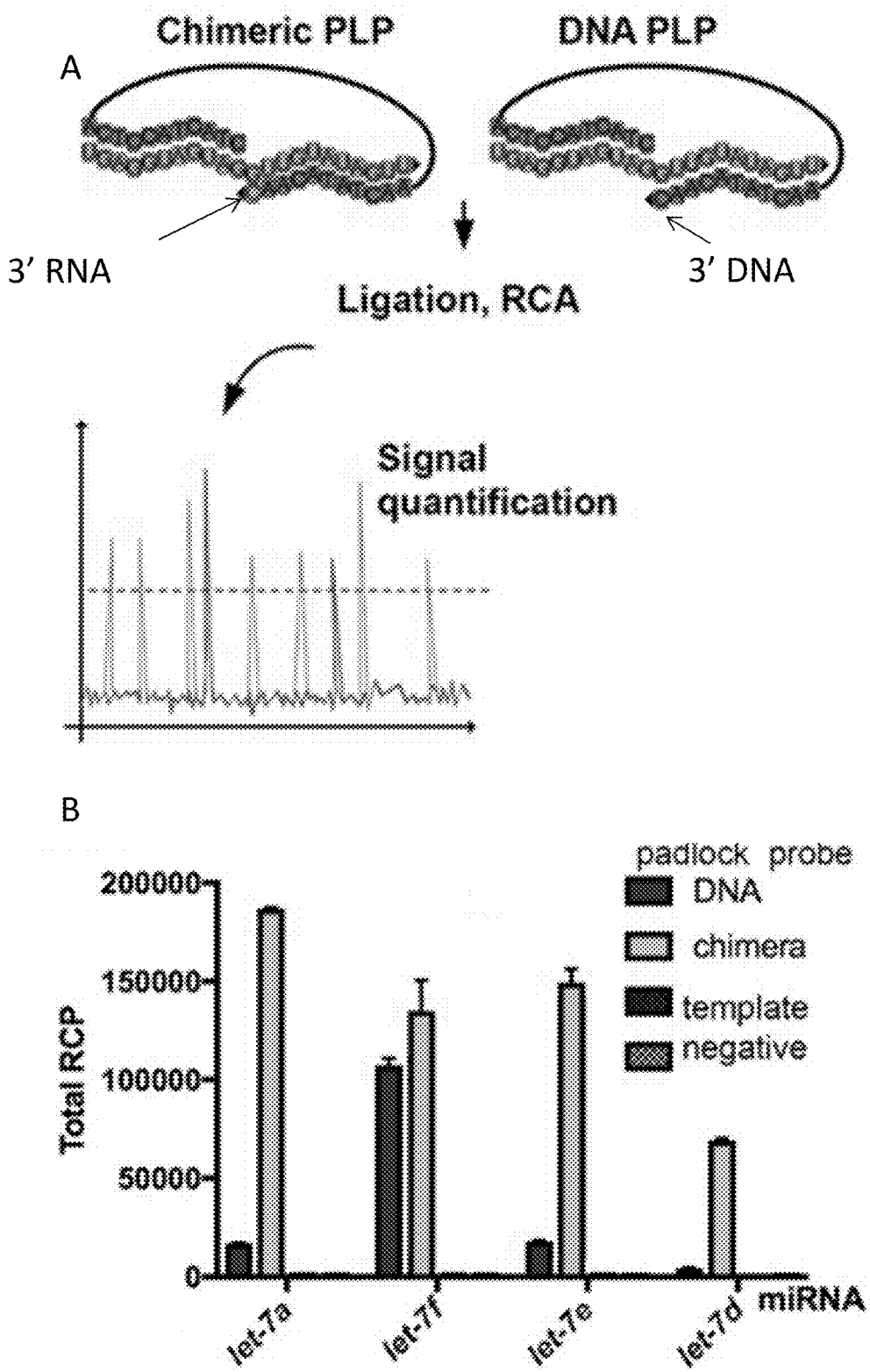
Figure 2:
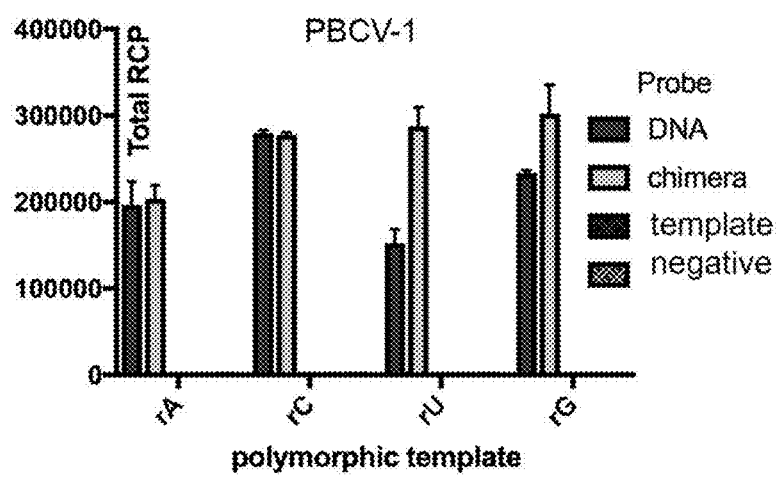
Figure 2:
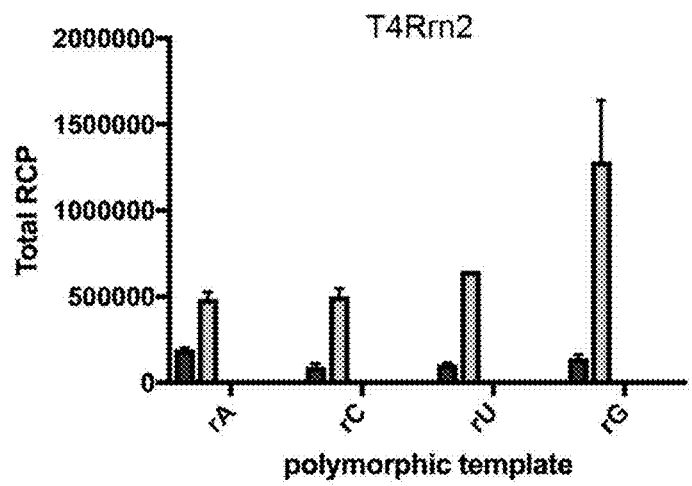
Figure 3:
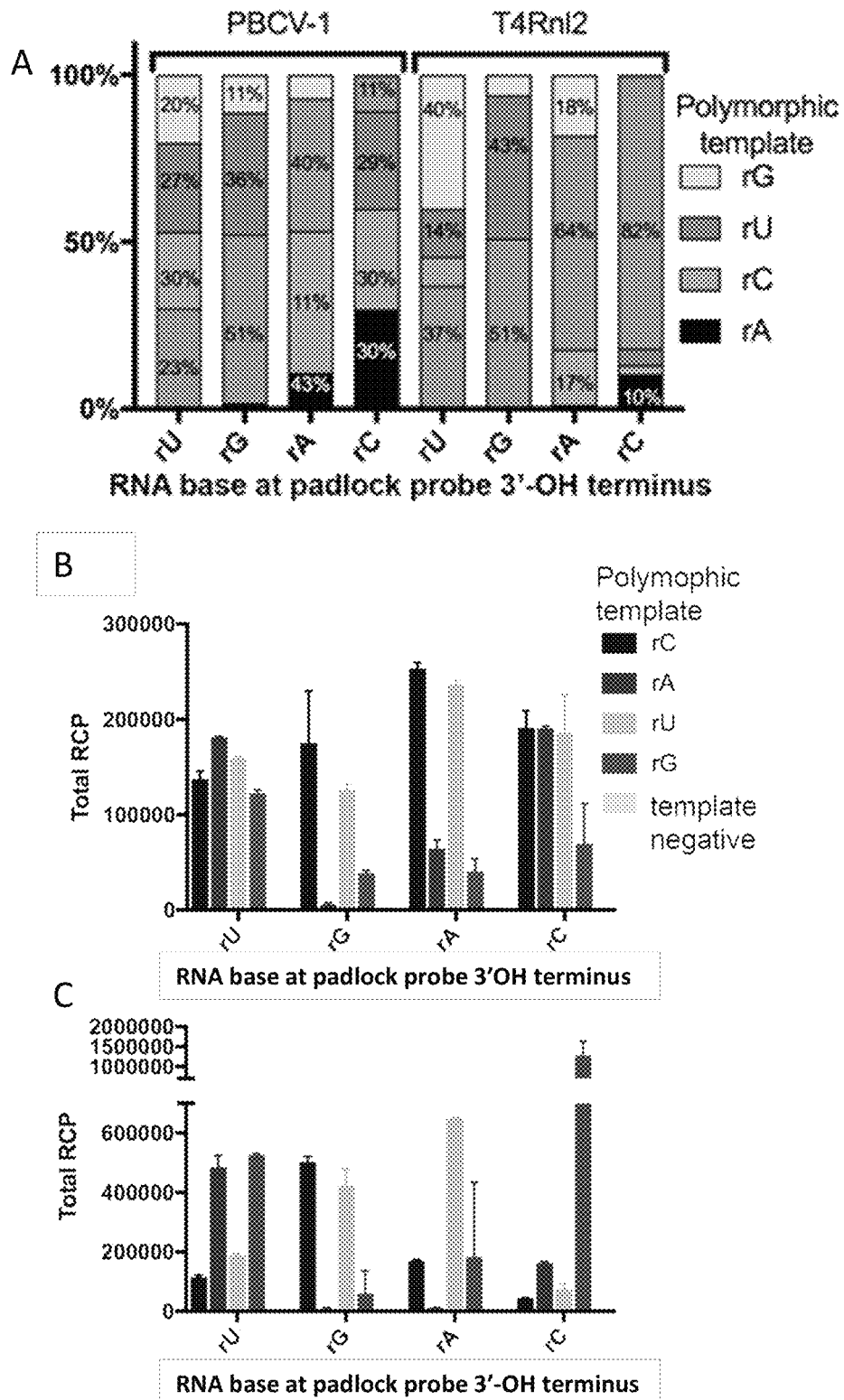

PBCV-1 ligase catalysed highly efficient end-joining when 3' RNA containing PLPs were ligated on miRNA targets (FIG. 1B). For longer non-miRNA targets, ligation efficiency of chimeric and non-chimeric probes was similar (FIG. 2A). Since presence of RNA results in greater nucleic acid duplexes stability, we hypothesised that more stable duplexes would be ligated faster during the initial reaction stage. T4RnI2 efficiently ligated chimeric padlock probes, while relatively lower activity was seen for DNA padlock probes (FIG. 2B). Our finding that PBCV-1 readily accepts chimeric padlock probes as substrates, motivated us to systematically characterise the ligation fidelity on synthetic targets having a polymorphic position in the centrally located nucleotide (FIG. 3 and table 1). To measure the effect of mismatched chimeric substrates on PBCV-1 and T4RnI2 ligase end-joining activity, four chimeric padlock probes, differing with a terminal 3' nucleotide (rA, rU, rG, rC,), were hybridised with four different RNA targets each, ligated and amplified with RCA (FIG. 3). PBCV-1 ligase was highly tolerant towards most 3' RNA mismatches (FIG. 3A, 3B). T4RnI2 on the other hand, was moderately accurate ligating rC/rG (82%) and rA/rC (64%) but showed poor end-joining fidelity towards other combinations (FIG. 3A, 3C).

Effect of Various RNA Substitutions on RNA Templated iLock Probe Activation, Ligation Efficiency and Fidelity for PBCV-1 as Well as T4RnI2

Figure 4:
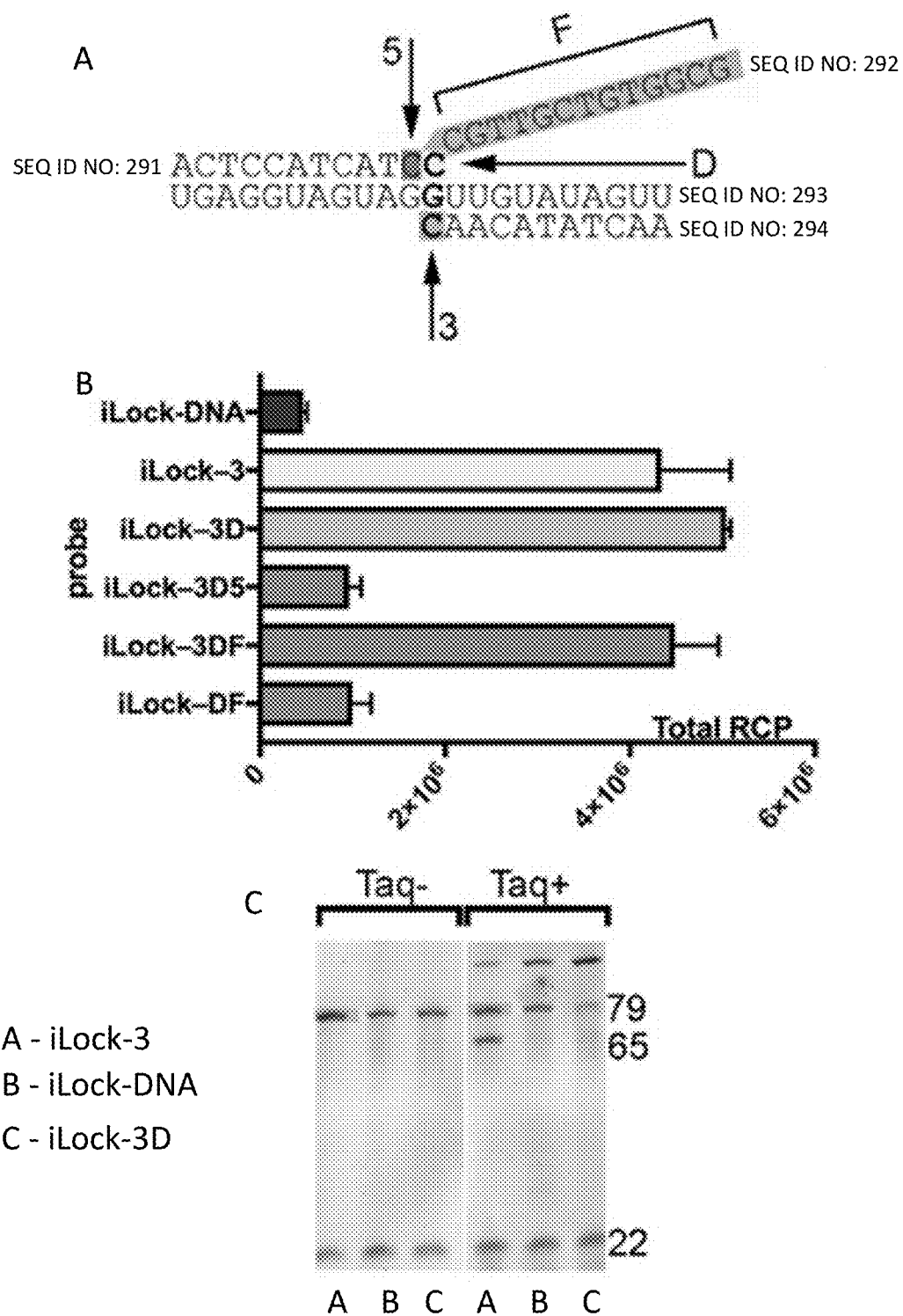

In our previous study, we have utilized structure-specific 5' flap cleavage activity of Taq DNA polymerase, used in the invader assay, to activate padlock probe molecules for ligation. We have shown that this iLock probe assay increases ligase-based RNA detection fidelity (Krzywkowski supra). As PBCV-1 ligase was fairly tolerant for majority of the chimeric 3' mismatches tested, we tested how presence of RNA substitutions in various position of an iLock probe will affect probe activation and ligation, compared to a DNA iLock probe. Multiple iLock probes, targeting let-7a miRNA, were designed (table 2), containing RNA substitutions in various probe positions (FIG. 4A). One chimeric probe (called "3") had the RNA substitution at the 3' terminus. In the "3D" probe, the terminal 3' and the displaced base of the 5' flap was substituted with RNA. The "3D5" probe had in addition to the substitutions in the "3D" probe, an additional RNA base at the position 3' to the "D" position. This RNA base would become the 5'-phosphate donor end in a ligation reaction after successful iLock activation. Lastly, we designed a probe with the terminal 3' and the complete 5' flap as RNA bases ("3DF"), and a probe where only the 5' flap was composed of RNA ("DF") (i.e. lacking the 3' RNA).

Figure 5:
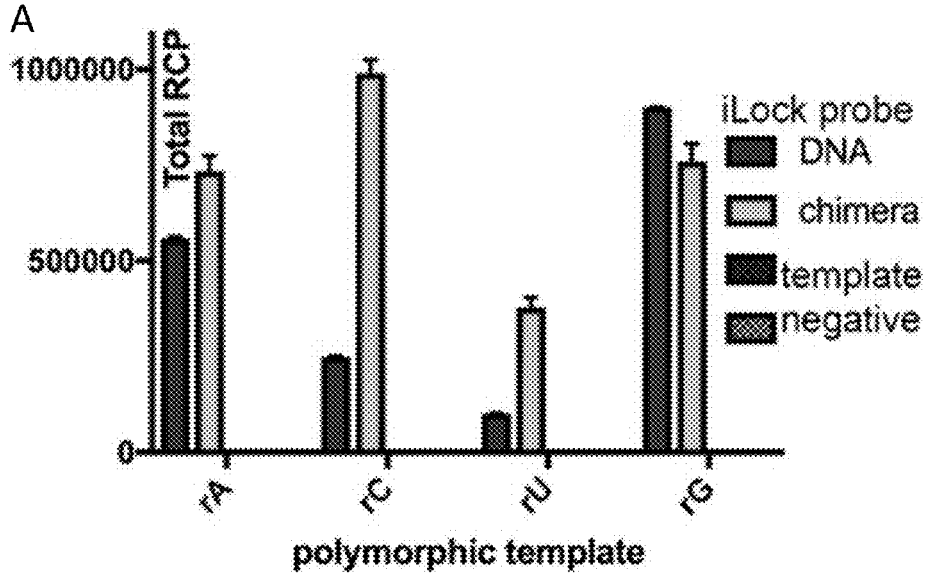
Figure 5:
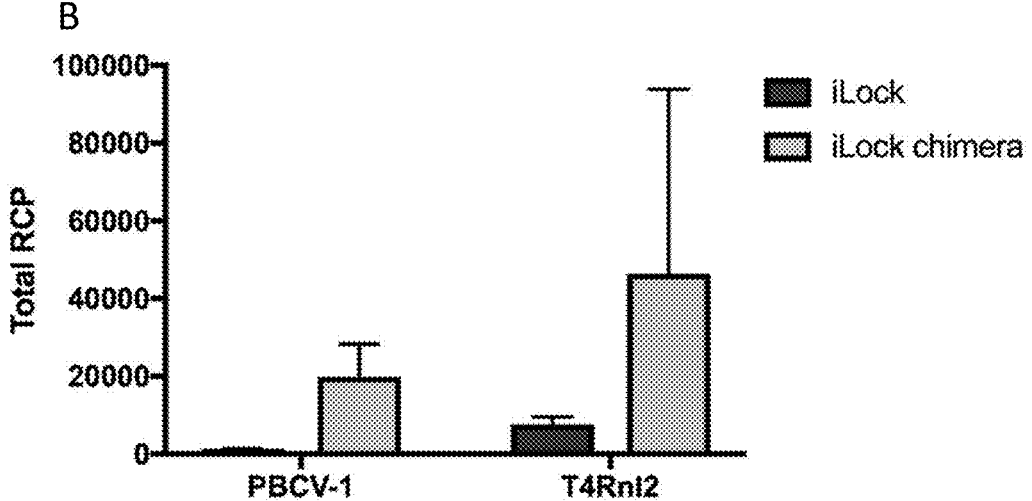
Figure 6:
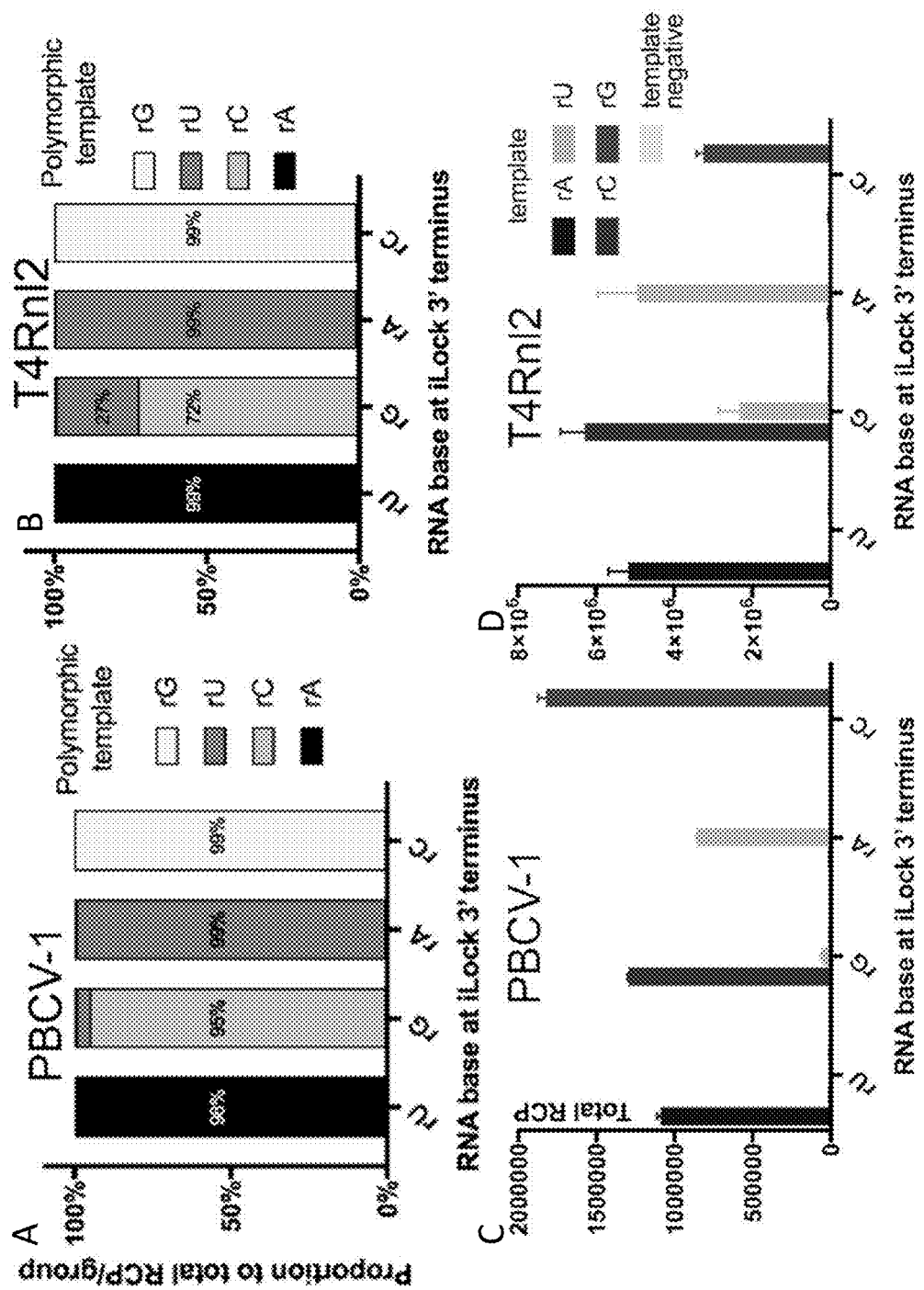

Compared to a non-chimeric let-7a iLock, iLock-3 greatly increased detection of let-7a miRNA. According to PAGE of ligated iLock probes (FIG. 4C), only a fraction of non-chimeric iLock probes was activated (cleaved) at given conditions and even smaller fraction was ligated (FIG. 4C, lane 4). Virtually all activated iLock-3 probes became ligated as evident by a quantitative gel-shift in the FIG. 4C (lane 5), as well as the total number of RCA products generated with iLock-3 probe (FIG. 4B). When the flap nucleotide displaced by an invading terminal 3' RNA was substituted with RNA, as in iLock-3D, an additional efficiency increase was observed. The majority of iLock-3D was activated and ligated (FIG. 4C). A similar effect was observed for the iLock-3DF probe, where whole 5' flap sequence was RNA, while the positive effect was lost in the absence of a terminal 3' RNA base (FIG. 4B). Interestingly, iLock-3D5 probe, containing 3'-(rN)/5'-(rN) after activation, showed significantly lower performance than an iLock probe with a deoxyribonucleotide at the (5) position. Significantly increased performance of iLock-3D probes was observed for other miRNAs we have tested (miR21) using both PBCV-1 and T4RnI2 ligase (FIG. 5). Similarly, in a repeated experiment with other iLock-3D probes increased performance was also observed using let-7f as a template, for both PBCV-1 and T4RnI2 (FIG. 27). To test if accuracy of RNA sensing with chimeric iLock-3D probes is maintained, we targeted the four polymorphic RNA templates (table 2) with four chimeric iLocks-3D probes. Chimeric iLock probes showed excellent fidelity towards matching rC/rG, rA/rU and rU/rA probe pairs (FIG. 6). iLock-3D probes showed no ligation products when templates were omitted. T4RnI2 displayed full compatibility with the iLock RNA detection assay, readily ligating targets-matching 3'-OH(rN)/5'-p(N) iLock probes (FIG. 6B). rG/rC pair was detected with relatively lower fidelity for both PBCV-1 and T4RN12, showing rG/rU mis-ligation of 5% and 27% respectively (FIG. 6A, 6B). In a further experiment, both PBCV-1 and T4RnI2 displayed full compatibility with the iLock RNA detection assay, readily ligating targets matching 3'-OH(rN)/5'-p(n) iLock probes (FIGS. 28A-B, FIG. 29, A-B). rG/rC pair was detected with relatively lower fidelity for both enzymes, showing rG/rU mis-ligation of 21% and 11%, respectively. Thus, as can be seen from FIG. 28A-B, chimeric ilocks have better performance than DNA ilocks.

Multiplexed Detection of Let-7 Isoforms Using Chimeric iLock Probes

Figure 7:
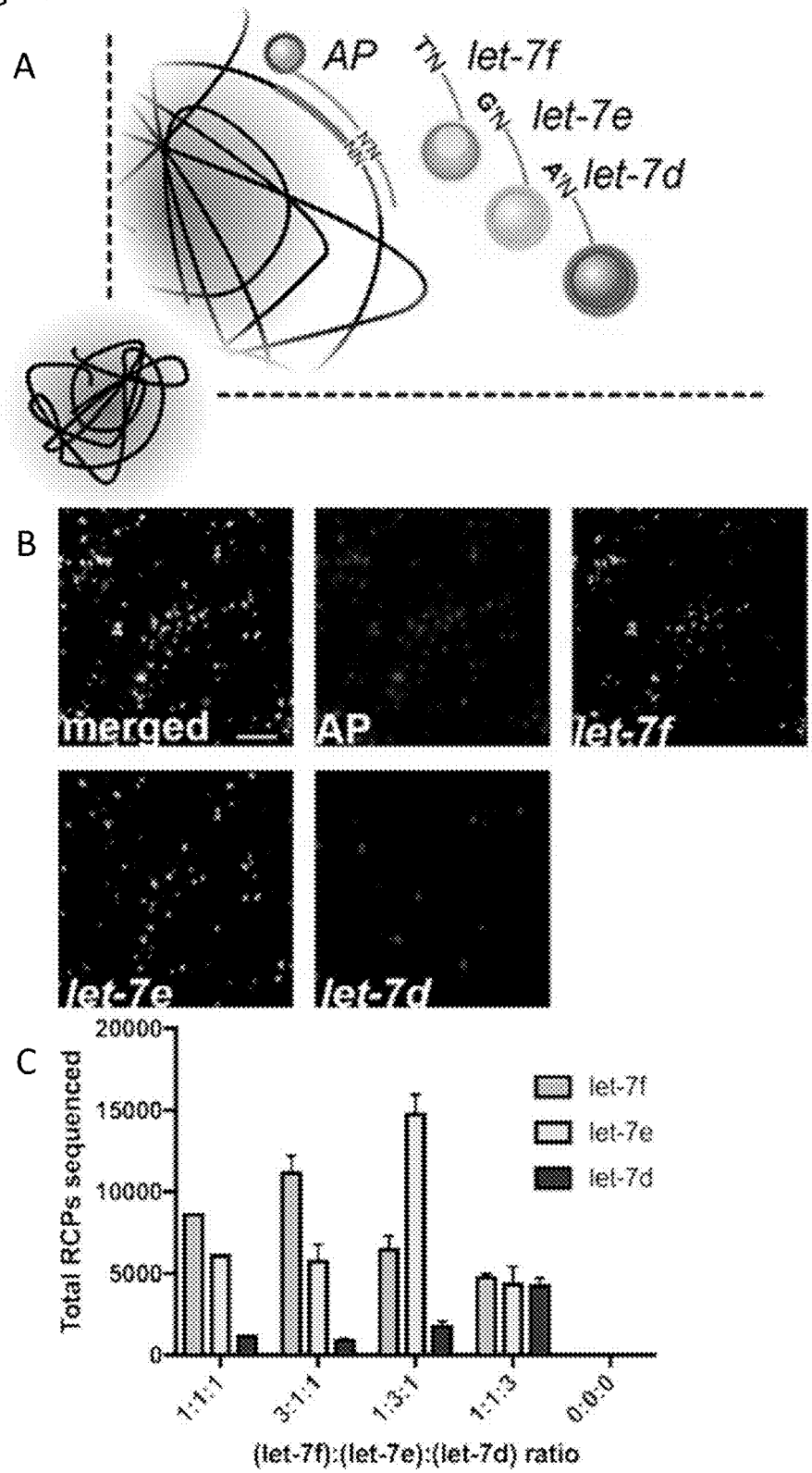

High multiplexing capacity is one of the most advantageous feature of padlock probes. Differentiation of amplified products, originated from different padlock probes, is typically achieved by using unique, probe-specific decorator oligonucleotides, labelled with fluorophores with different emission spectra. Alternatively, unique barcode sequence can be embedded in the padlock probe backbone that can be decoded using next-generation sequencing-by-ligation chemistry. To assess compatibility of chimeric iLock probes with sequencing-by-ligation readout, we have redesigned four let-7 family iLock-3D probes as described in methods section (table 3). To evaluate if barcoded iLock-3D probes could be utilized in multiplexed miRNA profiling, we have combined let-7f, let-7e, let-7d miRNAs in four different stoichiometric ratios. Ideally, ratios would be accurately reflected in miRNAs-specific sequencing reads. The iLock probes were applied in multiplex and the amplified products were fixed onto a glass surface. The barcodes of the RCPs were decoded using sequencing-by-ligation chemistry. Since only three iLock probes were used in this experiment, it was enough to sequence the first barcode position to decode which miRNA was detected. The iLock probes showed similar relative efficiency on the miRNA pool (FIG. 7). In samples where the concentration of one miRNA was increased, the signal increased for the corresponding iLock probe, while the signal for the other targets remained stable (FIG. 7C).

Example 2— Ligation of DNA Padlock Probes, and Chimeric Probes Comprising 1 or 2 Ribonucleotides at their 3' End Materials and Methods The ligation reactions were performed with 1 nM final concentration of DNA padlock probe or chimeric padlock probe with either 1 or 2 terminal 3' ribonucleotide bases, and 2 nM final concentration of synthetic KRAS RNA template or KRAS DNA template. Oligonucleotide sequences are shown in Table 6. Reactions were incubated in ligation buffer containing 1 U/µL RNAseinhibitor, 0.2 mg/mL BSA and 1× SplintR buffer or T4RNA ligase II buffer and 0.25 U/µL (low conc) or 1.25 U/µL (high conc) SplintR ligase, or 0.2 U/µL (low conc) or 1 U/µL (high conc) T4 RNA ligase II, respectively, in final volume of 10 µL for 30 min at 37 C. After that the circles were amplified with Rolling circle amplification in RCA reaction buffer, as described above, with a final circle concentration of 100 pM. Finally, the RCA products were labelled with Cy3-labelled detection probes in final concentration of 10 pM. Labelled RCA products were digitally counted.

Results

Figure 8:
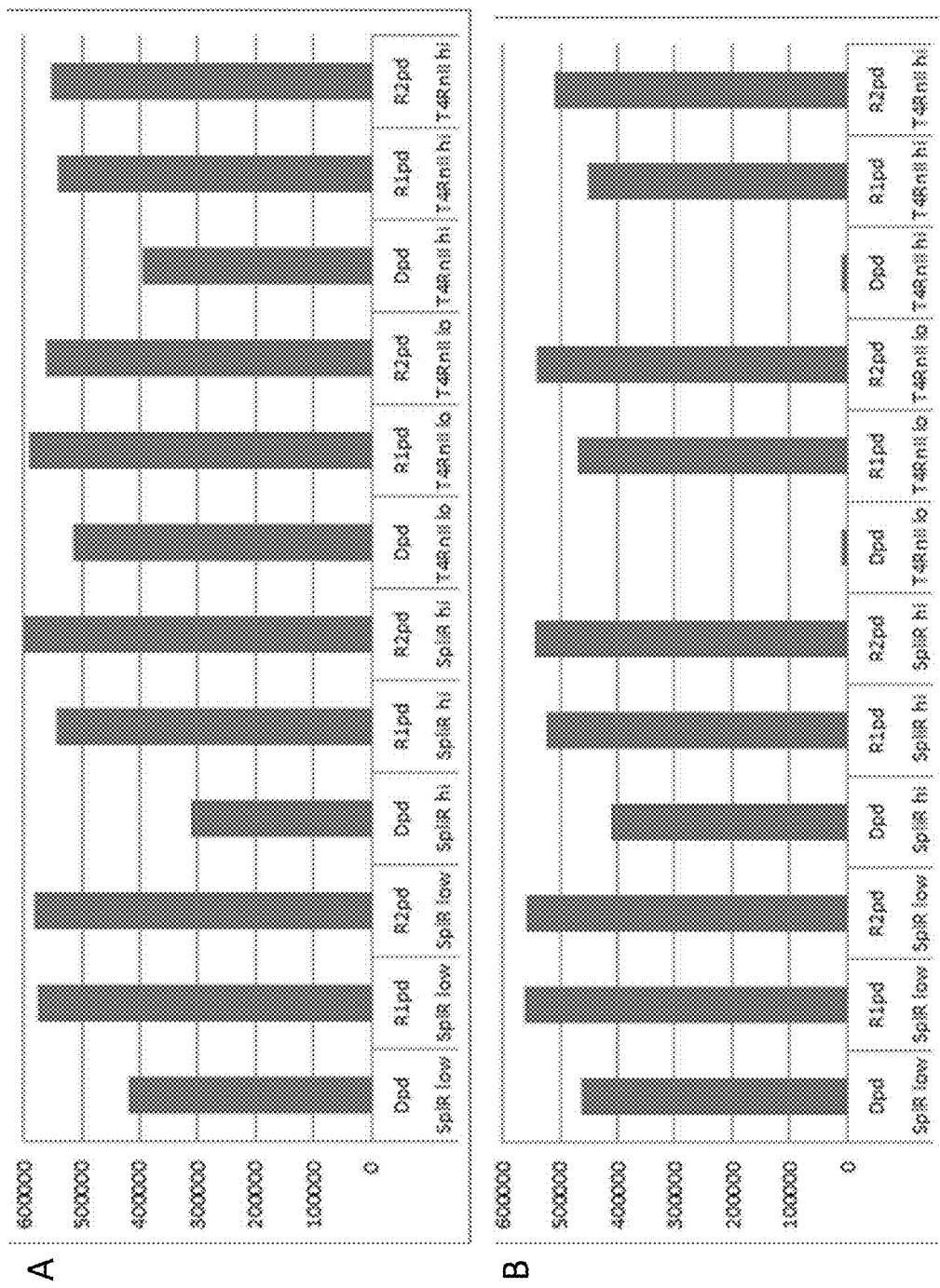

Both chimeric padlock probes, with 1 or 2 terminal 3' ribonucleotide bases generate more countable RCA products than pure DNA padlock probes, both for SplintR ligase and T4 RNA ligase II, and both on RNA templates and on DNA templates (FIG. 8). An increased ligase concentration did not have any effect on chimeric padlock probes, but a slightly negative effect on DNA padlock probes. There was no difference in RCA product count between chimeric padlock probes with 1 or 2 terminal 3' ribonucleotide-bases.

On RNA templates the activity of Splint R ligase and T4 RNA ligase II are similar (FIG. 8A). On DNA templates the difference between DNA padlock probes and chimeric padlock probes is similarly high for SplintR ligase as on RNA templates, while a very strong increase in RCP counts was recorded for ligating chimeric padlock probes on DNA templates with T4 RNA ligase II (FIG. 8B). T4 RNA ligase II does not accept 3' DNA and 5' DNA ends when templated by DNA, but readily accepts probes with 3' RNA ends when templated by DNA.

In conclusion, the use of chimeric probes makes ligation reactions with both SplintR ligase and T4 RNA ligase II on RNA templates more efficient than conventional DNA probes. Chimeric probes enable usage of T4 RNA ligase II for ligation reactions on DNA templates.

Figure 9:
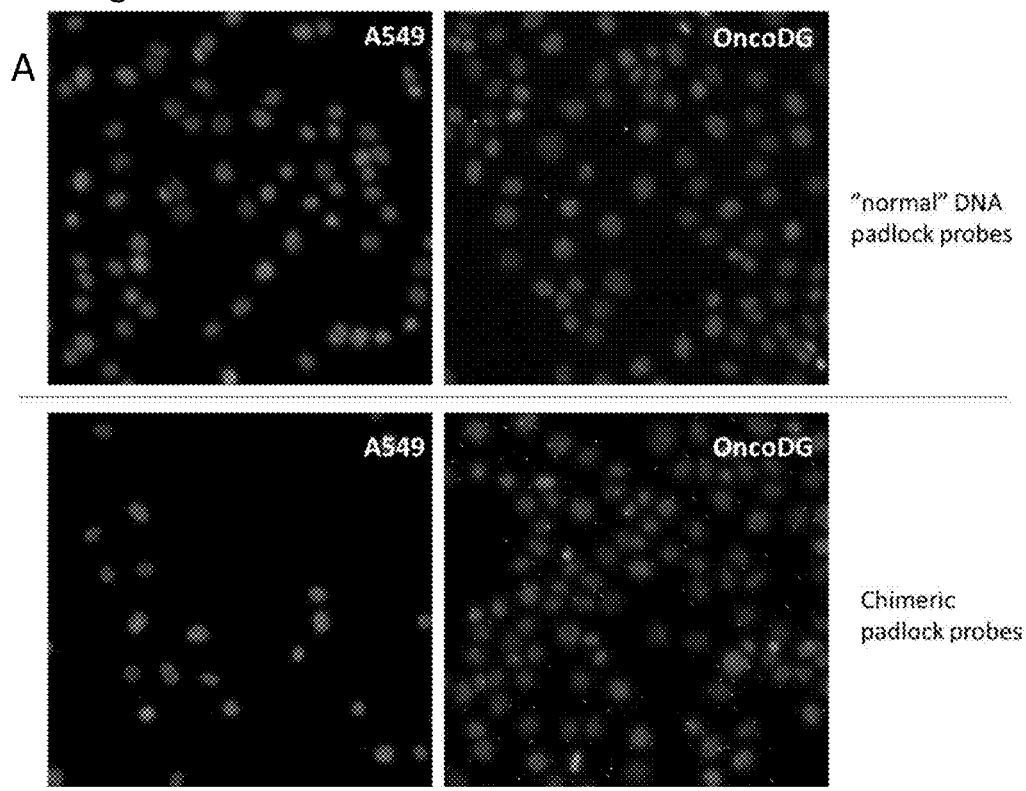
Figure 9:
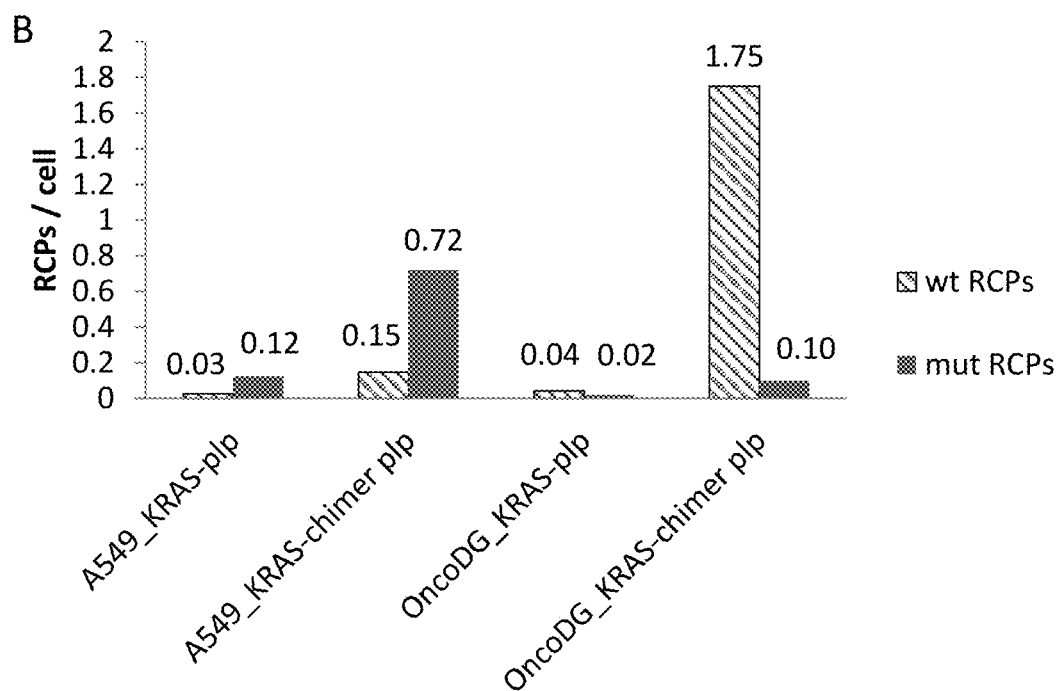
Figure 10:
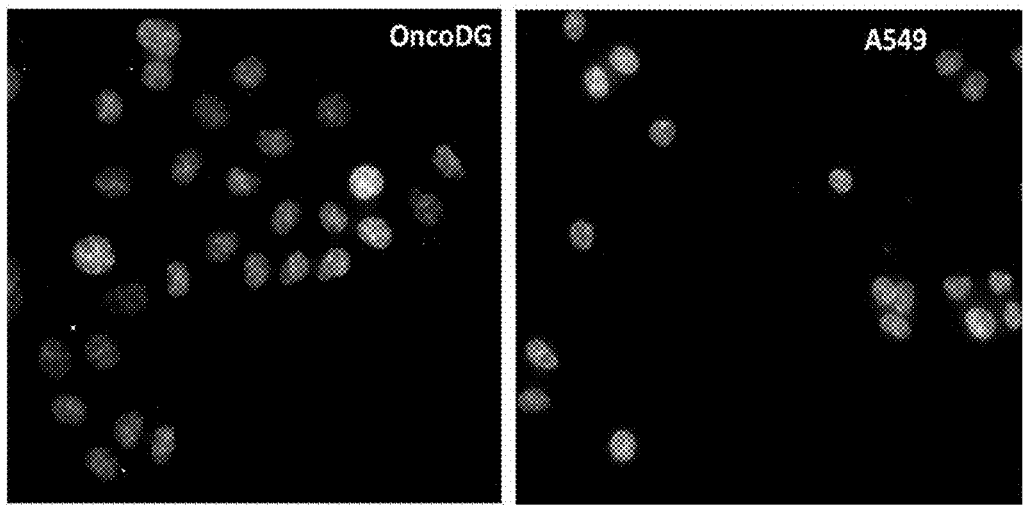
Figure 10:
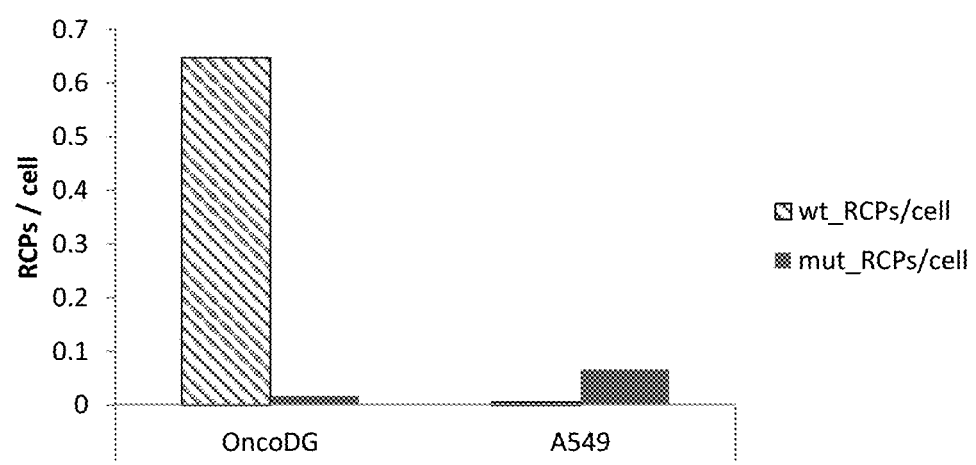

Example 3—In Situ KRAS Point Mutation Detection Using Chimeric Padlock Probes and Chimeric iLock Probes Materials and Methods ONCO-DG-1 and A-427 cell lines were cultured in RPMI culture medium without L-Glutamine supplemented with 10% FBS 2 mM L-Glutamine and 1× Penicillin-Streptomycin (PEST). A-549 was cultured in DMEM supplemented 10% FBS and 1×PEST. When confluent, all cell lines were seeded on Superfrost Plus slides and allowed to attach for 12 h. The cells were then fixed in 3% paraformaldehyde in DEPC-treated PBS (DEPC-PBS) for 15 min at room temperature. After fixation, slides were washed twice in DEPC-PBS and dehydrated through an ethanol series of 70%, 85% and 100% for 4 min each. Secure seal chambers were mounted on the slides, the cells were hydrated by a brief wash with PBS-T (DEPC-PBS with 0.05% Tween20 followed by a permeabilization with 0.1 HCl in $H_2O$ for 1 min at room temperature. Cells were washed twice in DEPC-PBS-T and then DNA or chimeric probes in final concentration of 50 nM were added in hybridization buffer containing 2×SSC, 20& Formamide and 0.4 U/µL RNAseinhibitor. Oligonucleotide sequences are shown in Table 6. Probes were hybridized for 60 min at 37° C. Then the probe hybridization mixture was removed and the cells were washed in pre-warmed (37° C.) wash buffer containing 2×SSC and 25% Formamide for 15 min at 37° C. and once in pre-warmed (37° C.) wash buffer containing 2×SSC and 20% Formamide for 15 min at 37° C. Cells were washed once in PBS-T. Then ligation reaction mix was added to the DNA/chimeric padlock probe experiments (FIG. 9) and invader reaction mixture was added to the DNA/chimeric iLock experiment (FIG. 10). Ligation reaction mixture contained SplintR ligase buffer, 0.2 mg/mL BSA, 0.8 U/µL RNAseinhibitor and 0.25 U/µL SplintR ligase. The ligation reaction was incubated for 60 min at 37° C. The invader reaction mixture contained the same as the ligation reaction and additional 0.1 U/µL Taq DNA polymerase. The invader reaction mixture was incubated for 60 min at 37° C. Subsequently, all experimental reactions were washed with PBS-T twice. 100 nM RCA primer was hybridized to the circles in situ in 2×SSC and 20% Formamide hybridization buffer for 30 min at room temperature. The cells were washed twice in PBS-T. Next, RCA reaction mixture was added containing 1× phi29 reaction buffer, 0.25 mM dNTP, 0.2 mg/mL BSA, 1 U/µL phi29 polymerase and 5% Glycerol and incubated at 37 C for 3 hours. Subsequently, cells were washed in PBS-T twice and detection probes were hybridized to the RCA products in situ (Cy3 labelled probes to KRAS wild type probes, Cy5 labelled probes to KRAS mutant probes) in 2×SSC and 20% Formamide hybridization buffer for 30 min at room temperature. Cells were washed in PBS-T three times, the nuclei stained with DAPI, washed three times again and then mounted in Slowfade mounting medium. Cells were imaged in fluorescent microscope with 20× objective and RCA products quantified using Cell profiler software.

Results

Chimeric padlock probes resulted in a higher in situ RNA detection efficiency on both A549 and OncoDG1 cell lines compared to DNA padlock probes (FIG. 9B). Moreover, the ratio of specific/unspecific RCPs per cell in both A549 and in OncoDG1 is increased for chimeric padlock probes over DNA padlock probes (more mutant RCPs than wild type RCPs are detected in A549 cells (carrying a KRAS codon 12 point mutation) and more wild type RCPs than mutant RCPs are detected in OncoDG1 cells (KRAS wild type), making it possible to more accurately detect point mutations with chimeric probes directly on RNA in situ. In order to further increase the specificity for point mutations, we applied chimeric iLock probes in situ and found specific detection of KRAS wild type mRNA in OncoDG1 cells and detected the KRAS codon 12 point mutation in A549 cells (FIG. 10).

In summary, chimeric probes strongly increase the in situ RNA detection efficiency, making in situ RNA analysis more sensitive, cost- and time-efficient than classic cDNA approaches. Moreover, compared to DNA padlock probes chimeric padlock probes, and especially chimeric iLock probes show a higher specificity, making RNA analysis in situ more powerful and accurate.

Example 4—Gap Fill iLock Probes

Materials and Methods

Figure 11A:
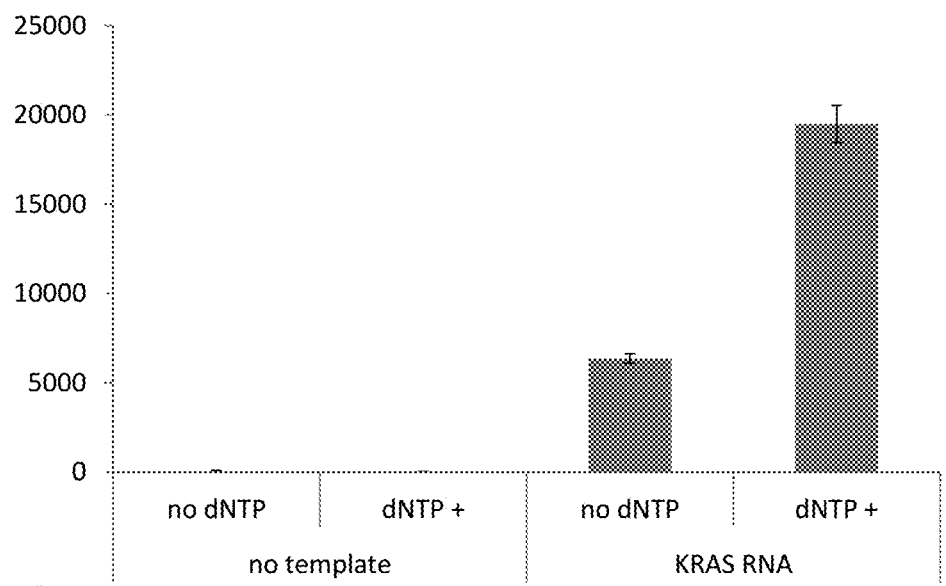
Figure 11B:
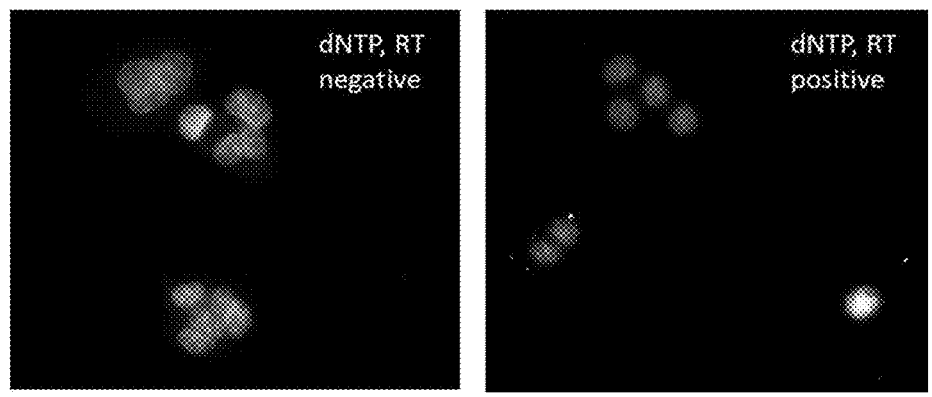
Figure 11:
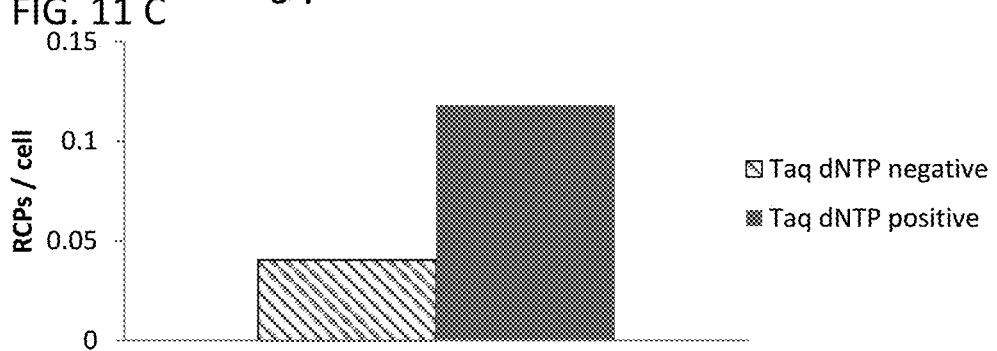
Figure 12:
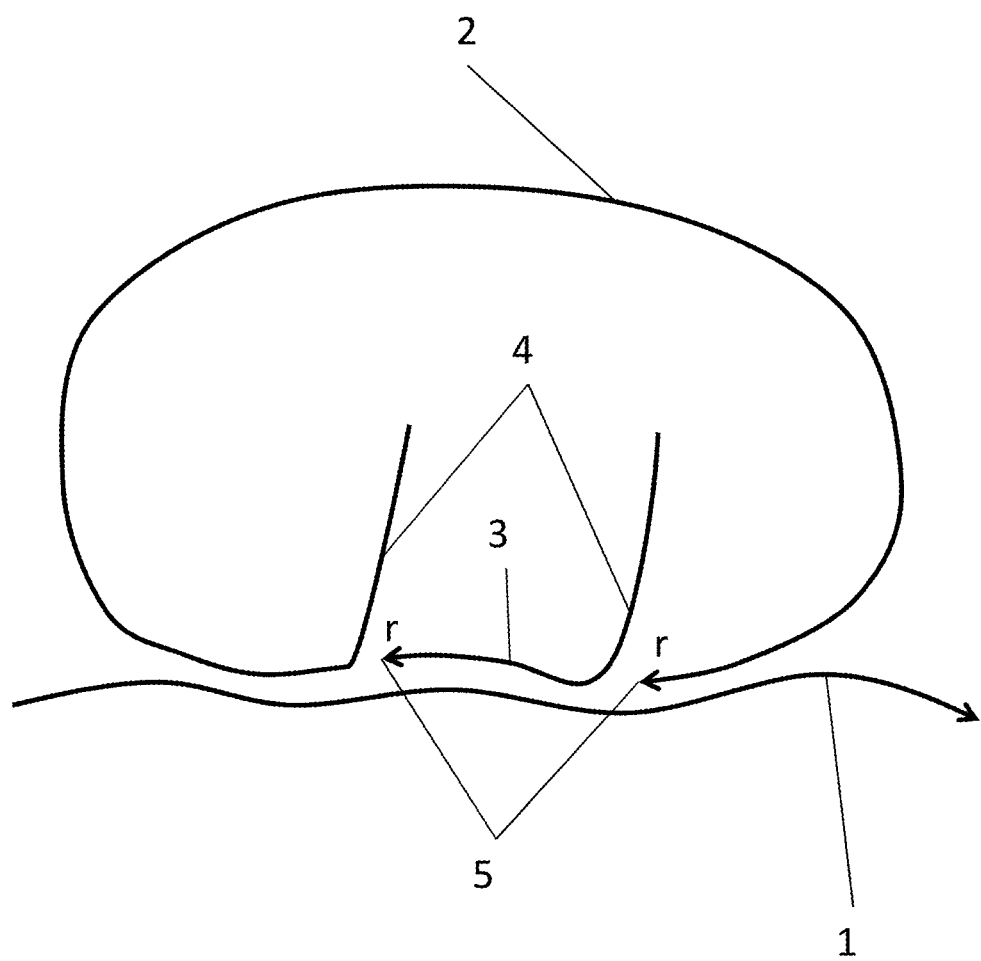

In-Solution Gap-Fill iLock Reaction:
The ligation reactions were performed with 10 nM final concentration of Gapfill ILock probe and 30 nM final concentration of synthetic KRAS RNA template (or no template in the negative control). Oligonucleotide sequences are shown in Table 7. Reactions were incubated in reaction buffer containing 1 U/μL RNAseinhibitor, 1 U/μL reverse transcriptase, 25 μM dNTP (or no dNTP in the gapfill negative control), 0.2 mg/mL BSA, 1× SplintR ligase buffer, 0.1 U/μL Taq DNA polymerase and 0.25 U/μL SplintR ligase in final volume of 10 μL for 60 min at 37° C. After that the circles were diluted 10× in PBS-T (to a theoretical concentration of 1 nM) and then amplified with Rolling circle amplification in RCA reaction buffer, as described above, with a final circle concentration of 100 pM. Finally, the RCA products were labelled with Cy3-labelled detection probes in final concentration of 10 pM and digitally counted.
In Situ Gapfill iLock Reaction
OncoDG1 cells were prepared and treated, as described in Example 3. Gapfill iLock probes were hybridized to the KRAS RNA in situ in 50 nM concentration with same conditions as in Example 3 After washing, gapfill polymerization invader mixture was added to the cells containing 1 U/μL RNAseinhibitor, 10 U/μL reverse transcriptase, 25 μM dNTP (or no dNTP in the gapfill negative control), 0.2 mg/mL BSA, 1× SplintR ligase buffer, 0.1 U/μL Taq DNA polymerase and 0.25 U/μL SplintR ligase and incubated on the cells for 60 min at 37° C. The cells were washed twice in PBS-T. Next, RCA reaction mixture was added containing 1× phi29 reaction buffer, 0.25 mM dNTP, 0.2 mg/mL BSA, 1 U/μL phi29 polymerase and 5% Glycerol and incubated at 37° C. for 3 hours. Subsequently, cells were washed in PBS-T twice and Cy3 labelled detection probes were hybridized to the RCA products as described above. Cells were washed in PBS-T three times, the nuclei stained with DAPI, washed three times again and then mounted in Slowfade mounting medium. Cells and RCA products were imaged in fluorescent microscope with 20× objective and RCA products quantified using Cell profiler software.
Results
RCA products from in-solution gap-fill polymerization-invader reactions were quantified and plotted in in FIG. 11A. When RNA template was present, RCA products were counted, indicating that the reaction worked sufficient. A significantly lower number of RCPs were counted when no template was present (template negative) indicating that gap-fill iLock probes could not be extended, and, hence, the 5' flap could not be removed and could not be ligated to the 3' end. In a control reaction, in which RNA template was present but no dNTPs were added, a significantly lower number of RCPs was counted than in the positive reaction (with template and dNTP), indicating that gap-filling through polymerization and triplex formation was limited, significantly reducing the cleavage of the flap, and hence, generating less ligation products (FIG. 11A). The same trend was visible in the in situ reaction (FIGS. 11B-C).

Example 5—Use of Phi29 as a Reverse Transcriptase Enzyme

Materials and Methods

Oligonucleotides
Oligonucleotide sequences are shown in Table 8 and Table 9. Probes were provided as described in Example 1. Ligation reactions were performed on synthetic KRAS mRNA templates. Padlock probes were designed such that upon RNA hybridisation, probe undergoes circularisation forming a nick between terminal arms. For convenient size assessment of rolling circle products (RCP), a reporter sequence was embedded in the sequence linking the probe arms (backbone). Complementary decorators were used for RCP staining by hybridising to the reporter sequence. For real-time RCA assessment, amplified DNA was stained with SybrGold dye.
Real-time RCA. To assess the effect of RNA bases on reverse-transcription performance by Phi29 polymerase, 20 nM of padlock probes were mixed with 10 nM of RNA template supplemented with 4 U RNase Inhibitor (DNA Gdansk), 3.75 U of PBCV-1 DNA ligase (SplintR, M0375S, NEB) in the respective buffer in a final volume of 15 μL. The reactions were incubated at 37° C. for 30 min. Following the ligation, 2 μL ligation volume (circles) was mixed in 18 μL RCA reaction mix containing 1×Phi29 reaction buffer (Thermo Fisher), 125 μM dNTP (DNA Gdansk), 0.2 mg/mL BSA (NEB) and 1× SybrGold (S11194, Invitrogen) to a final concentration of 2 nM circles. To ensure simultaneous initiation of RCA across all samples, circles were put in the tube lids and spun down using table-top centrifuge into the pre-disposed master mix. RCA was immediately initiated and SybrGold incorporation monitored using a Mx3005P qPCR System (Agilent Genomics) at 37° C. for 60 min, followed by Phi29 inactivation at 65° C. for 2 min.
To investigate whether RCA efficiency of RNA-rich circles can be stimulated by addition of reverse transcriptase, 100 U of RNaseH(−) TranscriptME Reverse Transcriptase (DNA Gdansk) were added to the RCA reaction mixture.
Sequencing of RCA Products Generated from RNA Containing Circles
Monomerization
In order to sequence the incorporated bases within the RCA products that correspond to the RNA bases within the circular templates, the RCA products were first monomerized by restriction digestion. First, RCA products from the real-time RCA measurements, as described above, were diluted in PBS-Tween 0.05% to a concentration of 100 pM. Next, RCA products were digested with AluI restriction enzyme in a reaction mixture containing 1×Phi29 DNA polymerase buffer, 2 mg/mL BSA, 100 nM restriction oligonucleotide (AluI KRAS RO—Table 9), 120 mU/μL AluI (NEB) and 10 pM final concentration of RCA products during 10 min incubation at 37° C. and subsequent heat inactivation at 65° C. for 2 min. After complete digestion of the 10 pM RCA products, the RCA monomer concentration is approximately 10 nM (1 hour RCA of an 80 base circle yields ~1000× amplification). The RCA monomers were diluted to 100 pM in PBS-Tween 0.05%.
Sequencing Library Preparation of RCA Monomers
The RCA monomers were first tagged with Illumina adapter sequences during a PCR reaction, containing 1×Taq DNA polymerase buffer (NEB), 1.5 mM MgCl$_2$ (NEB), 250

µM dNTP, 1× SybrGold, 25 mU/µL Taq DNA polymerase (NEB), 0.5 µM forward primer PE1 (table 9), 0.5 µM reverse primer PE2 (table 9) and final concentration of 10 pM RCA monomers. The PCR reaction was started with 5 min denaturation at 95° C. and cycled between 95° C. for 15 sec, 55° C. for 30 sec and 70° C. for 20 sec for 20 cycles. The reaction was monitored in the qPCR instrument and the reaction was stopped before the amplification reached saturation. After the first PCR step (Extension step), 1 µl of the PCR products were spiked into index PCR mixture containing 1× Phusion HF Buffer (Thermo Scientific), 0.2 mM d(A,T,G,C)TP (Thermo Scientific), 1% DMSO, 250 nM index PCR primers (table 11), each sample was labelled with unique combination of 1 of 7 different forward and 1 of 3 different reverse index primers) and programmed for an initial 2 min at 95° C., and 2 cycles of 95° C. for 15 sec, 60° C. for 1 min and 72° C. for 1 min, and an extra cycle of 72° C. for 3 min. The indexed PCR products were diluted 200 times into PCR mixture containing 1× Phusion HF Buffer (Thermo Scientific), 0.2 mM d(A,T,G,C)TP (Thermo Scientific), 1% DMSO, 500 nM P5 and P7 primers and programed at 2 min at 95° C., and 15 cycles of 95° C. for 15 sec, 60° C. for 30 sec and 72° C. for 30 sec. The PCR products were pooled and purified using QIAquick PCR Purification Kit and sequenced by NSQ® 500 hi-Output KT v2 (75 CYS) in NextSeq® 550 system (Illumina). The reads containing correct primer sequences at the expected positions were extracted and analysed with WebLogo.

Morphological Assessment of RCP Size and Intensity

To measure RCA product size and intensities, the RCA products from the real-time RCA reaction were diluted to a final concentration of 20 pM, labelled with 5 nM final decorator probe concentration in standard hybridization conditions. 10 µL of the fluorescently labelled RCA products were applied to Superfrost glass slides (Thermo Fisher), spread out by a 20×20 mm coverslip (Menzel) and left to bind electrostatically to the positively charged surface during 15 min incubation. Coverslips were removed, slides were briefly washed in PBS, mounted in mounting medium and imaged on a Zeiss Axioplan fluorescent microscope with 20× magnification in the Cy3 channel. Images were exported as original black-white (BW) pictures and processed with Cell Profiler software. Briefly, each image was pre-processed using automated top-hat filtering. Objects were identified using manually adjusted thresholding and separated based on objects intensity. The average fluorescence intensity and object size was recorded, exported as a csv file and processed in R! Studio.

Results

Figure 13:
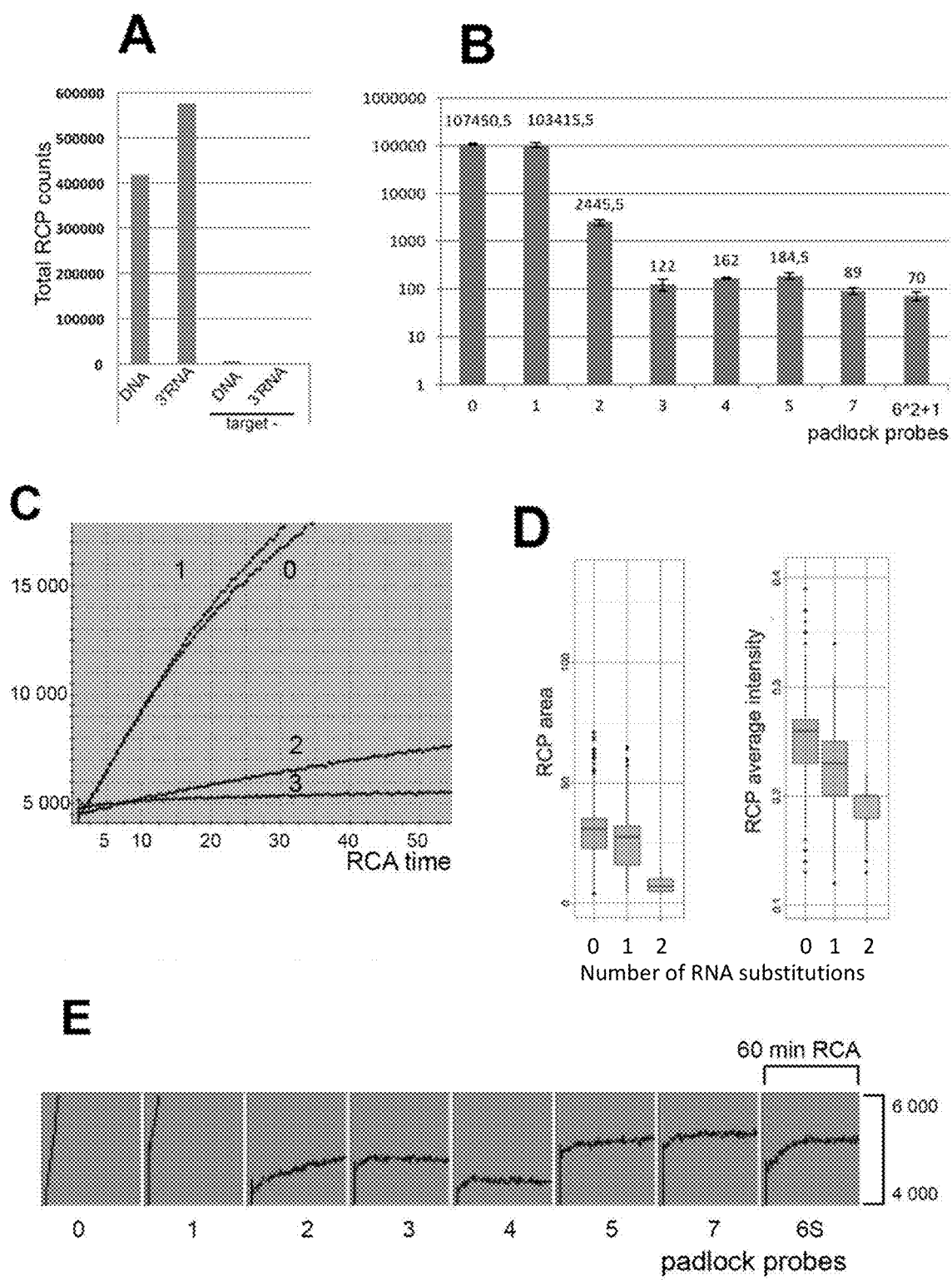

Phi29 DNA Polymerase Accepts Chimeric Circles as Rolling Circle Amplification (RCA) Templates We have observed that circularized chimeric padlock probes containing both RNA and DNA nucleotides can be used as substrates for RCA, suggesting that Phi29 DNA polymerase possesses a reverse-transcriptase activity. To investigate this activity, we have circularized a variety of RNA/DNA chimeric padlock probes containing 1-7 RNA substitutions in a DNA probe backbone and used the circularized probes as templates during RCA (FIG. 13).

The RCA reaction was monitored in real-time by Sybr-Gold incorporation. Additionally, the RCA products were digitally counted and their size and intensity (i.e. morphology) assessed.

We observed that PBCV-1 readily sealed both pure DNA probe and chimeric 3'-(rN)/5'(N) probe nicks and that Phi29 polymerase accepted both pure DNA and RNA-containing circles as templates for RCA (FIG. 13A). The higher number of RCA products from the 3' RNA probes is most likely due to increased ligation efficiency of chimeric probes, as described in detail in Example 1. When no template is added during the ligation reaction, probes are not ligated and cannot be amplified (FIG. 13A, target-).

Next, we aimed to investigate RCA efficiency of chimeric DNA/RNA circles without the bias of the ligation reaction. For this purpose we added RNA substitution in the circle backbone that do not participate in the ligation reaction. Consequently, all probes contained the same target-complementary DNA probe arm sequences (contributing to forming the ligation substrate) and were ligated on the same RNA target. We then investigated how an increasing number of RNA substitutions affect the RCA reaction efficiency by counting RCA products (FIG. 13B) and monitoring the amplification reaction in real-time (FIG. 13C). Padlock probes having sequences SEQ ID NOs:119, 120, 124, 131, 110, 111 and 112, being a DNA probe and chimeric probes having 0, 1, 2, 3, 4, 5 and 7 consecutive ribonucleotides, were used.

We have observed no effect on the RCA efficiency when a single RNA was substituted in the probe (circle) backbone (FIGS. 13B and 13C, FIGS. 32A and 32B). A strong inhibition of RCA (approximately 90%) was observed when circles were substituted with 2 consecutive RNA nucleotides (FIGS. 13B and 13C, FIGS. 32A and 32B). For circles with more than 2 RNA substitutions, no amplification was detected (FIG. 13E, FIG. 32C). When rolling circle products (RCP) were imaged using epi-fluorescence microscopy, the average size and intensity of RCPs was decreased for circles with 2 consecutive RNA substitutes (FIG. 13D). More than two consecutive RNA substitutions (3-7) led to complete RCA inhibition and no RCPs were detected in these samples.

We have additionally investigated whether RCA of RNA-rich circles can be recovered by supplying a M-MuLV reverse transcriptase during the RCA reaction. However, under the reaction conditions used, RCA activity did not recover in the presence of the reverse transcriptase. In contrast, the amplification rate was significantly decreased by addition of M-MuLV reverse transcriptase (lower panel of curves) in comparison to RCA reaction without additional reverse transcriptase (FIG. 19).

Phi 29 DNA Polymerase Preferentially Reverse Transcribes RNA Pyrimidines During RCA In the previous experiment, DNA bases in the circles backbone were increasingly substituted with RNA bases. Strong amplification inhibition was observed for circles with rGrA and rGrArC substitutions. In order to study if there is some sequence dependency in RCA efficiency of RNA containing circles, we monitored RCA rate in real-time using circles with single rU/rA/rC/rG RNA base, as well as, di- and trinucleotide long homo-nucleotide stretches (Table 9). We observed efficient RCA for all single RNA substitutions (FIG. 18A). For the dinucleotide RNA substitutions, we observed the highest RCA rate for rCrC circles followed by rUrU circles, while rArA and rGrG circles were substantially inhibited. For trinucleotide RNA circles, only rCrCrC circles generated detectable RCA, however, at a rate substantially slower than rCrC-containing circles (FIG. 18A). A number of the ribonucleotide probes SEQ ID NOs: 108-112, 124-127, 131-134, 137 and 139 contained further hetero-nucleotide ribonucleotide stretches. Experiments were repeated using probes SEQ ID NOs:267-281 (Table 13) which did not have the additional ribonucleotide stretches and similar results were observed (FIGS. 24A-D and FIG. 25).

To investigate whether RCA can be recovered for longer mixed RNA/DNA stretches, we interspaced 1 and 2 DNA bases in stretches of 3 and 6 RNA bases, respectively (FIG. 18 B). Circles containing rGArCGrU sequence in the backbone were amplified, while no RCA was detected for circles with 6 interspaced RNA substitutions, or for circles with 5 and 7 consecutive RNA bases (FIG. 18B).

Manganese Ions Increase RNA-Dependent RCA Activity of Phi29 DNA Polymerase

Figure 24A:
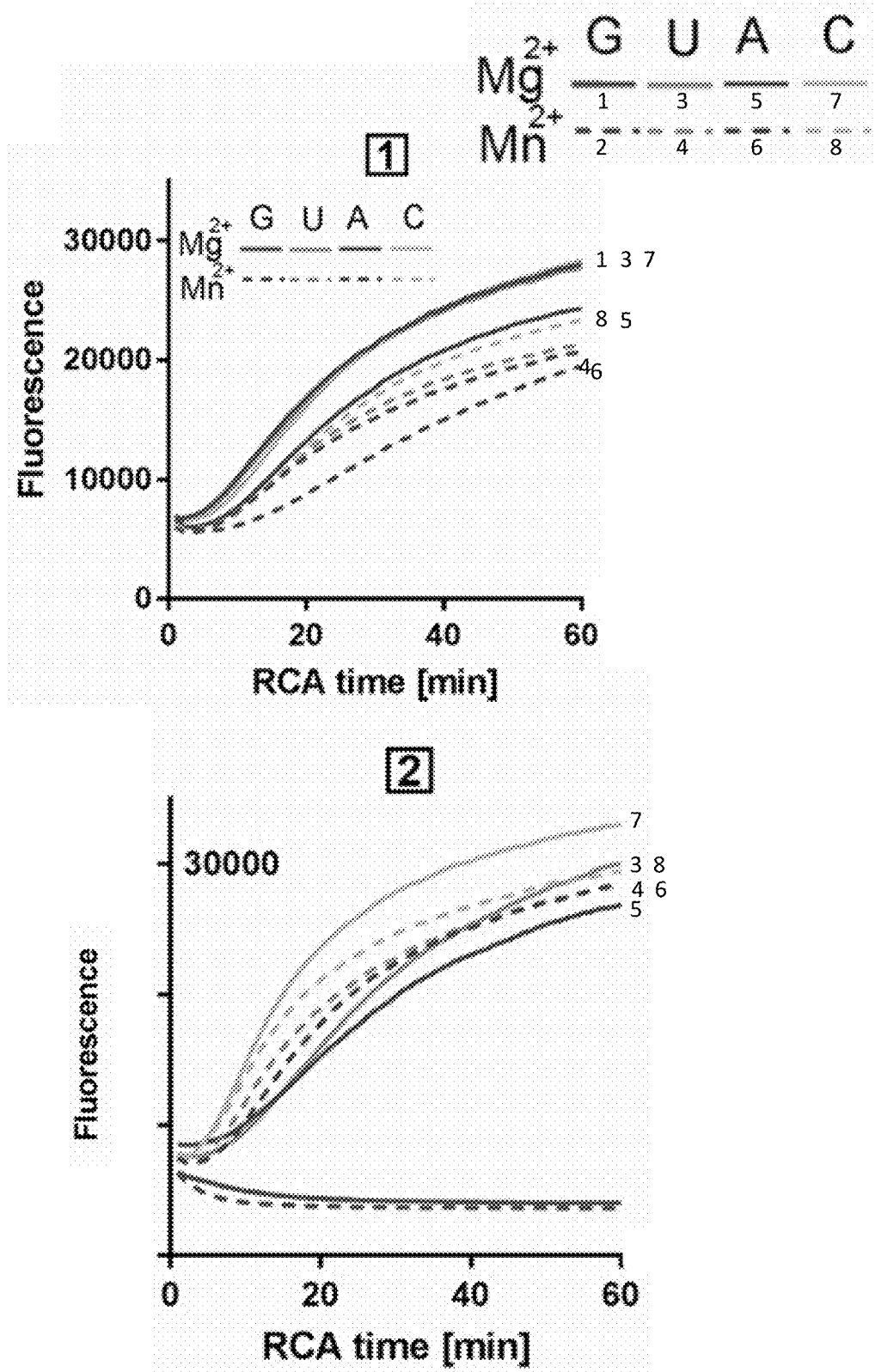
Figure 24B:
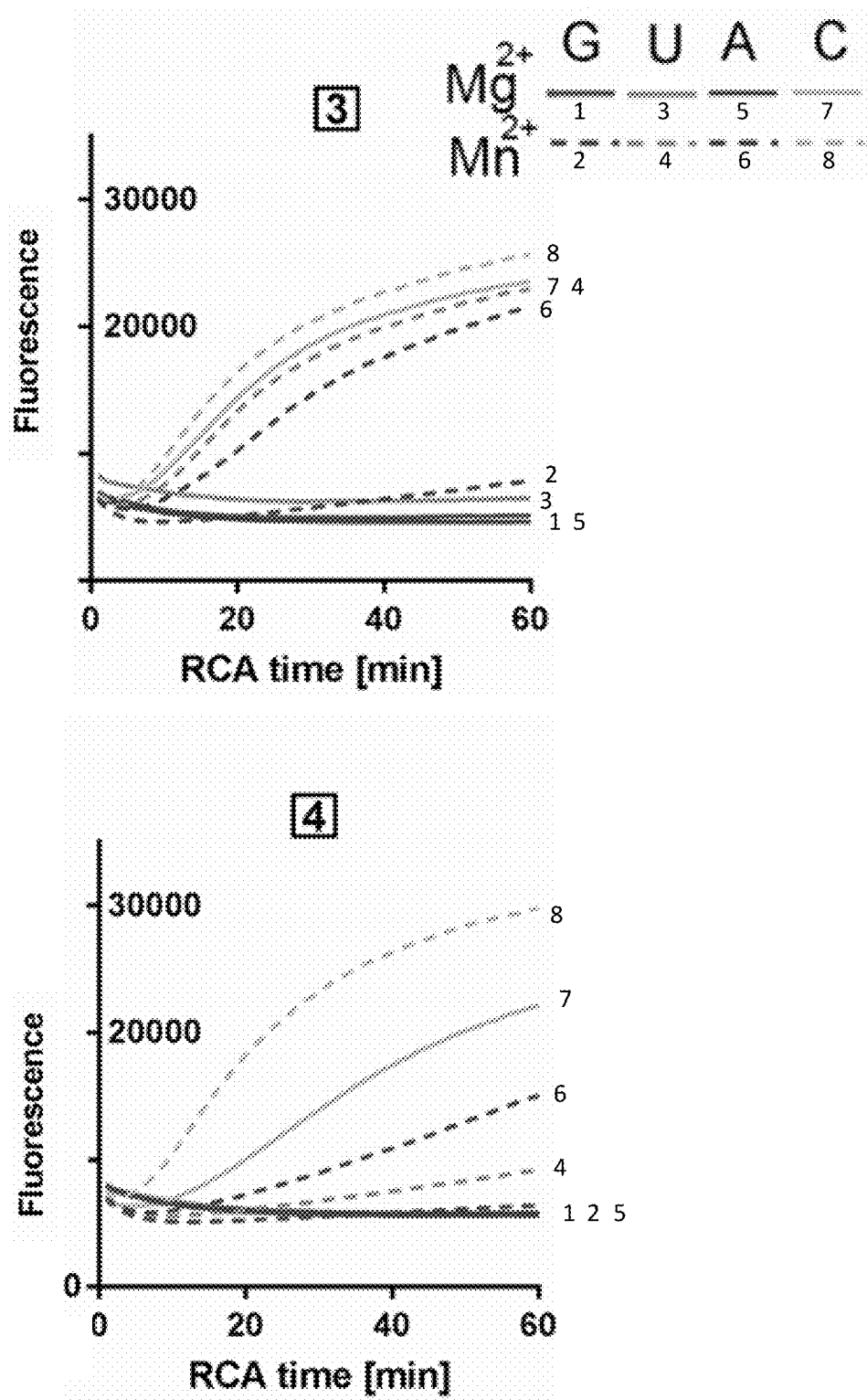
Figure 24C:
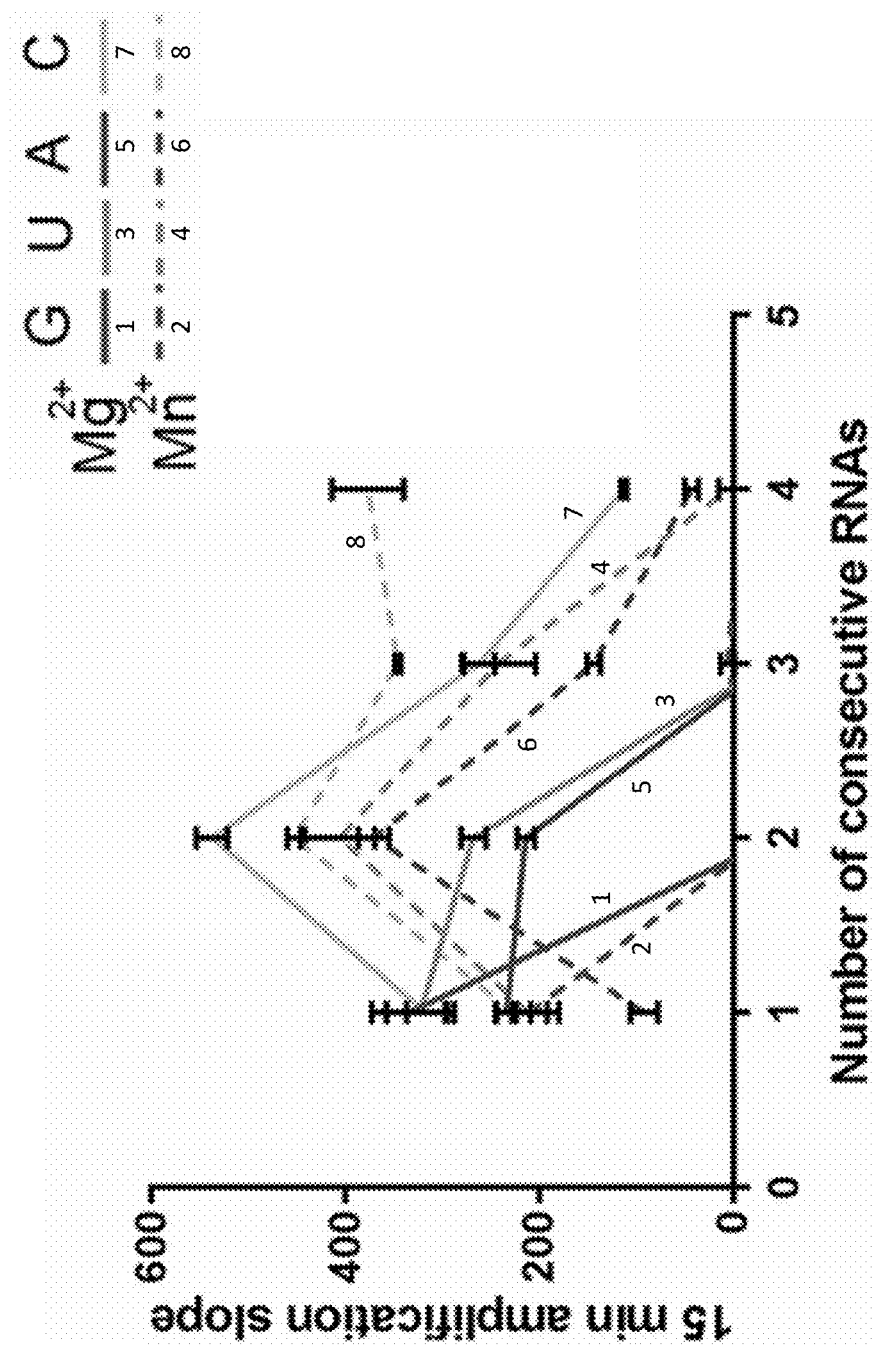
Figure 24D:
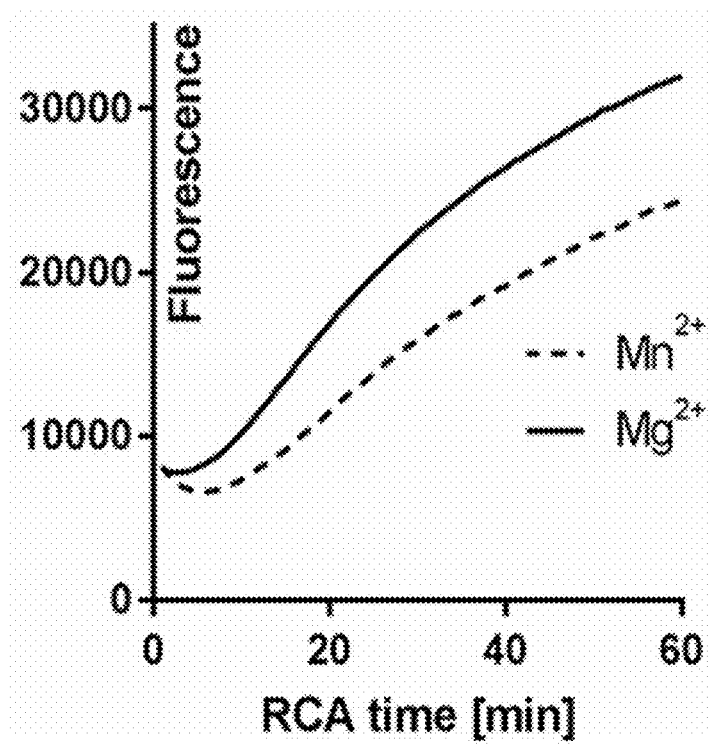

As certain DNA-dependent DNA polymerases are able to reverse-transcribe RNA in the presence of $Mn^{2+}$, we compared phi29 DNA polymerase RCA rates with $Mg^{2+}$ and $Mn^{2+}$. Using $Mn^{2+}$ as a cofactor, phi29 DNA polymerase in addition to rC also efficiently amplified single, dinucleotide and trinucleotide rU and rA stretches (FIGS. 24A-D). Interestingly, amplification rates of rCrC-, rUrU and rArA-circles were higher when compared to single RNA substituted circles, which was also true for rCrC with $Mg^{2+}$ as cofactor (FIGS. 24A-C). To investigate whether RCA can be recovered if multiple RNA bases are mixed with DNA-bases, multiple chimeric constructs were amplified with $Mg^{2+}$ and $Mn^{2+}$ (FIG. 25). According to our observations, phi29 DNA polymerase was able to engage in efficient $Mn^{2+}$-dependent RCA when RNA bases were interspaced with DNA (FIG. 25), Table 12). Interestingly, circular chimeric substrate with as many as 8 RNA bases was well amplified when substitutions were organised in a uniformly dispersed pattern (FIG. 25).

Sequencing of Rolling Circle Products Demonstrates Ability of Phi29 DNA Polymerase to Reverse Transcribes RNA Since the Phi29 polymerase amplification rate was inversely proportional to the number of RNA bases in the substrate, we considered that the enzyme may ignore RNA positions during RCA, introducing single, or double nucleotide deletions in amplified product. To validate this hypothesis, circles containing single and double RNA substitutions (rAr/Ur/G/rC/rArA/rUrU/rGrG/rCrC, Table 9) were amplified and RCA rate was monitored in real-time as described earlier. Following amplification, sequencing libraries were prepared from the different amplification products, and then sequenced using Illumina NextSeq® 550 system. Full length sequencing reads were extracted from the dataset, sequencing reads were aligned and base frequency was calculated for each position in the padlock probe backbone (FIG. 20).

According to our observations, Phi29 DNA polymerase incorporated the expected DNA nucleotides in the amplified RCP where template sequence was RNA. For circles with no RNA substitutions, >99% of sequenced monomers showed correctly incorporated base at R1 padlock probe region (here called accuracy) highlighted in the FIG. 20 (99.68%, RT accuracy for position R1 for DNA padlock probe). When R1 position was substituted with rA, rC, rG or rU, the RT accuracy was 99.88%, 99.70%, 96.07%, 99.88% respectively, While the rA, rC, and rU was copied with better accuracy than sequencing, or at least not worse than for dG in the investigated position, rG stands out with higher replication error. Interestingly, this higher incorporation error was observed not only for the R1 position, but for all following cytosine bases in the padlock probe backbone. When both R1 and R2 positions were substituted with rArA, rCrC, rGrG and rUrU, RT accuracy for the R1/R2 site was 99.81/99.59%, 99.82/99.86%, 93.01/89.7% and 99.93/99.94% respectively. Similarly to circles with a single rG substitution in R1, all dinucleotide RNA substrates demonstrated higher error rate for non-RNA cytosines across probe backbone sequence.

In a further experiment, when R1 position was substituted with rA, rC, rG or rU, the average error rate was 0.111%, 0.153%, 2.259% and 0.084% respectively FIG. 30, FIG. 31, FIG. 33). While the rA, rC, and rU was copied with the same accuracy as DNA (as measured by sequencing), rG stands out with higher replication error. Interestingly, this higher incorporation error was observed not only for the R1 position, but for all guanosine bases in the padlock probe backbone (visible as high error rate peaks in FIG. 31 and FIG. 33) and higher thymine frequencies for the rG padlock probe logo graphs in FIG. 30. When both R1 and R2 positions were substituted with rArA, rCrC, rGrG and rUrU, the error rate for the R1/R2 site was 0.269/0.561%, 0.107/0.109%, 2.827/2.231% and 0.144/0.220% respectively. Similarly to circles with a single rG substitution in R1, all dinucleotide RNA substrates demonstrated higher error rate for non-RNA guanosines across probe backbone sequence (FIG. 3C).

We demonstrate limited reverse transcription activity of Phi29 DNA polymerase. We show that single RNA substitutes in circular templates have no impact on RCA efficiency. We have found, however, that amplification was suppressed when more consecutive RNA bases were substituted in the circular template sequence. In order to characterize this novel activity of Phi29 polymerase, we amplified circular templates containing either one, two, or three consecutive RNA bases rA, rG, rC or rU with Phi29 Polymerase and monitored the RCA rate in real time. Moreover, we tested various combinations of different RNA bases and interspacing RNA bases with DNA bases. Our data demonstrate a preference for circular substrates containing pyrimidine RNA bases, since circles with 3 consecutive pyrimidine bases could still be amplified, but not circles with 3 consecutive purine bases. Interestingly, interspacing circles with 3 RNA substitutions with DNA bases led to a partial recovery of the RCA efficiency, indicating that RCA of RNA containing circles is restricted to single RNA base substitutions or very short stretches of consecutive RNA bases. The attempt to increase RCA efficiency of circles containing longer stretches of RNA bases by addition of reverse transcriptase failed. Instead, RCA was suppressed in the presence of dedicated reverse transcriptase, potentially due to blocking of circular substrates for Phi29 DNA polymerase binding.

Our data clearly illustrates that the mechanism, by which the polymerase copies RNA containing circles, is reverse transcription, as we found the matching DNA base incorporated into the RCA products with high frequency (>99% for rA, rU and rC, ~96% for rG). The overall incorporation accuracy on RNA substitutes was not different from the accuracy on pure DNA substrates.

Example 6—In Situ Detection of mRNA Using Chimeric Probes

Materials and Methods

BjHtert and MEF cells were cultured in growth medium consisting of Dulbecco's modified Eagle medium (DMEM; Invitrogen), 10% fetal bovine serum (Sigma), and 1% penicillin-streptomycin mix (PEST; Gibco). Both cell lines were grown in a humidified cell incubator at 37° C. in the presence of 5% CO2. Prior the experiments, cells were dislodged from the culture flask using trypsin-EDTA 0.25% solution (T4049 Sigma) and grown in 150-mm cell culture dishes with 5 submerged microscope slides over-night. Slides with the attached cells were washed twice with PBS, fixed in freshly prepared diethyl pyrocarbonate (DEPC)-treated PBS containing 3.4% formaldehyde for 15 min on ice. Thereafter, slides were washed twice with DEPC-PBS, dehydrated in an ethanol gradient (70%, 85%, and 99%; 3 min each), air dried, and stored at 80° C. At the experiment day, cells were thawed, dried and, for each experimental condition tested, isolated by covering with an 8 mm diameter and 50 ul volume Secure Seal chamber (Invitrogen). Cells were rehydrated with DEPC-TBS buffer. Each incubation step was followed by two DEPC-PBS-T washes ((DEPC)-treated PBS containing 0.05% Tween 20 as a surfactant agent). All incubations were performed in a humid chamber to avoid evaporation of the reaction mixture.

Probes for both ACTB transcripts (Table 4) were pooled and pre-hybridised (pool 1: non-chimeric PLPs, pool 2: chimeric PLPs, pool 3: iLocks, pool 4: chimeric iLocks) in final concentration 0.1 µM in hybridisation buffer (475 mM Tris-HCl at pH 8; 0.95 mM EDTA, 760 mM NaCl are shown in Table 4. 0.8 U/µL RNase Inhibitor (DNA Gdansk) in 50 uL reaction volume at 37° C. for 2 hours. Unhybridised probes were removed by stringent washing using pre-heated (37° C.) TBS-Tween buffer, twice. The ligation reaction was performed by adding 0.5 U/µL SplintR ligase (NEB), 1× SplintR buffer, 0.8 U/µL RNase Inhibitor in DEPC-ddH2O. iLock ligation and activation (for iLock probes) was conducted simultaneously by adding Taq DNA polymerase in final concentration 0.1 U/µL. Slides were incubated 2 hours at 37° C. and washed twice with DEPC-PBS-T.

Rolling circle amplification reaction was conducted by adding 1 U/µL phi29 DNA polymerase (Monserate), 1× phi29 DNA polymerase buffer, 0.25 mM dNTPs (Thermo Scientific), 0.2 µg/µL BSA (NEB), 5% glycerol and DEPC-ddH2O in 50 µL final reaction volume for 6 hours at 37° C. and washed twice with DEPC-PBS-T.

Finally, decorator oligonucleotides were hybridised to RCA products at 0.1 µM final concentration in hybridisation buffer (2×SSC, 20% formamide, ddH2O) with Hoechst 33342 (Thermo Scientific) in DEPC-PBS at room temperature for 30 minutes. Cells were washed twice with DEPC-PBS-T, dehydrate by passing through an ethanol series (70, 85, and 99.5% ethanol, each for 3 min) and coverslip were mounted with Slow-Fade medium (Thermo Scientific). Signals in cells were quantified using CellProfiler software and analysed in R!.

Results

Though probes were pooled together, only the expected signal was observed in cells (FIG. 21A). Moreover, chimeric padlock probes worked more efficiently (generated more detectable RCA products) when compared to non-chimeric padlock probes. iLock probes generated significantly less signal when compared to conventional padlock probes, indicating that further optimisation of the protocol is required to ensure efficient probe activation and RNA detection in situ. Analysis of the data however, revealed that the expected signal was also observed for chimeric and non-chimeric iLock probes, and signal was also higher for chimeric iLock probes (FIG. 21B).

Example 7— Detection of miR21 on a Solid Support Using DNA PLPs, Chimeric PLPs, and DNA and Chimeric iLock Probes In this example, miR21 is immobilised on the slide surface and detected in situ. miR21 is prepared with a 5' biotin moiety separated from the target sequence with 16× rU linker. miR21 is detected with conventional and chimeric padlock probes as well as non- and chimeric-iLock probes. Target and probe sequences are shown in Table 5.

Materials and Methods 8 mm diameter and 50 ul volume Secure Seal chambers (Invitrogen) were put on neutravidin coated microscope slides (PolyAn). In total, six Secure seal silicone chambers were used. miR21 target (miR21_BIO) was diluted to 50 nM final concentration in 1× labelling solution (2×SSC, 20% formamide) incubated at room temperature, 1 hour on gentle shaking. In one instance, miR21 target was intentionally omitted (negative control). After miR21 was immobilised, chambers were washed with PBS-Tween 20 (0.05%) 3×. Chamber where no ligation or activation was taking place (coating control) was kept in PBS until the end of the experiment.

Padlock probes, iLock probes and "coating control" probes (antimiR21_FAM) were hybridised to immobilised targets at final concentration 10 pM (padlock and iLock probes) or 50 nM (for antimiR21_FAM probe). Probes were hybridised in the hybridisation buffer (475 mM Tris-HCl at pH 8; 0.95 mM EDTA, 760 mM NaCl at 45° C. for 15 minutes and at room temperature for 3 hours on gentle shaking. Chambers were then washed with PBS-Tween 20 (0.05%) 2×.

The ligation reaction was performed by adding 0.5 U/uL SplintR ligase (NEB), 1× SplintR buffer, in DEPC-ddH2O. iLock ligation and activation (for iLock probes) was conducted simultaneously by adding Taq DNA polymerase in final concentration 0.1 U/uL. Slides were incubated for 1 hour at 37° C. and washed twice with DEPC-PBS-T.

Rolling circle amplification reaction was conducted by adding 0.5 U/µL phi29 DNA polymerase (Monserate), 1× phi29 DNA polymerase buffer, 0.125 mM dNTPs (Thermo Scientific), 0.2 µg/µL BSA (NEB), 5% glycerol and DEPC-ddH2O in 50 µL final reaction volume for 3 hours at room temperature and washed twice with DEPC-PBS-T.

Finally, decorator oligonucleotides were hybridised to RCA products at 0.1 pM final concentration in hybridisation buffer (2×SSC, 20% formamide, ddH2O) in DEPC-PBS at room temperature for 1 hour. Cells were washed twice with DEPC-PBS-T, dehydrated in 99% ethanol for 3 min and coverslip were mounted with Slow-Fade medium (Thermo Scientific). Signals in cells were quantified using CellProfiler software.

Results

Our data demonstrates efficient immobilisation of biotinylated miRNA target on neutravidin coated microscope slide as no fluorescence was detected from labelled, complementary probe when miR21 was not immobilised. Results of detection are shown in FIG. 22B. Traditional padlock probes generated ~7800 RCA products (RCPs)/field of view (fov) while ~36 000 RCPs/fov were quantified when chimeric padlock probes were used. Concordant with the example where ACTB mRNAs were detected in BjhTERT and MEF cultured cells, iLock probes generated less signal in comparison to padlock probes. Chimeric iLock probes generated ~3 000 RCP/fov while non-modified iLock probes only ~195 RCPs/fov.

Example 8—In Situ Multiplexed Gene Expression Profiling and Cell Type Analysis Using Chimeric Padlock Probes and In Situ Sequencing in Mouse Brain Tissue Sections Materials and Methods A P30 mouse brain was, right after surgical removal and without any fixation, imbedded into OCT medium and directly frozen on dry ice, and thereafter stored at −80° C. until usage. 10 μm sections were then cut with a cryostat and sections collected on Superfrost glass slides. Sections were then shortly fixated in 3.7% PFA in DEPC treated PBS for 5 min at room temperature. After that the sections were washed once in DEPC-PBS Tween 0.05% and permeabilized with 0.1 M HCl for 5 min at room temperature. After the permeabilization, slides were washed twice in DEPC-PBS and dehydrated through an ethanol series of 70%, 85% and 100% for 2 min each. Secure seal chamber was mounted on the slide covering the tissue section, and the tissue was hydrated by a brief wash with PBS-T (DEPC-PBS with 0.05% Tween). To target mRNAs with chimeric padlock probes (PLPs), the section was, after the brief rehydration wash, immersed into chimeric PLP hybridization mixture containing 2×SSC buffer, 20% Formamide, 0.05 M KCl, 0.2 mg/mL BSA, 1 U/μL RNAse inhibitor and 50 nM chimeric PLPs. The hybridization was performed at 45° C. over-night. After that the section was washed 2× in pre-warmed buffer (2×SSC, 20% Formamide) at 37° C. for 15 min. Finally, the section was washed 2× in PBS-T. Then ligation reaction mix was added to the section, containing 1× SplintR ligase buffer, 0.2 mg/mL BSA, 0.8 U/μL RNAse inhibitor and 0.25 U/μL SplintR ligase. The ligation reaction was incubated for 60 min at 37° C. The sections were washed 2× in PBS-T. Next, the section was immersed in rolling circle amplification mixture, containing 1× phi29 polymerase buffer, 0.25 mM dNTPs, 0.2 mg/mL BSA, 1 U/μL phi29 polymerase, 5% Glycerol and 50 nM RCA primer. RCA was performed for 3h at 37° C. Subsequently, section was washed in PBS-T twice and detection probes (serving as anchor probes in the in situ sequencing reaction) were hybridized to the RCA products in situ in 2×SSC and 20% Formamide hybridization buffer for 30 min at room temperature.

For in situ sequencing, as previously described in Ke et al. (2013, Nature methods), the section was immersed into sequencing by ligation mixture, containing 1× T4 ligation buffer, 1 mM ATP, 0.2 mg/mL BSA, 0.1 U/μL T4 DNA ligase and 100 nM each of sequencing library base 1 (for sequencing the first barcode position, sequencing library base 2 for sequencing the 2nd barcode position, etc.). The sequencing reaction was incubated for 1 h at room temperature. The section was then washed 3× in PBS-T and the nuclei stained with DAPI, washed three times again, a short ethanol series was performed as described above, and then the tissue was mounted in Slowfade mounting medium. The tissue section was then imaged in fluorescent microscope with 20× objective. To sequence the 2nd base the sections were first washed in ethanol to remove mounting medium, then the sections were washed 2× in 100% formamide to strip off the anchor and ligated sequencing probes. The sections were washed 3× in PBS-T and then the sequencing by ligation mix for the second base (same composition as above) was added to the sections and the procedure was repeated for the 3rd and 4th position. Images of the sequencing reactions were then processed through Cell profiler software and Matlab scripts, as described previously in Ke et al (Nat methods 2013).

Results

Multiplexed in situ gene expression profiling using cDNA synthesis and subsequent targeting of the cDNA by DNA padlock probes (PLPs) is usually limited to high expressed genes, due to the low efficiency of cDNA synthesis. Targeting directly the RNA with PLPs has until now been difficult because of the low probe ligation efficiency of enzymes on RNA and insufficient specificity resulting in false positive signals. In this experiment, we show very efficient ligation of chimeric PLPs on RNA (FIG. 23). We applied chimeric PLPs on mouse brain tissue sections targeting 18 different genes with 5 probes for each gene (90 probes in total) (Table 10). The probes were barcoded with sequencing barcodes that could later be decoded by in situ sequencing. The probes were first hybridized to the RNA and then after a wash, probes were ligated using SplintR ligase. The use of T4RNA ligase 2 may further increase the specificity, as we have shown increased specificity and efficiency with T4 RNA ligase 2 (see previous examples). The ligated probes were amplified with RCA and the barcodes in the RCA products sequenced with sequencing by ligation chemistry, as described previously in Ke et al (Nat methods 2013). The overall expression pattern that was received with the direct RNA approach using chimeric PLPs was very comparable to that received by the traditional cDNA targeting approach (data not shown). For simplicity, general stain of all RCA products is presented in this example. Besides the advantage of high sensitivity for the chimeric PLP direct RNA approach, the assay costs are lower, as the cDNA synthesis step is associated to high costs for the reverse transcriptase, and the assay can be performed faster, since the cDNA synthesis step is omitted. Overall, chimeric probes show a promising potential for highly multiplexed RNA analysis in tissue sections combined with in situ sequencing read-out.

TABLE 1

| SEQ ID NO: | Name | 5' modification | Sequence (5'-3') |
|---|---|---|---|
| 1 | hsa_KRAS | | rArArCrUrUrGrUrGrGrUrArGrUrU rGrGrArGrCrUrGrGrUrGrGrCrGrU rArGrGrCrArArGrArGrUrGrCrC |
| 2 | KRASwt_PLP | Phos | AGCTCCAACTACCAC(10A)AGTAGCCG TGACTATCGACT(10A)CTTGCCTACGC CACC |
| 3 | hsa_let-7e | | rUrGrArGrGrUrArGrGrArGrGrUrU rGrUrArUrArGrUrU |
| 4 | hsa_let-7d | | rArGrArGrGrUrArGrUrArGrGrUrU rGrCrArUrArGrUrU |
| 5 | let7-a_PLP_1 | Phos | CTACTACCTCA(10A)CCTCAATGCACA TGTTTGGCTCC(10A)AACTATACAAC |
| 6 | let7-f_PLP_1 | Phos | CTACTACCTCA(10A)CCTCAATGCACA TGTTTGGCTCC(10A)AACTATACAAT |
| 7 | let7-e_PLP_1 | Phos | CTCCTACCTCA(10A)CCTCAATGCACA TGTTTGGCTCC(10A)AACTATACAAC |
| 8 | let7-d_PLP_1 | Phos | CTACTACCTCT(10A)CCTCAATGCACA CTGTTTGGCTCC(10A)AACTATGCAA |
| 9 | let7-a_PLP_RNA_1 | Phos | CTACTACCTCA(10A)CCTCAATGCACA GTTTTGGCTCC(10A)AACTATACAArC |
| 10 | let7-f_PLP_RNA_1 | Phos | CTACTACCTCA(10A)CCTCAATGCACA TGTTTGGCTCC(10A)AACTATACAArU |
| 11 | let7-e_PLP_RNA_1 | Phos | CTCCTACCTCA(10A)CCTCAATGCACA TGTTTGGCTCC(10A)AACTATACAArC |
| 12 | let7-d_PLP_RNA_1 | Phos | CTACTACCTCT(10A)CCTCAATGCACA TGTTTGGCTCC(10A)AACTATGCAArC |

TABLE 1-continued

| SEQ ID NO: | Name | 5' modification | Sequence (5'-3') |
|---|---|---|---|
| 13 | benchm_templ_C | | rUrCrUrCrGrCrUrGrUrCrArU*rCrCrCrUrArUrArUrCrCrUrCrG |
| 14 | benchm_templ_A | | rUrCrUrCrGrCrUrGrUrCrArU*rArCrCrUrArUrArUrCrCrUrCrG |
| 15 | benchm_templ_G | | rUrCrUrCrGrCrUrGrUrCrArU*rGrCrCrUrArUrArUrCrCrUrCrG |
| 16 | benchm_templ_U | | rUrCrUrCrGrCrUrGrUrCrArU*rUrCrCrUrArUrArUrCrCrUrCrG |
| 17 | 3'T_PLP_2 | Phos | ATGACAGCGAGA(10A)AGTAGCCGTGACTATCGACT(10A)CGAGGATATAGGT |
| 18 | 3'G_PLP_2 | Phos | ATGACAGCGAGA(10A)AGTAGCCGTGACTATCGACT(10A)CGAGGATATAGGG |
| 19 | 3'A_PLP_2 | Phos | ATGACAGCGAGA(10A)AGTAGCCGTGACTATCGACT(10A)CGAGGATATAGGA |
| 20 | 3'C_PLP_2 | Phos | ATGACAGCGAGA(10A)AGTAGCCGTGACTATCGACT(10A)CGAGGATATAGGC |
| 21 | 3'rT_PLP_2 | Phos | ATGACAGCGAGA(10A)AGTAGCCGTGACTATCGACT(10A)CGAGGATATAGGrT |
| 22 | 3'rG_PLP_2 | Phos | ATGACAGCGAGA(10A)AGTAGCCGTGACTATCGACT(10A)CGAGGATATAGGrG |
| 23 | 3'rA_PLP_2 | Phos | ATGACAGCGAGA(10A)AGTAGCCGTGACTATCGACT(10A)CGAGGATATAGGrA |
| 24 | 3'rC_PLP_2 | Phos | ATGACAGCGAGA(10A)AGTAGCCGTGACTATCGACT(10A)CGAGGATATAGGrC |
| 25 | Decorator probe_1 | Cy3 | CCTCAATGCACATGTTTGGCTCCa |
| 26 | Decorator probe2_2 | Cy3 | AGTAGCCGTGACTATCGACTa | r[N]: RNA oligonucleotide; (10A): linker; a: last four bases of the decorator probe were 2' O-methylRNA to prevent oligo hydrolysis by Phi29 polymerase; italics: decorator sequence.

TABLE 2

| SEQ ID NO: | Name | 5' modification | Sequence (5'-3') |
|---|---|---|---|
| 27 | hsa_let-7a | | rUrGrArGrGrUrArGrUrArGrGrUrUrGrUrArUrArGrUrU |
| 28 | let-7a_PLP | Phos | CTACTACCTCA(7A)CCTCAATGCACATGTTTGGCTCC(7A)AACTATACAAC |
| 29 | iLock_1 | | CGCGTGTCGTTGCCCTACTACCTCA(10A)CCTCAATGCACATGTTTGGCTCC(10A)AACTATACAAC |
| 30 | iLock-3_1 | | CGCGTGTCGTTGCCCTACTACCTCA(10A)CCTCAATGCACATGTTTGGCTCC(10A)AACTATACAArC |
| 31 | iLock-3D_1 | | CGCGTGTCGTTGCrCCTACTACCTCA(10A)CCTCAATGCACATGTTTGGCTCC(10A)AACTATACAArC |
| 32 | iLock-3D5_1 | | CGCGTGTCGTTGCrCrCTACTACCTCA(10A)CCTCAATGCACATGTTTGGCTCC(10A)AACTATACAArC |

TABLE 2-continued

| SEQ ID NO: | Name | 5' modification | Sequence (5'-3') |
|---|---|---|---|
| 33 | iLock-3DF_1 | | rCrGrCrGrTrGrTrCrGrTrTrGrCrCCTACTACCTCA(10A)CCTCAATGCACATGTTTGGCTCC(10A)AACTATACAArC |
| 34 | iLock-DF_1 | | rCrGrCrGrTrGrTrCrGrTrTrGrCrCCTACTACCTCA(10A)CCTCAATGCACATGTTTGGCTCC(10A)AACTATACAAC |
| 35 | benchm_templ_C | | rUrCrUrCrGrCrUrGrUrCrArU*rCrCrCrUrArUrArUrCrCrUrCrG |
| 36 | benchm_templ_A | | rUrCrUrCrGrCrUrGrUrCrArU*rArCrCrUrArUrArUrCrCrUrCrG |
| 37 | benchm_templ_G | | rUrCrUrCrGrCrUrGrUrCrArU*rGrCrCrUrArUrArUrCrCrUrCrG |
| 38 | benchm_templ_U | | rUrCrUrCrGrCrUrGrUrCrArU*rUrCrCrUrArUrArUrCrCrUrCrG |
| 39 | 3'T_iLock_3 | | TATATCCCTATATTATGACAGCGAGA(10A)AGTAGCCGTGACTATCGACT(10A)CGAGGATATAGGT |
| 40 | 3'G_iLock_3 | | TATATCCCTATATGATGACAGCGAGA(10A)AGTAGCCGTGACTATCGACT(10A)CGAGGATATAGGG |
| 41 | 3'A_iLock_3 | | TATATCCCTATATAATGACAGCGAGA(10A)AGTAGCCGTGACTATCGACT(10A)CGAGGATATAGGA |
| 42 | 3'C_iLock_3 | | TATATCCCTATATCATGACAGCGAGA(10A)AGTAGCCGTGACTATCGACT(10A)CGAGGATATAGGC |
| 43 | 3'U_iLock_RNA_3 | | TATATCCCTATATrUATGACAGCGAGA(10A)AGTAGCCGTGACTATCGACT(10A)CGAGGATATAGGrU |
| 44 | 3'G_iLock_RNA_3 | | TATATCCCTATATrGATGACAGCGAGA(10A)AGTAGCCGTGACTATCGACT(10A)CGAGGATATAGGrG |
| 45 | 3'A_iLock_RNA_3 | | TATATCCCTATATrAATGACAGCGAGAG(10A)AGTAGCCGTGACTATCGACT(10A)CAGGATATAGGrA |
| 46 | 3'C_iLock_RNA_3 | | TATATCCCTATATrCATGACAGCGAGA(10A)AGTAGCCGTGACTATCGACT(10A)CGAGGATATAGGrC |
| 47 | Decorator probe_1 | Cy3 | CCTCAATGCACATGTTTGGCTCCa |
| 48 | Decorator probe_2 | Cy3 | TGCGTCTATTTAGTGGAGCCa |
| 49 | Decorator probe_3 | Cy3 | AGTAGCCGTGACTATCGACTa |

TABLE 3

| SEQ ID NO: | Name | Sequence (5'-3') |
|---|---|---|
| 50 | hsa_let-7a | rUrGrAGrGrUrArGrUrArGrGrUrUrGrUrArUrArGrUrU |
| 51 | hsa_let-7f | rUrGrArGrGrUrArGrUrArGrArUrUrGrUrArUrArGrUrU |
| 52 | hsa_let-7e | rUrGrArGrGrUrArGrGrArGrGrUrUrGrUrArUrArGrUrU |
| 53 | hsa_let-7d | rArGrArGrGrUrArGrUrArGrGrUrUrGrCrArUrArGrUrU |
| 54 | let-7a_seqRNA | AAAGATGCGATACrACTACCTCA*TGCGTCTATTTAGTGGAGCCC*GCTATCTTCTTTAACTATACAACCTrA |
| 55 | let-7e_seqRNA | AAAATGTCGTTGCrCCTCCTACCTCA*TGCGTCTATTTAGTGGAGCCG*CCTATCTTCTTTAACTATACAArC |
| 56 | let-7d_seqRNA | AAAATGTCGTTGCrCCTACTACCTCT*TGCGTCTATTTAGTGGAGCCA*TCTATCTTCTTTAACTATgCAArC |
| 57 | let-7f_seqRNA | AAAATGTCGTTGCrUCTACTACCTCA*TGCGTCTATTTAGTGGAGCC*TACTATCTTCTTTAACTATACAArU |
| 58 | let-7a_seq | AAAGATGCGATACACTACCTCA*TGCGTCTATTTAGTGGAGCCC*GCTATCTTCTTTAACTATACAACCTA |
| 59 | let-7e_seq | AAAATGTCGTTGCCCTCCTACCTCA*TGCGTCTATTTAGTGGAGCCG*CCTATCTTCTTTAACTATACAAC |
| 60 | let-7d_seq | AAAATGTCGTTGCCCTACTACCTCT*TGCGTCTATTTAGTGGAGCCA*TCTATCTTCTTTAACTATGCAAC |
| 61 | let-7f_seq | AAAATGTCGTTGCTCTACTACCTCA*TGCGTCTATTTAGTGGAGCC*TACTATCTTCTTTAACTATACAAT |
| 62 | Decorator probe | Cy3-*TGCGTCTATTTAGTGGAGCC*a |
| 63 | anchor primer | AlexaFluor750-TGCGTCTATTTAGTGGAGCCa |
| 64 | seqlibb 1T | pTNNNNNNNNN-FITCb |
| 65 | seqlibb 1G | PGNNNNNNNNN-Cy3b |
| 66 | seqlibb 1A | pANNNNNNNNN-Cy5b |
| 67 | seqlibb 1C | PCNNNNNNNNN-TexasRedb |

TABLE 4

| SEQ ID NO: | Name | Sequence (5'-3') |
|---|---|---|
| 68 | Mouse ACTB | GGCCTGTACACTGACTTGAGACCAATAAAAGTGCACACCTTACCTTACACAAC |
| 69 | Human ACTB | TACCTGTACACTGACTTGAGACCAGTTGAATAAAAGTGCACACCTTAAAAATGAAAAAAAAAAAAAAAAAAAAAAAAAAAAAAAAAAAAAAA |
| 70 | Mouse PLP | TAAGGTGTGCAAAAAGTAGCCGTGACTATCGACTAAAAGTAGCCGTGACTATCGACT GTTTGTGTAAGG |
| 71 | Human PLP | TAAGGTGTGCAAGTCGGAAGTACTACTCTCTAAAAGTCGGAAGTACTACTCTCTTTTTTTTTCATTTT |
| 72 | Mouse CPLP | TAAGGTGTGCAAAAAGTAGCCGTGACTATCGACTAAAAGTAGCCGTGACTATCGACTGTTTGTGTAAGrG |
| 73 | Human cPLP | TAAGGTGTGCAAGTCGGAAGTACTACTCTCTAAAAGTCGGAAGTACTACTCTCTTTTTTTTTCATTTrU |
| 74 | Mouse iLock | TAtaTCcctatatGTAAGGTGTGCAAAAAGTAGCCGTGACTATCGACTAAAAGTAGCCGTGACTATCGACTGTTTGTGTAAGG |
| 75 | Human iLock | TAtaTCcctatatTTAAGGTGTGCAAGTCGGAAGTACTACTCTCTAAAAGTCGGAAGTACTACTCTCTTTTTTTTTCATTTT |
| 76 | Mouse ciLock | TAtaTCcctatatrGTAAGGTGTGCAAAAAGTAGCCGTGACTATCGACTAAAAGTAGCCGTGACTATCGACTGTTTGTGTAAGrG |
| 77 | Human ciLock | TAtaTCcctatatrUTAAGGTGTGCAAGTCGGAAGTACTACTCTCTAAAAGTCGGAAGTACTACTCTCTTTTTTTTCATTTrU |

TABLE 5

| SEQ ID NO: | Name | Sequence (5'-3') |
|---|---|---|
| 78 | miR21_BIO | rUrUrUrUrUrUrUrUrUrUrUrUrUrUrUrArCrUrUrArUrCrArGrArCrUrGrArUrGrUrUrGrA |
| 79 | >miR21B2DO_PLP | /5Phos/CTGATAAGCTAGCCGAATCTAAGAGTAGCCGTGACTATCGACTAAAACTACACCA |
| 80 | >miR21B2DO_iLock | ccgtcgctgcgtTCTGATAAGCTAAAAAAAAGTAGCCGTGACTATCGACTAAAAAAATCAACATCAGT |
| 81 | > miR21 B2DO_rPLP | /5Phos/CTGATAAGCTAGCCGAATCTAAGAGTAGCCGTGACTATCGACTAAAACTACACCATCAACATCAGrU |
| 82 | >miR21B2DO_RiLock | ccgtcgctgcgtrUCTGATAAGCTAAAAAAAAGTAGCCGTGACTATCGACTAAAAAAATCAACATCAGrU |
| 83 | >B2DO_Cy3 | /Cy_3/AGTAGCCGTGACTATCGACT |
| 84 | >antimiR21_FAM | FAM/TCAACATCAGTCTGATAAGCTA | antimiR21 FAM is a "coating control" complementary to miR21, for visualising successful miR21 coating on the slide

TABLE 6

| SEQ ID NO: | Name | Sequence (5'-3') |
|---|---|---|
| 85 | KRAS DNA template | ACATTTTCATTATTTTTATTATAAGGCCTGCTGAAAATGACTGAATATAAACTTGTGGTAGTTGGAGCTGGTGGCGTAGGCAAGAGTGCCTTGACGATA |
| 86 | wt KRAS PLP | AGCTCCAACTACCACAAAGTCGATAGTCACGGCTACTCAGACGTAACGCGTTCAGTGATGCCCTTGCCTACGCCACC |

TABLE 6-continued

| | | |
|---|---|---|
| 87 | KRAS RNA template | rArArCrUrUrGrUrGrGrUrArGrUrUrG rArGrCrUrGrGrUrGrGrCrGrUrArGrC rArArGrArGrUrGrCrC |
| 88 | chim wt KRAS PLP | AGCTCCAACTACCACAAAGTCGATAGTCACGG CTACTCAGACGTAACGCGTTCAGTGATGCCCT TGCCTACGCCACrC |
| 89 | chim wt KRAS PLP_2 | AGCTCCAACTACCACAAAGTCGATAGTCACGG CTACTCAGACGTAACGCGTTCAGTGATGCCCT TGCCTACGCCArCrC |
| 90 | mut KRAS PLP | AGCTCCAACTACCACAACCTCAATGCACATGT TTGGCTCCCAGACGTAACGCGTTCAGTGATGC CCTTGCCTACGCCACT |
| 91 | chim mut KRAS PLP | AGCTCCAACTACCACAACCTCAATGCACATGT TTGGCTCCCAGACGTAACGCGTTCAGTGATGC CCTTGCCTACGCCACrU |
| 92 | RCA primer | CAT CAC TGA ACG C*G*T |
| 93 | mut DO-Cy5 | CCTCAATGCACATGTTTGGCTCC |
| 94 | wt DO-Cy3 | AGTCGATAGTCACGGCTACT |
| 95 | KRAS wt invader chim 3-5 | TAtaTCcctatatrCAGCTCCAACTACCACAA AGGTCGATAGTCACGGCTACTCAGACGTAACC GTTCAGTGATGCCCTTGCCTACGCCACrC |
| 96 | KRAS wt invader chim 3 | TAtaTCcctatatCAGCTCCAACTACCACAAA GTCGATAGTCACGGCTACTCAGACGTAACGCG TTCAGTGATGCCCTTGCCTACGCCACrC |
| 97 | KRAS mut invader chim 3-5 | TAtaTCcctatatrUAGCTCCAACTACCACAA CCTCAATGCACATGTTTGGCTCC CAGACGT AACGCGTTCAGTGATGCCCTTGCCTACGCCA CrU |
| 98 | KRAS mut invader chim 3 | TAtaTCcctatatTAGCTCCAACTACCACAAC CTCAATGCACATGTTTGGCTCC CAGACGTA ACGCGTTCAGTGATGCCCTTGCCTACGCCA CrU |

TABLE 7

| | | |
|---|---|---|
| 99 | KRAS gapfill invader | TAtaTCtctatatAGCTCCAACTACCACA AGTAGTCGATAGTCACGGCTACTCAGACG TAACGCGTTCAGTGATGAGTAGGC ACTCTTGCCTAC |
| 100 | invader_splint_chim | TAtaTCtctatatGCCACrC |
| 101 | invader_splint | TAtaTCtctatat GCCACC |
| 102 | splint | GCCACrC |
| 103 | splint_chim | GCCACC |
| 104 | RCA primer | CAT CAC TGA ACG C*G*T |
| 105 | DO-Cy3 | AGTCGATAGTCACGGCTACT |

TABLE 8

| SEQ ID NO | Name | 5' modification | Sequence (5'-3') |
|---|---|---|---|
| 106 | Kras_wt_RNA | | rArArCrUrUrGrUrGrGrUrArG rUrUrGrGrArGrCrUrGrGrUrG rGrCrGrUrArGrGrCrArArGrA rGrUrGrCrC |
| 107 | R_KRAS wt1_1 | Phos | AGCTCCAACTACCACAA [1] CArGACGTAACGCGTTCAGTGA TGCCCTTGCCTACGCCACC |
| 108 | R_KRAS wt1_2 | Phos | AGCTCCAACTACCACAA [1] CArGrACGTAACGCrGTTCAG TGATGCCCTTGCCTACGCCACC |
| 109 | R_KRAS wt1_3 | Phos | AGCTCCAACTACCACAA [1] CArGrArCGTAACGCrGTTCA GTGATGCCCTTGCCTACGCCACC |
| 110 | R_KRAS wt1_4 | Phos | AGCTCCAACTACCACAA [1] CArGrArCrGTAACGCrGTTCA GTGATGCCCTTGCCTACGCCACC |
| 111 | R_KRAS wt1_5 | Phos | AGCTCCAACTACCACAA [1] CArGrArCrGrUAACGCrGTTC AGTGATGCCCTTGCCTACGCCACC |
| 112 | R_KRAS wt1_7 | Phos | AGCTCCAACTACCACAA [1] CArGrArCrGrUrAACGCrG TTCAGTGATGCCCTTGCCTACG CCACC |
| 113 | R_KRAS wt1_6S | Phos | AGCTCCAACTACCACAA [1] CArGrACGrUrAArCrGTTC AGTGATGCCCTTGCCTACGCCA CC |
| 114 | R_KRAS wt1_DNA | | AGCTCCAACTACCAC (10A) [2] (10A) CTTGCCTACGCC ACC |
| 115 | R_KRAS wt1_RNA | Phos | AGCTCCAACTACCAC (10A) [2] (10A) CTTGCCTACGC CACrC |
| 116 | Decorator probe [1] | Cy3 | *CCTCAATGCACATGTTTGGCTC** |
| 117 | Decorator probe2 [2] | Cy3 | *AGTCGATAGTCACGGCTACT** | r[N]: RNA oligonucleotide; (10A): linker;
*: last four bases of the decorator probe were 2' O-methylRNA to prevent oligo hydrolysis by Phi29 polymerase; [1/2] decorator binding site and sequence

TABLE 9

| SEQ ID NO: | Name | Sequence (5'-3') |
|---|---|---|
| 118 | Kras_wt_RNA | rArArCrUrUrGrUrGrGrUrArGrUrGrGrArGrCrUrGrGrUrGrG rCrGrUrArGrGrCrArArGrArGrUrGrC |
| 119 | R_KRAS.0 | AGCTCCAACTACCACAAAGTCGATAGTCACGGCTACTCAGACGTAACGCG TTCAGTGATGCCCTTGCCTACGCCACC |
| 120 | R_KRAS.1G | AGCTCCAACTACCACAAAGTCGATAGTCACGGCTACTCArGACGTAACGC GTTCAGTGATGCCCTTGCCTACGCCACC |
| 121 | R_KRAS.1C | AGCTCCAACTACCACAAAGTCGATAGTCACGGCTACTCArCACGTAACGC GTTCAGTGATGCCCTTGCCTACGCCACC |
| 122 | R_KRAS.1A | AGCTCCAACTACCACAAAGTCGATAGTCACGGCTACTCArAACGTAACGC GTTCAGTGATGCCCTTGCCTACGCCACC |
| 123 | R_KRAS.1U | AGCTCCAACTACCACAAAGTCGATAGTCACGGCTACTCArUACGTAACGC GTTCAGTGATGCCCTTGCCTACGCCACC |
| 124 | R_KRAS.2G | AGCTCCAACTACCACAAAGTCGATAGTCACGGCTACTCArGrGCGTAACG rCrGTTCAGTGATGCCCTTGCCTACGCCACC |
| 125 | R_KRAS.2C | AGCTCCAACTACCACAAAGTCGATAGTCACGGCTACTCArCrCCGTAACG rCrGTTCAGTGATGCCCTTGCCTACGCCACC |
| 126 | R_KRAS.2A | AGCTCCAACTACCACAAAGTCGATAGTCACGGCTACTCArArACGTAACG rCrGTTCAGTGATGCCCTTGCCTACGCCACC |
| 127 | R_KRAS.2U | AGCTCCAACTACCACAAAGTCGATAGTCACGGCTACTCArUrUCGTAACG rCrGTTCAGTGATGCCCTTGCCTACGCCACC |
| 128 | AluI_KRAS_R0 | CGCCACCAGCTCCAACTA |
| 129 | PE1 | <u>ACACTCTTTCCCTACACGACGCTCTTCCGATCT</u>*CTGGTGGCGTAGGCAAG GGC* |
| 130 | PE2 | <u>GTGACTGGAGTTCAGACGTGTGCTCTTCCGATCT</u>*CTCCAACTACCACAAA GTCG* |
| 131 | R_KRAS.3G | AGCTCCAACTACCACAAAGTCGATAGTCACGGCTACTCArGrGrGTTAAC GrCrGTTCAGTGATGCCCTTGCCTACGCCACC |
| 132 | R_KRAS.3C | AGCTCCAACTACCACAAAGTCGATAGTCACGGCTACTCArCrCrCGTAAC GrCrGTTCAGTGATGCCCTTGCCTACGCCACC |
| 133 | R_KRAS.3A | AGCTCCAACTACCACAAAGTCGATAGTCACGGCTACTCArArArAGTAAC GrCrGTTCAGTGATGCCCTTGCCTACGCCACC |
| 134 | R_KRAS.3U | AGCTCCAACTACCACAAAGTCGATAGTCACGGCTACTCArUrUrUCGTAA CGrCrGTTCAGTGATGCCCTTGCCTACGCCACC |
| 135 | R_KRAS.5 | AGCTCCAACTACCACAAAGTCGATAGTCACGGCTACTCArGrArCrGrUA ACGCGTTCAGTGATGCCCTTGCCTACGCCACC |
| 136 | R_KRAS.6S | AGCTCCAACTACCACAAAGTCGATAGTCACGGCTACTCArGrACrUrAA CrGrCGTTCAGTGATGCCCTTGCCTACGCCACC |
| 137 | R_KRAS.3 | AGCTCCAACTACCACAAAGTCGATAGTCACGGCTACTCArGrArCGTAAC rGrCrGTTCAGTGATGCCCTTGCCTACGCCACC |
| 138 | R_KRAS.3S | AGCTCCAACTACCACAAAGTCGATAGTCACGGCTACTCArGArCrGrUAAC GCGTTCAGTGATGCCCTTGCCTACGCCACC |
| 139 | R_KRAS.2 | AGCTCCAACTACCACAAAGTCGATAGTCACGGCTACTCArGrACGTAACG rCrGTTCAGTGATGCCCTTGCCTACGCCACC |
| 140 | R_KRAS.7 | AGCTCCAACTACCACAAAGTCGATAGTCACGGCTACTCA rGrArCrGrUrArACGCGTTCAGTGATGCCCTTGCCTACGCCACC | r[N]: RNA oligonucleotide, bolded; italic: highlighted region where primer hybridises to the monomer, underlined: extension sequences highlighted that introduce binding sites for index primers; yellow: AluI restriction site, these padlock probes were used in the monomer sequencing experiment.

TABLE 10

| | | |
|---|---|---|
| 141 | Detection probe (seq anchor probe) | 5' Alexa750-TGCGTCTATTTAGTGGAGCC |
| 142 | Seq library 1st base-G | 5' phos-GNNNCTATC-3' Cy3 |
| 143 | RCA primer | 5'-GGCTCCACTAAATAGACG*C*A-3' thiophosphate (*) |
| 144 | Seq library 1st base-A | 5' phos-ANNNCTATC-3' Cy5 |
| 145 | Seq library 1st base-C | 5' phos-CNNNCTATC-3' Texred |
| 146 | Seq library 1st base-T | 5' phos-TNNNCTATC-3' Alexa488 |
| 147 | Seq library 2nd base-G | 5' phos-NGNNCTATC-3' Cy3 |
| 148 | Seq library 2nd base-A | 5' phos-NANNCTATC-3' Cy5 |
| 149 | Seq library 2nd base-C | 5' phos-NCNNCTATC-3' Texred |
| 150 | Seq library 2nd base-T | 5' phos-NTNNCTATC-3' Alexa488 |
| 151 | Seq library 3rd base-G | 5' phos-NNGNCTATC-3' Cy3 |
| 152 | Seq library 3rd base-A | 5' phos-NNANCTATC-3' Cy5 |
| 153 | Seq library 3rd base-C | 5' phos-NNCNCTATC-3' Texred |
| 154 | Seq library 3rd base-T | 5' phos-NNTNCTATC-3' Alexa488 |
| 155 | Seq library 4th base-G | 5' phos-NNNGCTATC-3' Cy3 |
| 156 | Seq library 4th base-A | 5' phos-NNNACTATC-3' Cy5 |
| 157 | Seq library 4th base-C | 5' phos-NNNCCTATC-3' Texred |
| 158 | Seq library 4th base-T | 5' phos-NNNTCTATC-3' Alexa488 |
| | Chimeric probe name | RNA directed chimeric probe sequence |
| 159 | Calb_1119_RNA | CATCGCAGCGGAGACGACAGCTGATTCCTTTGACTCACATTGCGTCTATTTAGTGGAGCCAATGCTATCTTCTTTATACAGCGAAGAACTCATrG |
| 160 | Calb2_1328_RNA | CACACACGTCAAGAACACAACTGATTCCTTTGACTCACATTGCGTCTATTTAGTGGAGCCAATGCTATCTTCTTTGAAGCCAAAGAGAAAAGGArA |
| 161 | Calb2_164_RNA | ACCTTCAATGTACCCATTTCCTGATTCCTTTGACTCACATTGCGTCTATTTAGTGGAGCCAATGCTATCTTCTTTAAGAAGTTCTCTAGCTCTTrU |
| 162 | Calb2_500_RNA | AGGTTCATCATAGGGCCTGTCTGATTCCTTTGACTCACATTGCGTCTATTTAGTGGAGCCAATGCTATCTTCTTTTGGGTGTACTCCTGGAGCTrU |
| 163 | Calb2_937_RNA | GTCAAGAGAGTCAGGACAGCCTGATTCCTTTGACTCACATTGCGTCTATTTAGTGGAGCCAATGCTATCTTCTTTGGGGAGGTCTGGGAAGGAGrU |
| 164 | Calb2_DO3_CCAA_RNA | CTCATACAGATCCTTCAGCTGATTCCTTTGACTCACATTGCGTCTATTTAGTGGAGCCCAACTATCTTCTTTTTCATCTCCTTCTTGTTCTrU |
| 165 | Chod1_1164_RNA | CGGGCTAGTTTTTGATCTTCCTGATTCCTTTGACTCACATTGCGTCTATTTAGTGGAGCCAGTACTATCTTCTTTATCCACAGTGTAGACTGATrU |

TABLE 10-continued

| | | |
|---|---|---|
| 166 | Chod1_1798_RNA | AAAGCAAAGAAACAGAACAACTGATTCCTTTGACTCACATTGCGTCTAT TTAGTGGAGCCAGTACTATCTTCTTTTCCTAAACTTTATCGAACCrC |
| 167 | Chod1_2071_RNA | ATTCTATAGGCAACATGTGACTGATTCCTTTGACTCACATTGCGTCTAT TTAGTGGAGCCAGTACTATCTTCTTTACTCTGGGGAGCTATTTGCrA |
| 168 | Chod1_2252_RNA | GTTCTGCTTAGCATCACACTCTGATTCCTTTGACTCACATTGCGTCTAT TTAGTGGAGCCAGTACTATCTTCTTTTTAATCATTAATATCAGTGrU |
| 169 | Chod1_293_RNA | TCCTACTCCCTCCTTCCCAGCTGATTCCTTTGACTCACATTGCGTCTAT TTAGTGGAGCCAGTACTATCTTCTTTTTCCTTGCTTTCCTGCTGGrG |
| 170 | Chod1_789_RNA | GAACTGGGAGCTGCTTCCATCTGATTCCTTTGACTCACATTGCGTCTAT TTAGTGGAGCCAGTACTATCTTCTTTTCATCAGTGTACCAGTTTCrG |
| 171 | Chod1_916_RNA | TGTTGCACCTGTCGTCATTCCTGATTCCTTTGACTCACATTGCGTCTAT TTAGTGGAGCCAGTACTATCTTCTTTGCAGATGTAATTGTGCTTCrA |
| 172 | Cort_326_RNA | CCCGGGGGTACCCCCTCCGACGTGCTTGTGGTAGCAAATATGCGTCTAT TTAGTGGAGCCTGATCTATCTTCTTTCTTCCTGGCTCTTGGACArG |
| 173 | Cort_529_RNA | CAAAGCTGACATAAGAAGAACGTGCTTGTGGTAGCAAATATGCGTCTAT TTAGTGGAGCCTGATCTATCTTCTTTTTCTCACAGGGCAGGGGAGrG |
| 174 | Htr3a_1014_GGAC_RNA | AGTGTGTCTGACACGATGATCGTGCTTGTGGTAGCAAATATGCGTCTAT TTAGTGGAGCCGGACCTATCTTCTTTTACCGATGGCCGTTGCTGGrC |
| 175 | Htr3a_1309_GTAA_RNA | ATGGCTGCAGTGGTTTCCCACGTGCTTGTGGTAGCAAATATGCGTCTAT TTAGTGGAGCCGTAACTATCTTCTTTAAGTCCTGAGGTCCTCCAArC |
| 176 | Htr3a_1573_TAAC_RNA | CCAAATGGACCAGAGAGTGACGTGCTTGTGGTAGCAAATATGCGTCTAT TTAGTGGAGCCTAACCTATCTTCTTTGTGCCCACTCAAGAATAATrG |
| 177 | Htr3a_1750_TATT_RNA | AAGTCAGAGAGACAGACTGGCGTGCTTGTGGTAGCAAATATGCGTCTAT TTAGTGGAGCCTATTCTATCTTCTTTGCTTTAAAGCCATGATAGGrG |
| 178 | Htr3a_1927_TCGC_RNA | GCAAGACAATTTGCTTTTCTCGTGCTTGTGGTAGCAAATATGCGTCTAT TTAGTGGAGCCTCGCCTATCTTCTTTCAGAAGTCTCAGGCATCTArU |
| 179 | Htr3a_2045_TGGA_RNA | ATTATCCCCTGCTCCCATTGCGTGCTTGTGGTAGCAAATATGCGTCTAT TTAGTGGAGCCTGGACTATCTTCTTTTTAAGATATCATAGCATTTrU |
| 180 | Htr3a_21_AAGT_RNA | GTCCCAGGCAGACTGCTTTTCGTGCTTGTGGTAGCAAATATGCGTCTAT TTAGTGGAGCCAAGTCTATCTTCTTTCCACCCGCTGCCAACCTCArU |
| 181 | Htr3a_247_CAGC_RNA | GTCTGACAGCCTTAGTAGAGCGTGCTTGTGGTAGCAAATATGCGTCTAT TTAGTGGAGCCCAGCCTATCTTCTTTTTGTAGTTAGCCAGGAGGTrG |
| 182 | Htr3a_424_CGGT_RNA | AGTCCACTGCAGAAACTCATCGTGCTTGTGGTAGCAAATATGCGTCTAT TTAGTGGAGCCCGGTCTATCTTCTTTACATTGTCGAAGTCCTCAGrG |
| 183 | Htr3a_89_CACT_RNA | CTCAGAGCAGCCACTCAGGACGTGCTTGTGGTAGCAAATATGCGTCTAT TTAGTGGAGCCCACTCTATCTTCTTTCTTCCCAGATGTGGGAGGGrC |
| 184 | Htr3a_955_GCTC_RNA | AGAGACTCTCTCACCGCTGTCGTGCTTGTGGTAGCAAATATGCGTCTAT TTAGTGGAGCCGCTCCTATCTTCTTTAGAAGGAGTGTGATCTTGArA |
| 185 | Neurod6_1033_RNA | TAGAAGGATTCATATGCACTCTGATTCCTTTGACTCACATTGCGTCTAT TTAGTGGAGCCTTGCCTATCTTCTTTACTCAGGGGAGGTACTTTCrA |
| 186 | Neurod6_108_RNA | CTGCTAGTGACGTCACAGGGCTGATTCCTTTGACTCACATTGCGTCTAT TTAGTGGAGCCTTGCCTATCTTCTTTAGAGCTGGTACCCATGCCArU |
| 187 | Neurod6_1524_RNA | TGTGATACAGACAAGAGGGACTGATTCCTTTGACTCACATTGCGTCTAT TTAGTGGAGCCTTGCCTATCTTCTTTAGAGAGAGAGAATCACArG |
| 188 | Neurod6_168_RNA | TCTCATTGATCTCTAAAAAGCTGATTCCTTTGACTCACATTGCGTCTAT TTAGTGGAGCCTTGCCTATCTTCTTTATCTGTGTGTATCTGCACTrA |
| 189 | Neurod6_1688_RNA | AGACATTGAAGTATGCTGTGCTGATTCCTTTGACTCACATTGCGTCTAT TTAGTGGAGCCTTGCCTATCTTCTTTCATAACTGTACAACTGAAArU |
| 190 | Neurod6_2041_RNA | AACAATACAAAACAAGTGCTCTGATTCCTTTGACTCACATTGCGTCTAT TTAGTGGAGCCTTGCCTATCTTCTTTACCTGTACAGAAAAATCCTrG |
| 191 | Neurod6_228_RNA | TTTTCAGGCTGAGTGTCGCACTGATTCCTTTGACTCACATTGCGTCTAT TTAGTGGAGCCTTGCCTATCTTCTTTCATTTTGGATCTTCCAAATrC |

TABLE 10-continued

| | | |
|---|---|---|
| 192 | Neurod6_315_RNA | GTAGTGTTAACATGGTTCTTCTGATTCCTTTGACTCACATTGCGTCTAT<br>TTAGTGGAGCCTTGCCTATCTTCTTTTACGACAGACTCGTCAAACrG |
| 193 | Neurod6_495_RNA | TGTCTTCTTCCTCCTCTTCTCTGATTCCTTTGACTCACATTGCGTCTAT<br>TTAGTGGAGCCTTGCCTATCTTCTTTATTCTCATCTTCTTCCTCTrC |
| 194 | Neurod6_648_RNA | TGTCCAGAGCATCATTGAGGCTGATTCCTTTGACTCACATTGCGTCTAT<br>TTAGTGGAGCCTTGCCTATCTTCTTTGGGGACCACTTTTCGCAAArU |
| 195 | Neurod6_714_RNA | GTCGTAAAGTTTCTATTTTGCTGATTCCTTTGACTCACATTGCGTCTAT<br>TTAGTGGAGCCTTGCCTATCTTCTTTCCAGATGTAATTTTTGGCCrA |
| 196 | Neurod6_971_RNA | CCCATGCCCTGGGGAGTGGCTGATTCCTTTGACTCACATTGCGTCTAT<br>TTAGTGGAGCCTTGCCTATCTTCTTTGACTTGGAATTATCAAGAGrU |
| 197 | Nov_D02_ATGC_RNA | GGAGAAAGTTCATGACACTCTACGATTTTACCAGTGGCTGCGTCTATTT<br>AGTGGAGCCATGCCTATCTTCTTTGAGTCGGTTTGTCTATAArU |
| 198 | Pcp4_120_RNA | TCAGAAGGCAATGCTCAGGGCTGATTCCTTTGACTCACATTGCGTCTAT<br>TTAGTGGAGCCATCCCTATCTTCTTTGCTAGGTCCCACAGAACAGrC |
| 199 | Pcp4_181_RNA | TCCGGCACTTTGTCTCTCACCTGATTCCTTTGACTCACATTGCGTCTAT<br>TTAGTGGAGCCATCCCTATCTTCTTTTTGTCTTTTCCGTTGGTCGrC |
| 200 | Pcp4_305_RNA | ACTGAGACTGAATGGCCACACTGATTCCTTTGACTCACATTGCGTCTAT<br>TTAGTGGAGCCATCCCTATCTTCTTTTTTCTTCTGGAATTTTCTGrA |
| 201 | Pcp4_386_RNA | AACTTGGTGTCTTCAGGTGGCTGATTCCTTTGACTCACATTGCGTCTAT<br>TTAGTGGAGCCATCCCTATCTTCTTTTTCTTGATGGATGGTGGTTrG |
| 202 | Pcp4_472_RNA | TTCAGGTTTGTAGCAGGGTGCTGATTCCTTTGACTCACATTGCGTCTAT<br>TTAGTGGAGCCATCCCTATCTTCTTTATGGGTTTCTCTTCATGCArU |
| 203 | Pdela_1081_RNA | TTCTCTGTTGAGTCCGTCAGTCTACGAGTTTGCAGTCACGTGCGTCTAT<br>TTAGTGGAGCCATCGCTATCTTCTTTCTATAAGAGGAATGACAATrU |
| 204 | Pdela_120_RNA | ACTTTGGTTTTTCTTCAGGCTCTACGAGTTTGCAGTCACGTGCGTCTAT<br>TTAGTGGAGCCATCGCTATCTTCTTTAGCATGGACAATGCTGCGArA |
| 205 | Pdela_1216_RNA | TCACACACGGAGCCTTTTGTTCTACGAGTTTGCAGTCACGTGCGTCTAT<br>TTAGTGGAGCCATCGCTATCTTCTTTAGTCTGGGGCATAGCTCCCrA |
| 206 | Pdela_273_RNA | CATTTAAGGCAAATACATCATCTACGAGTTTGCAGTCACGTGCGTCTAT<br>TTAGTGGAGCCATCGCTATCTTCTTTGCTATGCTCCCCGCTTGCTrU |
| 207 | Pdela_334_RNA | AGATCATATCTGGTAAAGAGTCTACGAGTTTGCAGTCACGTGCGTCTAT<br>TTAGTGGAGCCATCGCTATCTTCTTTGAATCTTGAAGCGGTTGATrA |
| 208 | Pdela_469_RNA | ATATAATGCACAGTTTGAGTTCTACGAGTTTGCAGTCACGTGCGTCTAT<br>TTAGTGGAGCCATCGCTATCTTCTTTTGATACCTGTATGAAGCATrU |
| 209 | Pdela_615_RNA | TGTACAGAATAGCAACGTCCTCTACGAGTTTGCAGTCACGTGCGTCTAT<br>TTAGTGGAGCCATCGCTATCTTCTTTCTCAAGCACTGAGCGGTCGrU |
| 210 | Pdela_759_RNA | CTGTCGCTAAGACCATTTCATCTACGAGTTTGCAGTCACGTGCGTCTAT<br>TTAGTGGAGCCATCGCTATCTTCTTTCTGAAAATGCCCTGACATGrU |
| 211 | Pdela_904_RNA | CTGTAGTGCAACTTCCAAGTTCTACGAGTTTGCAGTCACGTGCGTCTAT<br>TTAGTGGAGCCATCGCTATCTTCTTTCCATTAGGGCCATGGTCCArU |
| 212 | Pdela_995_RNA | CTTCCGATCACAAAGTGGAGTCTACGAGTTTGCAGTCACGTGCGTCTAT<br>TTAGTGGAGCCATCGCTATCTTCTTTGACTGGGCAACCATTGTTGrA |
| 213 | Penk_1282_RNA | CAATACTGAGCTTCAAGACTTCTACGATTTTACCAGTGGCTGCGTCTAT<br>TTAGTGGAGCCGTACCTATCTTCTTTACAACATAGCCATAAGAGArC |
| 214 | Penk_286_RNA | CATGGGCTGTAGGAGAGAAGTCTACGATTTTACCAGTGGCTGCGTCTAT<br>TTAGTGGAGCCGTACCTATCTTCTTTCAAAGCCTCAGGAACCGCGrC |
| 215 | Penk_638_RNA | GATATAGCTCGTCCATCTTCTCTACGATTTTACCAGTGGCTGCGTCTAT<br>TTAGTGGAGCCGTACCTATCTTCTTTTTCTTCTTCTGGCTCCATGrG |
| 216 | Penk_83_RNA | TGCCTGGGACTATTCTATCTTCTACGATTTTACCAGTGGCTGCGTCTAT<br>TTAGTGGAGCCGTACCTATCTTCTTTGTTTCCTGCTGTTCTAGTGrA |
| 217 | Penk_882_RNA | AGTTGGGGGCTTCTTTTGAGTCTACGATTTTACCAGTGGCTGCGTCTAT<br>TTAGTGGAGCCGTACCTATCTTCTTTGCTCTTTTGCTTCATCTTCrC |

TABLE 10-continued

| | | |
|---|---|---|
| 218 | Plcxd2_D03_GAAA_RNA | GCACTCCTACACAATGACTGATTCCTTTGACTCACATTGCGTCTATTTAGTGGAGCCGAAACTATCTTCTTTGAAGATGGTGAGGGTArU |
| 219 | Plcxd2_D03_GGCC_RNA | GTGGTAGAAAATGAGAACCTGATTCCTTTGACTCACATTGCGTCTATTTAGTGGAGCCGGCCCTATCTTCTTTTGCTTGTAGAAGGGACrA |
| 220 | Rorb_2282_RNA | TCATTCAGAATTGGATTCCACTGATTCCTTTGACTCACATTGCGTCTATTTAGTGGAGCCAAATCTATCTTCTTTATAACCACCAAAGTGAAGTrU |
| 221 | Rorb_4479_RNA | TCAATTTTCTGCCTTAAGCCCTGATTCCTTTGACTCACATTGCGTCTATTTAGTGGAGCCAAATCTATCTTCTTTAAGAAGAAAAAGAAGTTCArU |
| 222 | Rorb_536_RNA | ATGTGAGGTCATAGATAGGTCTGATTCCTTTGACTCACATTGCGTCTATTTAGTGGAGCCAAATCTATCTTCTTTGGTAAACAAGTTGGGTACArG |
| 223 | Rorb_6395_RNA | GAGAAAGTGTCACAGATTTGCTGATTCCTTTGACTCACATTGCGTCTATTTAGTGGAGCCAAATCTATCTTCTTTAGGTACAATTAAGAGAAAGrG |
| 224 | Rorb_8435_RNA | TAGTTGTTAGGGAGTGCTGCCTGATTCCTTTGACTCACATTGCGTCTATTTAGTGGAGCCAAATCTATCTTCTTTAAGTAATAGAAAACTCTTTrU |
| 225 | Rorb_D03_CCGG_RNA | AGCCTTTTAAAGTCATATTTGGTCTGATTCCTTTGACTCACATTGCGTCTATTTAGTGGAGCCCCGGCTATCTTCTTAATCGGTCATCATAAAATACrU |
| 226 | Rprm_654_RNA | CGGTCCGTGATGGTGCGTGCTTGTGGTAGCAAATATGCGTCTATTTAGTGGAGCCTTGTCTATCTTCTTTGACAGGTTTGCGTTGCrU |
| 227 | Sst_432_AP1SWPLP_RNA | TAACAGGATGTGAATGTCTTCTACGATTTTACCAGTGGCCTGACTATCTTCTTTTAGGACAACAATATTAAAGrC |
| 228 | Synpr_1071_RNA | CATACTAGAGACTTTAAGCTICTACGATTTTACCAGTGGCTGCGTCTATTTAGTGGAGCCATTACTATCTTCTTTAAGGTAATCTATGCACATTrA |
| 229 | Synpr_1643_RNA | CCTCTCTGGATGCAAAGAAATCTACGATTTTACCAGTGGCTGCGTCTATTTAGTGGAGCCATTACTATCTTCTTTAACTATGGTGTCTAAATCTrG |
| 230 | Synpr_260_RNA | ATGTACACGACCGTGGCAGCTCTACGATTTTACCAGTGGCTGCGTCTATTTAGTGGAGCCATTACTATCTTCTTTGGTACTTGTTCTGGAAGAArA |
| 231 | Synpr_591_RNA | AAGGTATCTCTGTCCAGAGGTCTACGATTTTACCAGTGGCTGCGTCTATTTAGTGGAGCCATTACTATCTTCTTTTGCTTCTCCATGGGGTCTGrA |
| 232 | Synpr_D02_ATTA_RNA | CTTAAAAATTCTTCTGCTACTGGTCTACGATTTTACCAGTGGCTGCGTCTATTTAGTGGAGCCATTACTATCTTCTTCATTAATAATTGATTGAAACrU |
| 233 | Yjefn3_138_RNA | CACTAGCGTGCCCACATAGTCGTGCTTGTGGTAGCAAATATGCGTCTATTTAGTGGAGCCTTTACTATCTTCTTTGGCCTTGGTCACAGCCACCrG |
| 234 | Yjefn3_344_RNA | CTTCTCGCACTGCGTGGTCACGTGCTTGTGGTAGCAAATATGCGTCTATTTAGTGGAGCCTTTACTATCTTCTTTGACAGGAAGGGGATGTCCArU |
| 235 | Yjefn3_686_RNA | AAACTTTCGGCGGACGTCATCGTGCTTGTGGTAGCAAATATGCGTCTATTTAGTGGAGCCTTTACTATCTTCTTTTATTTTGGCAGGTGCAGGrC |
| 236 | Bgn_412_RNA | GGGCACAGTCTTCAGACCCATCTACGATTTTACCAGTGGCTGCGTCTATTTAGTGGAGCCCTATCTATCTTCTTTGTGTCAGGTGAGATCTCCTrU |
| 237 | Bgn_851_RNA | TCAGGGTCTCAGGGAGATCTTCTACGATTTTACCAGTGGCTGCGTCTATTTAGTGGAGCCCTATCTATCTTCTTTGTGGTCCAGGTGAAGTTCGrU |
| 238 | Bgn_1194_RNA | TCCCAGTAGGGCACAGGGTTTCTACGATTTTACCAGTGGCTGCGTCTATTTAGTGGAGCCCTATCTATCTTCTTTGGAAGGTGGCAGGCTGCACrU |
| 239 | Bgn_1577_RNA | AACAATGGCGGTGGCAGTGTTCTACGATTTTACCAGTGGCTGCGTCTATTTAGTGGAGCCCTATCTATCTTCTTTAGGAACACATGCCTGGATGrG |
| 240 | Bgn_2309_RNA | TCAGGGACCCAGGGGTGAGGTCTACGATTTTACCAGTGGCTGCGTCTATTTAGTGGAGCCCTATCTATCTTCTTTGACCATCACCTCCTACCACrA |
| 241 | Apq4_879_RNA | CTTAAGGCGACGTTTGAGCTCTGATTCCTTTGACTCACATTGCGTCTATTTAGTGGAGCCCATTCTATCTTCTTTGCGGCTTTGCTGAAGGCTTrC |
| 242 | Apq4_2186_RNA | AATTACACTCACAATGCCGACTGATTCCTTTGACTCACATTGCGTCTATTTAGTGGAGCCCATTCTATCTTCTTTTAATTCACACAAATGGGTArU |
| 243 | Apq4_3100_RNA | CACTGGAAATGACTGTTAAACTGATTCCTTTGACTCACATTGCGTCTATTTAGTGGAGCCCATTCTATCTTCTTTTGTACCATACTGAATGCTGrU |

TABLE 10-continued

| | | |
|---|---|---|
| 244 | Apq4_3673_RNA | CGGTGTATCTGTCAGTAGCTCTGATTCCTTTGACTCACATTGCGTCTAT TTAGTGGAGCCCATTCTATCTTCTTTTTTCCTCTCTGATCTCTGTrG |
| 245 | Apq4_4344_RNA | ACAGAGGCAGTGTCTCTGTGCTGATTCCTTTGACTCACATTGCGTCTAT TTAGTGGAGCCCATTCTATCTTCTTTGCTCTCTGGCTTCAATTGTrC |
| 246 | Pdgfra_296_RNA | TGGGAGGATAGAGGGTAATATCTACGAGTTTGCAGTCACGTGCGTCTAT TTAGTGGAGCCTGTCCTATCTTCTTTACAATCTTCTCATTCTCGTrU |
| 247 | Pdgfra_646_RNA | GGTATGATGGCAGAGTCATCTCTACGAGTTTGCAGTCACGTGCGTCTAT TTAGTGGAGCCTGTCCTATCTTCTTTCCGGATCTGTGGTGCGGCArA |
| 248 | Pdgfra_832_RNA | GTTGCTTTCAAGGCATAAACTCTACGAGTTTGCAGTCACGTGCGTCTAT TTAGTGGAGCCTGTCCTATCTTCTTTTCTCCAGATTCAGTTCTGArC |
| 249 | Pdgfra_1227_RNA | GGTAGGCCTGCACCTCCACCTCTACGAGTTTGCAGTCACGTGCGTCTAT TTAGTGGAGCCTGTCCTATCTTCTTTCCACGATATCCTGGGCGTCrG |
| 250 | Pdgfra_1544_RNA | CATCCAGTCGATTTCTGGAATCTACGAGTTTGCAGTCACGTGCGTCTAT TTAGTGGAGCCTGTCCTATCTTCTTTTTCTTAATATGCTTGCAGArU |

TABLE 11

List of PCR index primers used for monomer sequencing library preparation.

| SEQ ID NO: | Name | Sequence (5'-3') |
|---|---|---|
| 251 | fwd_index1 | AATGATACGGCGACCACCGAGATCTACACAGGCTATA<u>ACACTCTTTCCCTACACGAC</u> |
| 252 | fwd_index2 | AATGATACGGCGACCACCGAGATCTACACGCCTCTAT<u>ACACTCTTTCCCTACACGAC</u> |
| 253 | fwd_index3 | AATGATACGGCGACCACCGAGATCTACACAGGATAGG<u>ACACTCTTTCCCTACACGAC</u> |
| 254 | fwd_index4 | AATGATACGGCGACCACCGAGATCTACACTCAGAGCC<u>ACACTCTTTCCCTACACGAC</u> |
| 255 | fwd_index5 | AATGATACGGCGACCACCGAGATCTACACCTTCGCCT<u>ACACTCTTTCCCTACACGAC</u> |
| 256 | fwd_index6 | AATGATACGGCGACCACCGAGATCTACACTAAGATTA<u>ACACTCTTTCCCTACACGAC</u> |
| 257 | fwd_index7 | AATGATACGGCGACCACCGAGATCTACACACGTCCTG<u>ACACTCTTTCCCTACACGAC</u> |
| 258 | fwd_index8 | AATGATACGGCGACCACCGAGATCTACACGTCAGTAC<u>ACACTCTTTCCCTACACGAC</u> |
| 259 | rev_index1 | CAAGCAGAAGACGGCATACGAGATCGAGTAAT<u>GTGACTGGAGTTCAGACGTGT</u> |
| 260 | rev_index2 | CAAGCAGAAGACGGCATACGAGATTCTCCGGA<u>GTGACTGGAGTTCAGACGTGT</u> |
| 261 | rev_index3 | CAAGCAGAAGACGGCATACGAGATAATGAGCG<u>GTGACTGGAGTTCAGACGTGT</u> |
| 262 | P5primer | AATGATACGGCGACCACCGA |
| 263 | P7primer | CAAGCAGAAGACGGCATACGA | bolded: illumina index sequences used to differentiate monomers in pooled samples;
underlined: highlighted region indicating primer hybridisation site to the extended monomer.

TABLE 12

| SEQ ID NO: | Name | Sequence (5' → 3') |
|---|---|---|
| 264 | R_KRAS.D3 | AGCTCCAACTACCACAAAGTCGArUAGTCACGGCTACTCArGACGTAACGCGTTCAGrUGATGCCCTTGCCTACGCCACC |
| 265 | R_KRAS.D8 | AGCTCCAACTACCACAArAGTCGArUAGTCArCGGCTArCTCAGArCGTAACGrCGTTCAGrUGATGCrCCTTGCCTACGCCACC |

TABLE 13

| | | |
|---|---|---|
| 267 | R_KRAS.2G | AGCTCCAACTACCACAAAGTCGATAGTCACGGCTACTCArGrGCGTAACGCGTTCAGTGATGCCCTTGCCTACGCCACC |
| 268 | R_KRAS.2C | AGCTCCAACTACCACAAAGTCGATAGTCACGGCTACTCArCrCCGTAACGCGTTCAGTGATGCCCTTGCCTACGCCACC |
| 269 | R_KRAS.2A | AGCTCCAACTACCACAAAGTCGATAGTCACGGCTACTCArArACGTAACGCGTTCAGTGATGCCCTTGCCTACGCCACC |
| 270 | R_KRAS.2U | AGCTCCAACTACCACAAAGTCGATAGTCACGGCTACTCArUrUCGTAACGCGTTCAGTGATGCCCTTGCCTACGCCACC |
| 271 | R_KRAS.3G | AGCTCCAACTACCACAAAGTCGATAGTCACGGCTACTCArGrGrGTTAACGCGTTCAGTGATGCCCTTGCCTACGCCACC |
| 272 | R_KRAS.3C | AGCTCCAACTACCACAAAGTCGATAGTCACGGCTACTCArCrCrCGTAACGCGTTCAGTGATGCCCTTGCCTACGCCACC |
| 273 | R_KRAS.3A | AGCTCCAACTACCACAAAGTCGATAGTCACGGCTACTCArArArAGTAACGCGTTCAGTGATGCCCTTGCCTACGCCACC |
| 274 | R_KRAS.3U | AGCTCCAACTACCACAAAGTCGATAGTCACGGCTACTCArUrUrUCGTAACGCGTTCAGTGATGCCCTTGCCTACGCCACC |
| 275 | R_KRAS.3 | AGCTCCAACTACCACAAAGTCGATAGTCACGGCTACTCArGrArCGTAACGCGTTCAGTGATGCCCTTGCCTACGCCACC |

TABLE 13-continued

| | | |
|---|---|---|
| 276 | R_KRAS.2 | AGCTCCAACTACCACAAAGTCGATAGTCAC<br>GGCTACTCrGrACGTAACGCGTTCAGTGA<br>TGCCCTTGCCTACGCCACC |
| 277 | R_KRAS<br>wt1_2 | AGCTCCAACTACCACAA [1]<br>CArGrACGTAACGCGTTCAGTGATGCCCTT<br>GCCTACGCCACC |
| 278 | R_KRAS<br>wt1_3 | AGCTCCAACTACCACAA [1]<br>CArGrArCGTAACGCGTTCAGTGATGCCCT<br>TGCCTACGCCACC |
| 279 | R_KRAS<br>wt1_4 | AGCTCCAACTACCACAA [1]<br>CArGrArCrGTAACGCGTTCAGTGATGCCC<br>TTGCCTACGCCACC |
| 280 | R_KRAS<br>wt1_5 | AGCTCCAACTACCACAA [1]<br>CArGrArCrGrUAACGCGTTCAGTGATGCC<br>CTTGCCTACGCCACC |
| 281 | R_KRAS<br>wt1_7 | AGCTCCAACTACCACAA [1]<br>CArGrArCrGrUrArACGCGTTCAGTGATG<br>CCCTTGCCTACGCCACC |

SEQ ID NO: 266:
Bacteriophage Phi29 WT polymerase
MKHMPRKMYSCDFETTTKVEDCRVWAYGYMNIEDHSEYKIGNSLDEFMAW

VLKVQADLYFHNLKFDGAFIINWLERNGFKWSADGLPNTYNTIISRMGQW

YMIDICLGYKGKRKIHTVIYDSLKKLPFPVKKIAKDFKLTVLKGDIDYHK

ERPVGYKITPEEYAYIKNDIQIIAEALLIQFKQGLDRMTAGSDSLKGFKD

IITTKKFKKVFPTLSLGLDKEVRYAYRGGFTWLNDRFKEKEIGEGMVFDV

NSLYPAQMYSRLLPYGEPIVFEGKYVWDEDYPLHIQHIRCEFELKEGYIP

TIQIKRSRFYKGNEYLKSSGGEIADLWLSNVDLELMKEHYDLYNVEYISG

LKFKATTGLFKDFIDKWTYIKTTSEGAIKQLAKLMLNSLYGKFASNPDVT

GKVPYLKENGALGFRLGEEETKDPVYTPMGVFITAWARYTTITAAQACYD

RIIYCDTDSIHLTGTEIPDVIKDIVDPKKLGYWAHESTFKRAKYLRQKTY

IQDIYMKEVDGKLVEGSPDDYTDIKFSVKCAGMTDKIKKEVTFENFKVGF

SRKMKPKPVQVPGGVVLVDDTFTIK

---

What is claimed is:

1. A method of detecting a target RNA molecule in situ in a cell or tissue sample, the method comprising:
  (a) contacting the cell or tissue sample with a first oligonucleotide and a second oligonucleotide to hybridize the first oligonucleotide and the second oligonucleotide to the target RNA molecule,
    wherein the first oligonucleotide comprises a first target binding site at a 5' end,
    wherein the second oligonucleotide comprises (i) a second target binding site at a 3' end, and (ii) a ribonucleotide at a 3' terminus; and
    wherein a 5' terminus of the first oligonucleotide and the 3' terminus of the second oligonucleotide are adjacent to one another when hybridized to the target RNA molecule;
  (b) ligating the first and second oligonucleotides hybridized to the target RNA molecule to generate a circularized probe,
    wherein the 5' terminus of the first oligonucleotide is ligated to the 3' terminus of the second oligonucleotide, and
    wherein the 3' terminus of the first oligonucleotide is ligated to the 5' terminus of the second oligonucleotide;
  (c) amplifying the circularized probe by rolling circle amplification (RCA) to generate an RCA product; and
  (d) detecting the RCA product at a location in the cell or tissue sample, thereby detecting the target RNA molecule at the location in the cell or tissue sample.

2. The method of claim 1, wherein the second oligonucleotide comprises at least one additional ribonucleotide, but no more than 2 consecutive ribonucleotides.

3. The method of claim 2, wherein two consecutive ribonucleotides are present at the 3' terminus of the second oligonucleotide.

4. The method of claim 1, wherein the second oligonucleotide does not comprise any additional ribonucleotides.

5. The method of claim 1, wherein the first oligonucleotide comprises a ribonucleotide at the 3' terminus.

6. The method of claim 1, wherein the first oligonucleotide comprises a deoxyribonucleotide comprising a 5' phosphate group at the 5' terminus.

7. The method of claim 1, wherein the 5' terminus of the first oligonucleotide does not comprise a ribonucleotide.

8. The method of claim 1, wherein the first and second oligonucleotides are ligated without gap-fill extension or hybridization of a gap oligonucleotide to the target RNA molecule to fill a gap between the 5' terminus of the first oligonucleotide and the 3' terminus of the second oligonucleotide.

9. The method of claim 1, wherein ligating the first and second oligonucleotides comprises using a DNA/RNA ligase.

10. The method of claim 9, wherein the DNA/RNA ligase is an RNA ligase.

11. The method of claim 9, wherein the DNA/RNA ligase is T4 DNA ligase, T4 RNA ligase 1, T4 RNA ligase 2, PBCV-1 ligase, or DraRN1 ligase.

12. The method of claim 1, further comprising contacting the cell or tissue sample with a third oligonucleotide, wherein the 3' end of the first oligonucleotide and the 5' end of the second oligonucleotide hybridize to the third oligonucleotide and are ligated using the third oligonucleotide as a ligation template.

13. The method of claim 12, wherein the cell or tissue sample is contacted with the third oligonucleotide subsequent to (a).

14. The method of claim 12, wherein the third oligonucleotide is prehybridized to the first oligonucleotide and the second oligonucleotide prior to (a).

15. The method of claim 12, wherein the first and second oligonucleotides are ligated without gap-fill extension or hybridization of a gap oligonucleotide to the third oligonucleotide to fill a gap between the 3' end of the first oligonucleotide and the 5' end of the second oligonucleotide.

16. The method of claim 12, wherein the first oligonucleotide comprises a 3' terminal deoxyribonucleotide and the second oligonucleotide comprises a 5' terminal deoxyribonucleotide.

17. The method of claim 16, wherein the third oligonucleotide is a DNA molecule.

18. The method of claim 17, wherein the 3' terminus of the first oligonucleotide is ligated to the 5' terminus of the second oligonucleotide using a DNA ligase.

19. The method of claim 18, wherein the 5' terminus of the first oligonucleotide is ligated to the 3' terminus of the second oligonucleotide using a DNA/RNA ligase.

20. The method of claim 19, wherein the DNA/RNA ligase is T4 DNA ligase, T4 RNA ligase 1, T4 RNA ligase 2, PBCV-1 ligase, or DraRN1 ligase.

21. The method of claim 1, wherein the circularized probe comprises no more than 2 consecutive ribonucleotides.

22. The method of claim 1, wherein the RCA comprises using a Phi29 DNA polymerase.

23. The method of claim 1, wherein:
  (i) the first oligonucleotide comprises one or more further sequences selected from the group consisting of a barcode sequence and a primer binding sequence;
  (ii) the second oligonucleotide comprises one or more further sequences selected from the group consisting of a barcode sequence and a primer binding sequence; or
  (iii) the first oligonucleotide and the second oligonucleotide each comprises one or more further sequences selected from the group consisting of a barcode sequence and a primer binding sequence.

24. The method of claim 1, wherein (c) comprises extending a primer hybridized to the circularized probe to generate the RCA product.

25. The method of claim 1, wherein the first oligonucleotide or the second oligonucleotide comprises a primer binding sequence such that the circularized probe comprises the primer binding sequence and wherein (c) comprises hybridizing a primer to the circularized probe and extending the primer to generate the RCA product.

26. The method of claim 1, wherein (c) comprises using a 3' portion of the target RNA molecule as a primer to generate the RCA product.

27. The method of claim 1, wherein the circularized probe comprises a barcode sequence that identifies the target RNA molecule.

28. The method of claim 27, wherein (d) comprises hybridizing fluorescently labeled detection oligonucleotides to the RCA product at the barcode sequence and using imaging to detect fluorescent signals associated with the RCA product.

29. The method of claim 1, wherein at least 10, at least 20, at least 100, or at least 1,000 different target RNA sequences are detected in parallel or sequentially at locations in the cell or tissue sample.

30. The method of claim 1, wherein the cell or tissue sample is a tissue section on a solid support.

\* \* \* \* \*